US010636322B2

(12) United States Patent
Wexler et al.

(10) Patent No.: US 10,636,322 B2
(45) Date of Patent: Apr. 28, 2020

(54) APPARATUS AND METHOD FOR ANALYZING IMAGES

(71) Applicant: OrCam Technologies Ltd., Jerusalem (IL)

(72) Inventors: Yonatan Wexler, Jerusalem (IL); Amnon Shashua, Mevasseret Zion (IL)

(73) Assignee: ORCAM TECHNOLOGIES LTD., Jerusalem (IL)

( * ) Notice: Subject to any disclaimer, the term of this patent is extended or adjusted under 35 U.S.C. 154(b) by 0 days.

(21) Appl. No.: 15/882,774

(22) Filed: Jan. 29, 2018

(65) Prior Publication Data
US 2018/0218643 A1 Aug. 2, 2018

Related U.S. Application Data

(63) Continuation of application No. 14/136,876, filed on Dec. 20, 2013, now Pat. No. 9,911,361.
(Continued)

(51) Int. Cl.
*G09B 21/00* (2006.01)
*G06K 9/00* (2006.01)
(Continued)

(52) U.S. Cl.
CPC .............. *G09B 21/008* (2013.01); *A61F 9/08* (2013.01); *G06F 1/163* (2013.01); *G06F 3/011* (2013.01);
(Continued)

(58) Field of Classification Search
CPC ....... G09B 21/006; G09B 21/008; A61F 9/08; G06F 1/163; G06F 3/011
(Continued)

(56) References Cited

U.S. PATENT DOCUMENTS 5,742,264 A 4/1998 Inagaki et al.
6,115,482 A 9/2000 Sears et al.
(Continued)

FOREIGN PATENT DOCUMENTS

EP 2065871 6/2009
EP 2490155 8/2012

OTHER PUBLICATIONS

U.S. Appl. No. 14/136,438, filed Dec. 20, 2013, entitled "Apparatus, Method, and Computer Readable Medium for Expedited Text Reading Using Staged OCR Technique,".
(Continued)

*Primary Examiner* — Jeffery A Williams
(74) *Attorney, Agent, or Firm* — Finnegan, Henderson, Farabow, Garrett & Dunner LLP

(57) ABSTRACT

Devices and a method are provided for providing feedback to a user. In one implementation, the method comprises obtaining a plurality of images from an image sensor. The image sensor is configured to be positioned for movement with the user's head. The method further comprises monitoring the images, and determining whether relative motion occurs between a first portion of a scene captured in the plurality of images and other portions of the scene captured in the plurality of images. If the first portion of the scene moves less than at least one other portion of the scene, the method comprises obtaining contextual information from the first portion of the scene. The method further comprises providing the feedback to the user based on at least part of the contextual information.

13 Claims, 121 Drawing Sheets

Related U.S. Application Data

(60) Provisional application No. 61/775,603, filed on Mar. 10, 2013, provisional application No. 61/799,649, filed on Mar. 15, 2013, provisional application No. 61/830,122, filed on Jun. 2, 2013.

(51) Int. Cl.

| | | |
|---|---|---|
| *G06F 1/16* | (2006.01) | |
| *G06F 3/01* | (2006.01) | |
| *H04M 1/725* | (2006.01) | |
| *A61F 9/08* | (2006.01) | |
| *G06K 9/18* | (2006.01) | |

(52) U.S. Cl.
CPC ........... *G06K 9/00442* (2013.01); *G06K 9/18* (2013.01); *G09B 21/006* (2013.01); *H04M 1/72522* (2013.01); *H04M 1/72577* (2013.01); *H04M 2250/52* (2013.01)

(58) Field of Classification Search
USPC .......................................................... 348/62
See application file for complete search history.

(56) References Cited

U.S. PATENT DOCUMENTS

| | | | |
|---|---|---|---|
| 6,948,937 | B2 | 9/2005 | Tretiakoff et al. |
| 7,627,142 | B2 | 12/2009 | Kurzweil et al. |
| 8,630,454 | B1 | 1/2014 | Wang et al. |
| 8,891,817 | B2 | 11/2014 | Wexler et al. |
| 8,902,303 | B2 | 12/2014 | Na'aman et al. |
| 8,908,021 | B2 | 12/2014 | Wexler et al. |
| 8,909,530 | B2 | 12/2014 | Wexler et al. |
| 8,937,650 | B2 | 1/2015 | Wexler et al. |
| 9,025,016 | B2 | 5/2015 | Wexler et al. |
| 9,095,423 | B2 | 8/2015 | Wexler et al. |
| 9,101,459 | B2 | 8/2015 | Wexler et al. |
| 9,189,973 | B2 | 11/2015 | Wexler et al. |
| 9,213,911 | B2 | 12/2015 | Wexler et al. |
| 2003/0086061 | A1 | 5/2003 | Pfleger |
| 2003/0095140 | A1* | 5/2003 | Keaton .................. G06F 3/011 715/700 |
| 2004/0233192 | A1 | 11/2004 | Hopper |
| 2005/0110875 | A1 | 5/2005 | Ma |
| 2005/0208457 | A1 | 9/2005 | Fink et al. |
| 2006/0017810 | A1 | 1/2006 | Kurzweil et al. |
| 2008/0107307 | A1 | 5/2008 | Altherr |
| 2009/0087024 | A1 | 4/2009 | Eaton et al. |
| 2009/0278766 | A1 | 11/2009 | Sako et al. |
| 2009/0313020 | A1 | 12/2009 | Koivunen |
| 2010/0073568 | A1 | 3/2010 | Van Ostrand et al. |
| 2010/0177970 | A1 | 7/2010 | King et al. |
| 2011/0044537 | A1 | 2/2011 | Cobb et al. |
| 2011/0091098 | A1 | 4/2011 | Yuille et al. |
| 2011/0228085 | A1 | 9/2011 | Hofman |
| 2012/0045090 | A1 | 2/2012 | Bobbitt et al. |
| 2012/0046947 | A1 | 2/2012 | Fleizach |
| 2012/0212406 | A1 | 8/2012 | Osterhout et al. |
| 2012/0212593 | A1 | 8/2012 | Na'aman et al. |
| 2013/0117025 | A1 | 5/2013 | Park et al. |
| 2013/0169536 | A1 | 7/2013 | Wexler et al. |
| 2013/0187835 | A1 | 7/2013 | Vaught et al. |
| 2013/0253980 | A1 | 9/2013 | Blom et al. |
| 2013/0271584 | A1 | 10/2013 | Wexler et al. |
| 2014/0003654 | A1 | 1/2014 | Beaurepaire |
| 2014/0160170 | A1 | 6/2014 | Lyons |
| 2015/0042562 | A1* | 2/2015 | Kurzweil ............... G06K 9/228 345/156 |

OTHER PUBLICATIONS

U.S. Appl. No. 14/135,727, filed Dec. 20, 2013, entitled "Systems and Method for Audible Facial Recognition,".

U.S. Appl. No. 14/137,033, filed Dec. 20, 2013, entitled "Apparatus and Method for Providing Failed-Attempt Feedback Using a Camera on Glasses,".

U.S. Appl. No. 14/137,263, filed Dec. 20, 2013, entitled "Apparatus and Method for Executing System Commands Based on Captured Image Data,".

U.S. Appl. No. 14/135,757, filed Dec. 20, 2013, entitled "Systems and Methods for Automatic Control of a Continuous Action,".

U.S. Appl. No. 14/137,373, filed Dec. 20, 2013, entitled "Apparatus and Method for Automatic Action Selection Based on Image Context,".

U.S. Appl. No. 14/135,762, filed Dec. 20, 2013, entitled "Systems and Methods for Performing a Triggered Action,".

U.S. Appl. No. 14/137,328, filed Dec. 20, 2013, entitled "Apparatus and Method for Performing Actions Based on Captured Image Data,".

U.S. Appl. No. 14/135,859, filed Dec. 20, 2013, entitled "Apparatus Connectable to Glasses,".

U.S. Appl. No. 14/137,446, filed Dec. 20, 2013, entitled "Apparatus and Method for Hierarchical Object Identification Using a Camera on Glasses,".

U.S. Appl. No. 14/135,928, filed Dec. 20, 2013, entitled "Systems and Methods for Processing Images,".

U.S. Appl. No. 14/135,775, filed Dec. 20, 2013, entitled "Systems and Methods for Providing Feedback Based on the State of an Object,".

U.S. Appl. No. 14/137,522, filed Dec. 20, 2013, entitled "Apparatus and Method for Using Background Change to Determine Context,".

U.S. Appl. No. 14/136,545, filed Dec. 20, 2013, entitled "Apparatus, Method, and Computer Readable Medium for Recognizing Text on a Curved Surface,".

U.S. Appl. No. 14/137,384, filed Dec. 20, 2013, entitled "Systems and Methods for Audibly Presenting Textual Information Included in Image Data,".

Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.

Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).

Office Action dated Feb. 3, 2015 in U.S. Appl. No. 14/137,328, 24 pages.

Office Action dated Jun. 19, 2015 in U.S. Appl. No. 14/137,328, 31 pages.

Office Action dated Oct. 14, 2015 in U.S. Appl. No. 14/137,328, 28 pages.

Office Action dated Feb. 2, 2016 in U.S. Appl. No. 14/137,328, 32 pages.

Office Action dated Aug. 11, 2016 in U.S. Appl. No. 14/137,328, 35 pages.

Zeigler et al., "Non-rigid Surface Detection for Gestural Interaction with Applicable Surfaces," *2012 IEEE Applications of Computer Vision (WACV)*, Jan. 9, 2012, 73-80.

European Patent Office, PCT International Search Report, International Application No. PCT/IB2014/001252, dated Oct. 14, 2014, 5 pages.

European Patent Office, Written Opinion of the International Searching Authority, International Application No. PCT/IB2014/001252, dated Oct. 14, 2014, 6 pages.

Office Action dated Jun. 3, 2014 in U.S. Appl. No. 14/137,328, 11 pages.

European Patent Office, PCT International Search Report, International Application No. PCT/IB2014/000850, dated Sep. 22, 2014, 4 pages.

European Patent Office, International Preliminary Report on Patentability, International Application No. PCT/IB2014/000850, dated Sep. 15, 2015, 5 pages.

\* cited by examiner

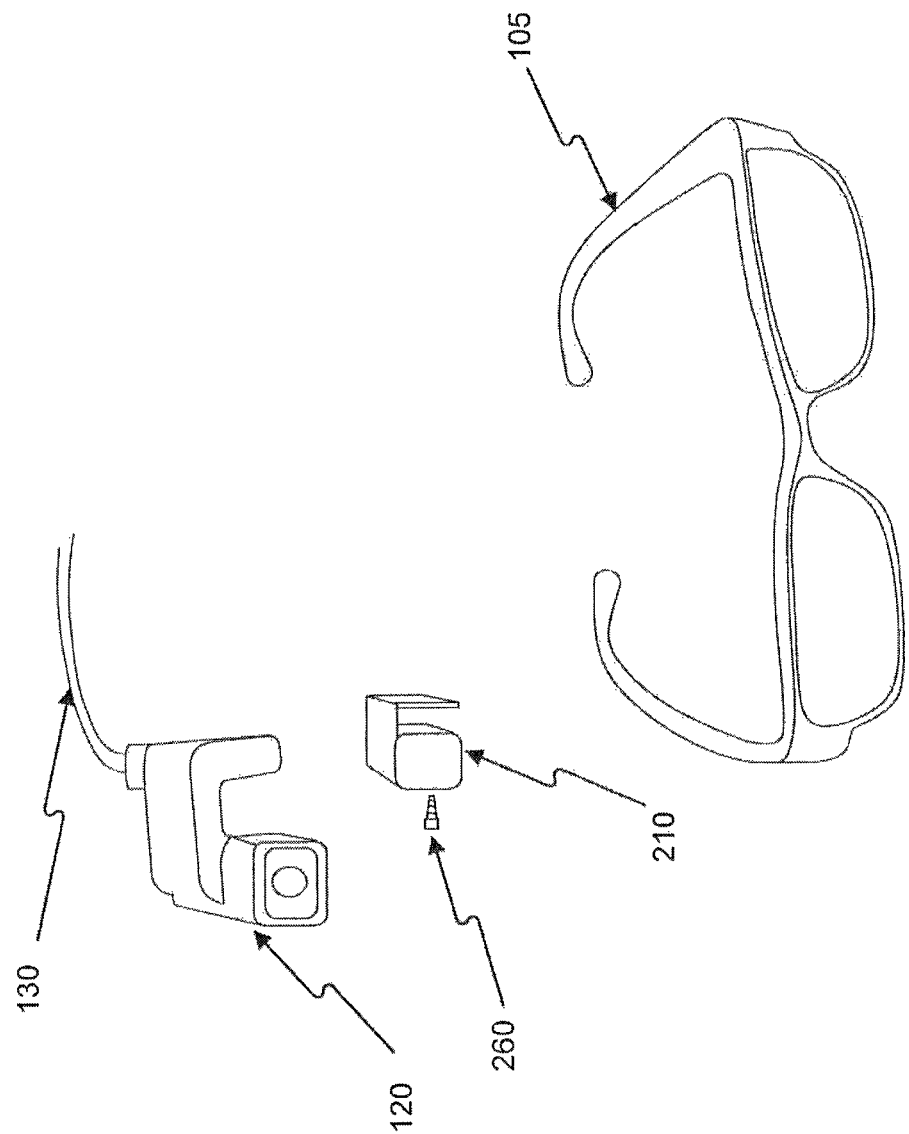

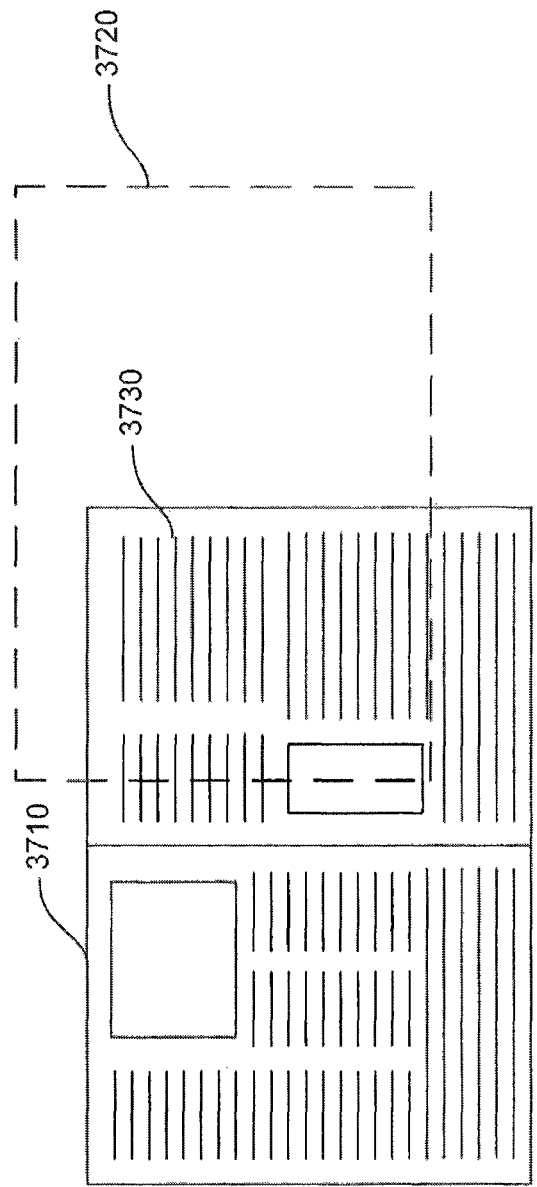
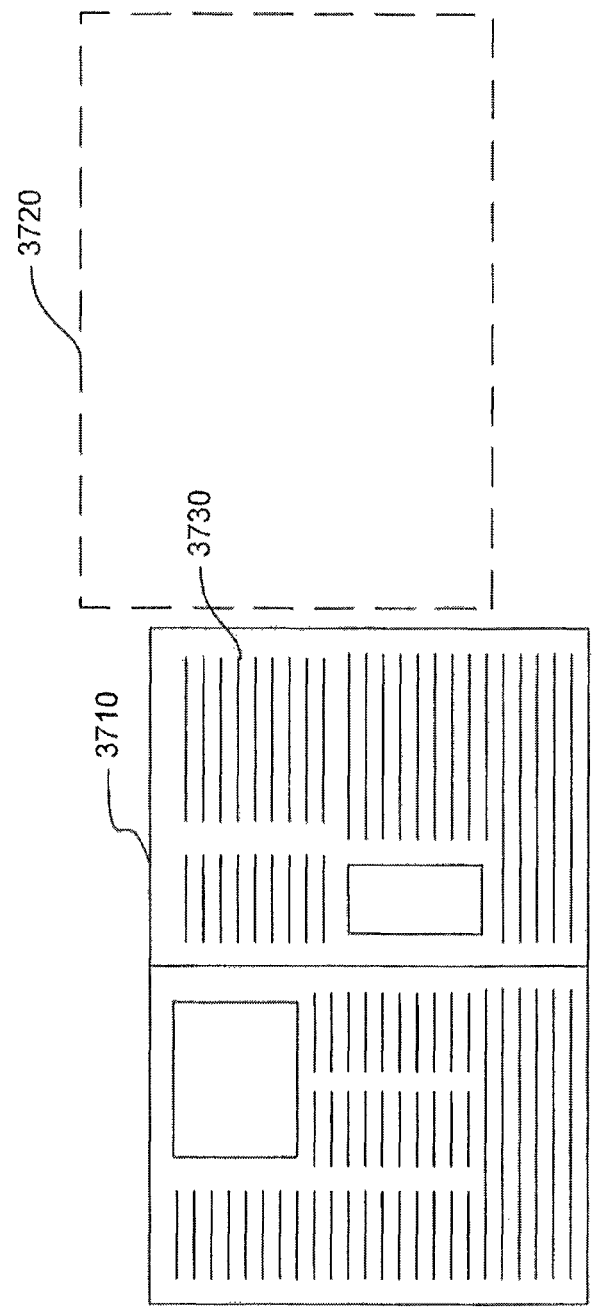
Fig. 37A
Fig. 37B

The following detailed description refers to the accompanying drawings. Wherever possible, the same reference numbers are used in the drawings and the following description to refer to the same or similar parts. While several illustrative embodiments are described herein, modifications, adaptations and other implementations are possible. ~5404

For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

APPARATUS AND METHOD FOR ANALYZING IMAGES

CROSS REFERENCE TO RELATED APPLICATIONS

This application is a continuation application under 37 C.F.R. § 1.53(b) of U.S. patent application Ser. No. 14/136,876, filed Dec. 20, 2013, pending, which claims the benefit of priority of U.S. Provisional Patent Application No. 61/775,603, filed Mar. 10, 2013, U.S. Provisional Patent Application No. 61/799,649, filed on Mar. 15, 2013, and U.S. Provisional Patent Application No. 61/830,122, filed on Jun. 2, 2013, the disclosures of which are all incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

Consistent with disclosed embodiments, an apparatus for providing feedback to a user is provided. The apparatus includes an image sensor configured to be positioned for movement with a head of the user as the head moves, and to capture real time images from an environment of the user. The apparatus also includes at least one processor device for determining contextual information based on the real time images. The processor device may be configured to monitor a plurality of images captured by the image sensor to determine whether relative motion occurs between a first portion of a scene captured in the plurality of images and other portions of the scene captured in the plurality of images. If the first portion of the scene moves less than at least one other portion of the scene, the processor device may also be configured to obtain contextual information from the first portion of the scene. Also, the processor device may be configured to provide the feedback to the user based on at least part of the contextual information.

Consistent with disclosed embodiments, an apparatus for providing feedback to a user is provided. The apparatus includes an image sensor for capturing real time images from an environment of the user, the image sensor configured to be positioned for movement with a head of the user as the head moves such that an aiming direction of the image sensor falls within a field of view of the user. The apparatus also includes at least one processor device for determining contextual information based on the real time images. The processor device may be configured to monitor the real time images captured by the image sensor to automatically determine whether an object in the user's field of view lingers within a plurality of the real time images. The processor device may also be configured to identify at least one object determined to linger within the plurality of real time images as an object of interest. Further, the processor device may be configured to obtain contextual information associated with the object of interest. The processor device may also be configured to provide the feedback to the user based on at least part of the contextual information.

Consistent with disclosed embodiments, a method for providing feedback to a user is provided. The method includes obtaining from an image sensor a plurality of images, wherein the image sensor is configured to be positioned for movement with a head of the user. The method also includes monitoring the plurality of images captured by the image sensor. The method further includes determining whether relative motion occurs between a first portion of a scene captured in the plurality of images and other portions of the scene captured in the plurality of images. If the first portion of the scene moves less than at least one other portion of the scene, the method further includes obtaining contextual information from the first portion of the scene. Also, the method further includes providing the feedback to the user based on at least part of the contextual information.

Consistent with disclosed embodiments, an apparatus for processing real time images of an environment of a user is provided. The apparatus includes a camera including an image sensor configured to be positioned for movement with a head of the user as the head moves, and to capture real time images. The apparatus also includes at least one processor device for determining contextual information based on the real time images. The processor device may be configured to monitor a plurality of images captured by the image sensor to determine whether relative motion occurs between a first portion of a scene captured in the plurality of images and other portions of the scene captured in the plurality of images. If the first portion of the scene moves less than at least one other portion of the scene, the processor device may also be configured to obtain contextual information from the first portion of the scene. Also, the processor device may be configured to adjust at least one parameter associated with the camera based on at least part of the contextual information.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 2E is an exploded view of FIG. 2D;

FIG. 37A is a schematic illustration of an object in the field of view of the apparatus;

FIG. 37B is a schematic illustration of an object outside of the field of view of the apparatus;

FIGS. 54A-54F illustrate exemplary level breaks within captured image data, according to disclosed embodiments;

FIG. 93 is a flow diagram of an exemplary process audibly presenting textual information disposed within captured image data, according to disclosed embodiments;

FIG. 94 is a flow diagram of an exemplary process for identifying portions of machine-readable text for audible presentation, according to disclosed embodiments;

FIG. 95 illustrates exemplary image data captured by an apparatus for aiding persons who have low vision, according to disclosed embodiments;

FIG. 96 illustrates exemplary image data captured by an apparatus for aiding persons who have low vision, according to disclosed embodiments;

FIG. 97 is a flow diagram of an exemplary process for identifying portions of textual information for audible presentation based on a logical structure of the textual information, according to disclosed embodiments; and FIG. 98 illustrates exemplary image data captured by an apparatus for aiding persons who have low vision, according to disclosed embodiments.

DETAILED DESCRIPTION

Figure 1:
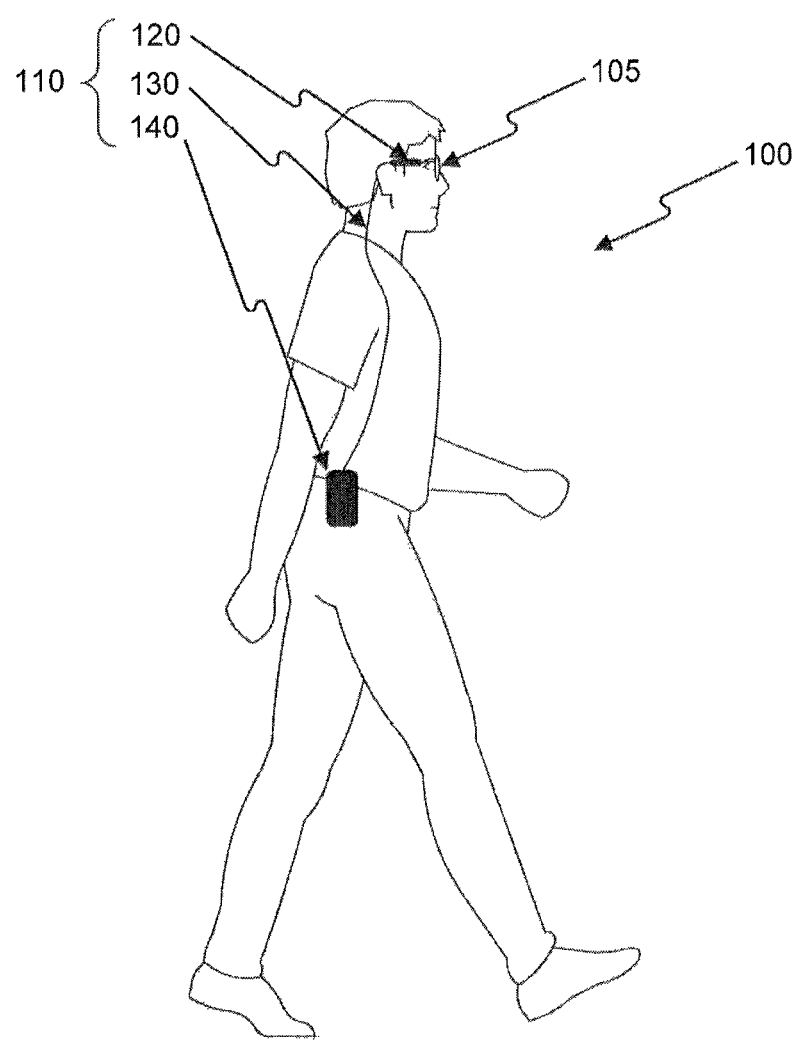
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
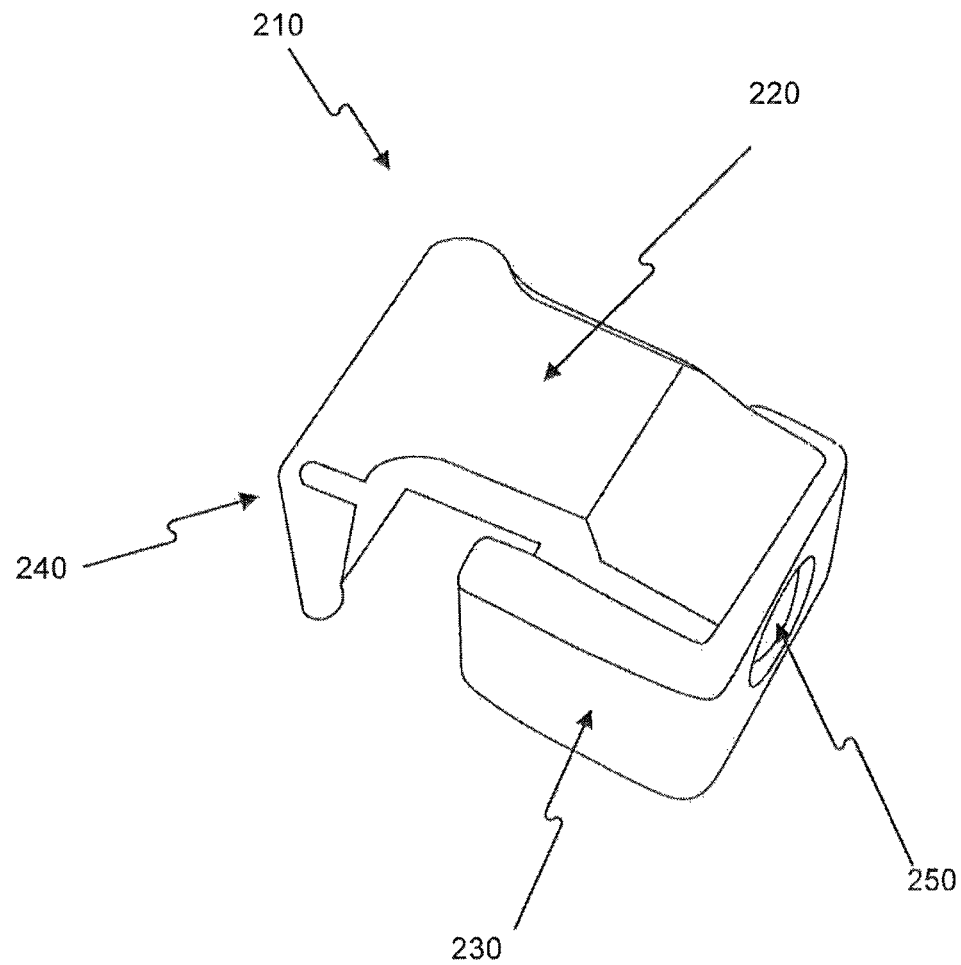
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. Support 210 may be mounted on glasses 105 such that support is permanently or detachably mounted on glasses 105. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
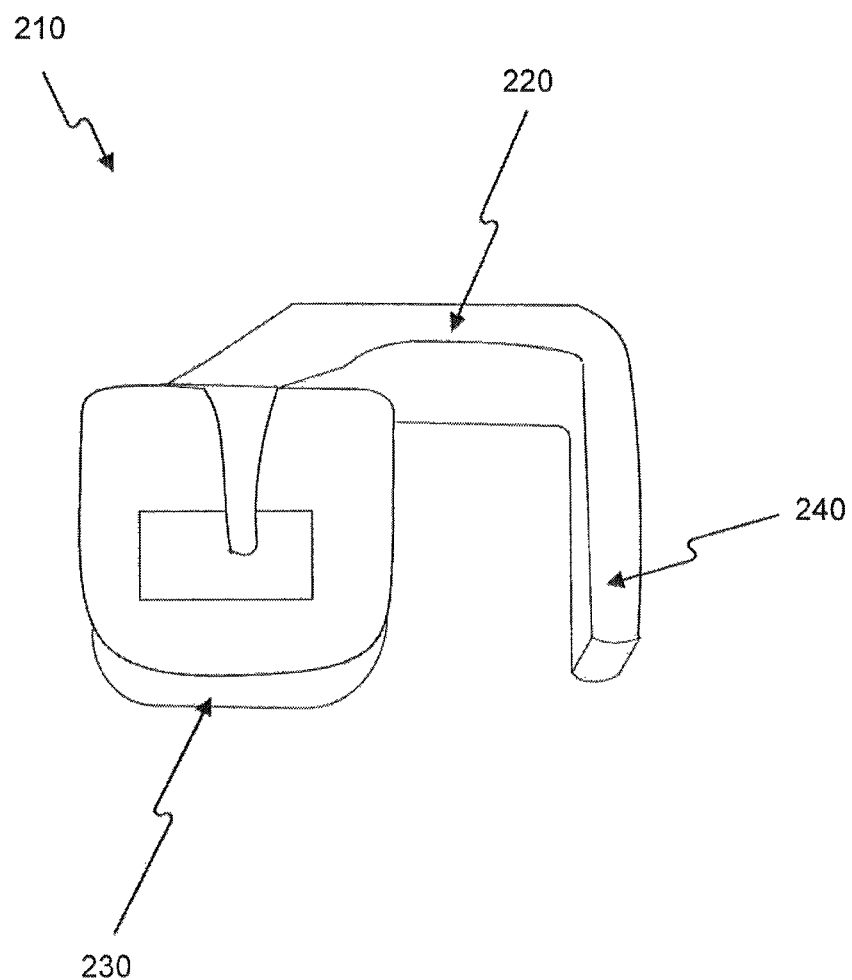
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

Figure 2C:
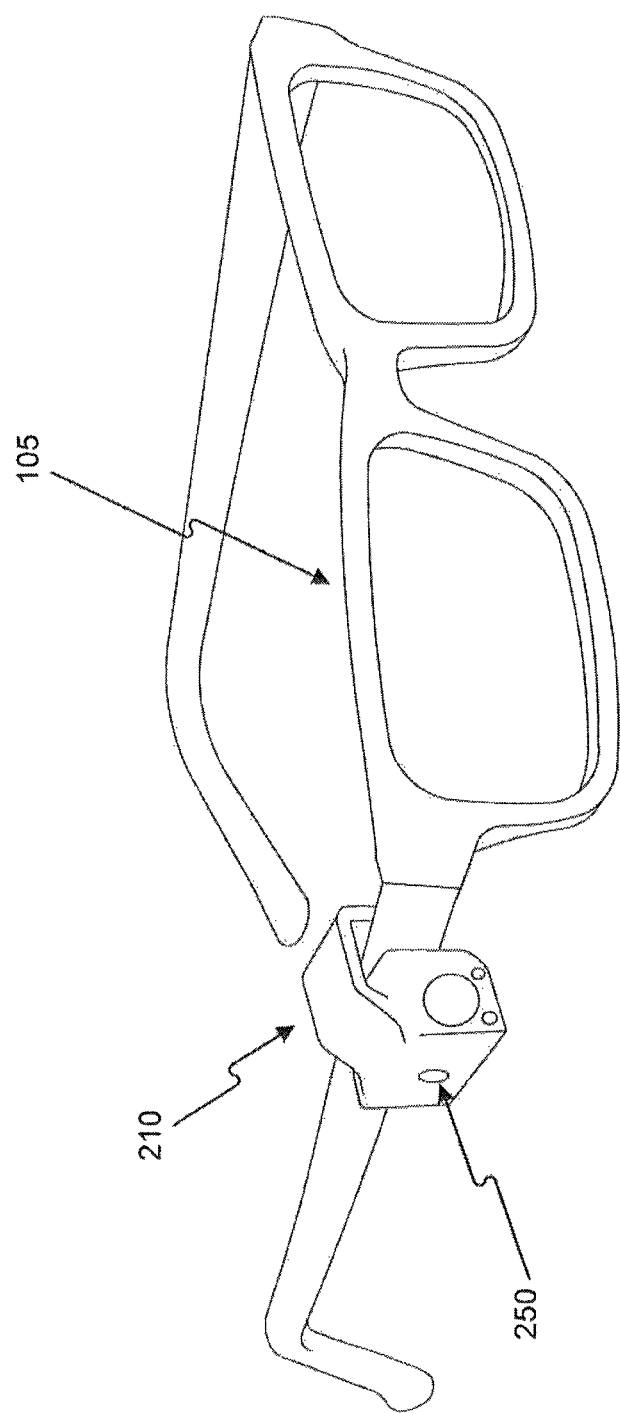
FIG. 2C is a schematic illustration of the support shown in FIG. 2A mounted on a pair of glasses.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
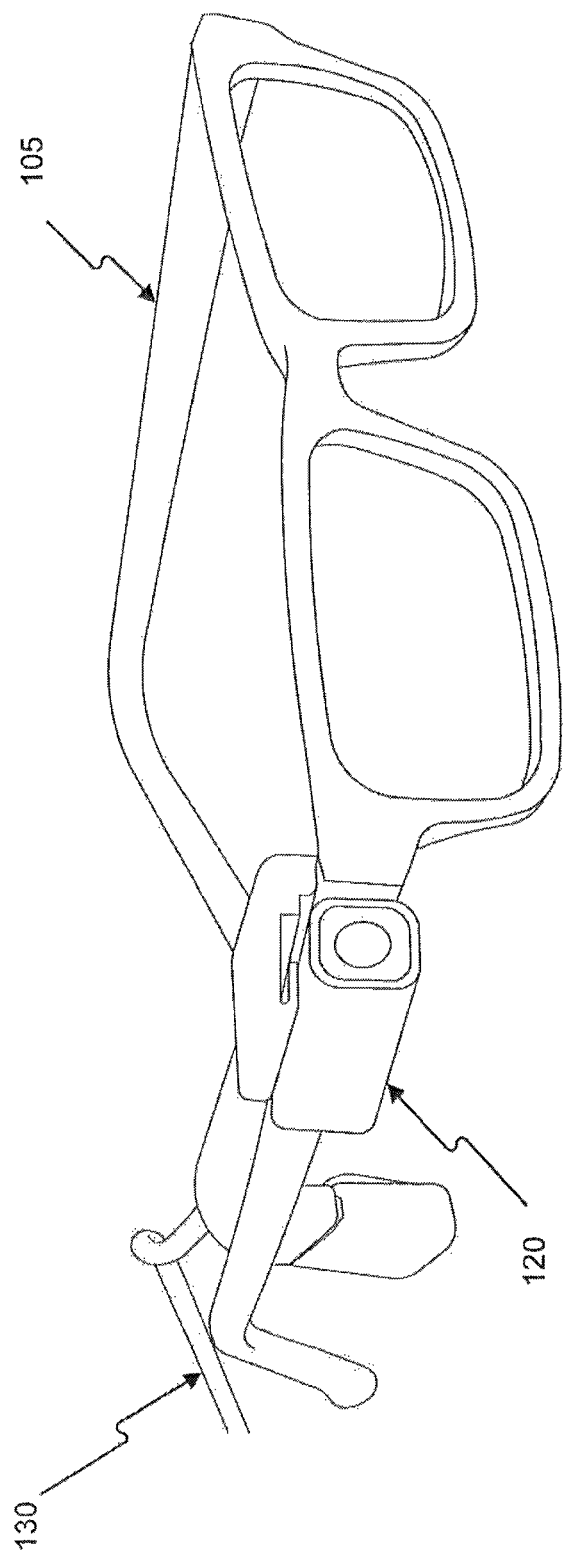
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment component may be internal or external to sensory unit 120.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
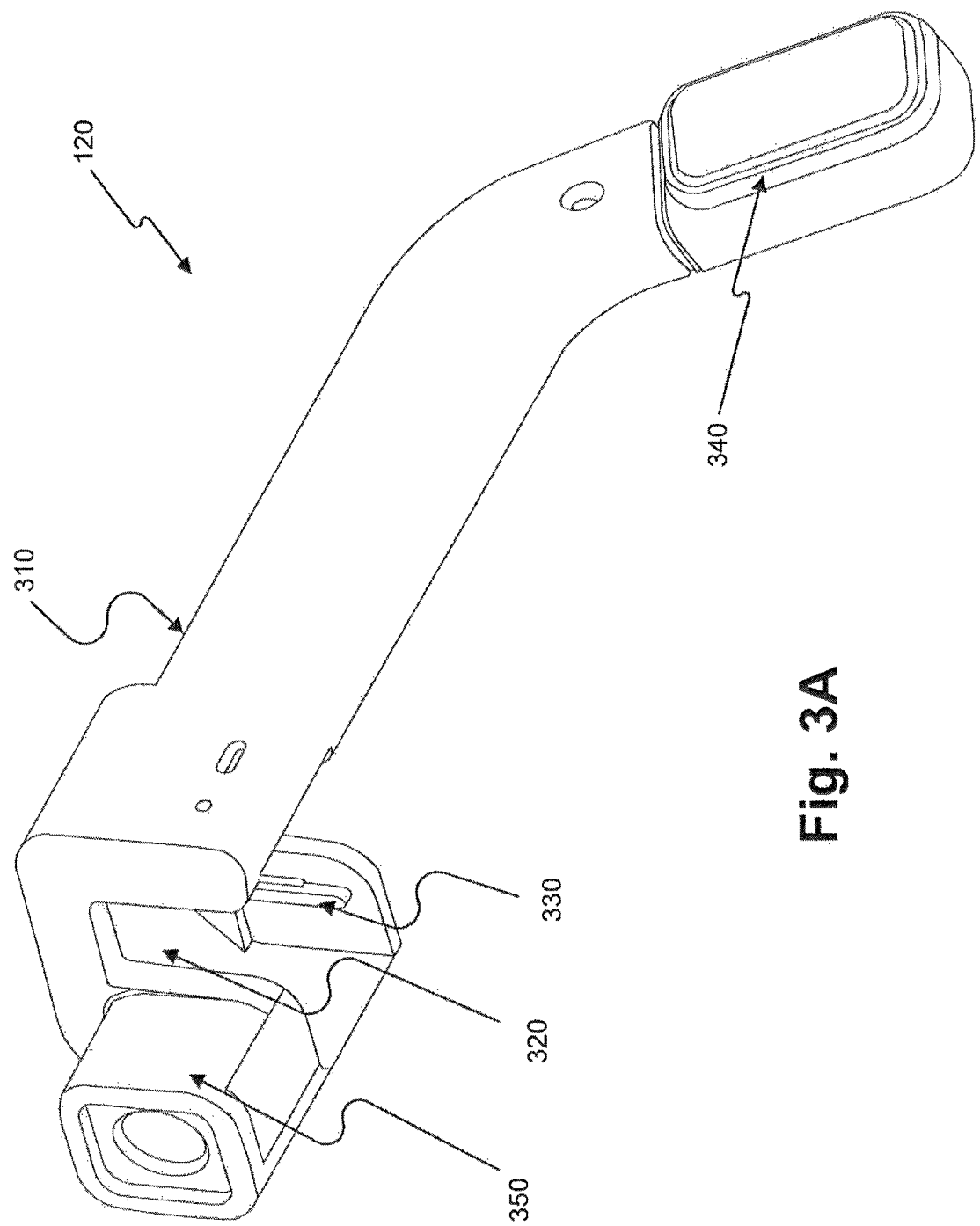
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. Housing 310 may be configured for selective attachment to support 210. Additionally, housing 310 may include the adjustment component discussed above in connection with FIG. 2D. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

Figure 3B:
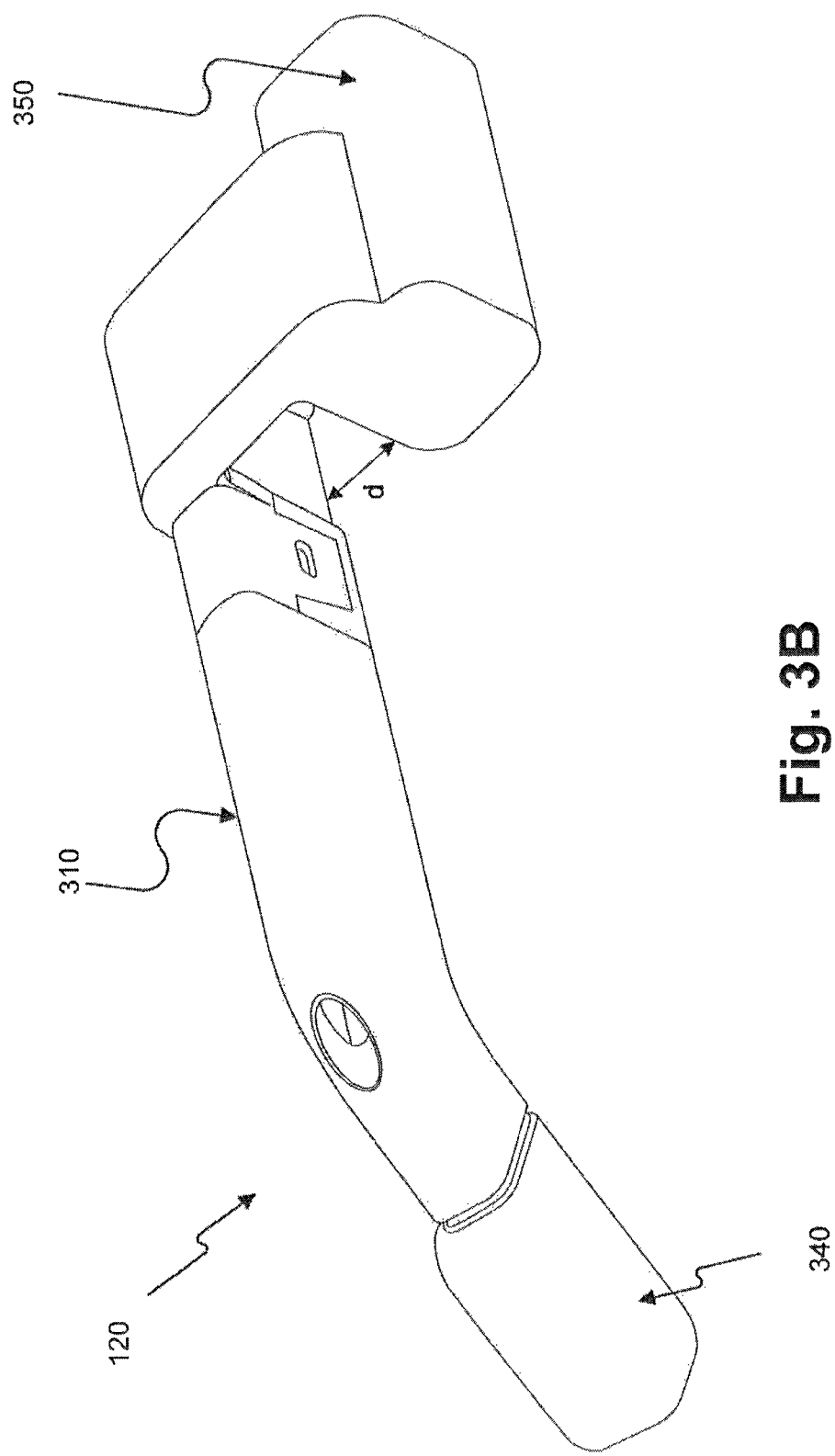
FIG. 3B is a schematic illustration of the sensory unit shown in FIG. 3A from a second viewpoint.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
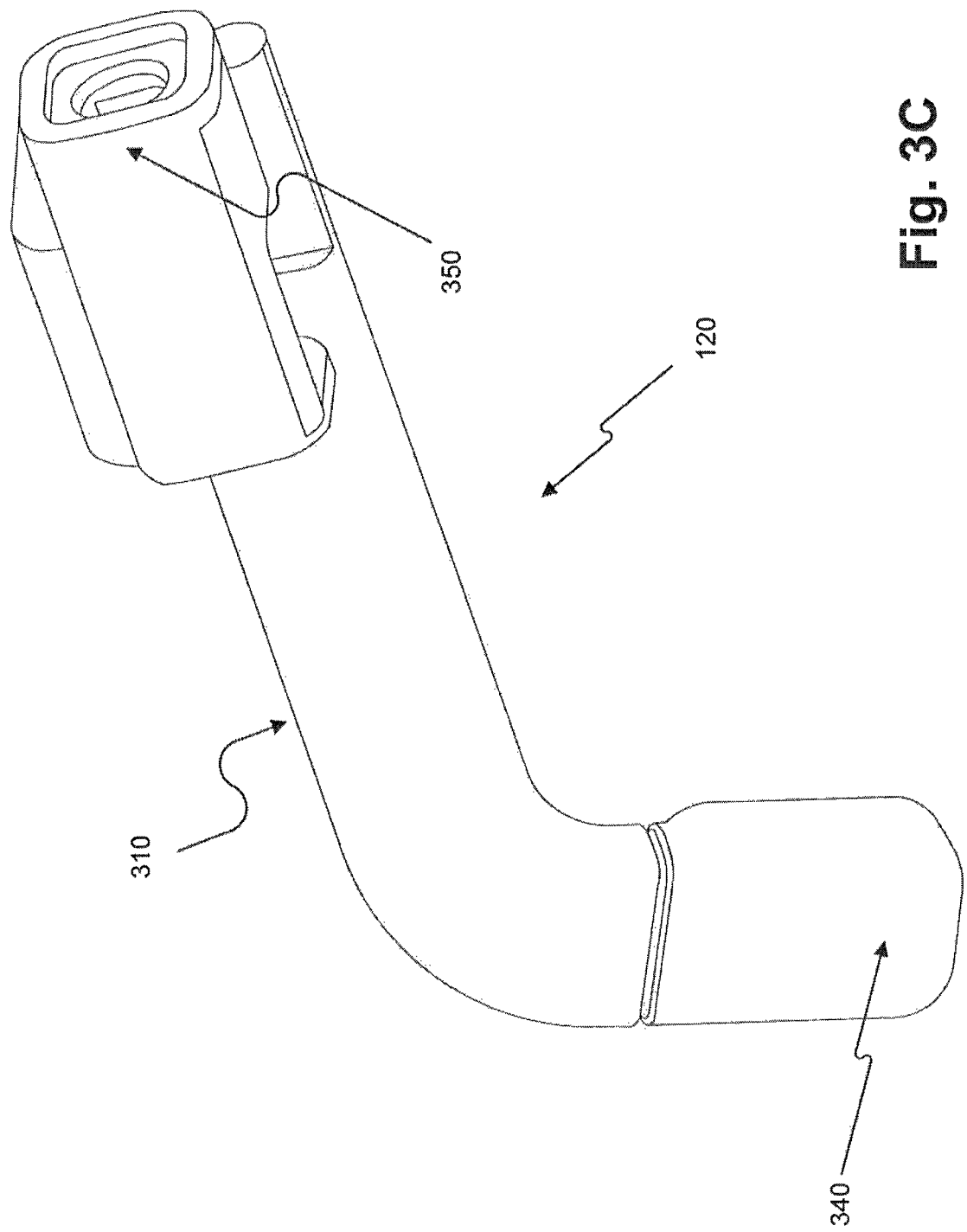
FIG. 3C is a schematic illustration of the sensory unit shown in FIG. 3A from a third viewpoint.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
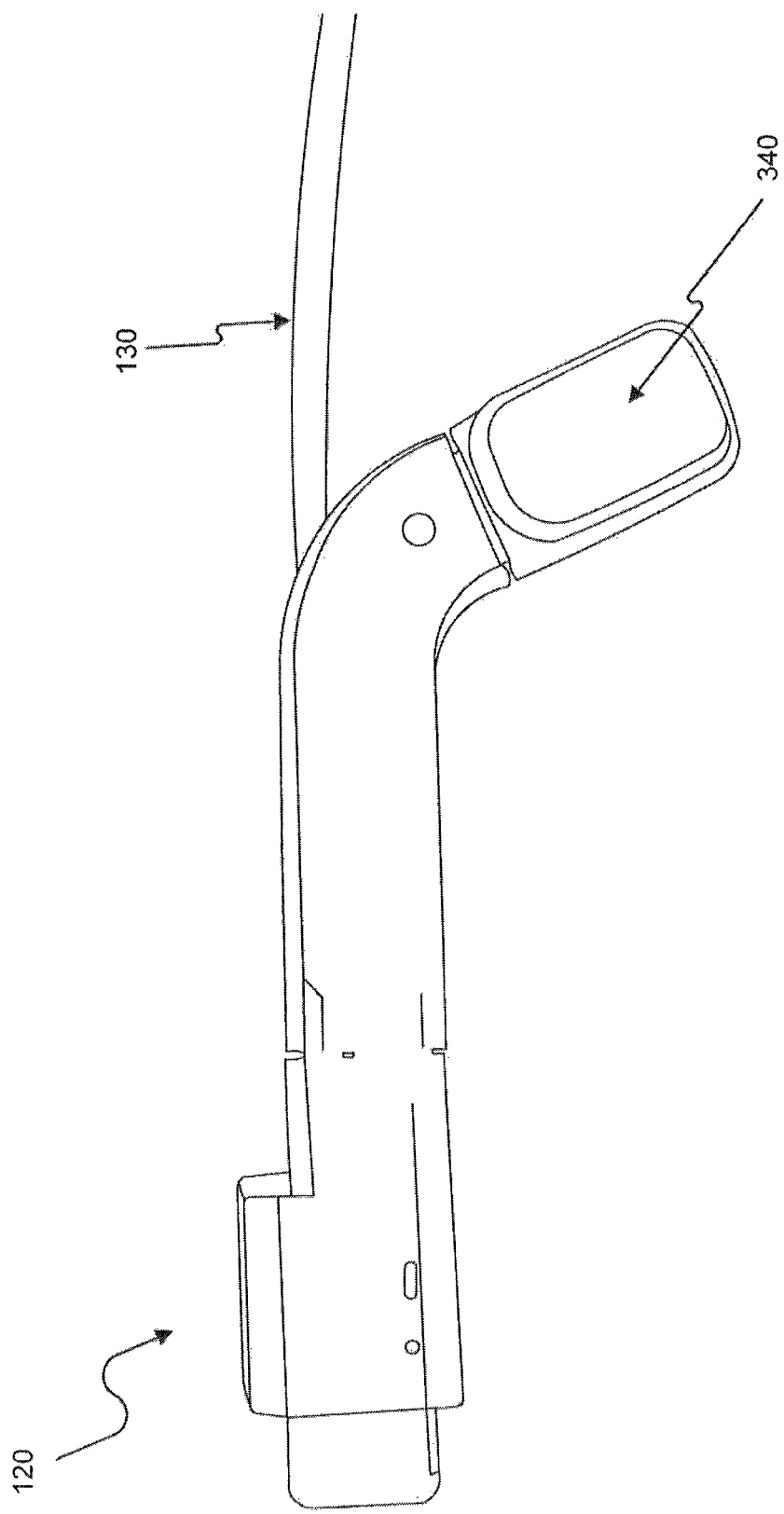
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3C. FIG. 3D shows the side of the U-shaped element that includes feedback-outputting unit 340.

Figure 3E:
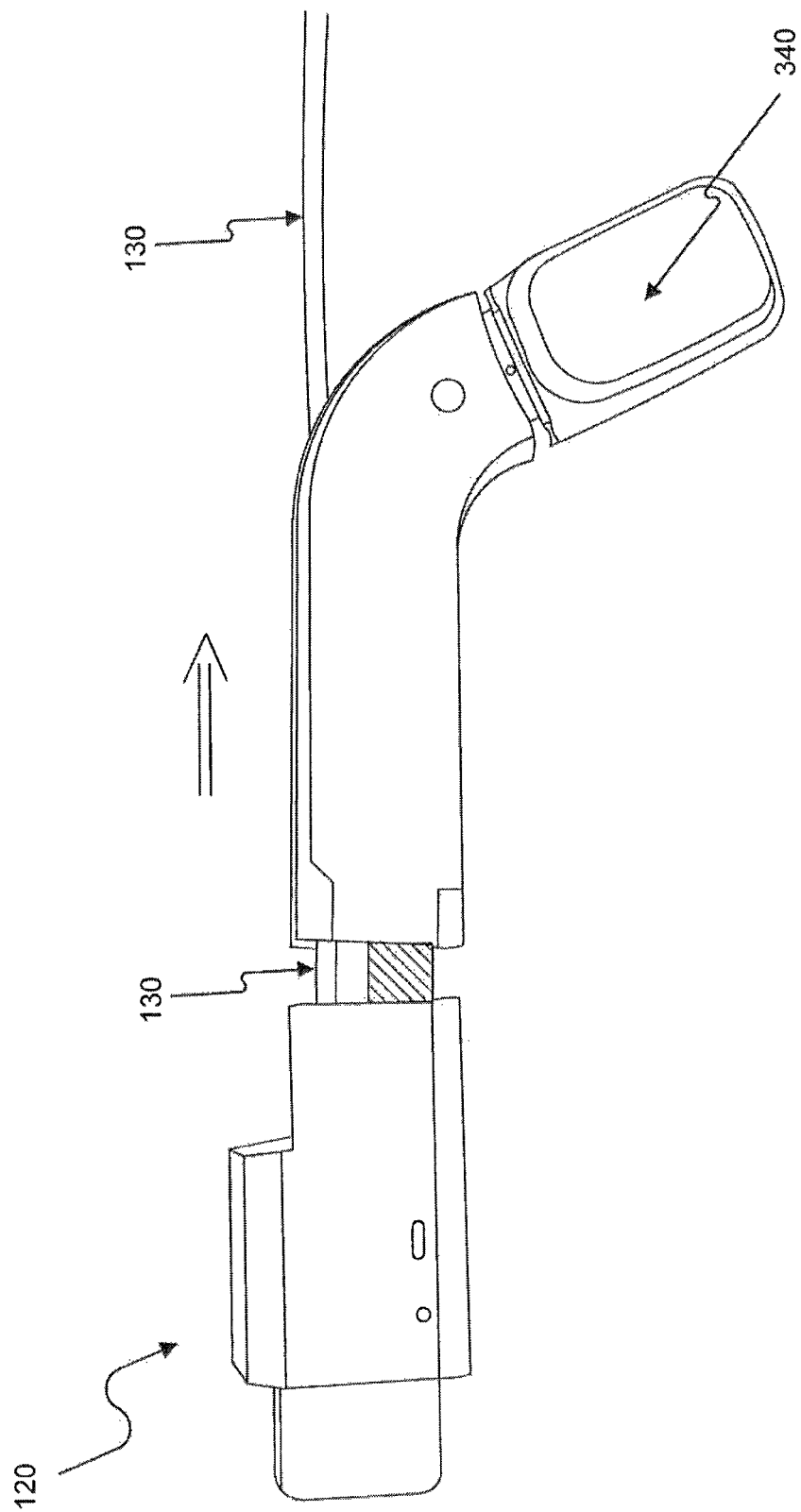
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

Figure 4A:
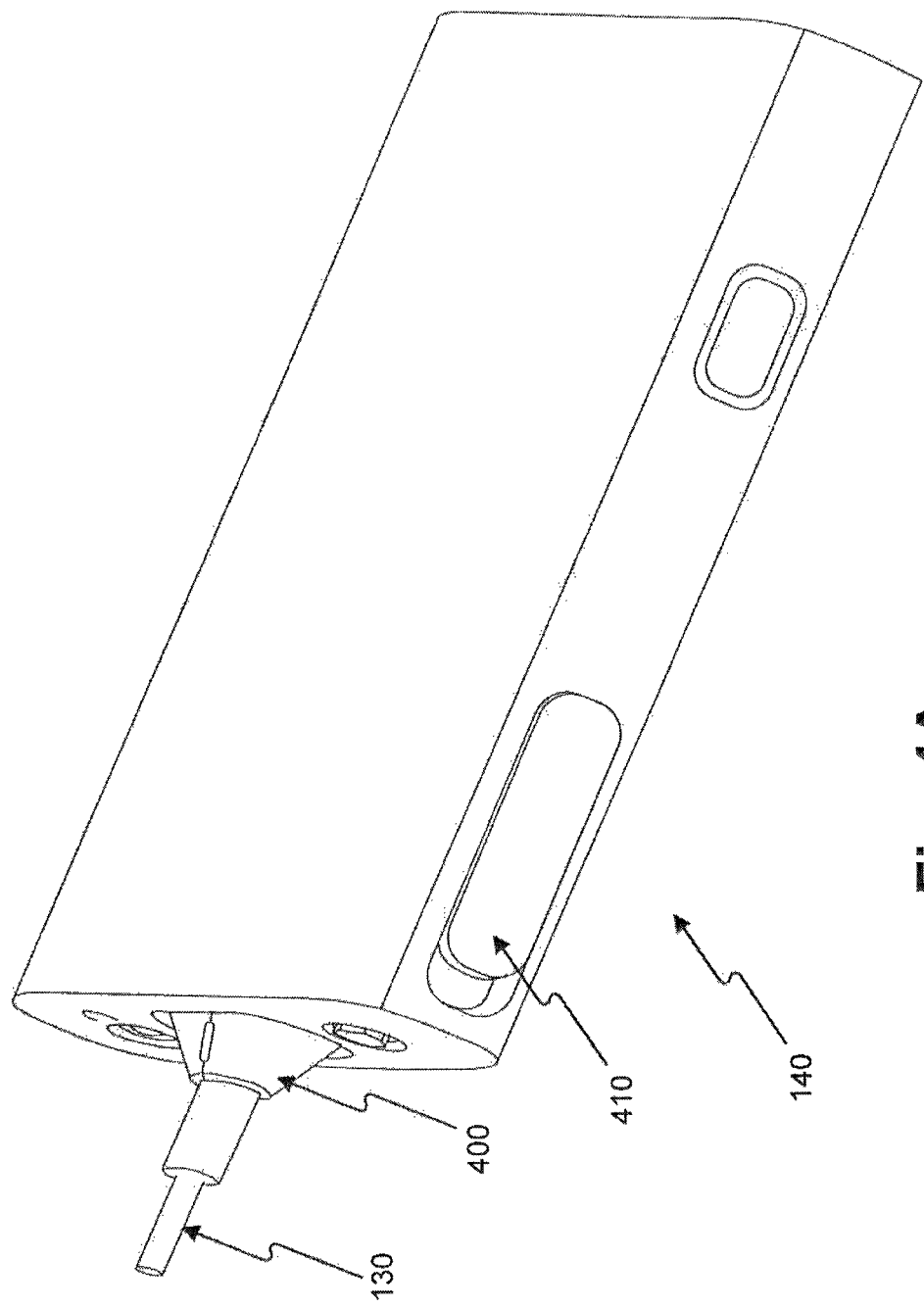
FIG. 4A is a schematic illustration of an example of a processing unit from a first viewpoint.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

Figure 4B:
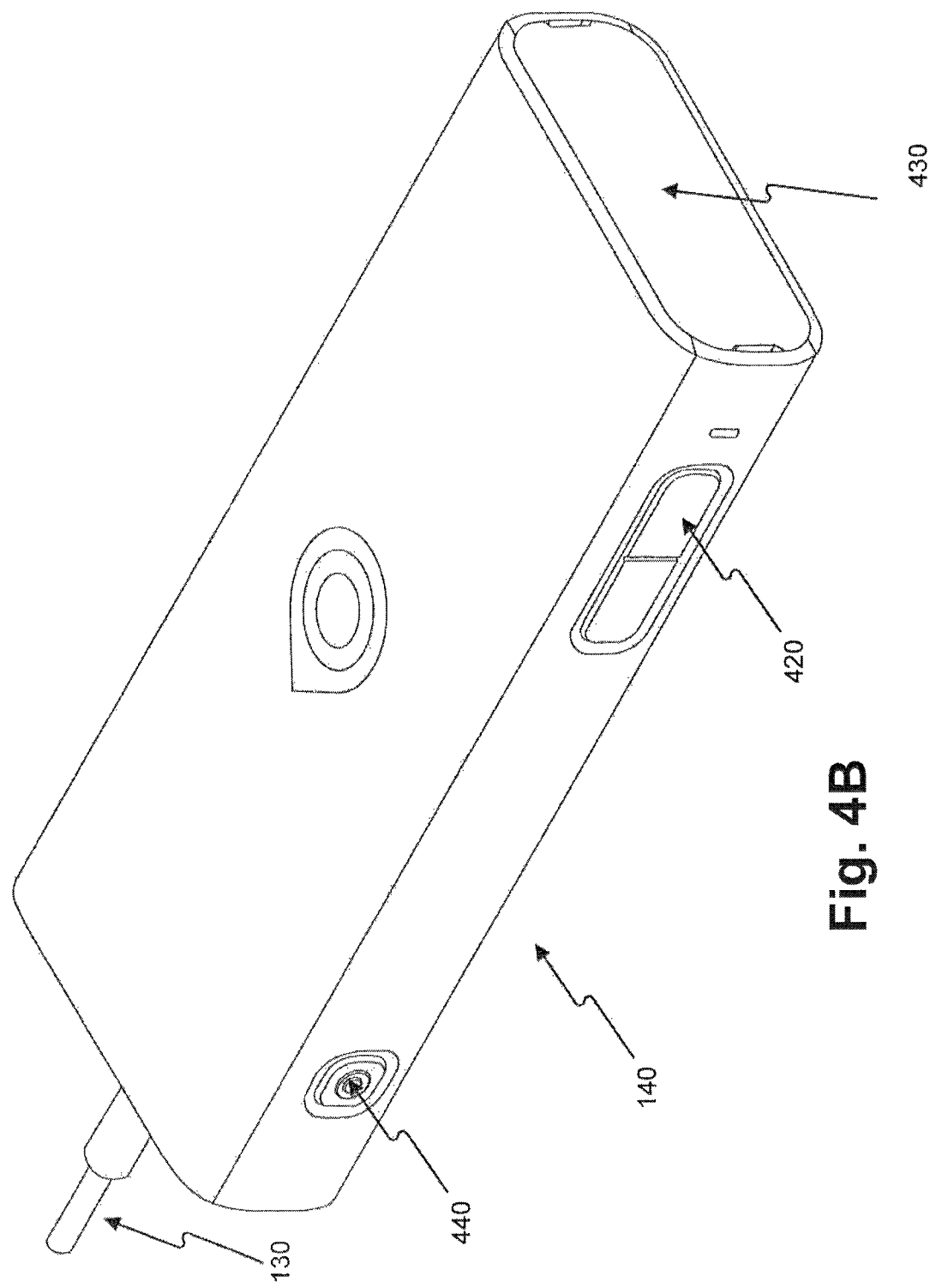
FIG. 4B is a schematic illustration of the processing unit shown in FIG. 4A from a second viewpoint.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

Figure 5A:
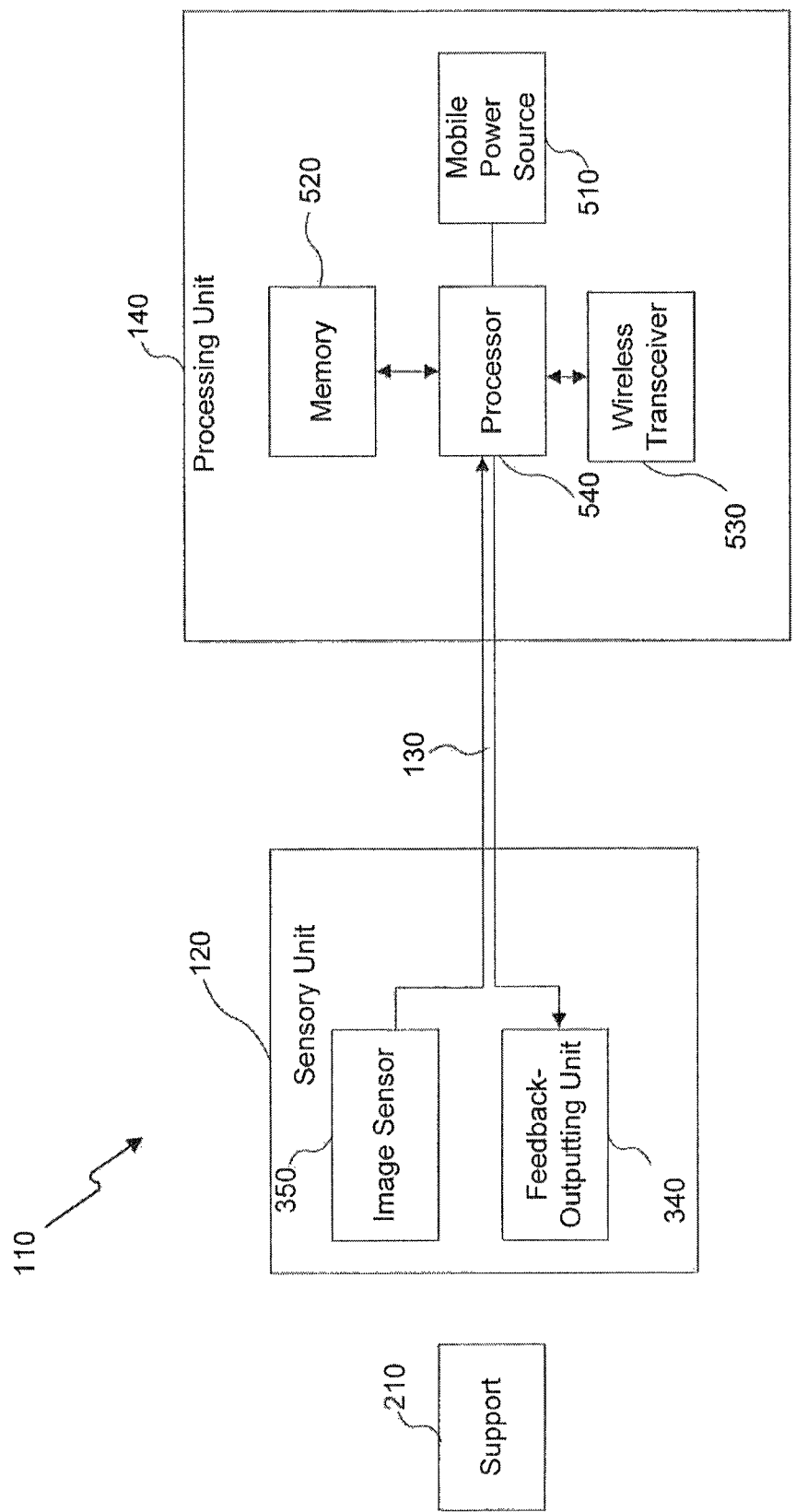
FIG. 5A is a block diagram illustrating an example of the components of an apparatus for aiding persons who have low vision according to a first embodiment.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit is 120 connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
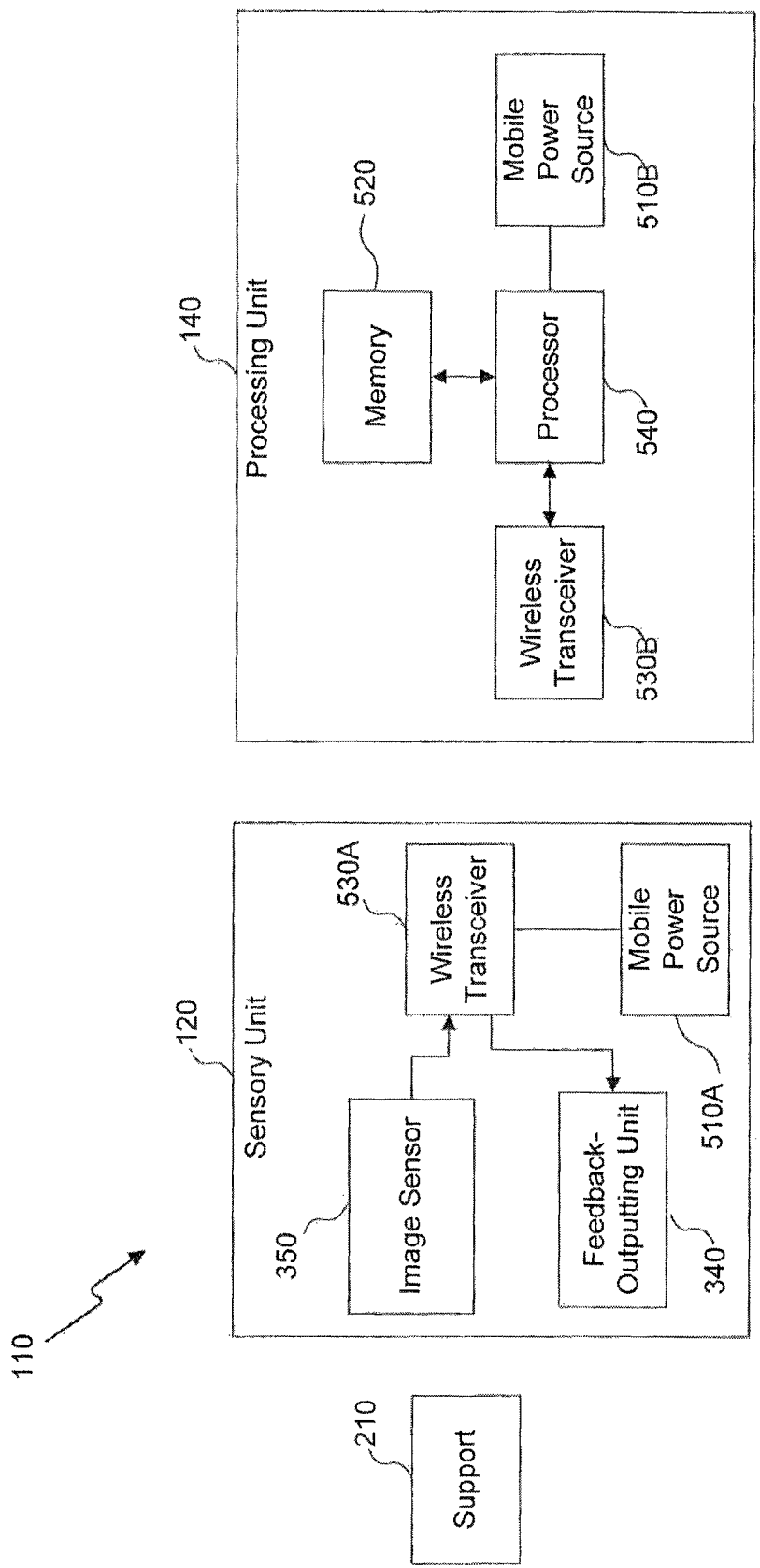
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
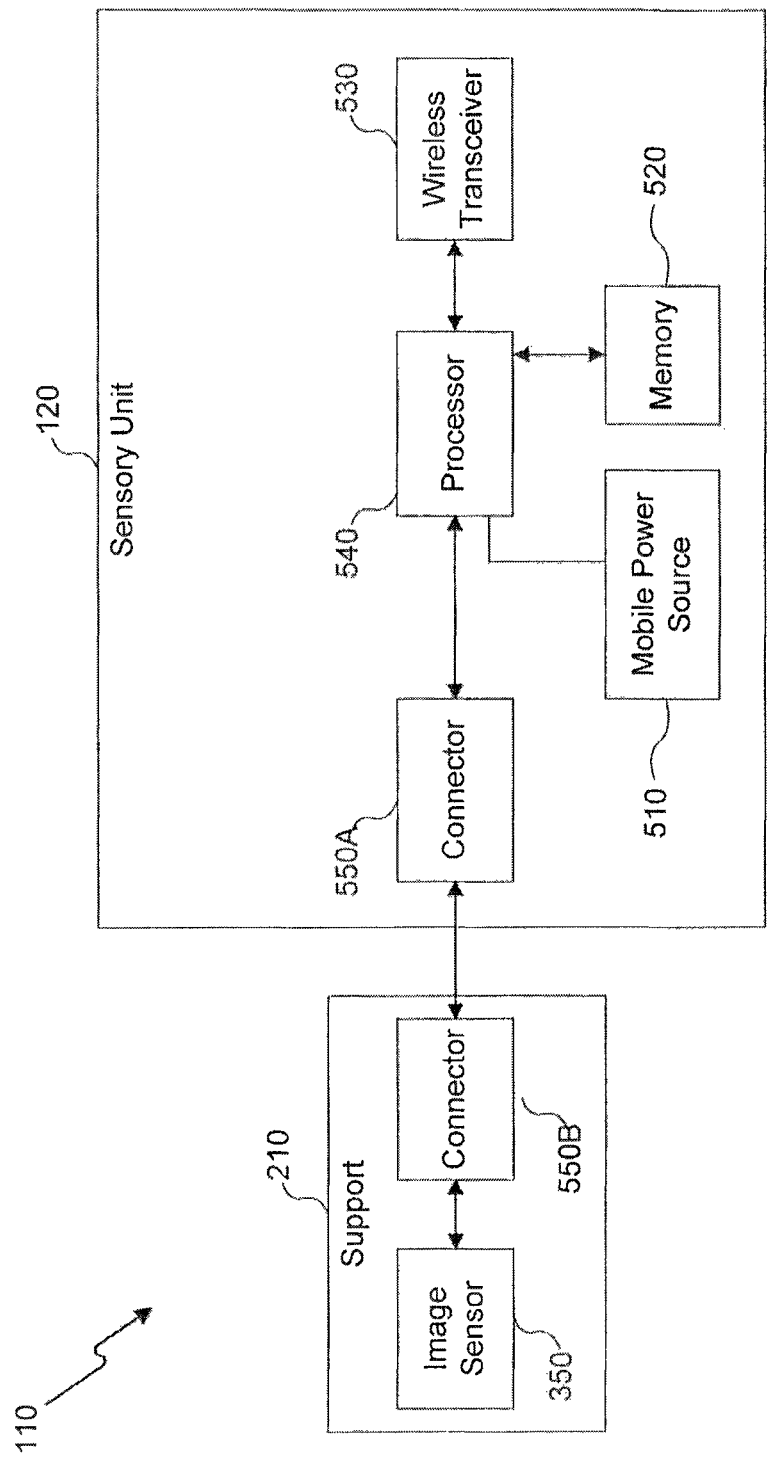
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120. Additionally, connectors 550A and 550B may allow power transmission from mobile power source 510A to image sensor 350 over wire 130. In some embodiments, connectors 550A and 550B may allow data from image sensor 350 to be provided to processor 540 over wire 130.

Figure 5D:
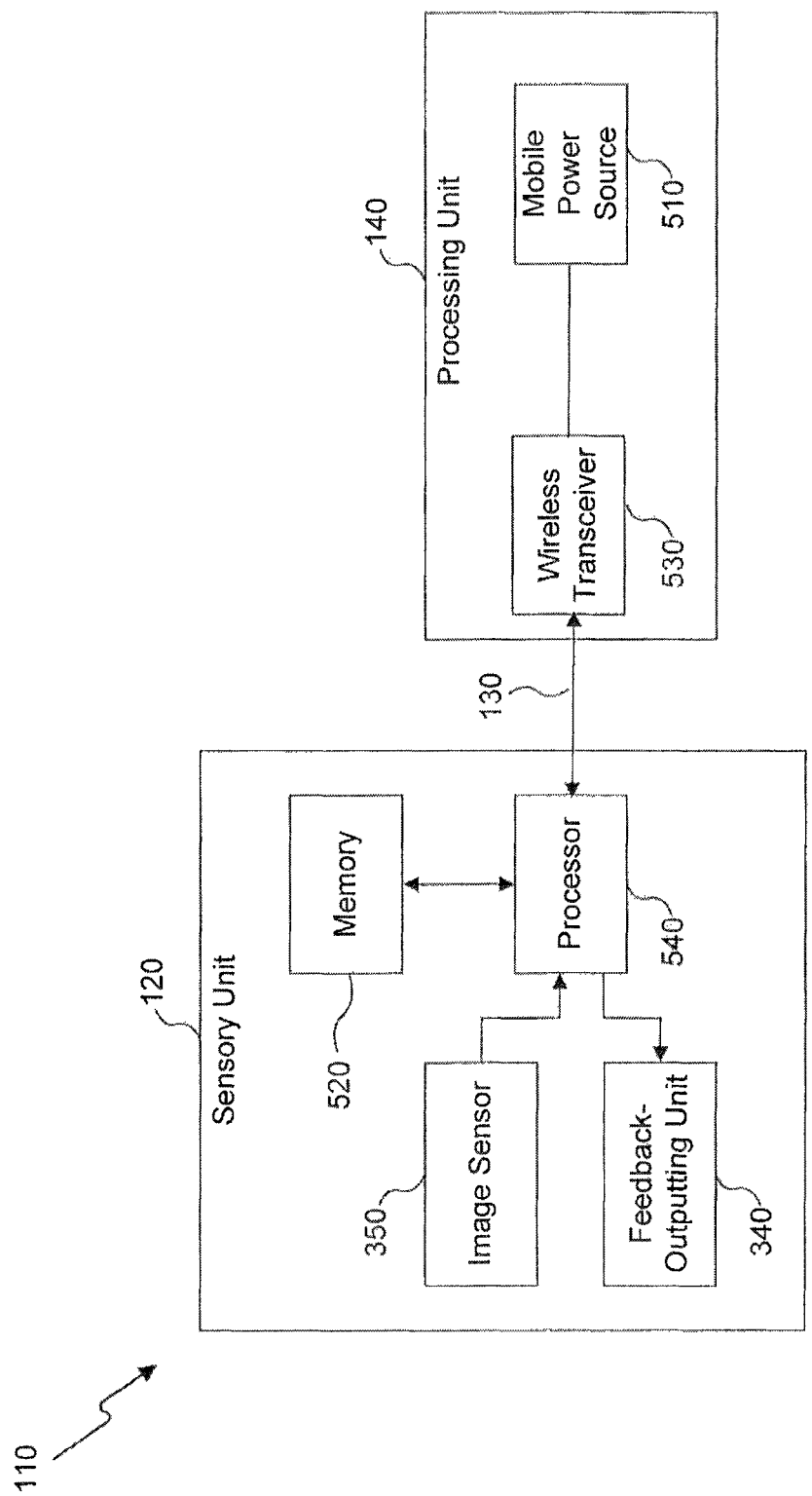
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, embodiments consistent with the present disclosure may provide a system, an apparatus, and a method for processing a text and for accelerating machine reading of the text.

Figure 6:
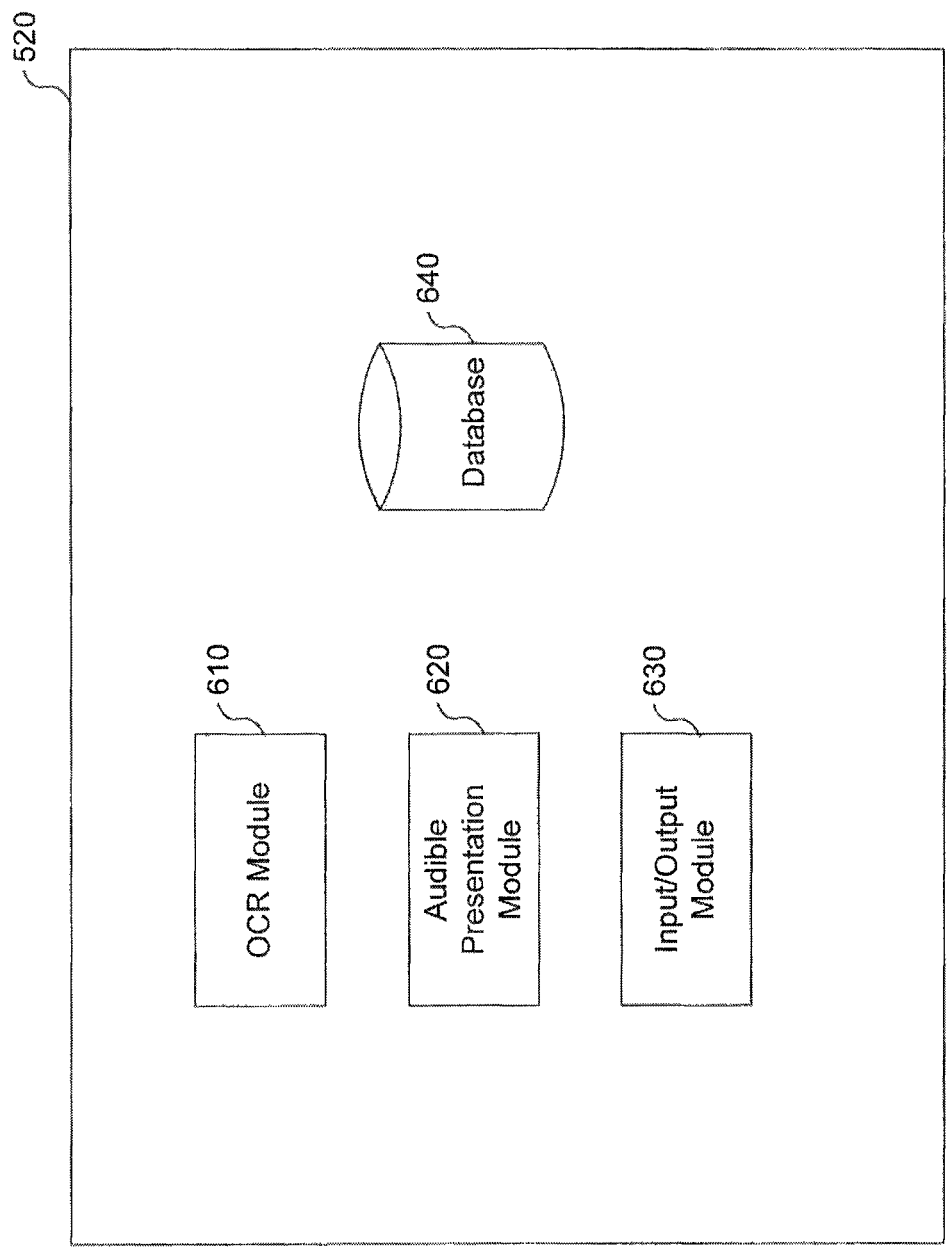
FIG. 6 is a block diagram illustrating an example of a memory storing software modules.

In some embodiments, text processing and accelerated text reading may be implemented using apparatus 110 with software instructions loaded into memory 520. The software instructions, when executed by processor 540, may perform various functions related to text recognition. FIG. 6 is a block diagram illustrating an example of a set of software instructions, organized in functional modules, which can be loaded into memory 520 for processing text and accelerating machine reading of the text.

Referring to FIG. 6, memory 520 may store an OCR module 610, which may include software instructions for perform OCR processing. OCR module 610 can generate a recognized representation of a text based on an image that includes the text. The recognized representation of the text may include a collection of letters, words, phrases, sentences, or any other suitable semantic symbols. In some embodiments, the recognized representation of the text may include audible reading of the text. The image containing the text may include a static image, a frame of a video stream, or any other graphical forms that contain at least a part of the text.

Memory 520 may store an audible presentation module 620, which may include software instructions for performing an audible presentation, such as reading aloud, of the recognized representation of the text generated by the OCR module 610. Audible presentation module 620 may execute the software instructions to perform an audible presentation after at least a part of the text has been recognized by OCR module 610. In some embodiments, audible presentation module 620 may simultaneously perform an audible presentation of the first part of the text while OCR module 610 is recognizing the second part of the text.

Memory 520 may store an input/output (I/O) module 630, which may include software instructions for performing image capture, audio output, user selection, or similar functions. For example, I/O module 630 may perform image capture from image sensor 350. In another example, I/O module 630 may perform audible feedback through feedback-outputting unit 340.

Memory 520 may store a database 640. Database 640 may contain data related to OCR, audible presentation, and/or input/output functions. For example, database 640 may store data of images or frames captured by image sensor 350 to be recognized by OCR module 610. Database 640 may store recognized representation generated by OCR module 610. Database 640 may store audible data to be presented to user 100 through feedback-outputting unit 340. Other forms of data related to the functions performed by modules 610, 620, and 630, including transitional or temporary data, may also be stored in database 640.

In other embodiments, database 640 may be located remotely from memory 520, and be accessible to other components of apparatus 110 (e.g., processing unit 140) via one or more wireless connections (e.g., a wireless network). While one database is shown, it should be understood that several separate and/or interconnected databases may make up database 640. Database 640 may include computing components (e.g., database management system, database server, etc.) configured to receive and process requests for data stored in memory devices associated with database 640 and to provide data from database 640.

OCR module 610, audible presentation module 620, and input/output module 630 may be implemented in software, hardware, firmware, a mix of any of those, or the like. For example, if OCR module 610, audible presentation module 620, and input/output module 630 are implemented in software, they may be stored in memory 520, as shown in FIG. 6. Other components of processing unit 140 and/or sensory unit 120 may be configured to perform processes to implement and facilitate operations of OCR module 610, audible presentation module 620, and input/output module 630. Thus, OCR module 610, audible presentation module 620, and input/output module 630 may include software, hardware, or firmware instructions (or a combination thereof) executable by one or more processors (e.g., processor 540), alone or in various combinations with each other. For example, OCR module 610, audible presentation module 620, and input/output module 630 may be configured to interact with each other and/or other modules of apparatus 110 to perform functions consistent with disclosed embodiments. In some embodiments, any of the disclosed modules (e.g., OCR module 610, audible presentation module 620, and input/output module 630) may each include dedicated sensors (e.g., IR, image sensors, etc.) and/or dedicated application processing devices to perform the functionality associated with each module.

In some embodiments, a system for perform accelerated machine reading of text may include an apparatus, e.g., apparatus 110. As described above, apparatus 110 may include processor 540 and memory 520. When user 100 uses apparatus 110 to recognize text, an image containing the text may be captured by apparatus 110. For example, image sensor 350 may be used to capture the image. The image may be a graphical presentation of one or more objects in an environment of user 100. For example, the image may be an image of a newspaper, a book, a flyer, a poster, a sign, a note, etc., or at least a part thereof or a combination thereof. The image may contain a plurality of elements, such as figure, text, etc.

Figure 7A:
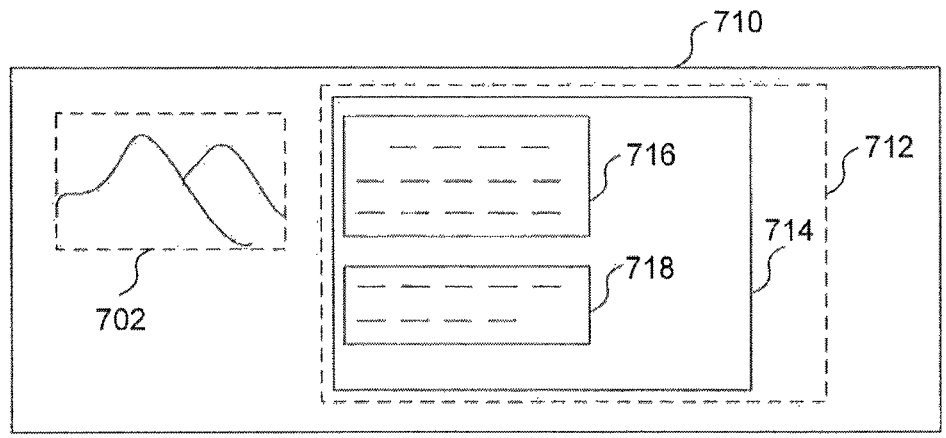
FIGS. 7A-7C are schematic illustrations of exemplary images containing text.
Figure 7B:
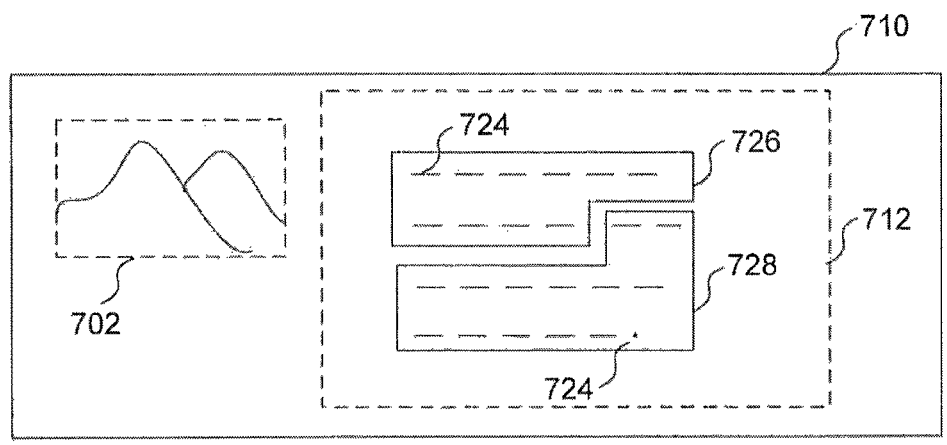
Figure 7C:
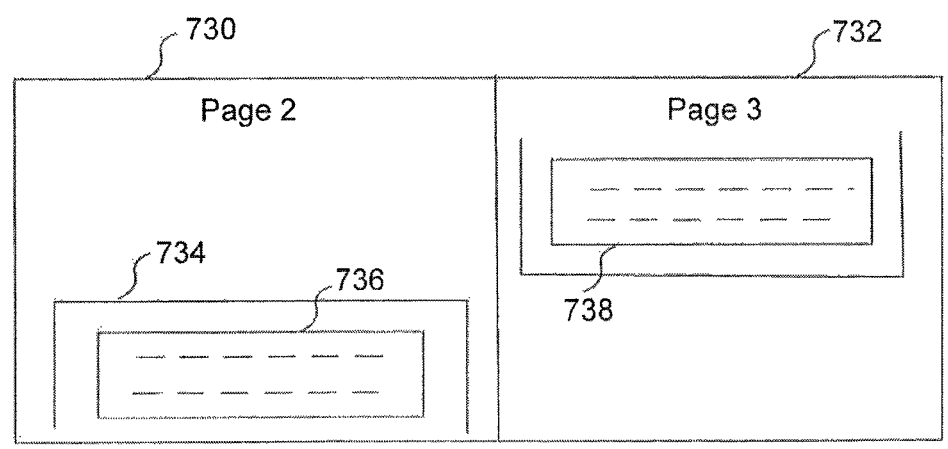

FIGS. 7A-7C are schematic illustrations of some exemplary images containing text. In FIG. 7A, image 710 may be an image of a newspaper, a book, a magazine, a poster, etc. Image 710 may contain a plurality of elements. For example, image 710 may contain a figure section 702. Figure section 702 may contain one or more graphical figures, such as a photo, a cartoon, an illustration, etc. Image 710 may contain a text section 712. Text section 712 may contain text, symbol, or other semantic representations. It is noted that figure section 702 and text section 712 may be intertwined with each other, such as in an advertisement or in a magazine cover. Therefore, figure section 702 and text section 712 are denoted in dashed lines to indicate that they are not necessarily separate sections. Text section 712 may include a text passage 714. Text passage 714 may include a paragraph of text, a section of text, one or more rows/columns of text, or any other forms of collection of text characters that can be grouped together. In one example, text passage 714 may be a logical collection of text characters, such as a paragraph of text that may run on one or more pages. In another example, text passage 714 may be a physical collection of text characters, such as text within a text box, within a callout region, within a marginal area, etc., which may or may not form a paragraph.

Text passage 714 may include multiple portions of text, such as text portions 716 and 718. A portion of text may be any subset of text passage 714. For example, text portions 716 and 718 may be substantially equal in terms of the number of characters. In another example, text portion 716 may contain more or less characters than text portion 718. For instance, text portion 716 may contain the first sentence or the first line of text passage 714, and text portion 718 may contain the subsequent sentence or the subsequent line of text passage 714. In some embodiments, text portions 716 and 718 may cover substantially all text content in text passage 714. In other embodiments, text portions 716 and 718 may cover a part of the text content in text passage 714. Text portion 718 may or may not be consecutive to text portion 716.

FIG. 7B shows an example in which text portions 726 and 728 may be parts of a same sentence 724. In some embodiments, sentence 724 may be a collection of text followed by a period, a question mark, or other punctuation marks that end a sentence. In other embodiments, sentence 724 may be a collection of text without any punctuation mark. In some embodiments, text portions 726 and 728 may cover substantially all text content of sentence 724. In other embodiments, text portions 726 and 728 may cover a part of the text content of sentence 724. Text portion 728 may or may not be consecutive to text portion 726.

FIG. 7C shows another example in which text portions 736 and 738 may be on different pages. In FIG. 7C, a text passage 734 may run across two pages 730 and 732. Text portion 736 may be on page 730 and text portion 738 may be on page 732. In some embodiments, text portion 736/738 may cover substantially all text content of text passage 734 that is on page 730/732, respectively. In other embodiments, text portion 736/738 may cover a part of text content of text passage 734 that is on page 730/732, respectively. Text portion 738 may or may not be consecutive to text portion 736.

When processor 540 performs OCR and audible presentation of text in an image, such as text passage 714 in image 710, processor 540 may break up text passage 714 into multiple portions, such as text portions 716 and 718, to accelerate the audible presentation process and to avoid delay between the moment when user 100 triggers a text recognition process and the moment when apparatus 110 starts to audibly read the text. For example, instead of performing OCR on the entire text content of passage 714 and starting to audibly read after all text characters have been recognized, apparatus 110 may be configured to perform OCR on text portion 716 first and start to audibly read text portion 716 right after text in portion 716 has been recognized, and while audibly reading text portion 716, simultaneously perform OCR on text portion 718. If the length of text portion 716 is properly controlled, audible reading can be started in a relatively short time period after user 100 triggers text recognition. In the following paragraphs, several embodiments will be described to implement the accelerated text reading technique.

Figure 8A:
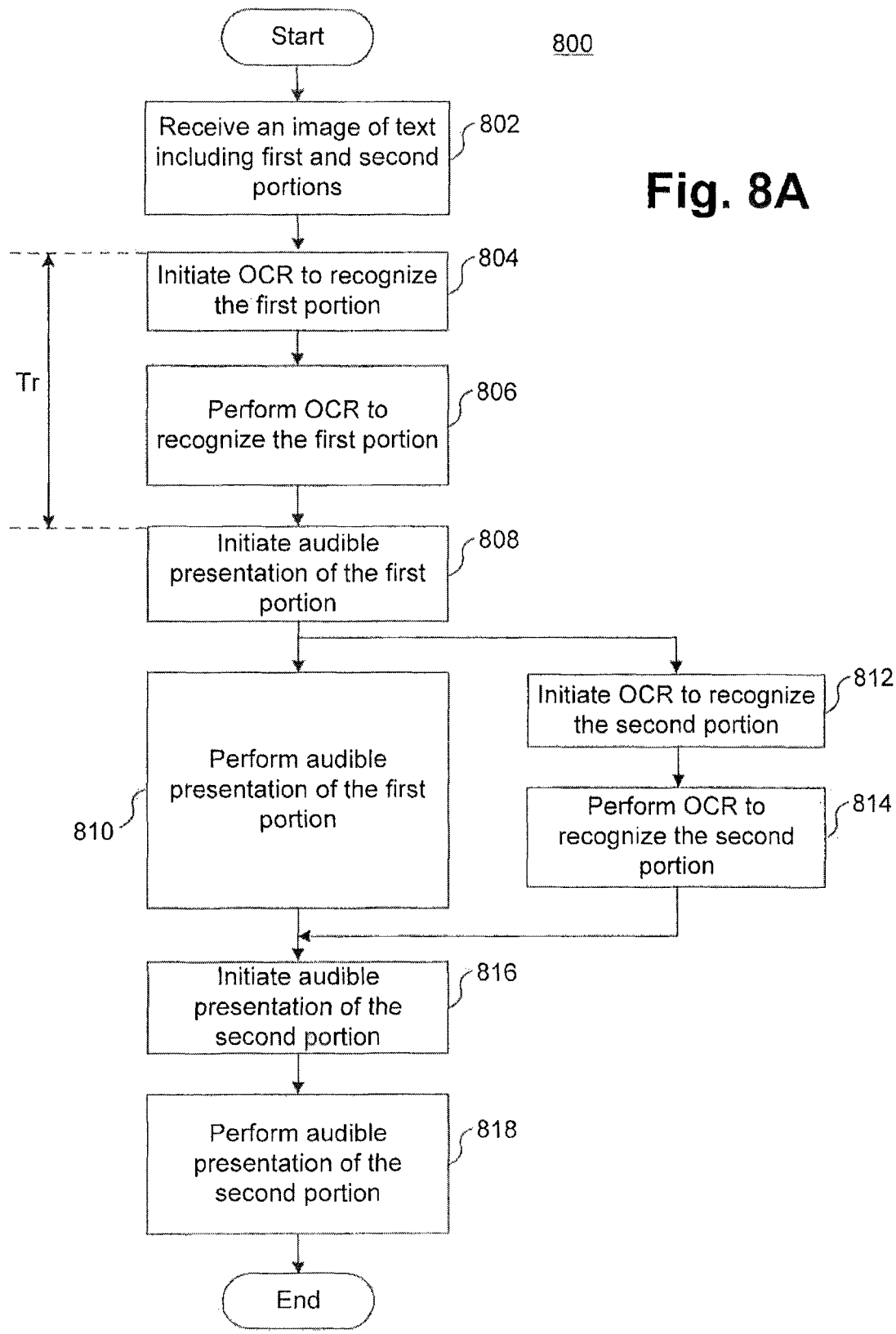
FIG. 8A is a flow chart of an exemplary process for accelerating machine reading of text, according to a first embodiment.

FIG. 8A is a flow chart of an exemplary process 800 for accelerating machine reading of text, according to a first embodiment. In step 802, processor 540 may be configured to receive an image of text (e.g., image 710) to be audibly read. Image 710 may include a first portion (e.g., portion 716) and a second portion (e.g., portion 718). For example, processor 540 may execute software instructions stored in I/O module 630 to receive image 710 captured by image sensor 350. In some embodiments, processor 540 may receive image 710 after user 100 triggers text recognition by, for example, pointing to a text, make an audible command, etc.

In step 804, processor 540 may initiate an OCR process to recognize text contained in text portion 716. As used herein, by initiating a process, it is meant that processor 540 starts the process. The action of initiation is complete after the process starts, but does not necessarily require the process to finish. For example, step 804 is considered complete after the OCR process starts. Step 804 is followed by step 806, in which processor 540 performs the OCR process to recognize text in text portion 716. Both steps 804 and 805 may be performed by processor 540 by executing software instructions stored in OCR module 610.

After processor 540 finishes the OCR process on text portion 716, process 800 proceeds to step 808, in which processor 540 initiates audible presentation of the recognized text of text portion 716. Processor 540 may execute software instructions stored in audible presentation module 620 to initiate the audible reading of the recognized text to user 100. For example, processor 540 may generate audible reading signals (e.g., analog and/or digital signals) based on the recognized text of text portion 716 using a text-to-voice algorithm stored in audible presentation module 620. The audible reading signals may then be transmitted to feedback outputting unit 340 through wire 130 or via a wireless communication channel established between wireless transceiver pair 530A and 530B. Feedback outputting unit 340 may convert the audible reading signals to audible feedback (e.g., readout, notification sound, vibration, etc.) to user 100 (e.g., using a speaker or a bone conduction headphone). In some embodiments, step 808 is immediately performed after OCR process on text portion 716 finishes. A time parameter Tr, referred to as the response time, may be used to measure the time interval from initiating OCR process on text portion 716 to initiating audible presentation of text portion 716. Response time Tr may be a measure of delay time experienced by user 100 after he triggers text recognition. In some embodiments, Tr may be controlled to be less than four seconds, less than two seconds, less than one second, or even shorter. An exemplary method of shortening Tr is to limit the number of characters in text portion 716. For example, text portion 716 may contain the first sentence, the first line, or even the first several words of text passage 714. As a result, the corresponding OCR process may take a relatively short period of time to finish.

After processor 540 initiates the audible presentation of text portion 716 (e.g., step 808 is complete), process 800 proceeds into two parallel branches. In one branch, as indicated by step 810, processor 540 performs the action to audibly present text portion 716 after the action is initiated in step 808. Similar to step 808, processor 540 may execute software instructions stored in audible presentation module 620 to audibly read the recognized text to user 100. In the other branch, as indicated by steps 812 and 814, processor 540 simultaneously initiates and performs OCR on the second portion of text, e.g., text portion 718. Depending on the length of text portion 716, the speed of audible reading, and the length of text portion 718, the OCR process on text portion 718 may finish before the completion of the audible presentation of text portion 716. In this case, process 800 may proceed to step 816, in which the audible presentation of text portion 718 is initiated automatically and immediately upon the completion of step 810. Then in step 818, processor 540 may perform the audible presentation of text portion 718 to user 100. User 100 can experience a seamless transition between the reading of text portion 716 and text portion 718 and enjoy a continuous reading of text without further delay.

It is noted that to provide continuous reading of text, method 800 may include additional steps similar to steps 810, 812, and 814 that are performed simultaneously in a staggered manner. For example, after step 814 finishes, processor 540 may receive a portion of text (e.g., a third portion) next to or subsequent to text portion 718 and initiate/perform OCR on the third portion at the same time when step 810, 816, and/or 818 is performed. Then, after step 818 finishes, processor 540 may initiate/perform audible reading of the third portion if the OCR process on the third portion is completed. The length of the text portion can be dynamically controlled such that whenever the reading of a text portion is finished, the next portion of text would be ready to read. In this way, user 100 is able to enjoy a continuous reading of text. In some embodiments, user 100 may not be even required to provide additional triggers after the first trigger.

In some embodiments, in order to improve user experience, the delay between the triggering of text recognition and starting of audible reading can be controlled to be within a tolerance threshold. In particular, response time Tr can be used as a condition parameter to start the audible presentation process.

Figure 8B:
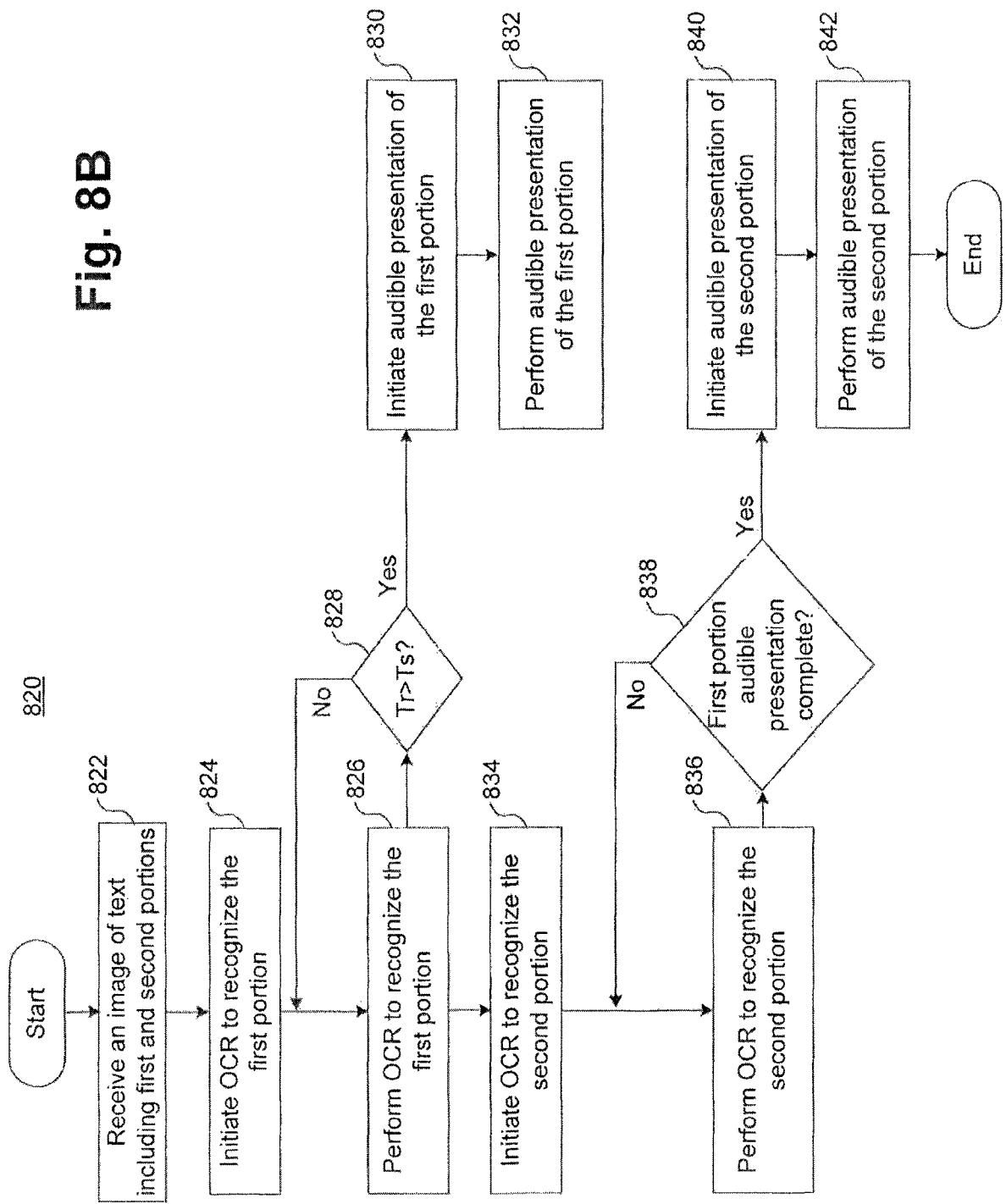
FIG. 8B is a flow chart of an exemplary process for accelerating machine reading of text, according to a second embodiment.

FIG. 8B is a flow chart of such an exemplary process 820 for accelerating machine reading of text, according to a second embodiment. In FIG. 8B, steps 822 and 824 are similar to steps 802 and 804 of FIG. 8A. In step 826, while processor 540 is performing OCR on the first portion (e.g., text portion 716), a condition is checked (step 828) to determine if response time Tr is longer than a threshold time Ts. The condition can be checked periodically during the course of performing OCR process on the first portion. Threshold time Ts may have a predetermined value, such as four seconds, two seconds, one second, etc. If Tr is not longer than Ts, then process 820 proceed back to step 826 to continue performing OCR until the next check of condition 828. If Tr is longer than Ts, the process 820 proceed to step 830, in which an audible presentation of the recognized part of the first text portion is initiated. Then in step 832, processor 540 performs the audible presentation of the recognized part. It is noted that the OCR step (e.g., step 826) and the audible presentation steps (e.g., steps 830 and 832) may be performed simultaneously. The recognized text, such as characters, words, phrases, etc., may be continuously saved in memory 520 (e.g., database 640) as they are generated from the OCR process. In the audible presentation steps (e.g., steps 830 and 832), the recognized text may be continuously read from memory 520 and audibly presented to user 100.

After the OCR process on the first text portion is completed (e.g., step 826 finishes), process 820 proceeds to step 834, in which processor 540 initiates OCR process to recognize the second portion of text (e.g., text portion 718). Then in step 836, processor 540 performs the OCR process on the second portion. It is noted that steps 834 and 836 may be performed in parallel to step 832. During the course of performing OCR on the second portion, a condition is checked (e.g., periodically) in step 838 to determine if the audible presentation of the first portion is completed. In other words, step 838 checks if step 832 is completed. If step 832 is not completed (i.e., the "No" branch of step 838), then process 820 proceeds back to step 836 to continue performing OCR on the second portion until the next check. If step 832 is completed (i.e., the "Yes" branch of step 838), then process 820 proceeds to step 840, in which processor 540 initiates the audible presentation of the second portion. Then in step 842, processor 540 performs the audible presentation of the second portion.

Similar to process 800, the OCR process (e.g., step 826 or 836) and the audible presentation process (e.g., step 832 or 842) may be performed in a staggered manner. For simplicity a detailed description of the staggered operation in process 820 is omitted.

Figure 8C:
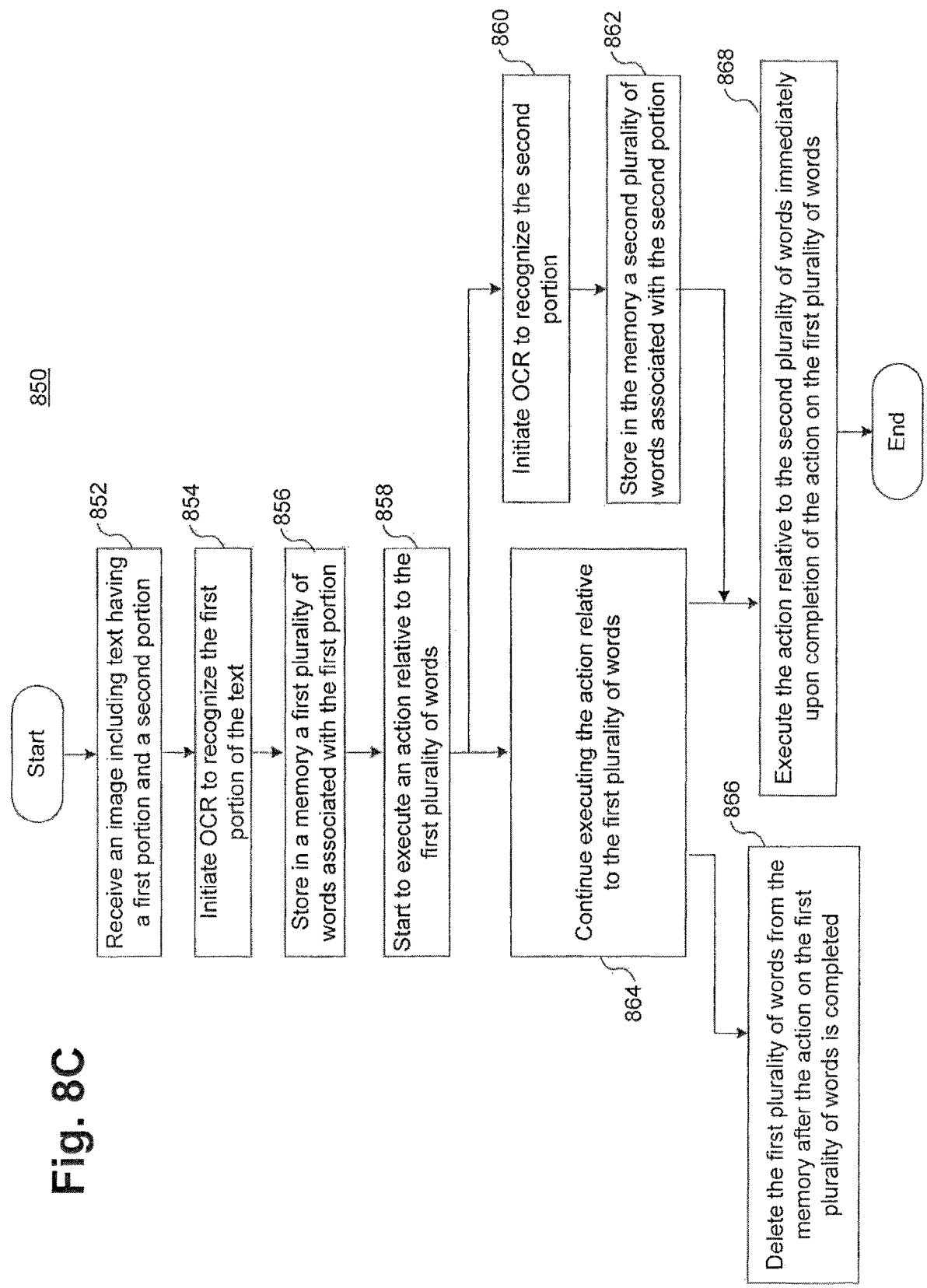
FIG. 8C is a flow chart of an exemplary process for accelerating machine reading of text, according to a third embodiment.

FIG. 8C is a flow chart of an exemplary process 850 for accelerating machine reading of text, according to a third embodiment. In FIG. 8C, steps 852 and 854 are similar to steps 802 and 804 of FIG. 8A. In step 856, as the OCR process initiated in step 854 starts to generate recognized results that associated with the first portion of text (e.g., text portion 716), such as a plurality of characters, words, phrases, etc., processor 540 stores the recognized results in memory 520 (e.g., in database 640). It is noted that the OCR process and the OCR result storage process (e.g., step 856) may be performed simultaneously. For example, step 856 may be performed after a certain number of words have been recognized. As these words being stored in memory 520, processor 540 may continue the OCR process.

After the first text portion have been recognized and the words associated with the first portion have been stored, process 850 may proceed to step 858, in which processor 540 may start to execute an action (e.g., audible presentation) relative to the stored words. For example, processor 540 may start read the stored words aloud to user 100. After step 858, processor 540 may simultaneously perform audible presentation of the recognized words associated with the first portion (e.g., step 864) and recognition of a second portion of text (e.g., text portion 718) in steps 860 and 862. For example, in step 860 processor 540 may initiate OCR process to recognize text portion 718. In step 862 processor 540 may store the recognized words associated with text portion 718 in memory 520.

After step 864 is completed, process 850 may proceed into two parallel branches. In step 868, processor 540 may perform audible presentation of the recognized words associated with text portion 718. In some embodiments, step 868 is performed immediately after the completion of step 864. In step 866, processor 540 may delete the recognized words associated with text portion 716 from memory 520 after these words have been audibly presented to user 100. Step 866 and step 868 may be performed in parallel.

Figure 8D:
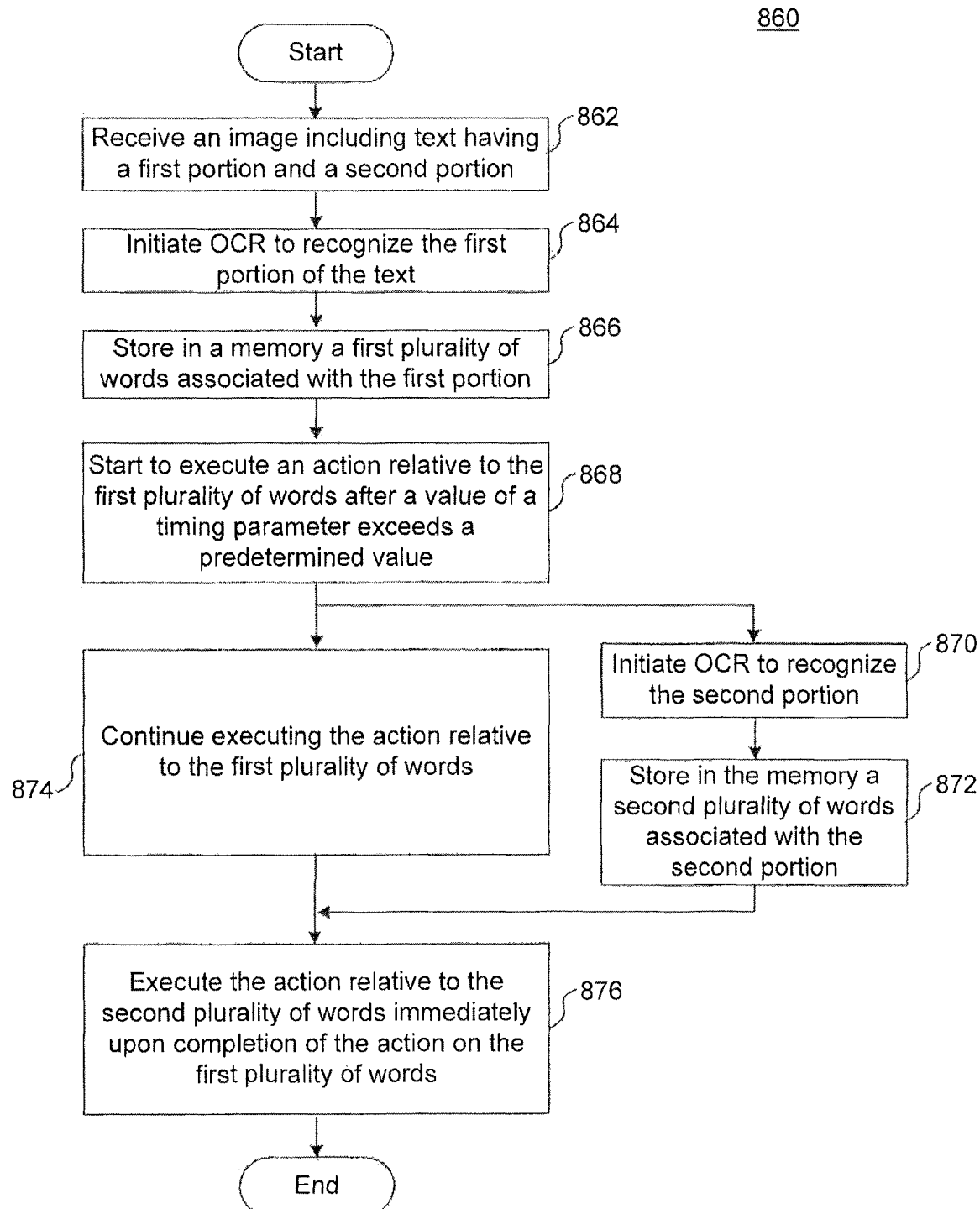
FIG. 8D is a flow chart of an exemplary process for accelerating machine reading of text, according to a fourth embodiment.

FIG. 8D is a flow chart of an exemplary process 860 for accelerating machine reading of text, according to a fourth embodiment. In FIG. 8D, steps 862, 864, and 866 are similar to steps 852, 854, and 856 of FIG. 8C. In step 868, processor 540 may periodically check a value of a timing parameter (e.g., Tr), and start to execute an action (e.g., audible presentation) relative to the recognized and stored words after Tr exceeds a predetermined value (e.g., Ts). Step 868 may be implemented in a similar manner to steps 826, 828, and 830 of FIG. 8B. After the audible presentation process is started, process 860 proceeds to steps 870, 872, 874, and 876, which are similar to steps 860, 862, 864, and 868 of FIG. 8C, respectively.

Figure 9A:
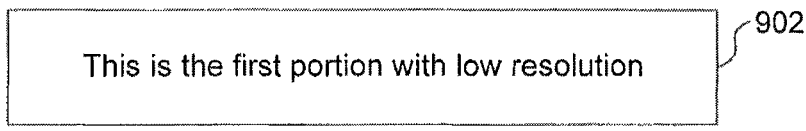
FIGS. 9A-9C are schematic illustrations of exemplary images of text portions.
Figure 9B:
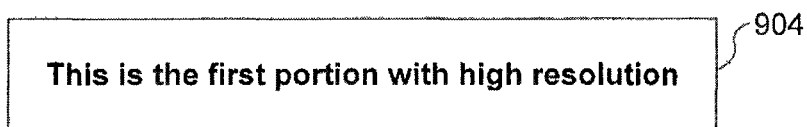
Figure 9C:
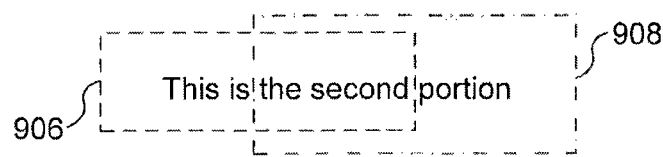

In some embodiments, multiple images may be captured and processed with respect to one text portion. FIGS. 9A-9C are illustrates some examples of such multiple images. FIG. 9A shows an image 902 of the first portion of text (e.g., text portion 716) with low resolution. FIG. 9B shows another image 904 of text portion 716 with high resolution. Images 902 and 904 may be captured by image sensor 350 using different resolution settings.

FIG. 9C shows multiple images of the second portion of text (e.g., text portion 718). Image 906 covers the left part of text portion 718, while image 908 covers the right part of text portion 718. However, none of images 906 and 908 includes all of text portion 718. The situation shown in FIG. 9C may occur when text portion 718 is on a curved surface or when text portion 718 appears on changing screens of an electronic device (e.g., computer, TV, mobile phone, etc.).

FIGS. 10A-10D are flow charts of exemplary processes for performing OCR on multiple images of a text portion. In the first exemplary process 1000 shown in FIG. 10A, in step 1002, processor 540 may initiate OCR to recognize the first image (e.g., image 902) of a text portion (e.g., text portion 716). In step 1004, processor 540 may perform OCR on image 902 to recognize text. In step 1006, processor 540 may initiate OCR to recognize the second image (e.g., image 904) of text portion 716. In step 1008, processor 540 may perform OCR on image 904 to recognize text.

After processor 540 performs OCR on images 902 and 904, processor 540 may combine the OCR results from images 902 and 904. For example, in step 1010, processor 540 may combine OCR results of low resolution image 902 and high resolution image 904 to generate a final result to audibly present to user 100.

Figure 10A:
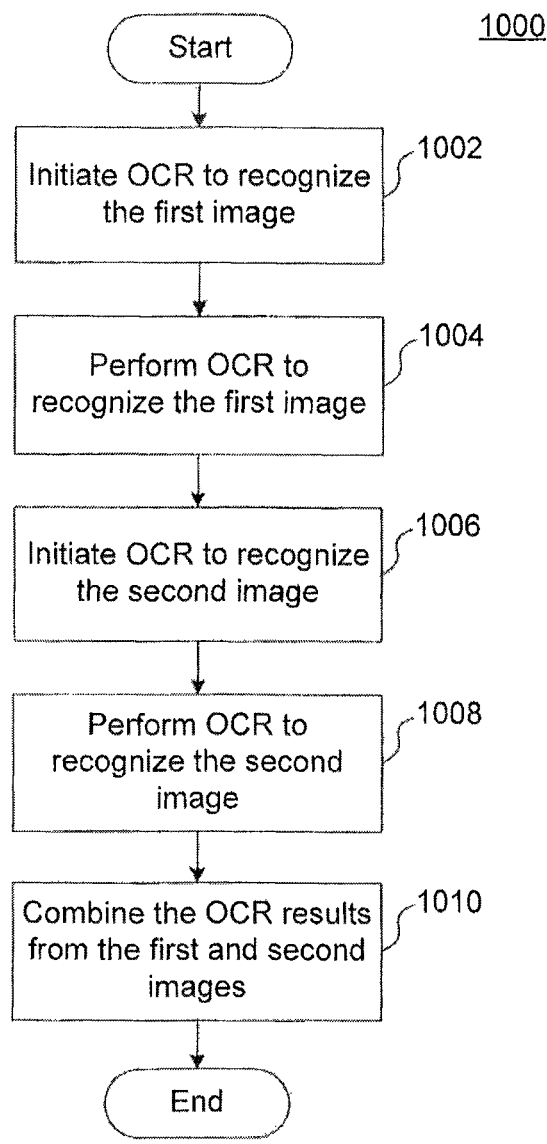
FIG. 10A is a flow chart of a first exemplary process for performing optical character recognition on multiple text images.
Figure 10B:
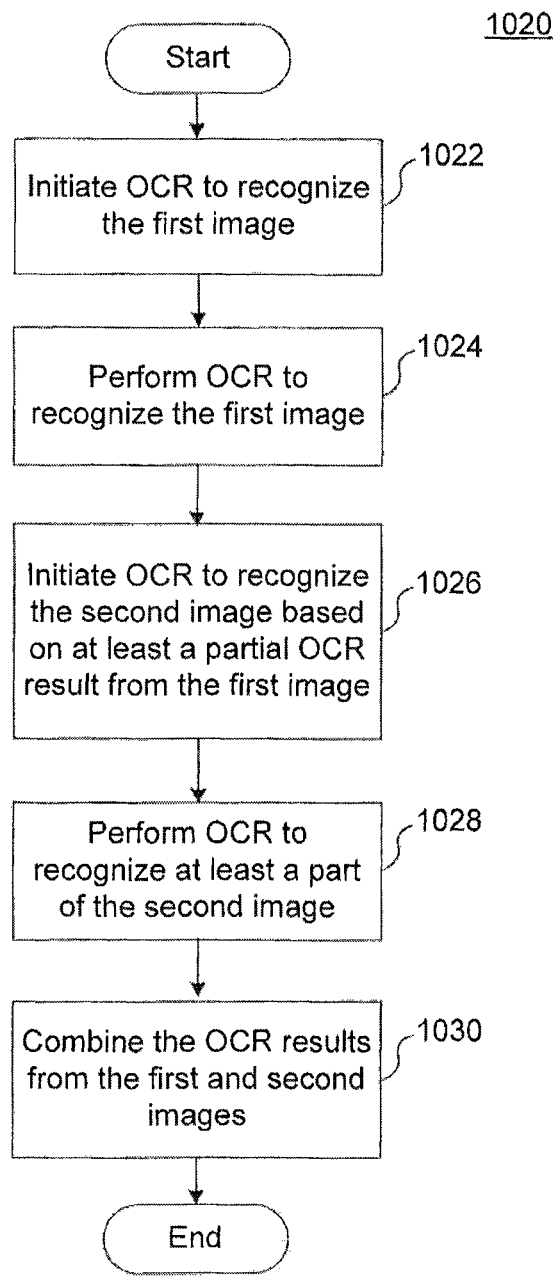
FIG. 10B is a flow chart of a second exemplary process for performing optical character recognition on multiple text images.

FIG. 10B is a flow chart of a second exemplary process 1020 for performing OCR on multiple text images. Steps 1022 and 1024 are similar to steps 1002 and 1004 of FIG. 10A. In step 1026, processor 540 may initiate OCR to recognize image 904 based on at least a partial OCR result from image 902. For example, the OCR result from image 902 may not be satisfactory due to low resolution, and only a part of text portion 716 is recognized in step 1024. Based on the partially recognized result from image 902, processor 540 may initiate OCR on image 904, which has a higher resolution than image 902, to recognize a part of (e.g., the unrecognized part of text portion 716 after step 1024) or the entire content of text portion 716. In step 1028, processor 540 may perform OCR on image 904 to recognize at least a part of image 904 (e.g., the unrecognized part of text portion 716). In step 1030, processor 540 may combine the OCR results from images 902 and 904. For example, processor 540 may combine the recognized part of image 902 with recognized part of image 904 to generate a final result to audibly present to user 100.

Figure 10C:
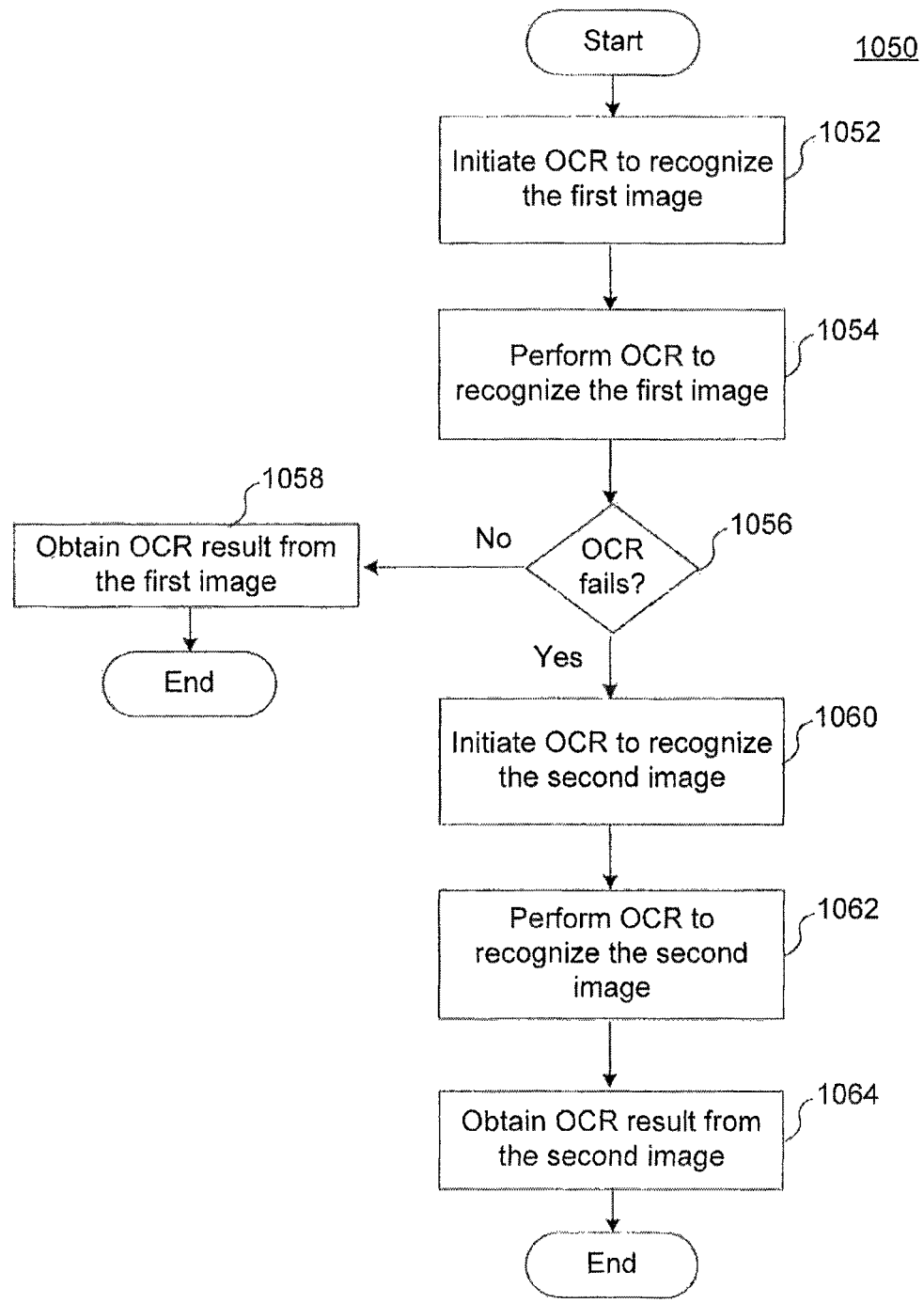
FIG. 10C is a flow chart of a third exemplary process for performing optical character recognition on multiple text images.

FIG. 10C is a flow chart of a third exemplary process 1050 for performing optical character recognition on multiple text images. Steps 1052 and 1054 are similar to steps 1002 and 1004 of FIG. 10A. In step 1056, processor 540 may determine if the OCR process performed on image 902 fails. The OCR process may be considered failed if a certain percentage (e.g., 80%, 60%, 50%, etc.) of text are not recognized. If the OCR does not fail, process 1050 proceeds to step 1058, in which processor 540 obtains an OCR result from image 902. If the OCR fails, process 1050 proceeds to step 1060. In step 1060, processor 540 initiates OCR to recognize image 904, which has a higher resolution than image 902. In step 1062, processor 540 performs OCR to recognize text in image 904. In step 1064, processor 540 obtains an OCR result from image 904.

Figure 10D:
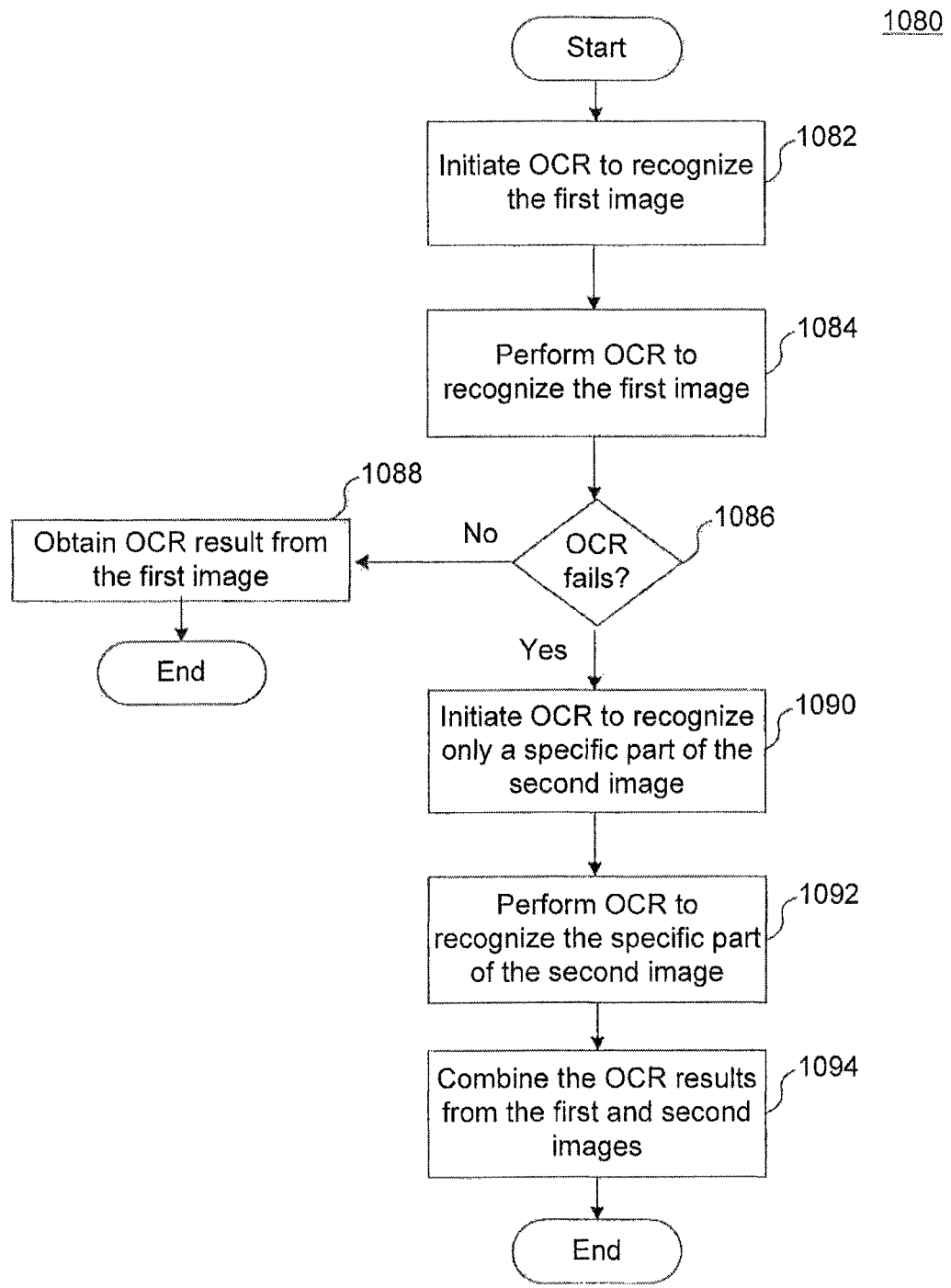
FIG. 10D is a flow chart of a fourth exemplary process for performing optical character recognition on multiple text images.

FIG. 10D is a flow chart of a fourth exemplary process for performing optical character recognition on multiple text images. Steps 1082, 1084, 1086, and 1088 are similar to steps 1052, 1054, 1056, and 1058 of FIG. 10C. In step 1090, processor 540 initiates OCR to recognize only a specific part of image 904. For example, although the OCR on image 902 is considered failed, there may be one or more parts in the OCR result from image 902 that are recognizable. Therefore, instead of performing OCR on the entire image of image 904, only one or more specific parts of image 904 are used in the OCR process in step 1090 to, for example, cover the unrecognized part(s) from the result of step 1084. In step 1092, processor 540 may perform OCR to recognize the specific part of image 904. In step 1094, processor 540 may combine the results from images 902 and 904 to generate a final result.

Figure 11:
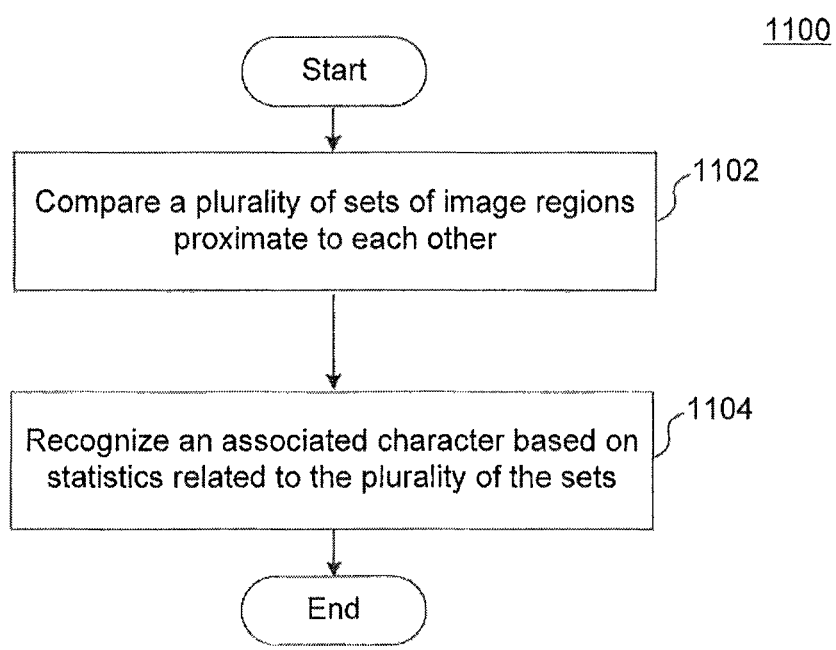
FIG. 11 is a flow chart of an exemplary process for performing optical character recognition.

FIG. 11 shows an exemplary process 1100 for performing OCR. Process 1100 may be a sub process of step 806 or 814 of FIG. 8A; step 826 or 836 of FIG. 8B; step 1004 or 1008 of FIG. 10A; step 1024 or 1028 of FIG. 10B; step 1054 or 1062 of FIG. 10C; or step 1084 or 1092 of FIG. 10D. In step 1102, processor 540 may compare a plurality of sets of image regions that are proximate to each other. For example, processor 540 may compare text regions of image to be recognized with a set of candidate image regions that have already been associated with text characters or representations. The comparison may yield likelihoods that the to-be-recognized image regions match one or more candidate image regions that have already established text association. In step 1104, processor 540 may recognize an associated character based on statistics related to the plurality of sets of image regions. For example, processor 540 may recognize a text character based on statistical results, e.g., the likelihoods of matching between the to-be-recognized image regions and the candidate image regions.

In some embodiments, processor 540 may be configured to recognize characters defined by a certain number of pixels. As used herein, a character is defined by X pixels when a substantial part of the character occupies X pixels of a digital image. It is noted that different character may occupy different number of pixels. In a black and white image, each pixel may only have a binary value (e.g., "0" or "1"; "True" or "False"; "Black" or "White"; etc.). In a gray scale image, each pixel may have a range of values indicating the degree of gray. In a color image, each pixel may have a vector value, such as (X, Y, Z), indicating the intensities of primary colors (e.g., red, green, and blue). In any case, a character in a digital image may occupy a number of pixels and the character is said to be defined by X number of pixels when a substantial part of the character occupies or covers X number of pixels. Processor 540 may be configured to perform OCR (e.g., using process 1100) to recognize characters defined by 15 or less pixels; 10 or less pixels; or even 6 or less pixels.

Figure 12A:
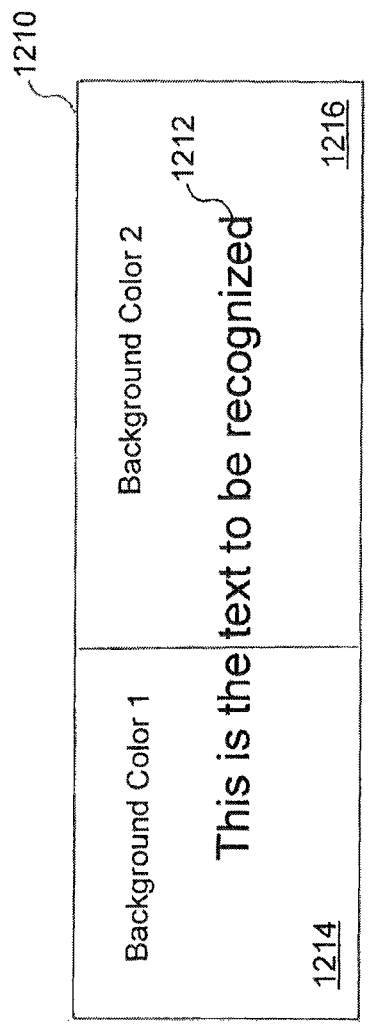
FIGS. 12A and 12B are schematic illustrations of text images having different colors.
Figure 12B:
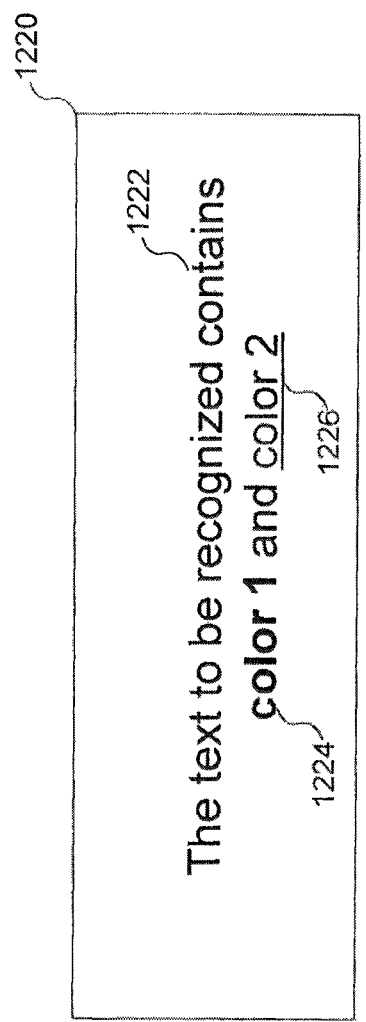

In some embodiments, processor 540 may be configured to recognize text images having different colors. FIGS. 12A and 12B are schematic illustrations of text images having different colors. In FIG. 12A, image 1210 contains text 1212. Image 1210 contains two background colors 1214 and 1216. In FIG. 12B, image 1220 contains text 1222. A part of text 1222 may have a first color 1224 and another part of text 1222 may have another color 1226. Processor 540 may be configured to recognize text 1212 or 1222 in image 1210 or 1220, respectively. In some embodiments, background or text colors may be used to indicate different text portions. For example, in FIG. 12A, text having background color 1214 (i.e., "This is the") may form a first portion (e.g., text portion 716, 726, or 736), and text having background color 1216 (i.e., "text to be recognized") may form a second portion (e.g., text portion 718, 728, or 738). In another example, referring to FIG. 12B, text having color 1224 (i.e., "color 1") may form a first portion (e.g., text portion 716, 726, or 736), and text having color 1226 (i.e., "color 2") may form a second portion (e.g., text portion 718, 728, or 738). Background or text colors may be an original color of an object (e.g., book, magazine, newspaper, etc.), or may be added/modified by user 100 (e.g., user 100 may highlight certain text). In some embodiments, processor 540 may identify different colors and use the color information to aid the OCR process.

As is evident from the foregoing, apparatus 110 may provide a wide range of functionality. More specifically, one embodiment consistent with the present disclosure provides an audible facial recognition function. Apparatus 110 may use the audible facial recognition function to identify individuals near a user of apparatus 110. In this way, in situations in which a visually-impaired user of apparatus 110 cannot identify or is unsure of the identity of a person nearby, apparatus 110 may be configured to recognize the individual and announce to the user an identifier of the nearby person.

Figure 13:
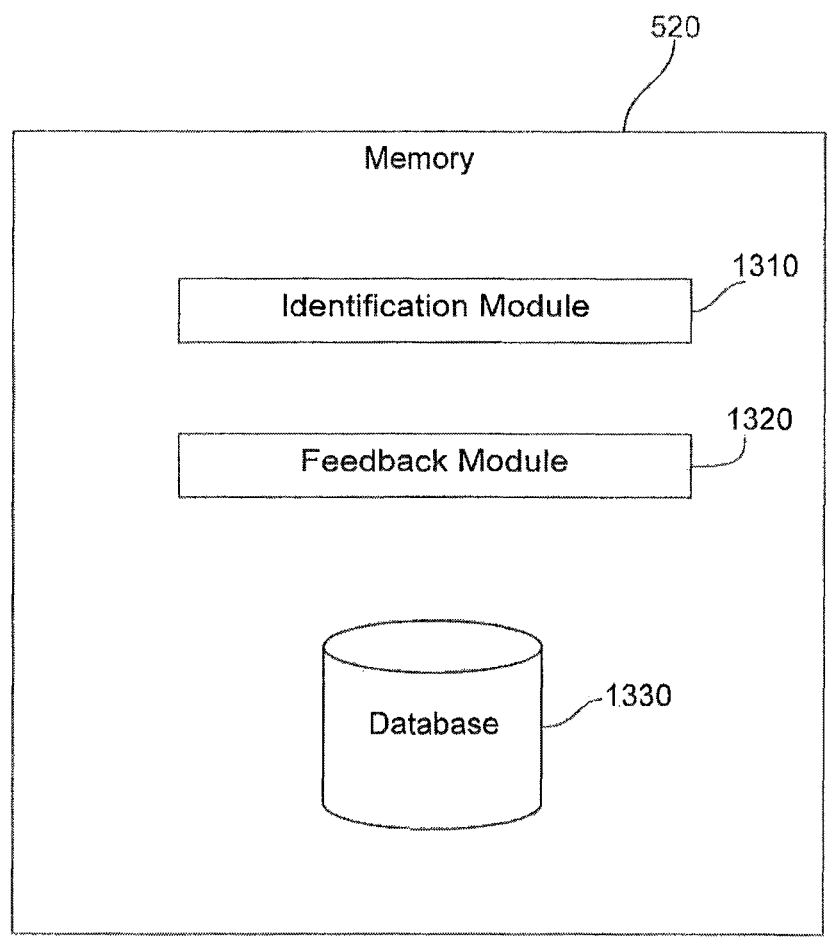
FIG. 13 is a block diagram illustrating an example of a memory configured to provide an audible facial recognition function, consistent with disclosed embodiments.

In some embodiments, memory 520 may include components configured to provide the audible facial recognition function. As shown in FIG. 13, memory 520 may include an identification module 1310, a feedback module 1320, and a database 1330. Identification module 1310 may be a component configured to identify a person based on data received from sensory unit 120. Feedback module 1320 may be a component configured to interact with a user to provide output to and receive input from the user. Database 1330 may be a component configured to store data associated with the audible facial recognition function and provide particular data when requested Identification module 1310 and feedback module 1320 may be implemented in software, hardware, firmware, a mix of any of those, or the like. For example, if identification module 1310 and feedback module 1320 are implemented in software, they may be stored in memory 520, as shown in FIG. 13. Other components of processing unit 140 and/or sensory unit 120 may be configured to perform processes to implement and facilitate operations of identification module 1310 and feedback module 1320. Thus, identification module 1310 and feedback module 1320 may include software, hardware, or firmware instructions (or a combination thereof) executable by one or more processors (e.g., processor 540), alone or in various combinations with each other. For example, identification module 1310 and feedback module 320 may be configured to interact with each other and/or other modules of apparatus 110 to perform functions consistent with disclosed embodiments. In some embodiments, any of the disclosed modules (e.g., identification module 1310 and feedback module 1320) may each include dedicated sensors (e.g., IR, image sensors, etc.) and/or dedicated application processing devices to perform the functionality associated with each module.

Database 1330 may include one or more memory devices that store information and are accessed and/or managed through a computing device, such as processing unit 140. In some embodiments, database 1330 may be located in memory 520, as shown in FIG. 13. In other embodiments, database 1330 may be located remotely from memory 520, and be accessible to other components of apparatus 110 (e.g., processing unit 140) via one or more wireless connections (e.g., a wireless network). While one database 1330 is shown, it should be understood that several separate and/or interconnected databases may make up database 1330. Database 1330 may include computing components (e.g., database management system, database server, etc.) configured to receive and process requests for data stored in memory devices associated with database 1330 and to provide data from database 1330.

In some embodiments, database 1330 may be configured to store identifying information associated with individual people. For example, database 1330 may be configured to store face-identifying information associated with a particular person. For the purposes of this disclosure, "face-identifying information" (also referred to herein as "facial information") may include any identifying information associated with the visual appearance of an individual. In some embodiments, face-identifying information may include information associated with the appearance of a person's face and/or head. In some embodiments, face-identifying information may include any combination of: one or more images of an individual's face, a list of features that describes a face, geometric information extracted from one or more images of a face, image statistics extracted from one or more images of the face, and any other information that can be used for face recognition. Further, in some embodiments, particular face-identifying information may include, for example, face shape information, face size information, facial features (e.g., facial hair, eye color, etc.), size and/or proportion of facial features, skin color, hair style, hair color, piercings, etc. It should be understood, however, that face-identifying information may not be limited to the physical appearance of a person's face. For example, face-identifying information may include information associated with the appearance of one or more other parts of the individual's body (besides the person's face) and/or the appearance of the individual's entire body. In some embodiments, other modalities may also be used to identify the person, such as the individual's voice.

Database 1330 may be configured to store face-identifying information for each of any number of different individuals. The face-identifying information for each individual may be derived from image data, such as image data collected by sensory device 120. The face-identifying information may be derived from a single image or multiple images of the individual. Face-identifying information from multiple images of an individual may be compiled and stored in a manner to create a collective and/or composite profile of that individual. For example, database 1330 may be configured to store multiple possible hair styles for one individual. Similarly, database 1330 may be configured to replace outdated face-identifying information with updated data, such as changes in a person's appearance (due to aging, for example).

Database 1330 may also be configured to collect and store one or more identifiers associated with one or more individuals. For example, database 1330 may be configured to store one or more identifiers associated with individuals for which face-identifying information is also stored. In some embodiments, identifiers may include any information that may identify an individual to a user of apparatus 110. For example, the identifier may be a person's name. Additionally or alternatively, identifiers may include other identifying information, such as other information about an individual (e.g., nickname, trait, descriptive term, etc.).

In some embodiments, identifiers may include audible identifiers. Audible identifiers may include any data that may be used to produce an audible output to announce information associated with the audible identifier. For example, an audible identifier may include a stored audio recording of identifying information (e.g., an audio recording of a person's name), which may be made either by the user or the individual they are trying to recognize. In another example, an audible identifier may be a text identifier configured to be converted to audio output. Apparatus 110 may be configured to output audible identifiers to a user of apparatus 110, such as via feedback-outputting unit 340. While audible identifiers are described herein, it should be understood that identifiers may be output to a user of apparatus 110 in any other manner, such as by being displayed as text on a display device.

In an exemplary embodiment, database 1330 may be configured to associate each stored audible identifier with one or more persons for which face-identifying information is also stored. In this way, apparatus 110 may be configured to receive face-identifying information associated with an individual, match the face-identifying information to stored face-identifying information associated with a particular person, and provide an associated audible identifier to identify the individual.

Figure 14:
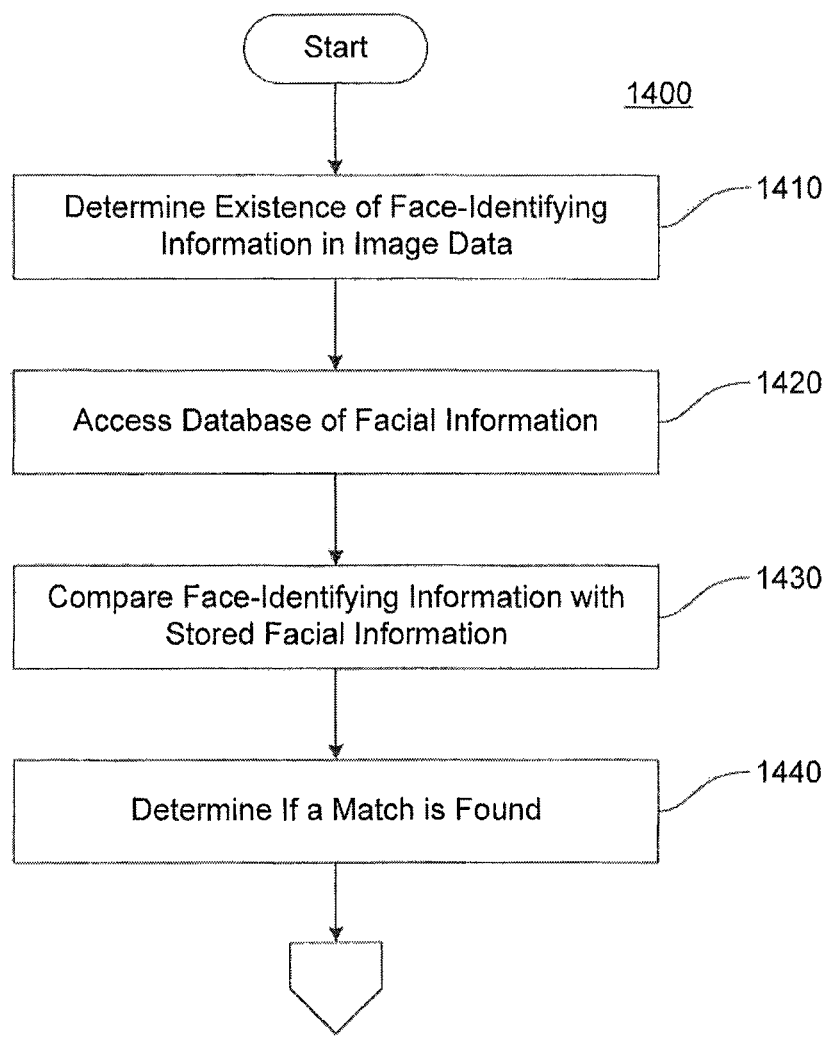
FIG. 14 is a flowchart of an example of a process for determining if an individual is recognized, consistent with disclosed embodiments.

FIGS. 14-17 depict examples of audible facial recognition processes, consistent with disclosed embodiments. FIG. 14 depicts an example of a process 1400 for determining if an individual is recognized, consistent with disclosed embodiments. In some embodiments, identification module 1310 may be configured to perform some or all of process 1400 to determine if an individual for which image data is received matches an individual for which face-identifying information is stored.

Identification module 1310 may be configured to receive image data as it is received from sensory unit 120. Identification module 1310 may process the received image data to determine the existence of face-identifying information in the image data (step 1410). Identification module 1310 may be configured to process images to identify portions of an image that are associated with a person present in the image, such as the person's face. Identification module 1310 may be configured to identify, for example, typical size and/or proportions of a face and/or head, particular facial features and/or an arrangement of facial features, or any other information that indicates that the image includes a person's face.

Identification module 1310 may proceed to communicate with database 1330 to access the database of stored facial information (step 1420). In some embodiments, identification module 1310 and/or database 1330 may be configured to perform one or more processes that provides identification module 1310 with access to search database 1330. For example, identification module 1310 may generate a request for access to a portion of database 1330 that stores facial information for the audible facial recognition function of apparatus 110.

After accessing database 1330, identification module 1310 may be configured to search the stored facial information by comparing the face-identifying information found in the image data with the stored facial information (step 1430). In some embodiments, identification module 1310 may be configured to perform one or more image- and/or data-matching processes that attempt to match some or all of face-identifying information identified in image data received from sensory unit 120 to facial information associated with a particular individual stored in database 1330.

For example, identification module 1310 may use one or more matching algorithms to search facial information associated with each individual stored in database 1330. The matching algorithm may be configured in any manner that allows identification module 1310 to compare received facial information with stored facial information and make a determination whether the results of the comparison indicate a match or if identification module 1310 should move to facial information associated with the next stored person.

In some embodiments, database 1330 may be configured to store statistical information associated with the audible facial recognition function of apparatus 110 in order to allow identification module 1310 to take statistical information into account when comparing face-identifying information. The statistical information may include, for example, frequency of specific matches of facial information, information about relationships between specific individuals, information about a time of specific matches, sound recording, information about location of specific matches, etc. Identification module 1310 may use the statistical information through use of a particular algorithm that indicates an order and/or priority for individuals to be searched. For example, identification may use a memory managing algorithm. The memory managing algorithm may use statistical information to determine an order of individuals to be searched while identification module 1310 attempts to find a match for received face-identifying information.

One example of a memory managing algorithm may use statistical information associated with the time a match of facial information for a particular individual was last found. The memory managing algorithm may determine an order of individuals to search based on this statistical information. The order may include attempting to match facial information associated with an individual for which a match was most recently found first, followed by facial information associated with an information was most recently matched before the first individual, and so on until the individual for which facial information was least recently matched.

Regardless of the processes and/or algorithms used to search the database of facial information, identification module 1310 may make a determination of whether a match was found (step 1440). Identification module 1310 may determine that a match has been found when stored facial information sufficiently matches the face-identifying information found in the real-time image data. Identification module 1310 may be configured to make a determination of whether information sufficiently matches based on the results of one or more comparison processes and/or algorithms that determine a likelihood that the received face-identifying information and the particular stored facial information are associated with the same person.

In some embodiments, identification module 1310 may be configured to stop search after finding facial information that sufficiently matches such that a likelihood of a match being correct is above a threshold value. In other embodiments, identification module 1310 may be configured to search each individual in the database and select a match based on the facial information associated with an individual that has the highest likelihood of being a match.

In some embodiments, identification module 1310 may be configured to use audio features to verify a potential match and/or find a match when no matching facial information is found. For example, apparatus 110 may be configured to capture and store audio features associated with the voice of individuals for which face-identifying information is stored in database 1330 (although it should be understood that only audio features may be stored for some individuals). During execution of process 1400, an input device associated with apparatus 110, such as a microphone, may capture an audio recording of the voice of an individual near the user (e.g., an individual in front of the user and found in the image data).

In some embodiments, after a potential match has been found using captured face-identifying information, identification module 1310 may compare the captured audio recording to stored audio features of the associated individual's voice. If the comparison results in a match (e.g., sufficient similarity of audible features above a certainty threshold), the match of an associated individual may be verified. If the comparison does not result in a match, identification module 1310 may continue to search database 1330 for another potential match of face-identifying information. In other embodiments, if a match between captured face-identifying information and stored facial information is not found, the audio recording may be compared to audio features stored in database 1330 to attempt to determine a match to identify an associated individual (e.g., an individual standing in front of the user).

Figure 15:
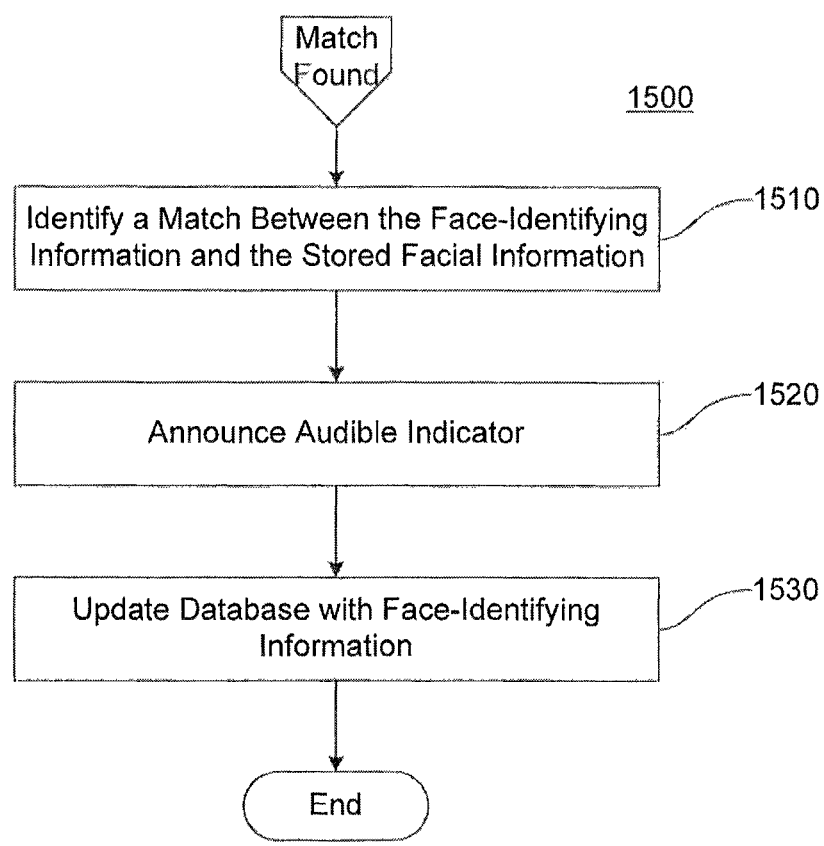
FIG. 15 is a flowchart of an example of a process that may be used in conjunction with the process of FIG. 14 when an individual is recognized.
Figure 16:
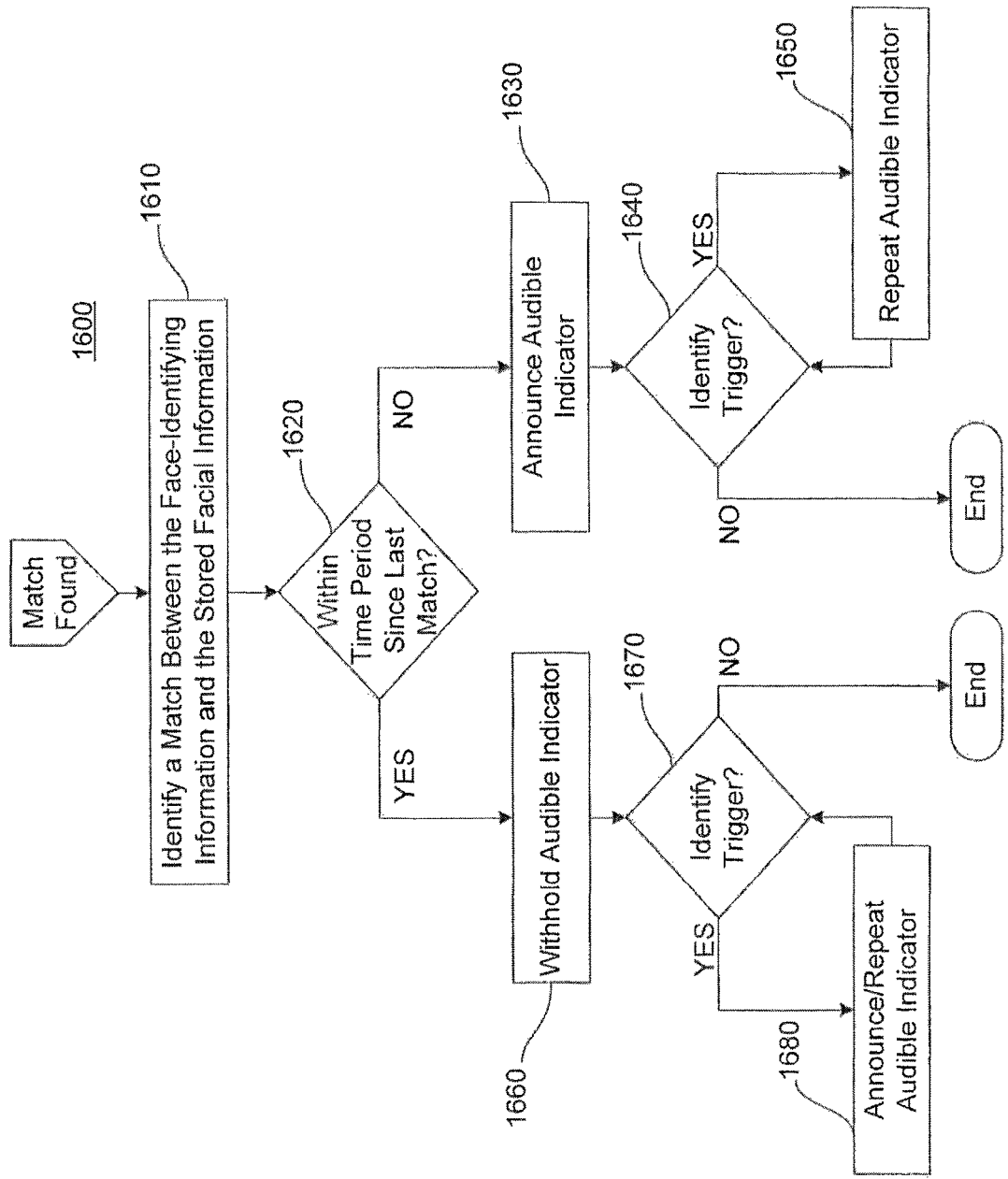
FIG. 16 is a flowchart of another example of a process that may be used in conjunction with the process of FIG. 14 when an individual is recognized.
Figure 17:
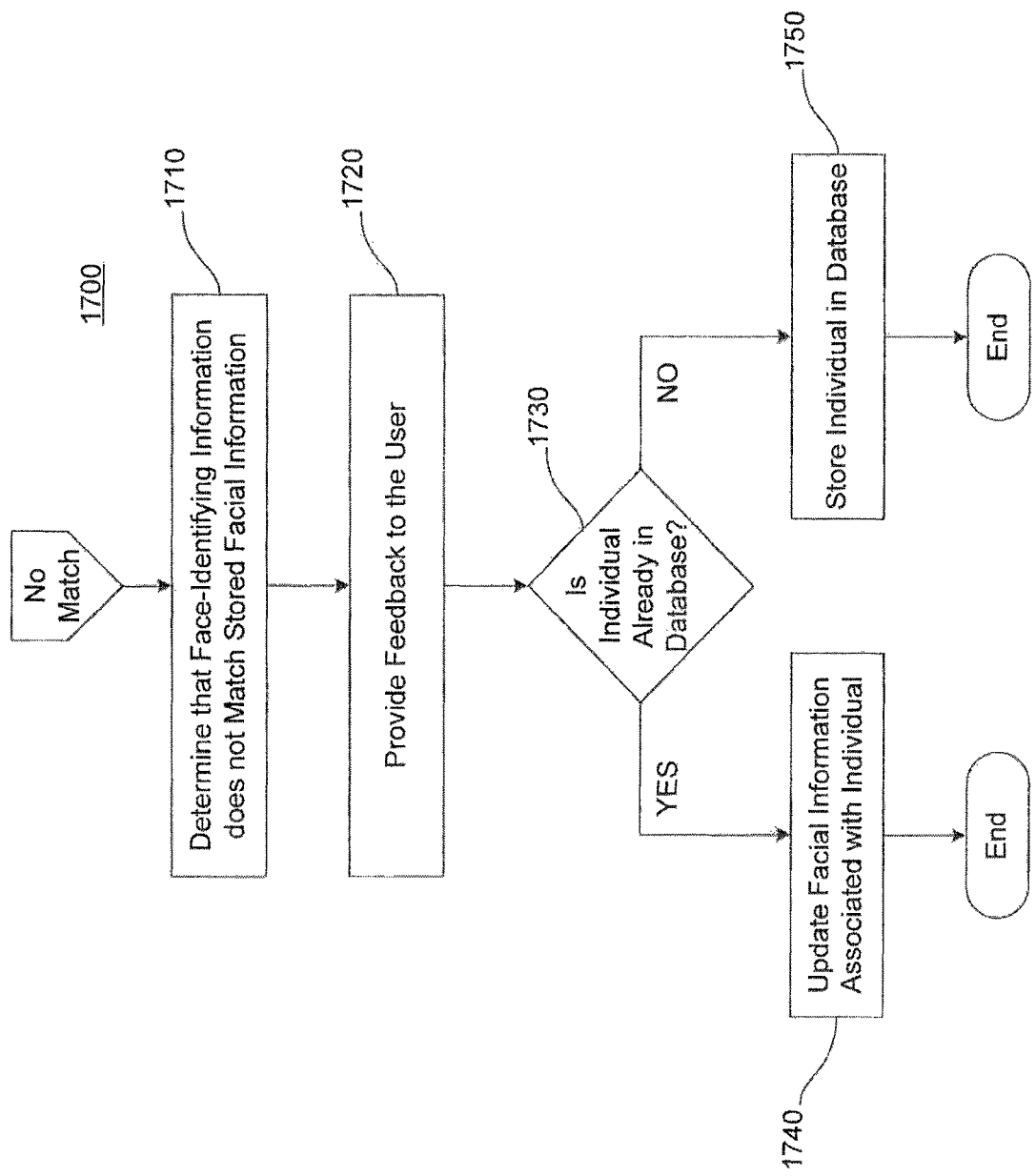
FIG. 17 is a flowchart of an example of a process that may be used in conjunction with the process of FIG. 14 when an individual is not recognized.

FIGS. 15 and 16 depict examples of processes that may be used after identification module 1310 determines that a match has been found. However, it should be understood that, in some instances, identification module 1310 may determine that the face-identifying information found in the image data does not match any stored facial information. FIG. 17 depicts an example of a process that may be used in such a scenario.

FIG. 15 depicts an example of a process 1500, consistent with disclosed embodiments. In certain aspects, process 1500 may be used in conjunction with process 1400 in instances where a match was found in step 1440 (e.g., a face identified in the real-time image data matches a face stored in the database of facial information). In these instances, identification module 1310 may identify that there is a match between the received face-identifying information and the stored facial information (step 1510).

In some situations, apparatus 110 (e.g., via process 1400 and/or 1500), may identify face-identifying information associated with more than one individual found in the image data (e.g., when two or more people are in front of a user of apparatus 110). Identification module 1310 may be configured to determine that there is more than one face in the image data, and perform process 1400 to determine if there is a match found for each face.

Feedback module 1320 may receive information indicating that the match has been identified. For example, feedback module 1320 may receive a notification from identification module 1310. In some embodiments, the notification may include an audible indicator associated with the matched facial information. In other embodiments, the notification may cause feedback module 1320 to access database 1330 to retrieve an audible indicator associated with the matched facial information, or identification module 1310 and/or feedback module 1320 may perform some other process that results in receipt of information associated with the audible indicator.

Feedback module 1320 may subsequently cause apparatus 110 (e.g., via feedback-outputting unit 340) to announce the audible indicator (step 1520). Feedback module 1320 may operate in conjunction with feedback-outputting unit 340 to provide the audible indicator to the user of apparatus 110. For example, apparatus 110 may generate an audible announcement via audio headphones or other speaker device. If matches are found for more than one face, feedback module 1320 (and/or identification module 1310) may be configured to determine which audible indicators to announce, and/or which order to announce them in, according to a pre-defined rule. For example, feedback module may announce each audible indicator in order of proximity to the user (e.g., closest individual identified first), or other order of priority (e.g., family members identified last).

Since the audible indicator may be associated with facial information matched to a face found in the image data, announcement of the audible indicator may indicate to the user of apparatus 110 an identity of a nearby person. In some embodiments, the audible facial recognition function of apparatus 110 may end after an audible identifier has been announced. However, as shown in FIG. 15, in some embodiments, process 1500 may continue by further processing the received face-identifying information.

For example, identification module 1310 may update database 1330 with the face-identifying information found in the image data (step 1530). For example, identification module 1310 may be configured to store the face-identifying information as additional facial information associated with an individual whose facial image is already stored in database 1330. In this way, the available information for that particular individual may be expanded to allow for more comprehensive matching of facial information. Similarly, identification module 1310 may be configured to update stored facial information stored in database 1330 with current facial information derived from the face identifying information in the real-time image data. In this way, the facial information associated with that particular individual may be updated to reflect changes in facial information, such as those due to aging, changes in style, etc.

FIG. 16 depicts an example of a process 1600, consistent with disclosed embodiments. In some aspects, process 1600 may be used in addition or as an alternative to process 1500 in instances where a match was found in step 1440 of process 1400. As with process 1500, process 1600 may include identification module 1310 identifying that there is a match between the received face-identifying information and the stored facial information (step 1610).

However, in some embodiments, further processing of the match determination may depend on additional information. For example, whether or not an audible indicator is announced to a user of apparatus 110 may depend on how recent the same individual was matched and identified. In this way, apparatus 110 may be prevented from repetitively announcing the identity of an individual who frequently reappears in the image data (e.g., in instances where the user and the individual are interacting with each other).

To provide this functionality, feedback module 1320 (and/or identification module 1310) may determine, when a match is found, whether a predetermined time period has passed since the associated individual was initially and/or most recently identified (step 1620). The predetermined time period may be any time period and may be selected based on any criteria. In some embodiments, the time period may be fixed for all situations. In other embodiments, the time period may depend on contextual and/or statistical information. In some embodiments, the time period may be selected by the user of apparatus 110.

If feedback module 1320 determines that the match is not within the predetermined time period (step 1620—NO), feedback module 1320 may be configured to cause apparatus 110 to announce an audible indicator associated with the matched individual (step 1630). Step 1630 may correspond to step 1520 of process 1500 or some other step by which apparatus 110 informs the user of apparatus 110 of the identity (or some other information) of the individual associated with the matched facial information.

In some embodiments, process 1600 may end after the audible indicator has been announced. In other embodiments, identification module 1310 may proceed to add to and/or update database 1330 with the received face-identifying information (e.g., step 1530 of process 1500). In still other embodiments, as shown in FIG. 16, process 1600 may continue with feedback module 1320 (and/or identification module 1310) looking for additional input from the user.

For example, feedback module 1320 may look for a trigger from the user of apparatus 110 (step 1640). The trigger may be any indication from the user of a request to perform an additional action. In some embodiments, the trigger may be associated with the user's desire to repeat the audible indicator. The trigger may be in the form of any input, such as an indication detected by sensory unit 120. For example, the trigger may be a pointing finger viewed by image sensor 350, or a voice command. In some embodiments, the trigger may include use of function button 410.

If feedback module 1320 identifies a trigger (step 1640—YES), feedback module 1320 may cause apparatus 110 to repeat the audible indicator to the user (step 1650). Feedback module 1320 may continue to look for triggers to repeat the audible indicator until it is determined that no additional triggers associated with that particular function are identified (step 1640—NO), which may occur after a predetermined period of time, after the individual leaves the image data, etc.

In some instances, feedback module 1320 may determine that a determined match of facial information occurred with the predetermined time period (step 1620—YES). In these instances, feedback module 1320 may withhold the audible identification of the individual (step 1660). In this way, apparatus 110 may refrain from announcing an audible identifier when the associated individual is merely reappearing in the image data within a predetermined time period since the individual was initially identified.

As with step 1630, process 1600 may end after step 1660, or it may be followed with an updating step (e.g., step 1530). However, in some instances, process 1600 may continue with feedback module 1320 looking for a trigger (step 1670). Step 1670 may correspond to step 1640 in that feedback module 1320 may look for a trigger as any indication that the user is requesting that the apparatus perform an additional process. For example, the user may desire for the audible identifier to be announced, even though the identification is determined to be within the predetermined time period.

Feedback module 1320 may identify a trigger associated with a user's desire to audibly re-identify (or initially identify) the associated individual during the predetermined time period (step 1670—YES). As was described with respect to step 1640, the trigger may take any form. For example, the trigger may include a pointing finger that is viewed by image sensor 350.

After feedback module 1320 identifies the trigger, feedback module 1320 may cause apparatus 110 to audibly re-identify (or initially identify) the associated individual during the predetermined time period (step 1680). As with step 1650, feedback module 1320 may continue to look for triggers to repeat the audible indicator until it is determined that no additional triggers associated with that particular function are identified (step 1670—NO), which may occur after a predetermined period of time, after the individual leaves the image data, etc. In some embodiments, feedback module 1320 may recognize that an individual has walked away and came back, causing re-identification of the associated individual, regardless of a time limit.

In some instances, individuals that appear in the real-time image data may not match individuals for which facial information is stored in database 1330. For example, the user of apparatus 110 may be in proximity to one or more persons that the user does not know or that the user knows but have not been stored in database 1330. FIG. 17 depicts an example process 1700, consistent with disclosed embodiments. In some embodiments, process 1700 may follow process 1400 in instances when no match was found for received face-identifying information.

After unsuccessfully searching stored facial information, identification module 1310 may determine that face-identifying information does not match stored facial information (step 1710). In some aspects, identification module 1310 may determine that the face-identifying information fails to match stored facial information with sufficient certainty to determine that the face associated with the face-identifying information is associated with an individual for which facial information is stored.

In some embodiments, feedback module 1320 may be configured to provide feedback to the user of apparatus 110 to indicate that no match was found between the received face-identifying information and the stored facial information (step 1720). For example, feedback module 1320 may receive a notification from identification module 1310 indicating that no match was found, and feedback module 1320 may perform one or more processes to notify the user. For example, feedback module 1320 may communicate with feedback-outputting unit 340 to cause feedback-outputting unit 340 to notify the user (e.g., make an audible announcement). It should be understood that step 1720 may be optional and that in some embodiments, no feedback to the user may be provided.

In some embodiments, feedback module 1320 (and/or identification module 1310) may be configured to store the received face-identifying information in database 1330. For example, feedback module 1320 may be configured to store facial information and an audible indicator for a non-recognized individual (e.g., a person for which face-identifying information was identified in the image data, but for which not match in database 1330 was found). In order to determine the face-identifying information that is associated with the correct individual, feedback module 1320 may determine if the face-identifying information is associated with an individual that is stored in database 1330 (step 1730).

In some instances, even though a match was not found, the face-identifying information may be associated with an individual already stored in database 1330, such as instances in which the individual's appearance has changed, or when the stored facial information is inaccurate or low-quality. Feedback module 1320 may determine whether the individual is already stored in database 1330 based at least in part on input from the user of apparatus 110. For example, the user may provide an audible indicator (e.g., via speech into a microphone) that feedback module 1320 (and/or identification module 1310) may determine matches a stored audible indicator associated with a stored individual.

If feedback module 1320 determines that the face-identifying information is associated with an individual already stored in database 1330 (step 1730—YES), feedback module 1320 (and/or identification module 1310) may store the face-identifying information to add to or update the stored facial information for that individual (step 1740). In this way, database 1330 may be configured to store more comprehensive facial information that may lead to more accurate matching of facial information in subsequent situations.

However, if feedback module 1320 determines that the face-identifying information is associated with an individual that is not stored in database 1330 (step 1730—NO), feedback module 1320 (and/or identification module 1310) may be configured to store information associated with the non-recognized individual in database 1330 (step 1750). For example, feedback module 1320 may be configured to store facial information and an audible indicator for the non-recognized individual. In some embodiments, feedback module 1320 may store facial information automatically and prompt the user of apparatus 110 to input an audible indicator to be associated with the individual. In other embodiments, feedback module 1320 may store the facial information and the audible indicator for the non-recognized individual upon identifying a trigger in the image data associated with the user's desire to add the non-recognized individual to the at least one database. In some embodiments, the trigger may be a pointing finger (e.g., the user points at the non-recognized individual).

Through process 1700, a user of apparatus 110 may expand database 1330 to store facial information associated with non-recognized individuals. Database 1330 may be configured to grow and adapt to include a more comprehensive and current catalog of facial information and individuals associated with the facial information. In this way, apparatus 110 may be configured to provide an audible facial recognition function that improves and expands over time.

While processes 1400, 1500, 1600, and 1700 have been described as examples, it should be understood that apparatus 110 may use any combination of these or any other processes to provide an audible facial recognition function. Additional or alternative functions of apparatus 110 may be used in conjunction with the audible facial recognition function to provide additional features to apparatus 110.

For example, in some embodiments, image sensor 350 may be configured to capture images in various resolutions. In performing one or more of processes 1400, 1500, 1600, and 1700 (or any other process), identification module 1310 (and/or feedback module 1320) may be configured to operate in a lower power consumption mode. In some embodiments, the low power consumption mode may include determining an existence of face-identifying information in image data take at a resolution lower that a resolution of image data used to compare face-identifying information in the real-time image data with facial information stored in database 1330.

In another example, in some embodiments, feedback module 1320 (and or identification module 1310) may be configured to look for a trigger from a recognized individual before audibly identifying that individual. For example, feedback module 1320 may be configured to determine if an individual is looking in a direction of the user of apparatus 110. If it is determined that the individual is looking in a direction of the user of apparatus 110, feedback module 1320 may cause apparatus 110 to audibly identify the individual. Feedback module 1320 may perform this function for more than one recognized individual. For example, feedback module 1320 may be configured to determine if two individuals are looking in a direction of the user of apparatus 110, and, if so, cause apparatus 110 to audibly identify both individuals.

The disclosed apparatus 110 may include the audible facial recognition function described herein in order to identify nearby individuals to a user of apparatus 110. User 110 may be a visually impaired user than may be unable to visually identify these individuals. Apparatus 110 may match detected faces to stored faces and provide audible feedback to assist these users in identifying people that are around them.

As is evident from the foregoing, apparatus 110 may provide a wide range of functionality. More specifically, one embodiment consistent with the present disclosure provides a method for informing user 100 that an object detected within the field of view of apparatus 110 is not found in one or more databases containing object information. As a result of this "failed attempt," apparatus 110 may assist the user in creating a new database entry for this new object to facilitate future rapid identification.

As used in this disclosure, a "representation" may comprise any audible or visual information associated with any object or locational setting perceived within the field of view of apparatus 110. As previously discussed, one or more such objects may be described in entries within one or more databases, which facilitate identification of the object by apparatus 110 and allow the apparatus to provide feedback to the user identifying the object.

A database may not contain information associated with each and every object or situation that a user such as user 100 may encounter in daily life. In these situations, apparatus 110 may receive image data and a signal from user 100 indicating a desire to know more about an object or situation within the image data in order to discover in rapid fashion that no information is known about the object. The ability to provide feedback on demand to the user regarding these "failed" identification attempts may be important to operation of apparatus 110. These failed attempts may provide opportunities to expand the device's capabilities, since the object can be associated with a new database entry that may be readily identified in the future. Further, the failed attempt feedback can provide confirmation to user 100 that apparatus 110 is working and operational, but simply does not have enough information to identify an object or situation.

As used in this disclosure, a "signal" from the user may include any audible input presented by user 100 to apparatus 110, or any visible activity recognizable by apparatus 110 indicating that user 100 needs help or wants information. "Information" relating to an object or a situation may include any descriptive knowledge or data associated with the entity, such as context, location, size, color, rate of motion, etc. As used herein, "feedback" generated and provided by apparatus 110 may comprise any audible, tactile, or visual information that the apparatus employs to update and inform user 100 about a particular system status, or about objects and situations perceived from the field of view of the apparatus. Apparatuses, systems, and methods for generating and providing "failed attempt" feedback will now be described in detail.

Figure 18:
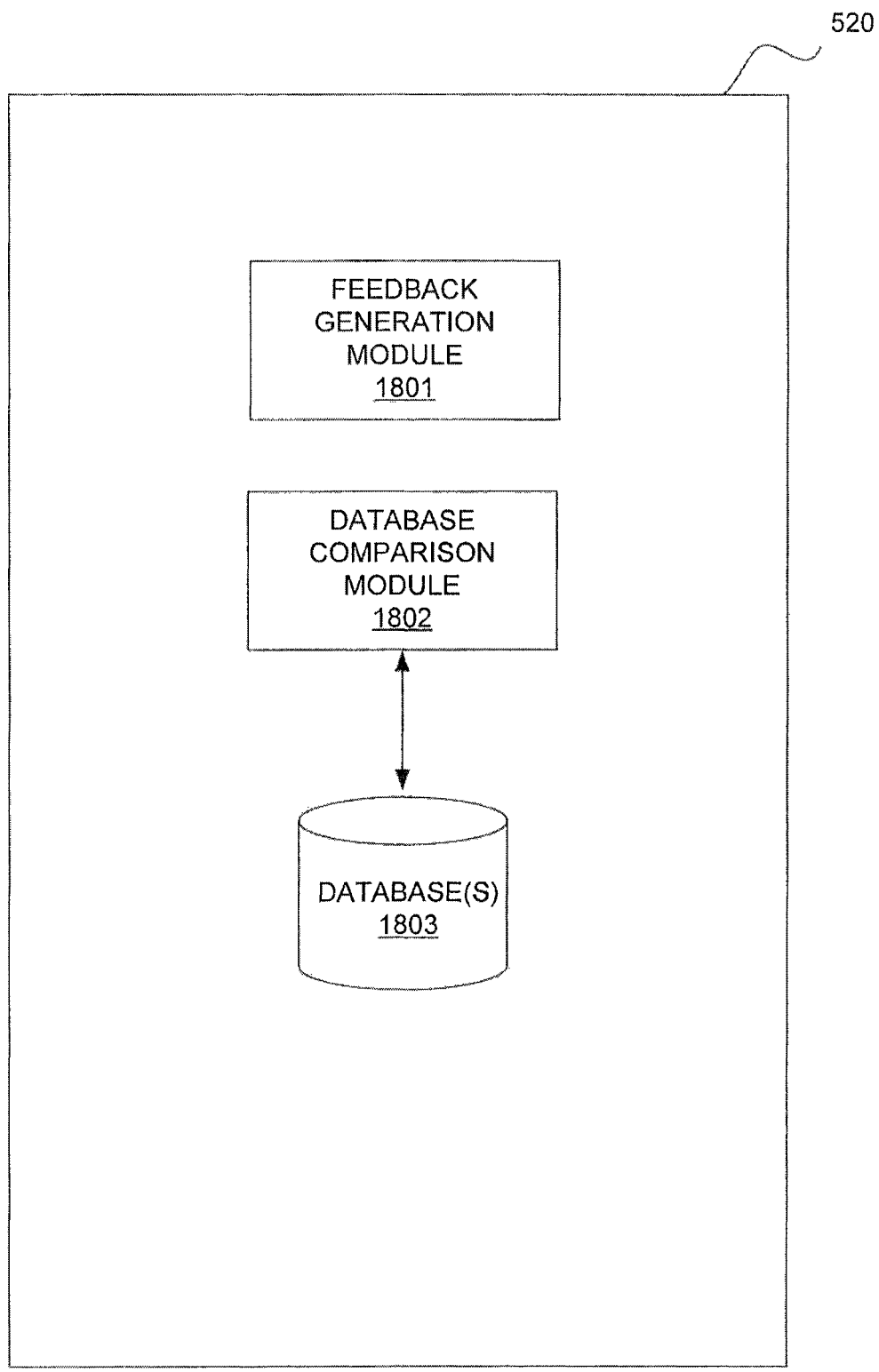
FIG. 18 is a block diagram illustrating an example of a memory contained within an apparatus for aiding persons who have low vision.

FIG. 18 is a block diagram illustrating memory 520 associated with apparatus 110 according to one embodiment. In the example shown in FIG. 18, memory 520 comprises a feedback generation module 1801, a database comparison module 1802, and one or more databases 1803.

Feedback generation module 1801 may provide functionality for apparatus 110 to generate and transmit information to user 100 in response to a query. Processor 540 may execute feedback generation module 1801 to generate and process feedback in a given context, then transmit the generated feedback to feedback-outputting unit 340 for output to user 100. In one embodiment, processor 540 and feedback-outputting unit 340 may be operatively connected via wire 130. In other embodiments, processor 540 and feedback-outputting unit 340 may be operatively connected via wireless transceiver(s) 530. As discussed above, in some embodiments, feedback generation module 1801 may generate audible feedback to user 100. In other embodiments, the feedback may be tactile in nature, such as a vibration.

Database comparison module 1802 may provide functionality for apparatus 110 to compare objects detected in the user's environment to objects in a database, such as database 1803 or remote databases 1902, to be described in detail below. In some embodiments, database comparison module 1802 may derive information from real time image data received from image sensor 350. In other embodiments, other software elements or processors may derive the information and provide it to database comparison module 1802. Processor 540 may execute database comparison module 1802 to access one or more of the described databases, and compare the information derived from the received real time image data with information in the databases. If the derived information corresponds to information found in one or more of the databases, database comparison module 1802 may provide an indication to feedback generation module 1801 to that effect. If the derived information is not found in any database searched by database comparison module 1802, apparatus 110 will generate and provide feedback relating to the failed attempt as discussed in further detail below in association with FIGS. 20-24.

Database(s) 1803 may comprise one or more databases that store information and are accessed and/or managed through memory 520. By way of example, databases 1803 may include document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 1803 may contain software code or macros that facilitate rapid searching and comparison by database comparison module 1802.

Feedback generation module 1801 and database comparison module 1802 may be implemented in software, hardware, firmware, a mix of any of those, or the like. For example, if feedback generation module 1801 and database comparison module 1802 are implemented in software, they may be stored in memory 520, as shown in FIG. 18. Other components of processing unit 140 and/or sensory unit 120 may be configured to perform processes to implement and facilitate operations of feedback generation module 1801 and database comparison module 1802. Thus, feedback generation module 1801 and database comparison module 1802 may include software, hardware, or firmware instructions (or a combination thereof) executable by one or more processors (e.g., processor 540), alone or in various combinations with each other. For example, feedback generation module 1801 and database comparison module 1802 may be configured to interact with each other and/or other modules of apparatus 110 to perform functions consistent with disclosed embodiments. In some embodiments, any of the disclosed modules (e.g., feedback generation module 1801 and database comparison module 1802) may each include dedicated sensors (e.g., IR, image sensors, etc.) and/or dedicated application processing devices to perform the functionality associated with each module.

Figure 19:
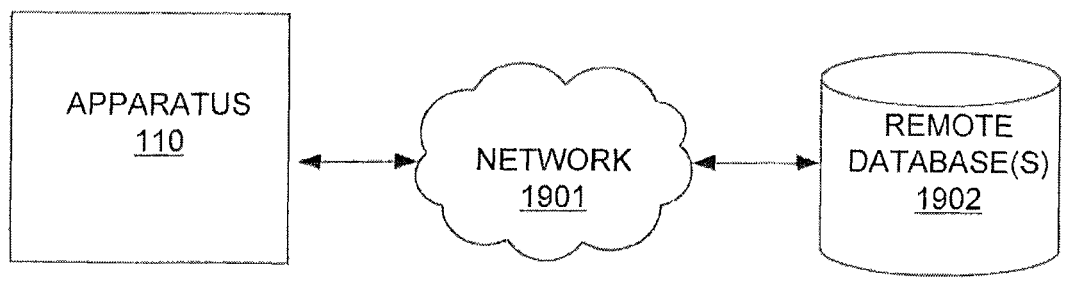
FIG. 19 is a block diagram illustrating an example of a system environment for aiding persons who have low vision.

FIG. 19 is an example illustration of a system 1900 for providing feedback to a visually-impaired user, consistent with a disclosed embodiment. As shown in system 1900, apparatus 110 and remote database(s) 1902 are configured to communicate over a network 1901. One of skill in the art will appreciate that although one apparatus and one remote database are depicted in FIG. 19, any number of these components may be provided. Furthermore, one of ordinary skill in the art will recognize that one or more components of system 1900 may be combined and/or divided into subcomponents.

Network 1901 provides communications between the various components in system 1900, such as apparatus 110 and remote database(s) 1902. In addition, the components in system 1900 may access legacy systems (not shown) via network 1901, or may directly access legacy systems, data stores, or other network applications. Network 1901 may be a shared, public, or private network, may encompass a wide area or local area, and may be implemented through any suitable combination of wired and/or wireless communication networks. Network 1901 may further comprise an intranet or the Internet.

Apparatus 110 may comprise any configuration of the apparatus illustrated in FIGS. 5A-5D. Apparatus 110 may configure wireless transceiver 530 to communicate with other components of system 1900 via network 1901, or may contain other components (not shown) which facilitate network communication.

Remote database(s) 1902 may, as described above in relation to databases 1803, comprise one or more databases that store information and are accessible by apparatus 110 via network 1901. Databases 1902 may contain or be linked to components (not shown) that facilitate communication over network 1901. By way of example, databases 1902 may be document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 1902 may contain software code or macros that facilitate rapid searching and comparison by database comparison module 1802 of apparatus 110.

Figure 20:
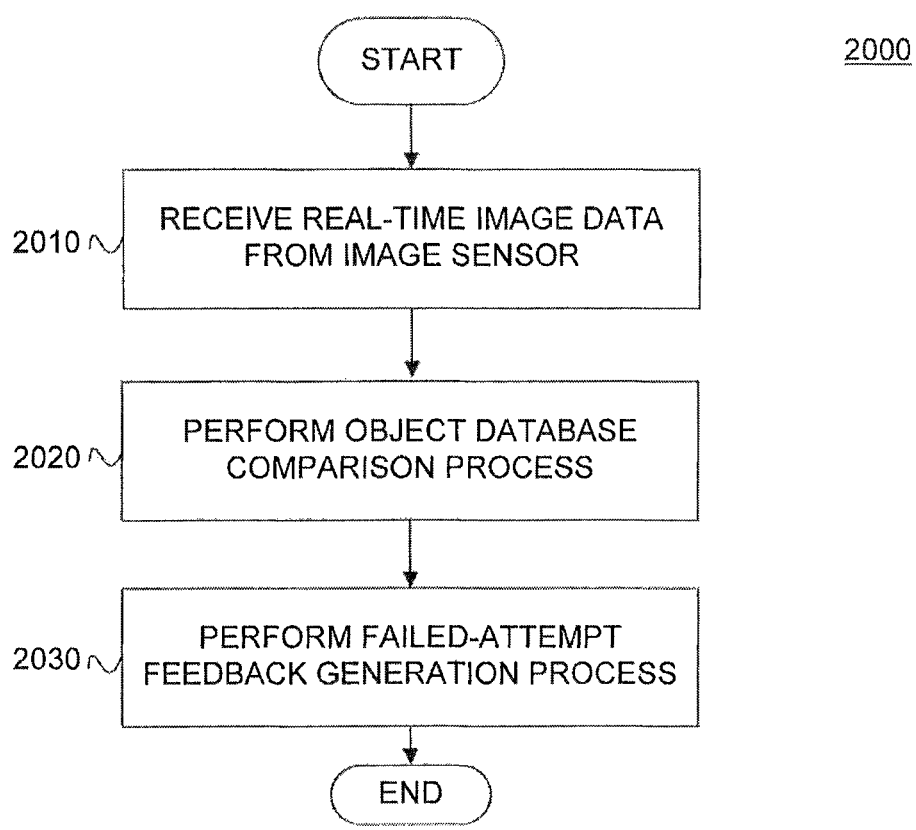
FIG. 20 is an example of a process for providing feedback to a person who has low vision, consistent with disclosed embodiments.

FIG. 20 illustrates an example process 2000 for providing feedback to a person who has low vision consistent with certain disclosed embodiments. Process 2000, as well as any or all of the individual steps therein, may be performed by various aspects of device 110, such as sensory unit 120, processing unit 140, support 210, or any subcomponents therein. For exemplary purposes, FIG. 20 is described as being performed by processor 540, executing software instructions stored within memory 520.

Processor 540 may receive real-time image data from an image sensor, such as image sensor 350 (Step 2010). In other embodiments, processor 540 may receive the image data from an intermediate component associated with sensory unit 120. The intermediate unit may, for example, perform image processing operations on the real-time image data before transmitting it to processor 540. In some embodiments, the real-time image data may be received as a single streaming video file. In other embodiments, the real-time image data may be received as a series of still images. When the image data is received, processor 540 may store the data in memory 520 or databases 1803.

Processor 540, via database comparison module 1802, may perform an object database comparison process, such as is described below in connection with FIG. 21 (Step 2020). In brief, according to some embodiments, database comparison module 1802 may select one or more databases, such as databases 1803 or remote databases 1902 to search for information relating to the objects in the received real-time image data associated with the user request. Database comparison module 1802 may then access the selected databases. As discussed previously, processor 540 may determine trigger information, either audio or visual, from the received real-time image data. Processor 540 may further determine context information from the real-time image data. Finally, database comparison module 1802 may perform an object database query process, such as is described below in connection with FIG. 22.

In Step 2030 of process 2000, processor 540, via feedback generation module 1801, may perform a failed-attempt feedback generation process, such as is described below in connection with FIG. 23. In brief, according to some embodiments, feedback generation module 1801 may configure the content of feedback to provide to user 100 when database comparison module 1802 determines that the object(s) identified in the real-time image data are not contained within databases 1803 or remote databases 1902. Feedback generation module 1801 may generate this "failed-attempt feedback," then provide it to user 100. Processor 540 may determine if user 100 wishes to add the representation of the object and an audible representation of the object to one or more of databases 1803 or remote databases 1902. If so, database comparison module 1802 may perform a database entry addition process, such as is described below in connection with FIG. 24.

Figure 21:
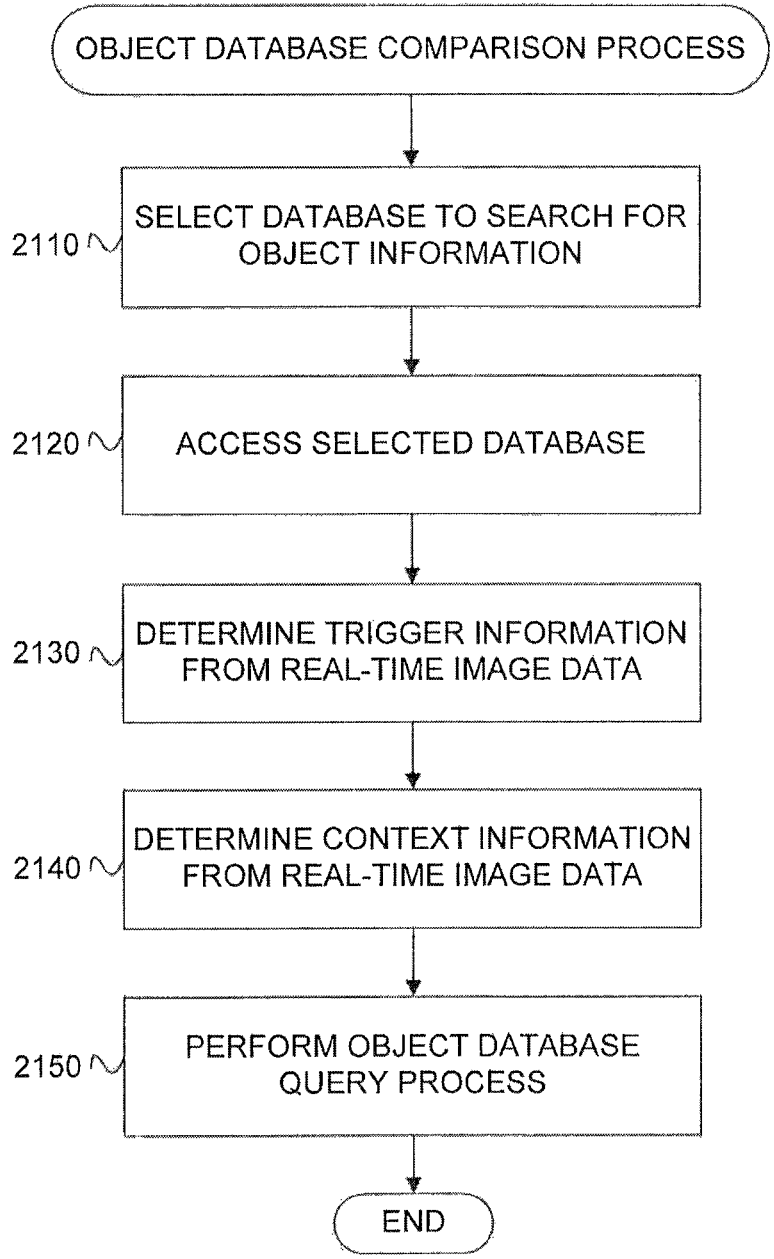
FIG. 21 is an example of an object database comparison process, consistent with disclosed embodiments.

FIG. 21 illustrates an example object database comparison process such as that described above in association with Step 2020 of process 2000 consistent with certain disclosed embodiments. Process 2020, as well as any or all of the individual steps therein, may be performed by various aspects of device 110, such as sensory unit 120, processing unit 140, support 210, or any subcomponents therein. For exemplary purposes, FIG. 21 is described as being performed by processor 540, executing software instructions stored within memory 520.

Processor 540, via database comparison module 1802, may select one or more databases to search for object information (Step 2110). The database may be a mobile database contained within apparatus 110, such as database(s) 1803 housed within memory 520. In other embodiments, the database may be one or more remote databases accessible over a network, such as remote database(s) 1902 accessible over network 1901. Once the target database(s) are selected, processor 540 may access the selected database(s) (Step 2120). In some embodiments, processor 540 may provide credentials that permit its access to the database, particularly for remote database(s) 1902 located on an external server.

Processor 540 may determine trigger information from the received real-time image data (Step 2130). As part of the determination, processor 540 may receive a request for object information from user 100 relating to one or more representations of objects in the environment of the user contained within the received real-time image data. In some embodiments, the trigger information may comprise audible cues received from a microphone (not shown) associated with apparatus 110. In other embodiments, the trigger information may comprise one or more visual signals performed by user 100 within the received real-time image data, such as a hand signal or other such trigger. In still other embodiments, processor 540 may be configured to determine a head movement of user 100, and use the head movement as the signal indicating the desire of the user to obtain information about a given object within the field of view of apparatus 110. It is understood that these are non-limiting examples, and that apparatus 110 may receive a request for object information via any manner of trigger information.

Processor 540 may determine context information from the received real-time image data that facilitates the retrieval of information (Step 2140). In some embodiments, processor 540 may execute software instructions to process the representations of the one or more objects in the real-time image data associated with the detected trigger information described above. In some embodiments, the processing may comprise image processing, such as image rotation, a change in the size of the image, image sharpening, cropping the image, enhancing the focus, etc. It is understood that these are non-limiting examples and that any manner of image processing may be applied to the real-time image data. In other embodiments, the processing may comprise optical character recognition (OCR), when the real-time image data comprises text. In these embodiments, the optical character recognition may facilitate recognition of the visualized text by processor 540, and facilitate formation of a search query for a database containing object information. Processor 540 may further derive or determine any other information contained in the received real-time image data relating to the context of the image, such as date, time, geographical location, etc.

In Step 2150, processor 540, via database comparison module 1802, may perform an object database query process, such as is described below in connection with FIG. 22. In brief, according to some embodiments, database comparison module 1802 may query one or more selected databases (such as database(s) 1803 or remote database(s) 1902) using information such as the determined trigger information and context information. Database comparison module 1802 may determine if an existing trigger and context matched set entry within the databases corresponds to the system status observed in the real-time image data. If so, processor 540, via feedback generation module 1801, may prepare audible or tactile feedback to user 100 identifying the object. If no existing trigger and context entry matches the current system status, database comparison module 1802 may determine whether or not there are further database entries to search, and may continue to compare trigger information and context information with the entries in the databases until they are exhausted. If the database entries are exhausted without matching the current system status, processor 540 may prepare "failed-attempt" feedback via feedback generation module 1801.

Figure 22:
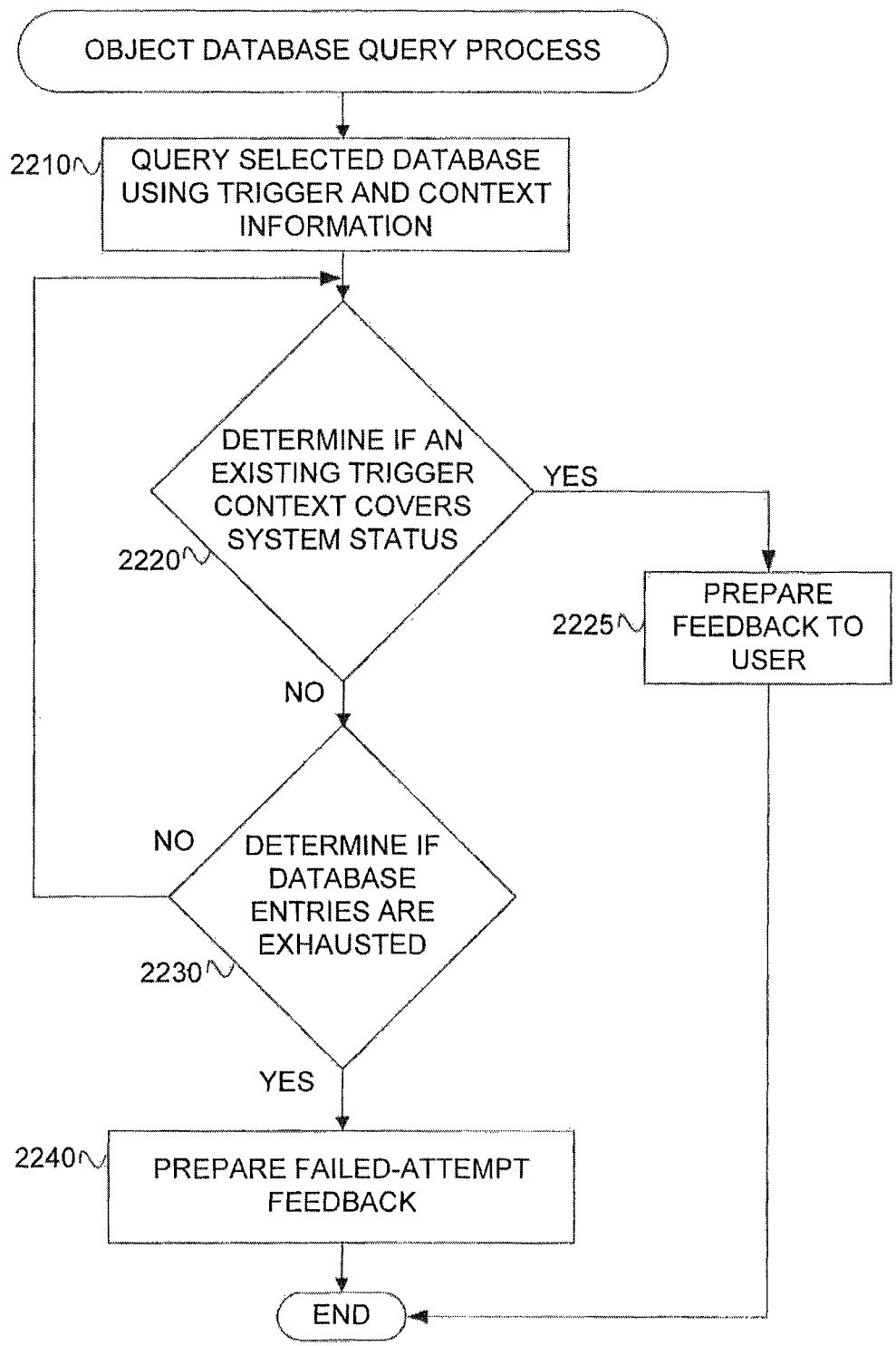
FIG. 22 is an example of an object database query process, consistent with disclosed embodiments.

FIG. 22 illustrates an example object database query process such as that described above in association with Step 2150 of process 2020 consistent with certain disclosed embodiments. Process 2150, as well as any or all of the individual steps therein, may be performed by various aspects of device 110, such as sensory unit 120, processing unit 140, support 210, or any subcomponents therein. For exemplary purposes, FIG. 22 is described as being performed by processor 540, executing software instructions stored within memory 520.

Processor 540, via database comparison module 1802, may query the selected databases, such as database(s) 1803 and/or remote database(s) 1902 (Step 2210). Database comparison module 1802 may form a query using trigger information or context information derived from the real-time image data, or a combination of the two. In some embodiments, additional audible or visual information may form a portion of the query, if the databases are configured to contain such information and if such information was derived from the image data by processor 540.

Database comparison module 1802 may determine if an existing database entry comprises trigger information and/or context information that covers or matches the current system status and the received real-time image data (Step 2220). If the status does match an existing entry (Step 2220: YES), then processor 540 may prepare feedback to user 100 identifying the object via feedback generation module 1801, and the process terminates (Step 2225).

Alternatively, if no database entry matches the present system status (Step 2220: NO), then database comparison module 1802 may determine if the database entries are exhausted, or if there are more entries to search (Step 2230). In alternative embodiments, database comparison module 1802 may also choose a different database to query at this stage with the same search query. In other embodiments, database comparison module 1802 may alter the search query. If there are more database entries to search, or if the database and/or query are otherwise modified (Step 2230: NO), then database comparison module 1802 repeats Steps 2220-2230 and continues to compare the search query with existing database entries.

If database comparison module 1802 determines that the database entries are exhausted (Step 2230: YES), then the comparison process ends. In some embodiments, the database comparison process may end due to other input, such as an expiration of a certain amount of time as measured by a timer associated with processor 540 (not shown). In other alternative embodiments, user 100 may provide input to apparatus 110 that halts the comparison process. After the database query comparison ends, processor 540 may begin to prepare feedback informing user 100 of the failed attempt and lack of object identification (Step 2240).

Figure 23:
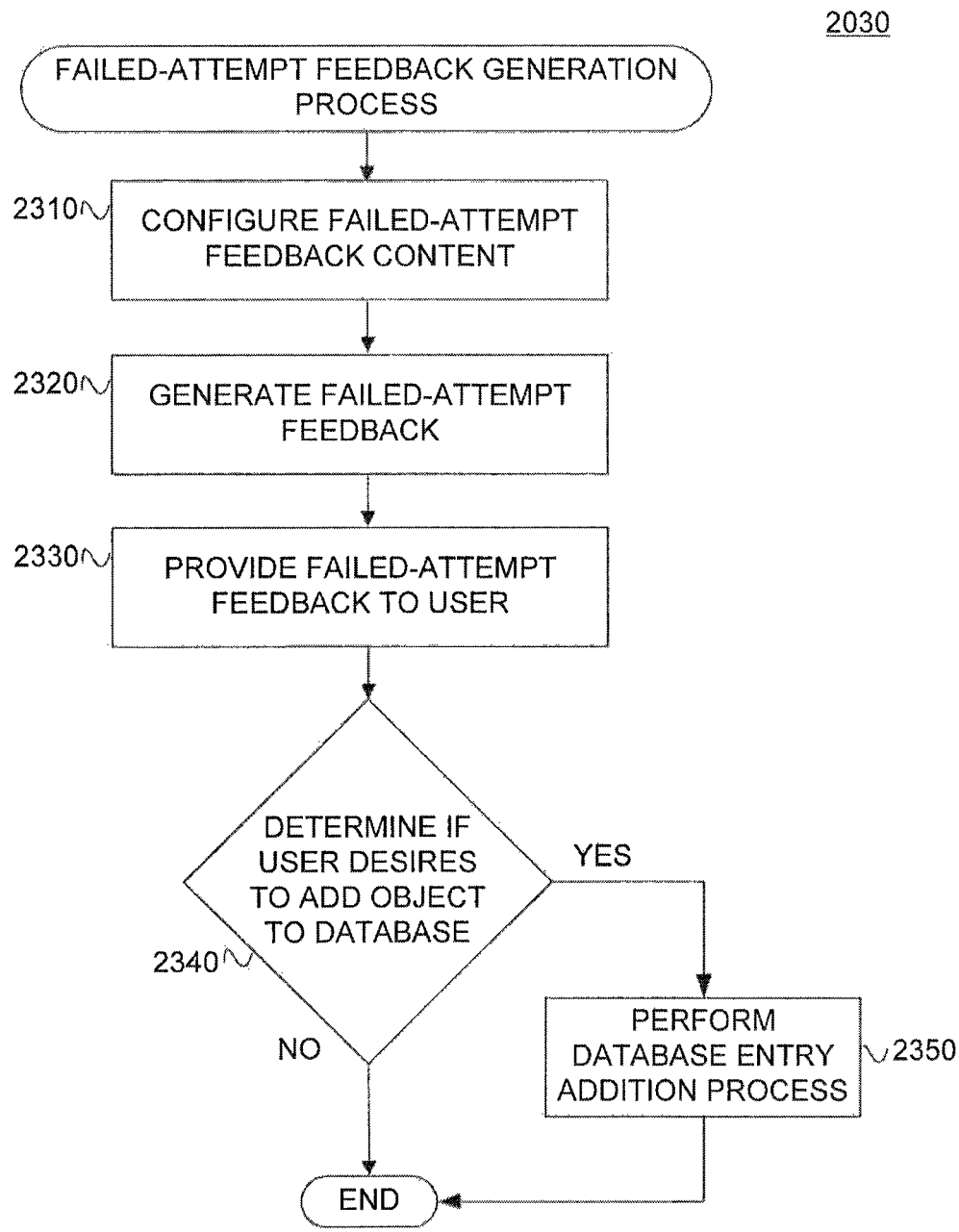
FIG. 23 is an example of a failed-attempt feedback generation process, consistent with disclosed embodiments.

FIG. 23 illustrates an example failed-attempt feedback generation process such as that described above in association with Step 2030 of process 2000 consistent with certain disclosed embodiments. Process 2030, as well as any or all of the individual steps therein, may be performed by various aspects of apparatus 110, such as sensory unit 120, processing unit 140, support 210, or any subcomponents therein. For exemplary purposes, FIG. 23 is described as being performed by processor 540, executing software instructions stored within memory 520.

Processor 540, via feedback generation module 601, may configure the content of the failed-attempt feedback (Step 2310). As discussed previously, the feedback may be in an audible form. In these embodiments, apparatus 110 may provide user 100 with audible feedback such as "SORRY; OBJECT NOT FOUND," or "NEW OBJECT DETECTED." In other embodiments, the feedback may be in a tactile form. For example, apparatus 110 may contain components that generate vibration, and these components may be configured to vibrate in a particular pattern signifying to user 100 when an object is not found in the database. It is understood that these are merely non-limiting examples, and that feedback generation module 1801 may configure any content for the feedback that may be relevant to the instant situation or context.

Once feedback generation module 1801 determines and configures the content of the failed-attempt feedback, feedback generation module 1801 may generate the feedback and transmit it to other components of apparatus 110 (Step 2320). In some embodiments, feedback generation module 1801 may access a pre-configured feedback file matching the determined content. A feedback file may comprise a set of software instructions stored in one or more of memory 520, database(s) 1803, or remote database(s) 1902 that contains software instructions encoding audible feedback that may be read and outputted by feedback generation module 1801 and feedback-outputting unit 430. In other embodiments, feedback generation module 1801 may generate a new feedback file. In these embodiments, the new feedback file may be stored for further use in one or more of memory 520, database(s) 1803, or remote database(s) 1902 via network 1901. Once the feedback file (whether audible, tactile, visual, or a combination thereof) is generated, feedback generation module 1801 may transfer or transmit the file to other components of apparatus 110 for output to user 100, such as feedback-outputting unit 340 and/or wireless transceiver 530. These components may then provide the failed-attempt feedback to user 100 (Step 2330).

In some embodiments, processor 540 may be configured to add new entries to one or more of database(s) 1803 or remote database(s) 1902. In these embodiments, after providing the nonvisual failed-attempt feedback to user 100, processor 540 may determine if user 100 desires to add a representation of the object to one or more accessible databases described above (Step 2340). If user 100 does not wish to add the object to the database, or if for some other reason apparatus 110 is not configured to do so (Step 2340: NO), then the process terminates. If user 100 does wish to add a representation of the "failed" object to the database (Step 2340: YES), then database comparison module 1802 may perform a database entry addition process (Step 2350), which will now be described in detail.

Figure 24:
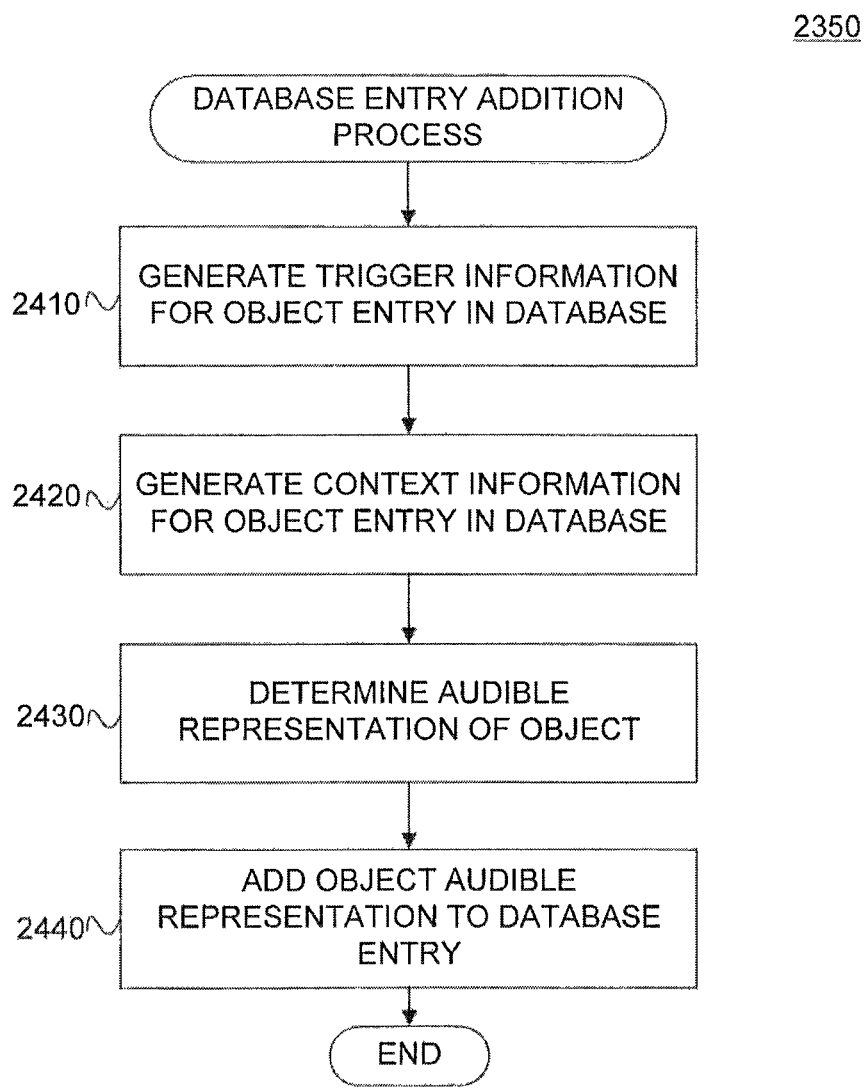
FIG. 24 is an example of a database entry addition process, consistent with disclosed embodiments.

FIG. 24 illustrates an example database entry addition process such as that described above in association with Step 2350 of process 2030 consistent with certain disclosed embodiments. Process 2350, as well as any or all of the individual steps therein, may be performed by various aspects of device 110, such as sensory unit 120, processing unit 140, support 210, or any subcomponents therein. For exemplary purposes, FIG. 24 is described as being performed by processor 540, executing software instructions stored within memory 520.

Processor 540, via database comparison module 1802, may generate trigger information to be associated with the new object in one or more of database(s) 1803 and remote database(s) 1902 (Step 2410). Database comparison module 1802 may use information derived previously from the real-time image data as discussed above, or may analyze a stored representation of the object anew. The trigger information may comprise a gesture, action, or other input that may invoke actions associated with the newly-identified object in the future. For example, if the new object is a bus (or other such motor vehicle), the trigger may comprise pointing at the object. Any trigger contemplated by one skilled in the art may be used that would be detectable by the components of apparatus 110.

Database comparison module 1802 may further generate context information to be associated with the database entry for the new object (Step 2420). Context information may comprise any information related to the object or the setting that facilitates unique identification. In some embodiments, the context information may comprise a geographical location based on GPS coordinates. For example, if the "new" object is a bus, as in the example above, context information relating to the bus may comprise the street on which the bus was seen, or the location of a bus stop where the bus had paused to gather passengers. In other embodiments, context information may comprise information relating to the date and time when the object was seen. Continuing the bus example, additional context information may include that the bus was at a particular bus stop on a particular day at a particular time of day. In other embodiments, context information may include additional information about the object itself. In the bus example, this might include the color of the bus. In these embodiments, context might further include text that was recognized via OCR as described above. The text may include the name of the organization associated with the bus, or identifying route information. Therefore, an example of a full picture of the context information for a given object, such as a bus, might include "Orange bus, Route 6, at the bus stop at Freedom Drive and Explorer Street at 4:00 PM on Thursdays. Route is the Northern Line going to the Airport." Any such contextual information may be determined by processor 540 and associated with the object in database(s) 1803 or remote database(s) 1902.

In some embodiments, processor 540, via feedback generation module 601 and/or database comparison module 1802, may determine an audible representation of the object to further complete the object's database entry (Step 2430). Carrying forward the example above, an example audible representation for the given situation might be "THIS IS A NORTHERN LINE ROUTE 6 BUS GOING TO THE AIRPORT." Feedback generation module 1801 may generate the content of the audible representation, in conjunction with feedback-outputting unit 340, and may add the audible representation of the object to its database entry (Step 2440). A particular object may have more than one audible representation associated with it. For example, if multiple triggers or multiple contexts are associated with the object, each of the triggers and/or contexts may be associated with its own audible representation. Feedback generation module 1801 may individually generate each of the necessary representations and associate them with the entry in the database.

As is evident from the foregoing, apparatus 110 may provide a wide range of functionality. More specifically, in embodiments consistent with the present disclosure, apparatus 110 may capture image data that includes textual and non-textual information disposed within a field-of-view of sensory unit 120, identify one or more system commands associated with the textual information and non-textual information, and subsequently execute the one or more system commands automatically or in response to an input received from a user of apparatus 110.

In certain aspects, "textual information" consistent with the disclosed embodiments may include, but is not limited to, printed text, handwritten text, coded text, text projected onto a corresponding surface, text displayed to the user through a corresponding display screen or touchscreen, and any additional or alternate textual information appropriate to the user and to apparatus 110. Further, the "non-textual information" may include, but is not limited to, images of various triggers (e.g., a human appendage, a cane, or a pointer), images of physical objects, images of persons, images of surroundings, and images of other non-textual objects disposed within the field-of-view of sensory unit 120.

In certain aspects, apparatus 110 may perform an OCR process on the textual information within the captured image data, and may subsequently identify the one or more system commands based on portions of the recognized text. In other aspects, apparatus 110 may detect elements of non-textual information within the captured image data, and may initiate the identification of the one or more system commands in response to the detected non-textual information.

Figure 25:
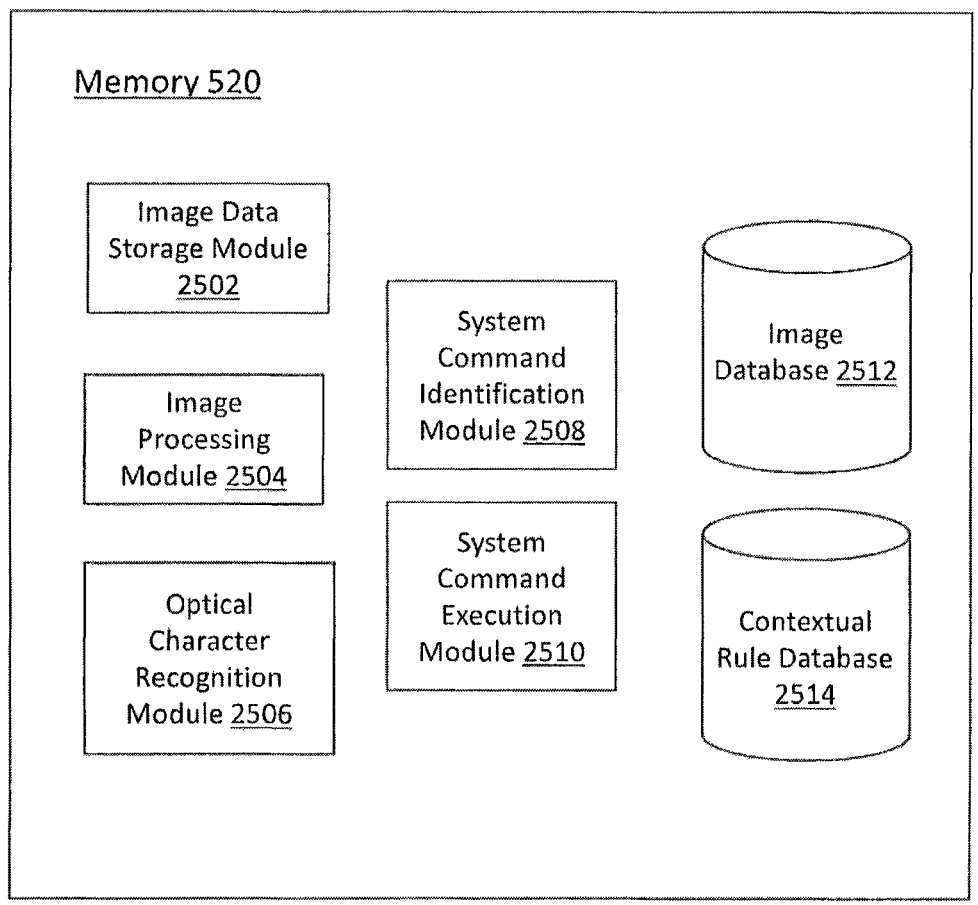
FIG. 25 illustrates an exemplary set of application modules and databases, according to disclosed embodiments.

In an embodiment, apparatus 110 may include a memory (e.g., memory 520) configured to store one or more applications and application modules that, when executed by a processor (e.g., processor 540), enable apparatus 110 identify and execute system commands based in textual and non-textual information within captured image data. In certain aspects, memory 520 may also be configured to store information that identifies the system commands and associates the system commands with elements of textual information (e.g., characters, words, phrases, and phrases), elements of non-textual information (e.g., images of triggers, physical objects, and persons), other system commands, and other events. FIG. 25 illustrates an exemplary structure of memory 520, in accordance with disclosed embodiments.

In FIG. 25, memory 520 may be configured to store an image data storage module 2502, an image processing module 2504, and an image database 2512. In one embodiment, image data storage module 2502, upon execution by processor 540, may enable processor 540 to receive data corresponding to one or more images captured by sensory unit 120, and to store the captured image data within image database 2512. In some aspects, the captured image data may include textual information (e.g., printed, handwritten, coded, projected, and/or displayed text) and non-textual information (e.g., images of physical objects, persons, and/or triggers), and processor 540 may store the image data in image database 2512 with additional data specifying a time and/or date at which sensory unit 120 captured the image data. In additional embodiments, image data storage module 2502 may further enable processor 540 to configure wireless transceiver 530 to transmit the captured image data to one or more devices (e.g., an external data repository or a user's mobile device) in communication with apparatus 110 across a corresponding wired or wireless network.

In an embodiment, image processing module 2504, upon execution by processor 540, may enable processor 540 to process the captured image data and identify elements of textual information within the captured image data. In certain aspects, textual information consistent with the disclosed embodiments may include, but is not limited to, printed text (e.g., text disposed on a page of a newspaper, magazine, book), handwritten text, coded text, text displayed to a user through a display unit of a corresponding device (e.g., an electronic book, a television a web page, or an screen of a mobile application), text disposed on a flat or curved surface of an object within a field-of-view of apparatus 110 (e.g., a billboard sign, a street sign, text displayed on product packaging), text projected onto a corresponding screen (e.g., during presentation of a movie at a theater), and any additional or alternate text disposed within images captured by sensory unit 120.

In certain aspects, processor 540 may perform a layout analysis of the image data to identify textual information within the captured image data. By way of example, processor 540 may perform a layout analysis to detect paragraphs of text, blocks of text, zones and/or regions that include text, logos, titles, captions, footnotes, and any additional or alternate portions of the image data that includes printed, handwritten, displayed, coded, and/or projected text.

Referring back to FIG. 25, memory 520 may also include an optical character recognition (OCR) module 2506 that, upon execution by processor 540, enables processor 540 to perform one or more OCR processes on elements of textual information disposed within the image data. In one embodiment, processor 540 may execute image processing module 2504 to identify portions of the captured image data that include textual information, and further, may execute OCR module 2506 to retrieve machine-readable text from the textual information.

Memory 520 may also be configured to store a system command identification module 2508, a system command execution module 2510, and a system command database 2514. In one embodiment, system command database 2514 may store linking information that associates one or more system commands with corresponding portions of captured image data. In some aspects, a system command may include one or more instructions that, when executed by processor 540, cause processor 540 to perform one or more actions or processes consistent with an operating system of apparatus 110. Further, in one aspect, linking information may associate a particular system command with an element of recognized text (e.g., a word, a phrase, or a paragraph), an element of non-textual information (e.g., an image of a physical object, a person, or a trigger), combinations thereof, and any additional or alternate indicia of linkages between captured image data and system commands.

In an embodiment, system command identification module 2508 may, upon execution by processor 540, enable processor 540 to access linking information stored within system command database 2514, and to identify one or more system commands associated with portions of the captured image data based on the linking information. For example, processor 540 may leverage the accessed linking information to determine that a portion of machine-readable text corresponds to a system command executable by processor 540. Additionally or alternatively, system command identification module 2508 may enable processor 540 to identify a system command associated with a particular image within the captured image data, and further, a system command associated with a particular trigger in the captured image data, taken alone or in conjunction with machine-readable text.

System command execution module 610 may, upon execution by processor 540, enable processor 540 to execute the identified system command and perform one or more actions and processes consistent with the operating system of apparatus 110. In one instance, the identified system command may enable processor 540 to modify an operational state of apparatus 110. For example, upon execution of the identified system command by processor 540, apparatus 110 may function in accordance with a "training" mode, a "sleep" mode, or an "airplane" mode, or other mode of operation consistent with the captured image data and the operating system of apparatus 110.

In other aspects, the identified system command may enable processor 540 to modify a configuration of apparatus 110. By way of example, upon execution of the identified system command, processor 540 may modify a configuration of one or more of sensory unit 120 and processing unit 130. Further, in additional embodiments, processor 540 may execute the identified system command to modify a configuration of an external device in communication with apparatus 110 across a corresponding wired or wireless communications network (e.g., a mobile telephone, a smart phone, or a tablet computer).

Additionally or alternatively, the identified system command may enable processor 540 to execute one or more applications and/or perform one or more actions supported by an operating system of apparatus 110. By way of example, processor 540 may initiate or terminate a recording of audio or video content, download a stored digital image (e.g., to image database 2512), transmit a stored digital image to an external device in communication with apparatus 110, update or restart the operating system of apparatus 110, and establish, modify, or erase a user customization of apparatus 110.

Further, in an embodiment, the identified system command may include a plurality of steps associated with corresponding system sub-commands, and processor 540 may be configured to execute sequentially the corresponding system sub-commands upon execution of system command execution module 2510. For example, the identified system command may update the operating system of apparatus 110, and the corresponding sub-commands may enable processor 540 to obtain an updated version of the operating system, replace the existing version of the operating system with the updated version, and restart apparatus 110 upon completion of the replacement.

In further embodiments, the identified system command may cause processor 540 perform an action on one or more files stored locally by apparatus 110, and additionally or alternatively, on one or more files stored within a data repository or external device accessible to apparatus 110 over a corresponding communications network. By way of example, upon execution of the identified system command, processor 540 may store image, video, and/or audio files in memory 520, overwrite one or more files stored within memory 520, and additionally or alternatively, transmit one or more files stored within memory 520 to the external device.

In other embodiments, image database 2512 and/or contextual rule database 2514 may be located remotely from memory 520, and be accessible to other components of apparatus 110 (e.g., processing unit 140) via one or more wireless connections (e.g., a wireless network). While two databases are shown, it should be understood that image database 2512 and contextual rule database 2514 may be combined and/or interconnected databases may make up the databases. Image database 2512 and/or contextual rule database 2514 may further include computing components (e.g., database management system, database server, etc.) configured to receive and process requests for data stored in associated memory devices.

Image data store module 2502, image processing module 2504, OCR module 2506, system command identification module 2508, and system command execution module 2510 may be implemented in software, hardware, firmware, a mix of any of those, or the like. For example, if the modules are implemented in software, they may be stored in memory 520, as shown in FIG. 25. Other components of processing unit 140 and/or sensory unit 120 may be configured to perform processes to implement and facilitate operations of image data store module 2502, image processing module 2504, OCR module 2506, system command identification module 2508, and system command execution module 2510. Thus, image data store module 2502, image processing module 2504, OCR module 2506, system command identification module 2508, and system command execution module 2510 may include software, hardware, or firmware instructions (or a combination thereof) executable by one or more processors (e.g., processor 540), alone or in various combinations with each other. For example, image data store module 2502, image processing module 2504, OCR module 2506, system command identification module 2508, and system command execution module 2510 may be configured to interact with each other and/or other modules of apparatus 110 to perform functions consistent with disclosed embodiments. In some embodiments, any of the disclosed modules (e.g., image data store module 2502, image processing module 2504, OCR module 2506, system command identification module 2508, and system command execution module 2510) may each include dedicated sensors (e.g., IR, image sensors, etc.) and/or dedicated application processing devices to perform the functionality associated with each module.

Figure 26:
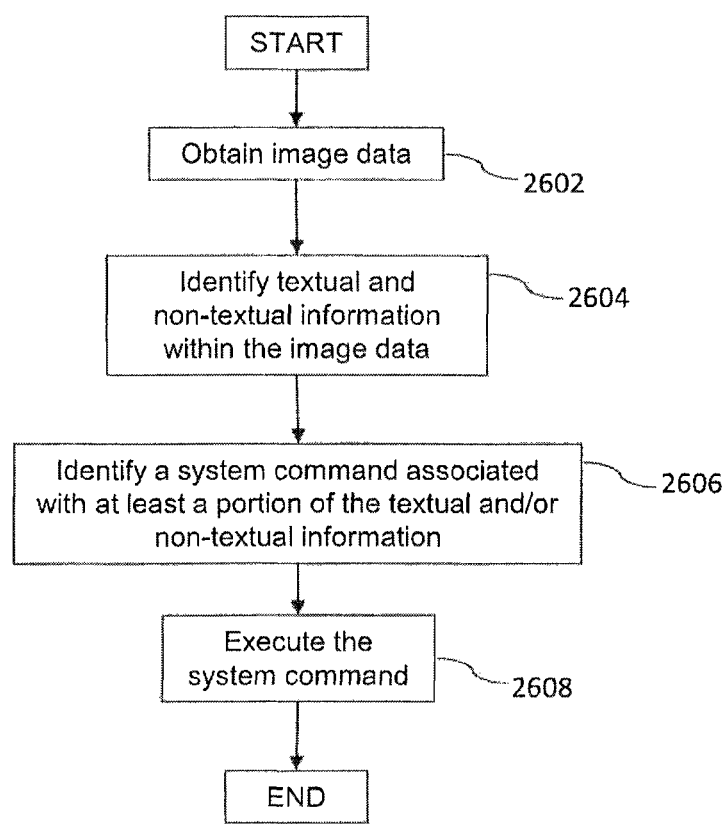
FIG. 26 is a flow diagram of an exemplary process for identifying and executing system commands based on captured image data, according to disclosed embodiments.

FIG. 26 is a flow diagram of an exemplary process 2600 for identifying and executing system commands based on captured image data, according to disclosed embodiments. As described above, sensory unit 120 may capture image data that includes textual information and non-textual information disposed within a corresponding field-of-view. Processing unit 130 may receive the captured image data, and processor 540 may execute one or more application modules to identify the textual and non-textual information, and to execute one or more system commands that correspond to the identified textual and non-textual information. Process 2600 provides further details on how processor 540 identifies and executes one or more system commands based on captured image data.

In step 2602, processor 540 may obtain captured image data. In some aspects, sensory unit 120 may capture one or more images, and the captured image data may be transmitted to processing unit 140 across wired or wireless communications link 130. Processor 540 may, in step 2602, obtain the captured image data directly from sensory module 120 across communications link 130, or alternatively, processor 540 may retrieve the captured image data from a corresponding data repository (e.g., image database 2512 of memory 520). By way of example, the captured image data may include one or more regions of printed, displayed, or projected information.

In step 2604, processor 540 may analyze the captured image data to identify portions of the captured image data that include textual information. As described above, the textual information may include, but is not limited to, printed, handwritten, projected, coded, or displayed text, and processor 540 may perform a layout analysis to detect the textual information within the captured image data. By way of example, the detected portions may include, but are not limited to, paragraphs of text, blocks of text, zones and/or regions that include text, logos, titles, captions, footnotes, and any additional or alternate portions of the captured image data that includes printed, handwritten, displayed, coded, and/or projected text.

Additionally or alternatively, processor 540 may analyze the captured image data using image processing techniques in step 2604 to identify non-textual information within the captured image data. In certain aspects, the non-textual information may include, but is not limited to, an image of a trigger (e.g., a human appendage or a cane), an image of a person (e.g., a police officer, a firefighter, or an airline employee), an image of a physical object (e.g., a streetlight and/or a pedestrian crossing signal, a particular vehicle, a map), and any additional or alternate image of relevant to the user of apparatus 110.

In step 2606, processor 540 may identify one or more system commands associated with the textual and non-textual information. In one embodiment, to identify the one or more system commands, processor 540 obtain linking information in step 2606 that associates the system commands with corresponding portions of textual information, non-textual information, or combinations of textual and non-textual information. In certain aspects, processor 540 may access system command database 2514 to obtain the linking information. Alternatively, processor 540 may obtain the linking information from a data repository in communication with apparatus 110 across a corresponding communications network using appropriate communications protocols.

For example, processor 540 may determine in step 2606 that a system command is associated with textual information when the linking information for that system command includes at least a portion of the textual information. Additionally or alternatively, processor 540 may also determine in step 2606 that the system command is associated with non-textual information when the linking information for that system command includes information identifying the non-textual information, either alone or in combination with textual information.

Processor 540 may execute the one or more identified system commands in step 2608. Upon execution of the one or more identified system commands by processor 540, exemplary process 2600 ends.

As described above, one or more of the executed system commands may correspond to an operation that modifies a functional state of apparatus 110 or an external device in communications with apparatus 110 (e.g., that causes apparatus 110 to enter a sleep mode, a training mode, or an airplane mode). The executed system commands may also correspond to processes performed by and supported by an operating system of apparatus 110, which include, but are not limited to, processes that initiate or terminate a recording of audio or video content, download a stored digital image (e.g., to image database 2512), perform an action on one or more files associated with a user of apparatus 110, transmit a stored digital image to an external device in communication with apparatus 110, update or restart the operating system of apparatus 110, backup stored content, obtain information indicative of a status of a battery of apparatus 110, obtain audible instructions regarding one or more functions of apparatus 110, and establish, modify, or erase a user customization of apparatus 110 (e.g., a volume associated with apparatus 110 or a gender of an audible narration provided by apparatus 110). Further, and consistent with the disclosed embodiments, at least one of the system commands may be associated with a plurality of steps, which correspond to system sub-commands executed sequentially by processor 540. The disclosed embodiments are, however, not limited to such exemplary system commands, and in additional embodiments, processor 540 may identify (e.g., step 2606) and execute (e.g., step 2608) any additional or alternate system command appropriate to processor 540, apparatus 110, and the captured image data.

Figure 27:
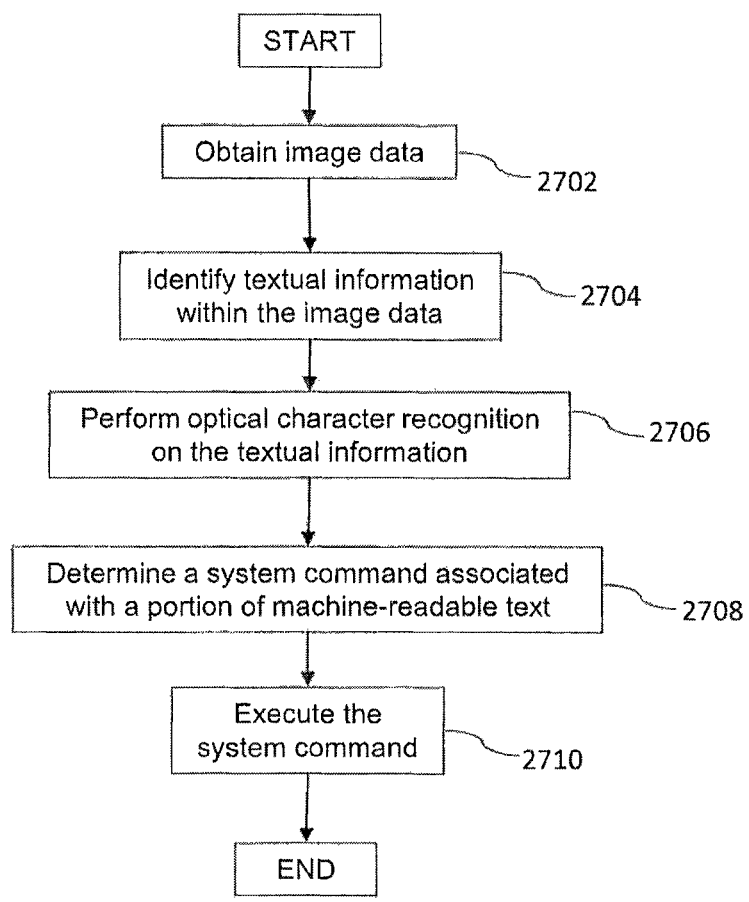
FIG. 27 is a flow diagram of an exemplary process for identifying and executing system commands based on textual information within captured image data, according to disclosed embodiments.

FIG. 27 is a flow diagram of an exemplary process 2700 for identifying and executing system commands based on text within captured image data, according to disclosed embodiments. As described above, sensory unit 120 of apparatus 110 may capture image data that includes textual information. In some embodiments, processor 540 of apparatus 510 may execute one or more application modules to identify the textual information within the captured image data, retrieve machine-readable text from the identified textual information, and execute one or more system commands associated with the machine-readable text. Process 2700 provides further details on how processor 540 identifies and executes one or more system commands based on text disposed within portions of captured image data.

In step 2702, processor 540 may obtain captured image data. In some aspects, sensory unit 120 may capture one or more images, and the captured image data may be transmitted to processing unit 140 across wired or wireless communications link 130. As described above, processor 540 may obtain the captured image data in step 2702 from sensory module 120 across communications link 130, or alternatively, processor 540 may retrieve the captured image data from a corresponding data repository (e.g., image database 2512 of memory 520). The captured image data may, in certain aspects, include at least one of textual information (e.g., printed text, handwritten text, displayed text, projected text, and coded text) and non-textual information (e.g., images of physical objects, persons, and triggers).

Processor 540 may analyze the captured image data in step 2704 to identify portions of the captured image data that include the textual information. In one embodiment, as described herein, processor 540 may perform a layout analysis to detect the textual information within the captured image data. By way of example, the detected textual information may include, but are not limited to, paragraphs of text, blocks of text, zones and/or regions that include text, logos, titles, captions, footnotes, and any additional or alternate portions of the image data that includes printed, handwritten, displayed, coded, and/or projected text.

In step 2706, processor 540 may perform an OCR process on the detected textual information to identify and retrieve machine-readable text. Further, in step 2708, processor 540 may identify one or more system commands associated with the recognized text based on linking information that associates the system commands with corresponding machine-readable text. In certain aspects, system command database 2514 may store the linking information, and in step 2708, processor 540 may access system command database 2514 to obtain the linking information, as described above.

Processor 540 may execute the one or more identified system commands in step 2710. Upon execution of the one or more identified system commands by processor 540, exemplary process 2700 ends.

As described above, one or more of the system commands may correspond to an operation that modifies a functional state of apparatus 110 or an external device in communications with apparatus 110 (e.g., that causes apparatus 110 to enter a sleep mode, a training mode, or an airplane mode). One or more of the system commands may also correspond to processes performed by and supported by an operating system of apparatus 110, which include, but are not limited to, processes that initiate or terminate a recording of audio or video content, download a stored digital image (e.g., to image database 2512), perform actions on one or more files associated with a user of apparatus 110, transmit a stored digital image to an external device in communication with apparatus 110, update or restart the operating system of apparatus 110, backup stored content, obtain information indicative of a status of a battery of apparatus 110, obtain audible instructions regarding one or more functions of apparatus 110, and establish, modify, or erase a user customization of apparatus 110 (e.g., a volume associated with apparatus 110 or a gender of an audible narration provided by apparatus 110). Further, and consistent with the disclosed embodiments, at least one of the system commands may be associated with a plurality of sequential steps, which correspond to system sub-commands executed sequentially by processor 540.

In the embodiments described above, processor 540 may identify system commands associated with one or more of textual information and non-textual information disposed within captured image data (e.g., step 2606 of FIG. 26 and step 2708 of FIG. 27), and may execute the identified system commands (e.g., in step 2608 of FIG. 26 and step 2710 of FIG. 27) without tactile or audible confirmation from a user.

In some instances, however, the executed system commands may be associated with significant and often irreversible impacts on an operation of apparatus 110. For example, the executed system commands may erase a user-established customization of apparatus 110, or alternatively, delete or modify one or more image filed stored by apparatus 110. In some embodiments, described below in reference to FIG. 28, processor 540 may execute the identified system commands in response to user input that confirms the user's intentions to execute the identified system commands.

Figure 28:
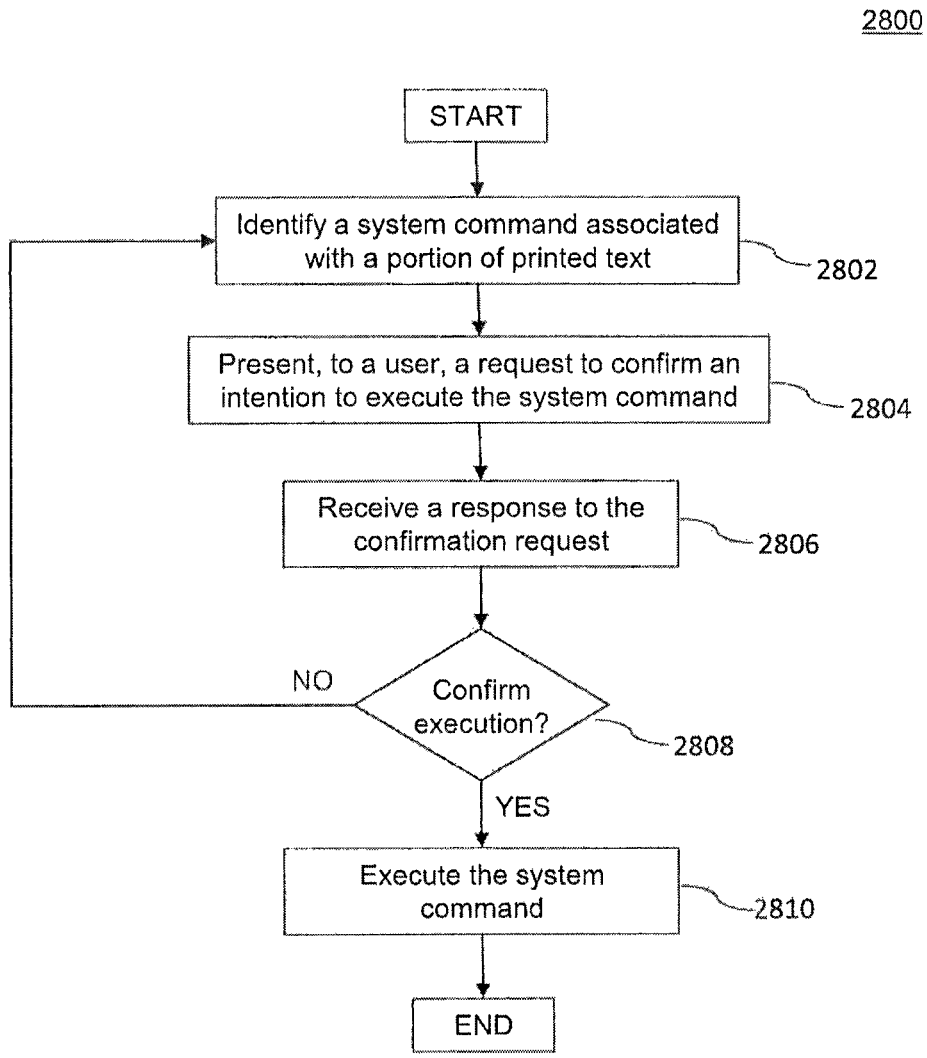
FIG. 28 is a flow diagram of an exemplary process for executing an identified system command, according to disclosed embodiments.

FIG. 28 is a flow diagram of an exemplary process 2800 for executing system commands based on received user confirmation, according to disclosed embodiments. As described above, processor 540 may identify one or more system commands associated with at least one of textual or non-textual information disposed within captured image data. In some embodiments, processor 540 may execute the identified system commands in response to confirmation of the user's intention to execute the identified system commands. Process 2800 provides further details on how processor 540 requests a confirmation of the user's intention to execute a system command, receives and processes input from the user, and executes the system command based on the received input.

In step 2802, processor 540 may identify a system command associated with textual information, non-textual information, or combinations of textual and non-textual information within captured image data. For example, as described above in reference to FIGS. 26 and 27, the identified system command may be associated with one or more portions of machine-readable text retrieved from the textual information using a corresponding OCR process, and additionally or alternatively, may be associated with elements of non-textual information disclosed within the captured image data.

Further, as described above, the identified system command may correspond to an operation that modifies a functional state of apparatus 110 or an external device in communications with apparatus 110 (e.g., that causes apparatus 110 to enter a sleep mode, a training mode, or an airplane mode). In other aspects, the identified system command may cause processor 540 to initiate or terminate a recording of audio or video content, download a stored digital image (e.g., to image database 2512), modify one or more files associated with the user, transmit a stored digital image to an external device in communication with apparatus 110, perform an operation on a stored file, update or restart the operating system of apparatus 110, backup stored content, obtain information indicative of status of a battery of apparatus 110, obtain audible instructions regarding one or more functions of apparatus 110, and establish, modify, or erase a user customization of apparatus 110 (e.g., a volume associated with apparatus 110 or a gender of an audible narration provided by apparatus 110). Further, and consistent with the disclosed embodiments, at least one of the system commands may be associated with a plurality of steps, which correspond to system sub-commands executed sequentially by processor 540.

Referring back to FIG. 28, processor 540 may request the user confirm an intention to execute of the identified system command in step 2804. In one embodiment, processor 540 may generate an audible request, which may be presented to the user through a speaker or a bone conduction headphone associated with processing unit 140. The disclosed embodiments are, however, not limited to such audible requests, and in further embodiments, processor 540 may generate and provide a textual request to the user (e.g., by transmitting the textual request as a message to a mobile communications device of the user in communication with apparatus 110), a tactile request to the user (e.g., a vibration of apparatus 110 of a predetermined intensity and duration), or through any additional or alternate mechanism appropriate to the user and to apparatus 110.

In step 2806, processor 540 may detect user input indicative of a response to the request for confirmation. In one embodiment, the detected user input may include an audible response to the requested spoken by the user into a microphone associated with apparatus 110. Additionally or alternatively, the user input may include a tactile response to the request for confirmation (e.g., the user may tap a sensor or other input device disposed on a surface of apparatus 110). The disclosed embodiments are, however, not limited to such exemplary user input, and in other embodiments, the user input may include any additional or alternate form or combination of inputs appropriate to the user and to apparatus 110.

Based on the detected user input, processor 540 may determine in step 908 whether the user confirmed the intention to execute of the identified system command. If processor 540 determine that the user confirms the execution (e.g., step 908; YES), processor 540 may execute the identified system command in step 2810, as described above. Exemplary process 2800 is then complete. Alternatively, if processor 540 determines that the user elects not to confirm the execution (e.g., step 2808; NO), exemplary process 2800 passes back to step 2802, and processor 540 identified an additional system command for execution, as described above.

Figure 29:
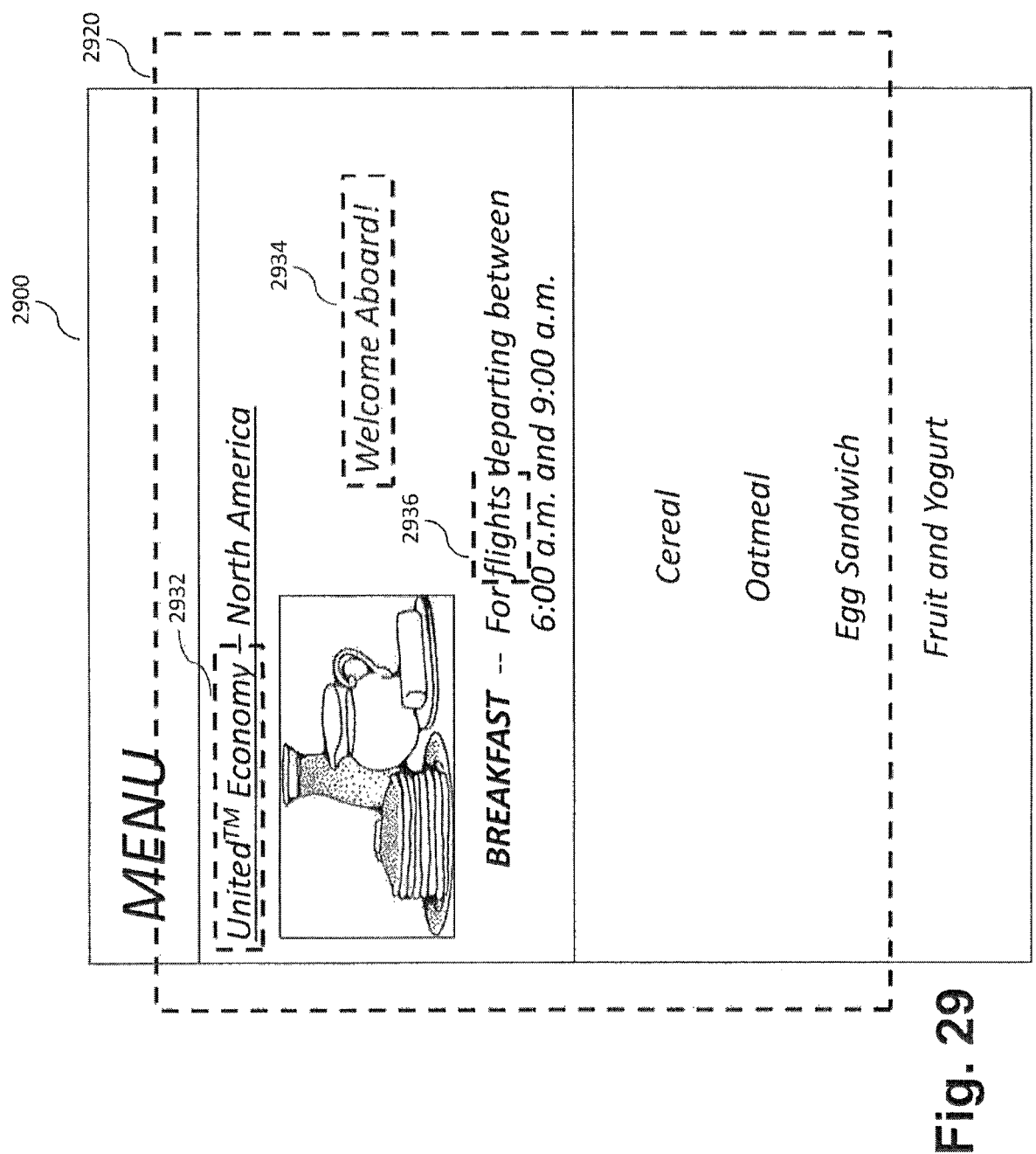
FIG. 29 illustrates exemplary image data captured by an apparatus for aiding persons who have low vision, according to disclosed embodiments.

Using the embodiments described above, apparatus 110 may capture image data that includes one or more of textual and non-textual information, identify a system command that corresponds to the textual and/or visual information, and subsequently execute the identified system command to modify an operational state of apparatus 110. By way of example, a user of apparatus 110 may board an airplane and, upon locating a corresponding seat, browse through materials placed within a pocket or storage accessible to the user (e.g., a seat-back pocket). As illustrated in FIG. 29, the user may access an in-flight menu 2900 for the trip, and apparatus 110 may capture an image that includes a portion 2920 of menu 2900 corresponding to a field-of-view of sensory unit 120.

As described above, processor 540 may identify textual information within the captured image, may perform an OCR process that retrieves machine-readable text from the textual information, and may access system command database 2514 to obtain linking information associating one or more system commands with corresponding portions of the recognized text. For example, as illustrated in FIG. 29, processor 540 may leverage the linking information to determine that text portion 2932 (e.g., "United™ Economy"), text portion 1034 (e.g., "Welcome Aboard!"), and text portion 2936 (e.g., "flights") each correspond to a system command that causes apparatus 110 to enter an airplane mode. In certain embodiments, processor 540 may execute the corresponding system command, which disposes apparatus 110 into an airplane mode for the duration of the flight.

Figure 30:
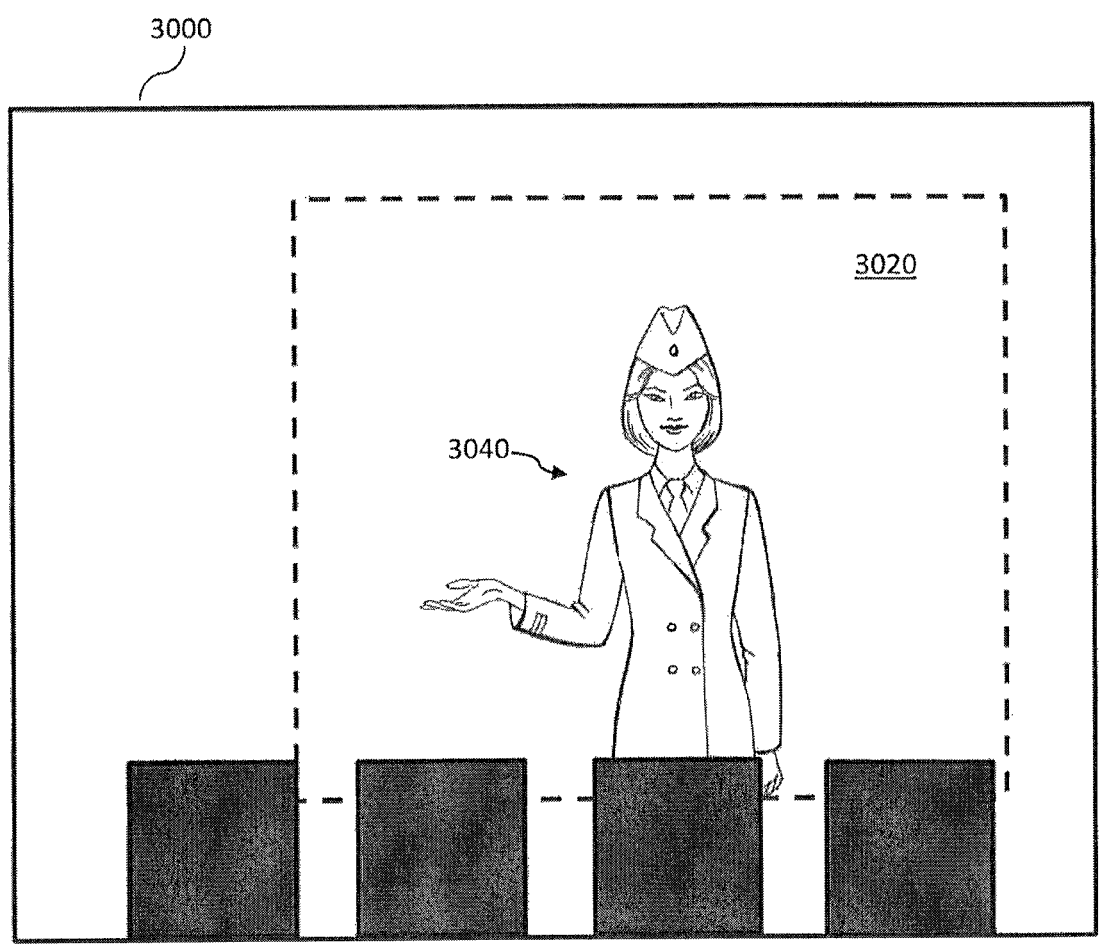
FIG. 30 illustrates exemplary image data captured by an apparatus for aiding persons who have low vision, according to disclosed embodiments.

The disclosed embodiments are, however, not limited to processes that identify system commands associated with machine-readable text, and in additional embodiments processor 540 may identify one or more system commands associated with non-textual information disposed within the captured image data. For example, as illustrated in FIG. 30, a user of apparatus 110 may view an in-flight safety video 3000 after boarding an airplane, and apparatus 110 may capture an image that includes a portion 3020 of in-flight safety video 3000. Processor 540 may analyze portion 3020 to identify an image 3040 of a flight attendant demonstrating a proper technique for securing the user's seat belt, and may leverage linking information to determine that image 3040 corresponds to a system command that causes apparatus 110 to enter the airplane mode. As described above, processor 540 may execute the corresponding system command, which places apparatus 110 into an airplane mode during the flight.

Figure 31:
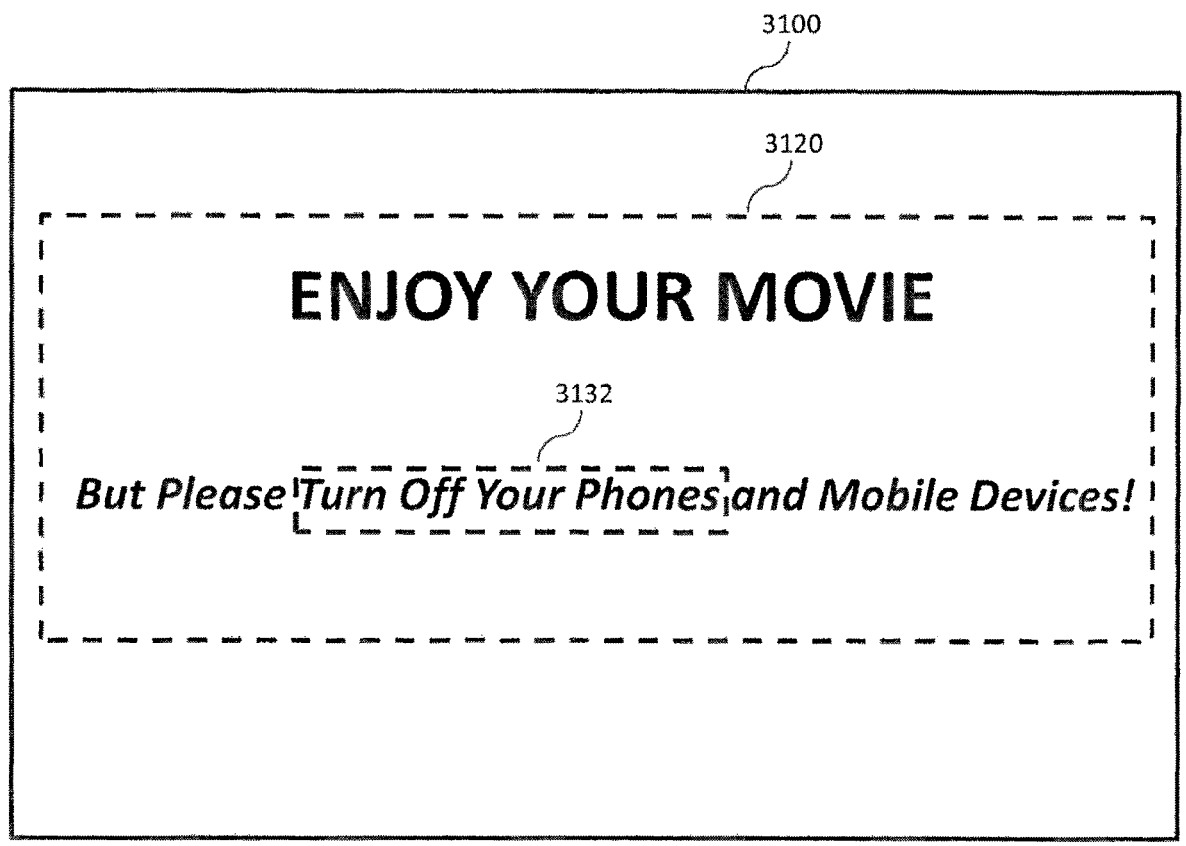
FIG. 31 illustrates exemplary image data captured by an apparatus for aiding persons who have low vision, according to disclosed embodiments.

In additional embodiments, described above, apparatus 110 may capture image data that includes textual and non-textual information projected onto a corresponding surface visible to a user of apparatus 110, and may identify and execute one or more system commands associated with the projected textual and/or non-textual information. By way of example, a user of apparatus 110 may visit a movie theater to view a recently released feature film. As illustrated in FIG. 31, the theater may project a reminder onto a screen 3100 asking viewers to turn off or silence their mobile communications devices, and apparatus 110 may capture an image that includes a portion 3120 of the reminder corresponding to a field-of-view of sensory unit 120.

Processor 540 may identify textual information within the captured image, may perform an OCR process that retrieves machine-readable text from the textual information, and may obtain linking information associating one or more system commands with corresponding portions of the recognized text. For example, as illustrated in FIG. 31, processor 540 may leverage the linking information to determine that text portion 3132 (e.g., "Turn Off Your Phones") corresponds to a system command that causes apparatus 110 to enter a "sleep" or "silent" mode. In certain embodiments, processor 540 may execute the corresponding system command, which places apparatus 110 into the corresponding sleep or silent mode for the duration of the feature.

Figure 32:
FIG. 32 illustrates exemplary image data captured by an apparatus for aiding persons who have low vision, according to disclosed embodiments.

Apparatus 110 may also capture image data including textual and non-textual information displayed to user of apparatus 110 through a display unit or touchscreen of a user device (e.g., a television, a smart phone, tablet computer, laptop, or desktop computer). For example, as illustrated in FIG. 32, the user may view a web page 3200 (or other electronic document, such as an email message or text message) that prompts the user to visit a corresponding "app store" and upgrade an operating system without cost, and apparatus 110 may capture an image that includes a portion 3220 of displayed web page 3200 corresponding to a field-of-view of sensory unit 120.

In certain aspects, processor 540 may identify textual information within the captured image, may perform an OCR process that retrieves machine-readable text from the textual information, and may obtain linking information associating one or more system commands with corresponding portions of the recognized text. For example, as shown in FIG. 32, processor 540 may leverage the linking information to determine that text portion 3232 (e.g., "Upgrade to the New OS") corresponds to a system command that causes apparatus 110 to retrieve and install an update to an operating system of apparatus 110. Processor 540 may then execute the corresponding system command, which causes apparatus 110 to obtain and install the corresponding update, and further, to restart apparatus 110 to complete an installation process.

Figure 33:
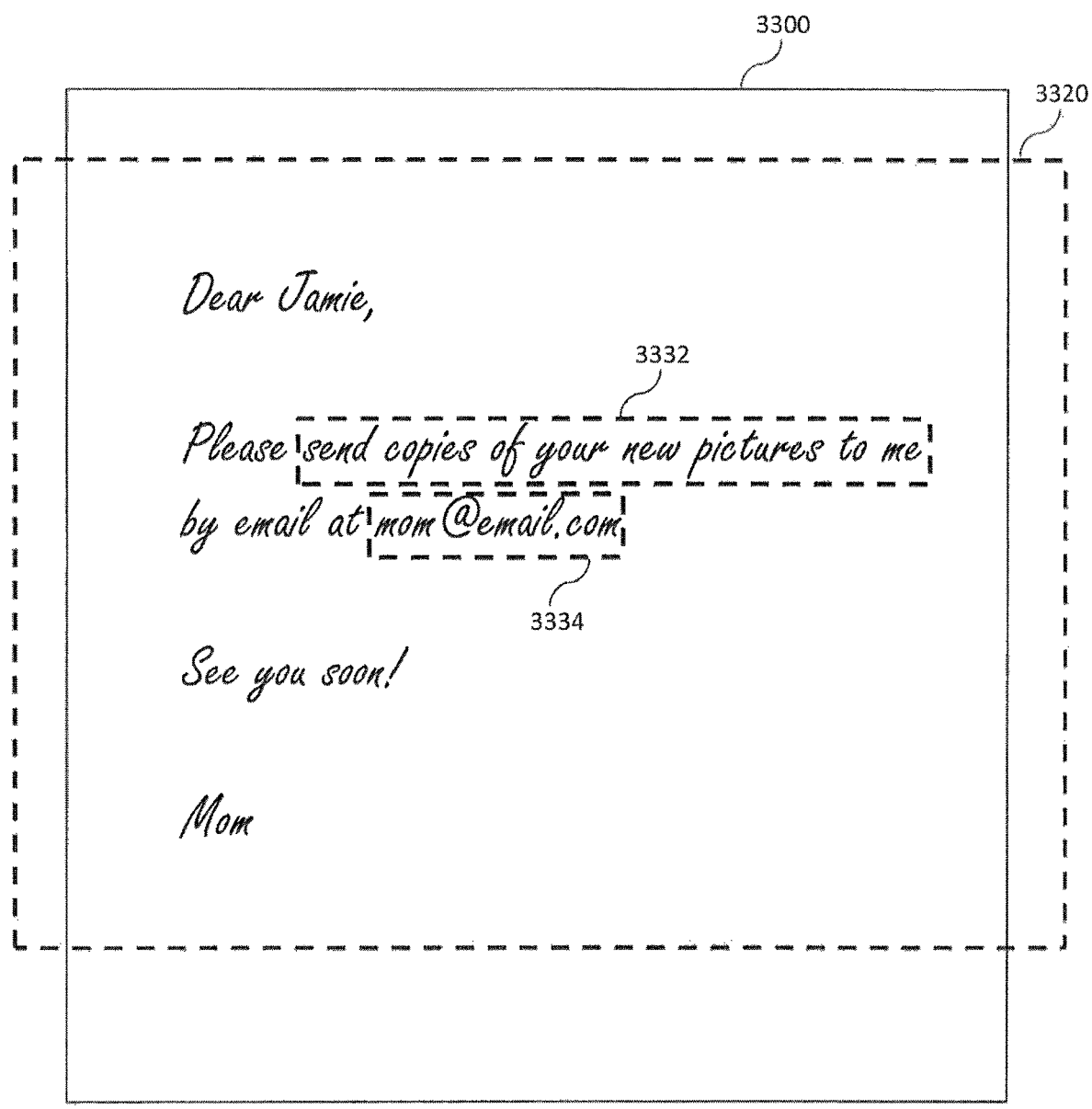
FIG. 33 illustrates exemplary image data captured by an apparatus for aiding persons who have low vision, according to disclosed embodiments.

Further, in additional embodiments, apparatus 110 may capture image data that includes handwritten textual information, and may identify and execute one or more system commands associated with the handwritten textual information. For example, as illustrated in FIG. 33, a user of apparatus 110 may receive a letter 3300 from his or her mother that asks the user to provide copies of digital images by email. In such an instance, apparatus 110 may capture an image that includes a portion 3320 of letter 3300 corresponding to a field-of-view of sensory unit 120.

Processor 540 may analyze the captured image data to identify the handwritten textual information, perform an OCR process that retrieves machine-readable text from the handwritten textual information, and obtain linking information associating one or more system commands with corresponding portions of the handwritten text. Using the linking information, processor 540 may determine that text portion 3332 (e.g., "send copies of your new pictures to me") corresponds to a system command that causes apparatus 110 to identify one or more stored digital images (e.g., within image database 2512), and download the identified digital images to a user device in communications with apparatus 110 over a corresponding wired or wireless communications network.

Processor 540 may execute the corresponding system command, which causes apparatus 110 to download the identified images to the user's communications device. Further, in additional embodiments, the executed system command may also provide instructions to the user's communications device to automatically transmit the downloaded photos to the user's mother at email address 3334.

In additional embodiments, apparatus 100 may identify and execute system commands based on combinations of textual and non-textual information disposed within captured image data. For example, a user of apparatus 110 may approach an exterior exit of a building, but may be unaware of a street onto which the exit leads. In such an instance, the user may point to an exit sign disposed above the exit door, and apparatus 110 may capture an image that include both the exit sign, with its corresponding textual information, and also an existence of the user's finger within the field-of-view of apparatus 110.

Figure 34:
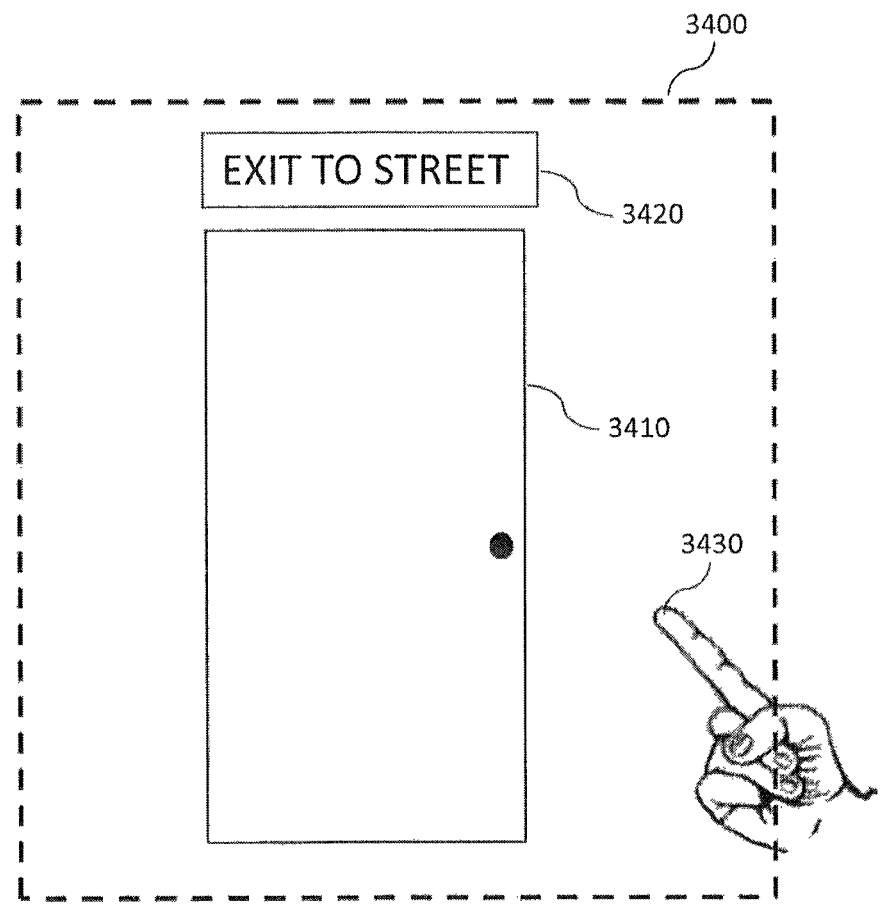
FIG. 34 illustrates exemplary image data captured by an apparatus for aiding persons who have low vision, according to disclosed embodiments.

By way of example, as illustrated in FIG. 34, a captured image 3400 may include an image of an exit door 3410, textual information corresponding to an exit sign 3420 (e.g., "EXIT TO STREET"), and an image of a trigger 3430 (which corresponds to the user's finger). In certain aspects, processor 540 may identify the existence of the textual information and non-textual information associated with trigger 3430, may identify a system command that corresponds to the presence of both the textual information (e.g., "EXIT TO STREET") and trigger 3430 within the captured image data, and execute the system command to provide positional information to the user of apparatus 110.

In an embodiment, upon execution of the identified system command, apparatus 110 may access a positioning system (e.g., a GPS unit) to obtain a current position of apparatus 110, and access a mapping system to identify a street onto which exit door 3410 leads. In certain aspects, the positioning and mapping systems may be executed by apparatus 110, or alternatively, may be executed by an external device in communication with apparatus 110 over a corresponding wired or wireless communications network. Processor 540 may then provide an audible indication of the determined street to the user of apparatus 110 (e.g., through a speaker or a bone conduction headphone associated with processing unit 140).

As is evident from the foregoing, apparatus 110 may provide a wide range of functionality. More specifically, one embodiment consistent with the present disclosure provides an automatic reaction function that allows apparatus 110 to automatically perform and/or suspend a continuous action, depending on various factors, such as objects in the image data, a focus of a user, a field-of-view of image sensor 350, and contextual information. Apparatus 110 may interpret information associated with these factors to determine an intention of the user, such as an intention to cause apparatus 110 to perform a continuous action and/or an intention to cause apparatus 110 to suspend performance of a continuous action. In this way, apparatus 110 may perform functions to automatically react to a user's movements and allow apparatus 110 to adapt to the user in real-time or near real-time.

In order to provide this functionality, apparatus 110 may include components (e.g., processing unit 140) configured to process real time images (e.g., images received from image sensor 350) to monitor a user's environment. In particular, apparatus 110 may be configured to monitor a field-of-view of apparatus 110. In some embodiments, the field-of-view of apparatus 110 may be an area of space that is detectable by image sensor 350. Apparatus 110 may be arranged such that its field-of-view corresponds at least partially with a visually-unimpaired user's typical field of view, such as an area in front of the user's face.

In some embodiments, the field-of-view of apparatus 110 may include the entire detectable area (e.g., the entire space covered by one detected image). In other embodiments, the field-of-view of apparatus 110 may include a portion of the entire detectable area. For example, the field-of-view of apparatus 110 may correspond to a focus of attention region. A focus of attention region may be a particular portion of the detectable area. The focus of attention region may correspond to an area that the user may be focusing, or intend to focus, his or her attention. For example, a focus of attention region may include a central area within the detectable area.

As described herein, the field-of-view of apparatus 110 may include any region of an image received in real-time image data, including any selected portion of the image and the entire image. In some embodiments, apparatus 110 may monitor the field-of-view of apparatus 110 in providing the automatic reaction function. Apparatus 110 may perform actions based on inputs identified in the field-of-view, and subsequently change the action as the field-of-view changes. In this way, apparatus 110 may be configured to automatically react to changes in the image data based on changes in the users' environment and/or movements of the user.

Figure 35:
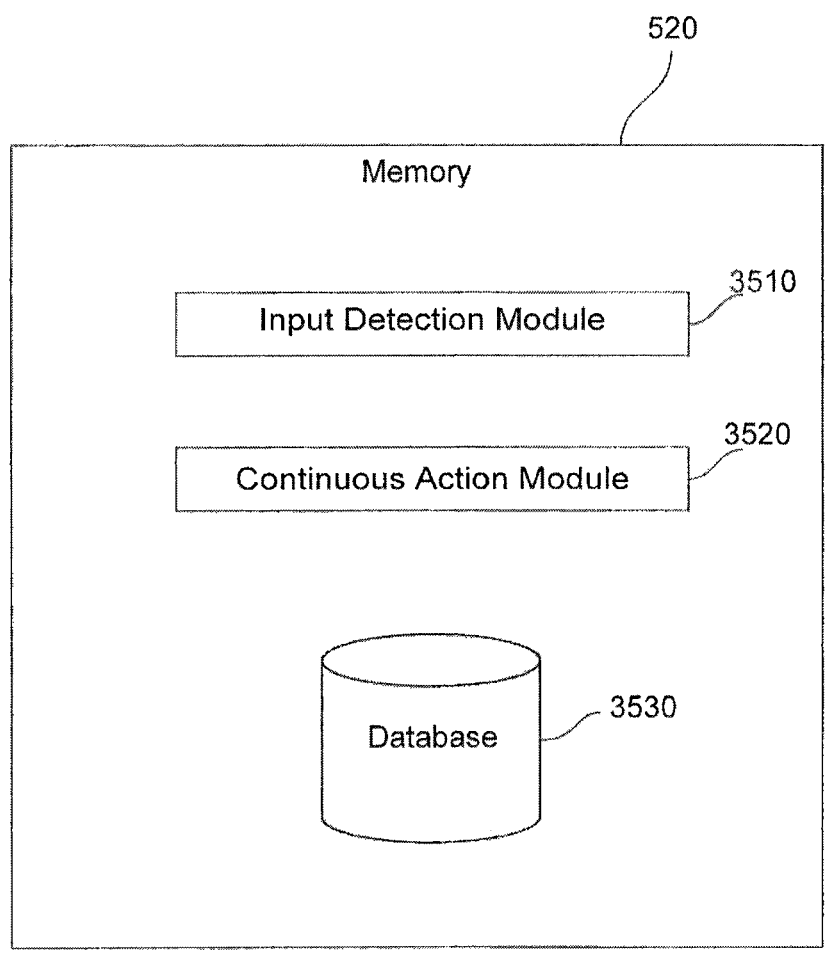
FIG. 35 is a block diagram illustrating an example of a memory that may be used in conjunction with an apparatus for aiding persons who have low vision.

In some embodiments, memory 520 may include components configured to provide the automatic reaction function. As shown in FIG. 35, memory 520 may include an input detection module 3510, a continuous action module 3520, and a database 3530. Input detection module 3510 may be a component configured to detect an input associated with the automatic reaction function. Continuous action module 3520 may be a component configured to manage a continuous action performed by apparatus 110. Database 3530 may be a component configured to store data associated with the automatic reaction function and provide particular data when requested.

Input detection module 3510 and continuous action module 3520 may be implemented in software, hardware, firmware, a mix of any of those, or the like. For example, if input detection module 3510 and continuous action module 3520 are implemented in software, they may be stored in memory 520, as shown in FIG. 35. Other components of processing unit 140 and/or sensory unit 120 may be configured to perform processes to implement and facilitate operations of input detection module 3510 and continuous action module

3520. Thus, input detection module 3510 and continuous action module 3520 may include software, hardware, or firmware instructions (or a combination thereof) executable by one or more processors (e.g., processor 540), alone or in various combinations with each other. For example, input detection module 3510 and continuous action module 3520 may be configured to interact with each other and/or other modules of apparatus 110 to perform functions consistent with disclosed embodiments. For example, in some embodiments, input detection module 3510 and continuous action module 3520 may each include dedicated sensors (e.g., IR, image sensors, etc.) and/or dedicated application processing devices to perform the disclosed functionality.

Database 3530 may include one or more memory devices that store information and are accessed and/or managed through a computing device, such as processing unit 140. In some embodiments, database 3530 may be located in memory 520, as shown in FIG. 35. In other embodiments, database 3530 may be located remotely from memory 520, and be accessible to other components of apparatus 110 (e.g., processing unit 140) via one or more wireless connections (e.g., a wireless network). While one database 3530 is shown, it should be understood that several separate and/or interconnected databases may make up database 3530. Database 3530 may include computing components (e.g., database management system, database server, etc.) configured to receive and process requests for data stored in memory devices associated with database 3530 and to provide data from database 3530.

In some embodiments, database 3530 may be configured to store data associated with the automatic reaction function of apparatus 110. For example, database 3530 may include recognized objects. In some embodiments, recognized objects may include images of objects that were previously stored via apparatus 110. Recognized objects may be objects that apparatus 110 is configured to identify in real-time image data received by image sensor 350. Recognized objects may include any physical object, a person, an area, an environment, a background, and any combination and/or grouping of these. Recognized objects may include a particular aspect of an object (e.g., shape, color, text, etc.).

In some embodiments, recognized objects may include triggers, including triggers associated with the automatic reaction function of apparatus 110. In some embodiments, triggers may include any stored image or portion of an image that apparatus 110 may recognize as an input indicating a particular intention of the user of apparatus 110. For example, a pointing finger, a specific object, a particular hand motion, change in the field-of-view of apparatus 110, change in the user's area of focus, and the like, may be triggers. In some embodiments, apparatus 110 may be configured to perform a process to match a trigger in real-time image data to a trigger stored in database 3530 and perform additional processing to determine a particular action associated with the trigger (e.g., performance of a continuous action).

Input detection module 3510 and continuous action module 3520 may be configured to communicate with each other and with database 3530. For example, input detection module 3510 may monitor real-time image data to look for any input in the field-of-view that may be matched to an input stored in database 3530. If a matching input is detected, input detection module 3510 may communicate with continuous action module 3520 to determine a particular continuous action associated with the detected input. Continuous action module 3520 may communicate with components of apparatus 110 to cause apparatus 110 to perform the determined continuous action. Input detection module 3510 may continue to monitor the field-of-view to determine if any additional inputs are in the real-time images. If additional inputs are found, input detection module 3510 may communicate with continuous action module 3520 to suspend, reinstitute, modify, change, or otherwise alter the continuous action.

As used herein, real-time image data may refer to image data captured in real-time or near real-time. For example, input detection module 3510 may monitor the field-of-view of apparatus 110 to detect inputs while continuous action module 3520 may determine whether to suspend, reinstitute, modify, change, or otherwise alter the continuous action. Accordingly, input detection module 3510 and continuous action module 3520 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 36:
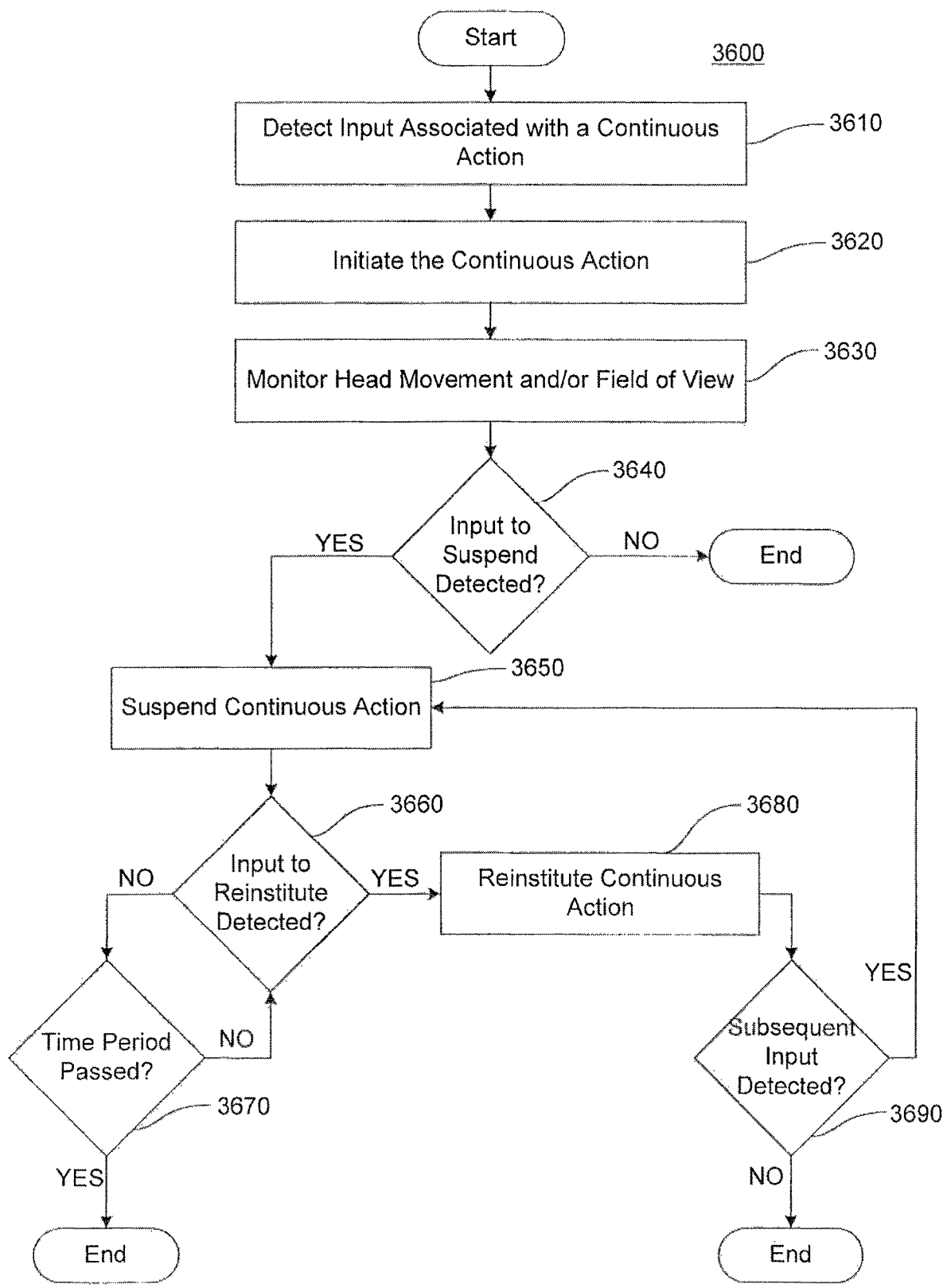
FIG. 36 is an example of a process for performing a continuous action in response to an input.

FIG. 36 depicts a flowchart of an example of a process 3600 for providing an automatic reaction function. In some embodiments, input detection module 3510 and/or continuous action module 3520 may be configured to perform at least a part of process 3600. To perform process 3600, apparatus 110 may include image sensor 350 positioned for movement with a head of a user of apparatus 110. Image sensor 350 may also be configured to capture real-time images in a field-of-view of image sensor 350 from the user's environment. Image sensor 350 may be configured to capture the real-time images as the user's head moves and/or the field-of-view of image sensor 350 changes (including changes in the environment).

In some embodiments, input detection module 3510 may be configured to monitor image data associated with one or more real-time images that are captured by image sensor 350. In some instances, input detection module 3510 may detect in the image data an input associated with a continuous action (step 3610). In some embodiments, the input may be the existence of an object. For example, input detection module 3510 may be configured to process the image data (associated with at least one image) to identify the existence of an object within a field-of-view of image sensor 350. Input detection module 3510 may be configured to identify the object, for example, by matching image data associated with the object to image data associated with one or more recognized images stored in database 3530.

In some embodiments, identification of an object may be a sufficient input for input detection module 3510 (and/or continuous action module 3520) to cause apparatus 110 to automatically react and perform additional processing and/or functions (e.g., perform a continuous action). In other embodiments, input detection module 3510 may monitor the image data for additional or alternative information to determine an input.

For example, input detection module 3510 may be configured to determine a head movement of the user. Input detection module 3510 may determine a head movement of the user, for example, by monitoring for changes in the field-of-view of image sensor 350, which may correspond to a particular head movement (e.g., changing direction of focus, nodding or shaking of the head, tilting of the head, etc.). In some embodiments, input detection module 3510 may use the head movement determination in identifying the object. For example, input detection module 3510 may detect a head movement of the user that indicates the user is changing their focus of attention to a particular region in which an object is located, without the user providing an additional indication. Input detection module 3510 may associate the head movement as a signal to identify the object in the region where the user has decided to look.

In another example, input detection module 3510 may be configured to monitor for a trigger in the image data. For example, input detection module 3510 may identify an object and a trigger in the field-of-view of image sensor 350. In some embodiments, identification of an object and a trigger may constitute an input that may cause an automatic reaction by apparatus 110 (e.g., performance of a continuous action). For example, input detection module 3510 may identify several objects in the field-of-view of image sensor 350. Input detection module may also detect a trigger, such as a finger of the user pointing to one of the objects. Based on the trigger, input detection module may determine that the automatic reaction should be associated with the object associated with the trigger (the object at which the finger is pointed).

In other embodiments, identification of a trigger may cause input detection module 3510 to perform a process to identify an object associated with the trigger (e.g., the user is pointing at an object), and cause an automatic reaction based on the identified object. In still other embodiments, identification of a trigger may itself be a sufficient input to cause an automatic reaction.

After input detection module 3510 determines that an input is present in the real-time image data, input detection module 3510 may cause apparatus 110 to have an automatic reaction to the input. In the example of process 3600, continuous action module 3520 may initiate a continuous action (step 3620). A continuous action may be any action, function, process, etc., that apparatus 110 may be configured to perform. Examples of continuous actions include audibly reading of text (e.g., text on an identified object, such as a newspaper), monitoring of a state of an object (e.g., the state of a device that changes indicators, such as a stop light), recording of a video stream (e.g., a video stream of an identified object), playing of a media file (e.g., a media file, such as an audio recording, associated with an identified object), audibly providing information (e.g., information associated with an identified object), and the like.

Continuous action module 3520 may be configured to determine which continuous action to initiate. In some embodiments, continuous action module 3520 may be configured to select which continuous action to initiate based on the type of the object identified. For example, continuous action module 3520 (and/or input detection module 3510) may determine that the identified object is an object with text (e.g., a newspaper, magazine, book, etc.) and determine that the continuous action is audible reading of the text. In another example, continuous action module 3520 may recognize that the user has turned a page in a book, and continue audible reading of the text on the next page. In other embodiments, continuous action module 3520 may be configured to select a continuous action to initiate based on a particular context associated with the identified object. The context may include contextual information, such as the time and/or the place that an image of the object was captured, the meaning of text written on the object, the identity of an object, the type of the object, the background of the object, the location of the object in the frame, the physical location of the user relative to the object, etc. After determining which continuous action should be used (e.g. audible reading of text on an object), continuous action module 3520 may initiate the continuous action (e.g., begin audible reading of text).

While the continuous action is being performed, input detection module 3510 may continue to monitor real-time image data for additional inputs. In some embodiments, input detection module 3510 may monitor the real-time image data for head movements of the user and/or changes in the field-of-view of the user (step 3630). In some aspects, input detection module 3510 may monitor for these movements and/or changes for inputs to suspend the continuous action being performed (step 3640).

An input to suspend the continuous action may be anything determined by input detection module 3510 as indicating a desire of the user of apparatus 110 to stop the performance of the continuous action and/or that performance of the continuous action is no longer possible. In one example, detection by input detection module 3510 that the identified object has moved outside of the field-of-view of image sensor 350 may be determined to be an input to suspend the continuous action. As has been described, the field-of-view of image sensor 350 may refer to an entire detectable region of image sensor 350 or a particular area of the detectable region, such as a focus of attention region.

In another example, identification by input detection module 3510 of a specific head movement may be determined to be an input to suspend the continuous action. For example, input detection module 3510 may identify a specific head movement that includes a movement causing the identified object to move outside of the field-of-view of image sensor 350. In some embodiments, the specific head movement may include two or more detected changes in the movement of the head of the user (e.g., nodding or shaking of the user's head).

In instances in which there is no input to suspend detected during performance of the continuous action (step 3640— NO), apparatus 110 may perform the continuous action until it is completed (or some other completing event, such as an error, change in the continuous action, etc.), and process 3600 may end. However, in instances in which an input to suspend is detected (step 3640—YES), apparatus 110 (via continuous action module 620, for example) may suspend the continuous action (step 3650). Examples of suspending continuous actions based on inputs to suspend include suspending audible reading of text when the user looks away from the text being read aloud (i.e., the text moves outside the field-of-view of image sensor 350), suspending monitoring of a state of an object when the user looks away from the object, suspending recording of a video stream of an object when the user looks away from the object, suspending playing of a media file associated with an object when the user looks away from the object, suspending audibly providing information associated with an object when the user looks away from the object, and the like.

In some embodiments, continuous action module 3520 (and/or input detection module 3510) may be configured to reinstitute the continuous action. For example, continuous action module 3520 may be configured to stop a particular action when the action is suspended, and return to the point at which performance was stopped and continue performance of the action at a later point in time. Input detection module 3510 may continue to monitor real-time image data, head movements of the user, and field-of-view of image sensor 350, to determine if any inputs to reinstitute the continuous action are detected (step 3660).

In some instances, input detection module 3510 may not detect an input to reinstitute the suspended continuous action (step 3660—NO). In some embodiments, input detection module 3510 may determine if a threshold time period has passed since the continuous action was suspended (step 3670). If a threshold time period has passed (step 3670—YES), input detection module 3510 and/or continuous action module 3520 may consider the continuous action completed and process 3600 may end. If the threshold time period has not passed (step 3670—NO) input detection module 3510 may continue to look for an input to reinstitute the suspended action (and remain prepared to restart the action at the point at which it was stopped).

In other instances, input detection module 3510 may detect an input to reinstitute the suspended continuous action (step 3660—YES). The input to reinstitute the suspended action may be anything detected by input detection module 3510 that indicates that the stopped continuous action should return to being performed. In one example, the input to reinstitute the continuous action may be identification of the identified object that caused initiation of the continuous action. For example, in situations in which a continuous action was suspended after the identified object moved outside of the field-of-view of image sensor 350, continuous action module 3520 may be configured to automatically reinstitute the suspended action when the object reappears in the field-of-view. In embodiments in which the action may only be reinstituted during a threshold time period, continuous action module 3520 may be configured to automatically reinstitute the suspended action if a time period, between a time the object moves outside the field-of-view and a time the object reappears in the field-of-view, is less than a predetermined threshold.

In other embodiments, the input to reinstitute the suspended action may include a trigger. In one example, continuous action module 3520 may be configured to reinstitute a suspended action after the object reappears in the field-of-view and a trigger is identified. For example, continuous action module 3520 may be configured to reinstitute a continuous action associated with an object after the object reappears in the field-of-view of image sensor 350 and identification module 3510 identifies that the user is pointing a finger at the object.

After an input to reinstitute the continuous action is detected, continuous action module 3520 may be configured to reinstitute the continuous action (step 3680). For example, a continuous action of audible reading text that was suspended may be reinstituted, and apparatus 110 may continue audible reading of the text from the point at which the reading was stopped. As the action continues, input detection module 3510 may continue to monitor for inputs, such as a subsequent input to suspend the continuous action (step 3690). A subsequent input to suspend the action may be the same or different action from the input detected in step 3640 (e.g., identified object moving outside of the field-of-view of image sensor 350).

If input detection module 3510 detects a subsequent input to suspend the continuous action (step 3690—YES), process 3600 may return to step 3650, and the continuous action may be suspended again. Processing may be repeated to determine if the suspended action is to be reinstituted or if the process will end. Several iterations of suspending and reinstituting the action may occur, depending on the situation (e.g., the user may look away from an object several times only to return to it each time). In instances in which no subsequent input to suspend the continuous action is detected (step 3690—NO), apparatus 110 may perform the continuous action until it is completed (or some other completing event, such as an error, change in the continuous action, etc.), and process 3600 may end.

Through process 3600, apparatus 110 may automatically perform an action based on image data captured by image sensor 350, which may allow apparatus 110 to automatically react as the user moves and/or the captured environment changes. FIGS. 37A-37B schematically illustrate an example of a scenario in which the automatic reaction function of apparatus 110 may be used. FIG. 37 illustrates an object 3710, such as a newspaper, which may be in the field-of-view 3720 of image sensor 350. Apparatus 110 may be configured to identify object 3710 as a newspaper and select a continuous action that audibly reads a particular section 3730 of the newspaper, such as based on identification of a finger pointing to section 3730 (not shown). Apparatus 110 may continue to audibly read section 3730 until completion. However, as shown in FIG. 37B, the object 3710 and/or section 3730 may leave the field-of-view 3720. The object 3710 and/or section 3730 may leave the field-of-view 3720, for example, when the user of apparatus 110 moves their head. When identification module 3510 determines that object 3710 has left the field-of-view 3720, audible reading of section 3730 may be suspended. The suspension of the continuous action may correspond to the user turning their attention to another object or a person in their environment, and thus a desire to stop the audible reading. As described in process 3600, if the object returns to the field-of-view 3720 (e.g., by the user moving his or her head or by moving the object), continuous action module 3520 may reinstitute the suspended action, and audible reading of section 3730 may restart at the point at which reading was stopped.

As is evident from the foregoing, apparatus 110 may provide a wide range of functionality. More specifically, one embodiment consistent with the present disclosure provides a method for providing user 100, who may be visually impaired, with information about one or more objects or situations detected within the field of view of apparatus 110. Apparatus 110 may be configured to identify a hand-related trigger in real-time image data. The apparatus may further identify in the image data one or more objects associated with the hand-related trigger, as well as a context associated with the object(s) and the hand-related trigger. Based on the identified context, apparatus 110 may select one of a plurality of alternative actions to execute. The capability to automatically select and execute actions may provide user 100 with the opportunity to more fully interact with their surrounding environment.

Figure 38:
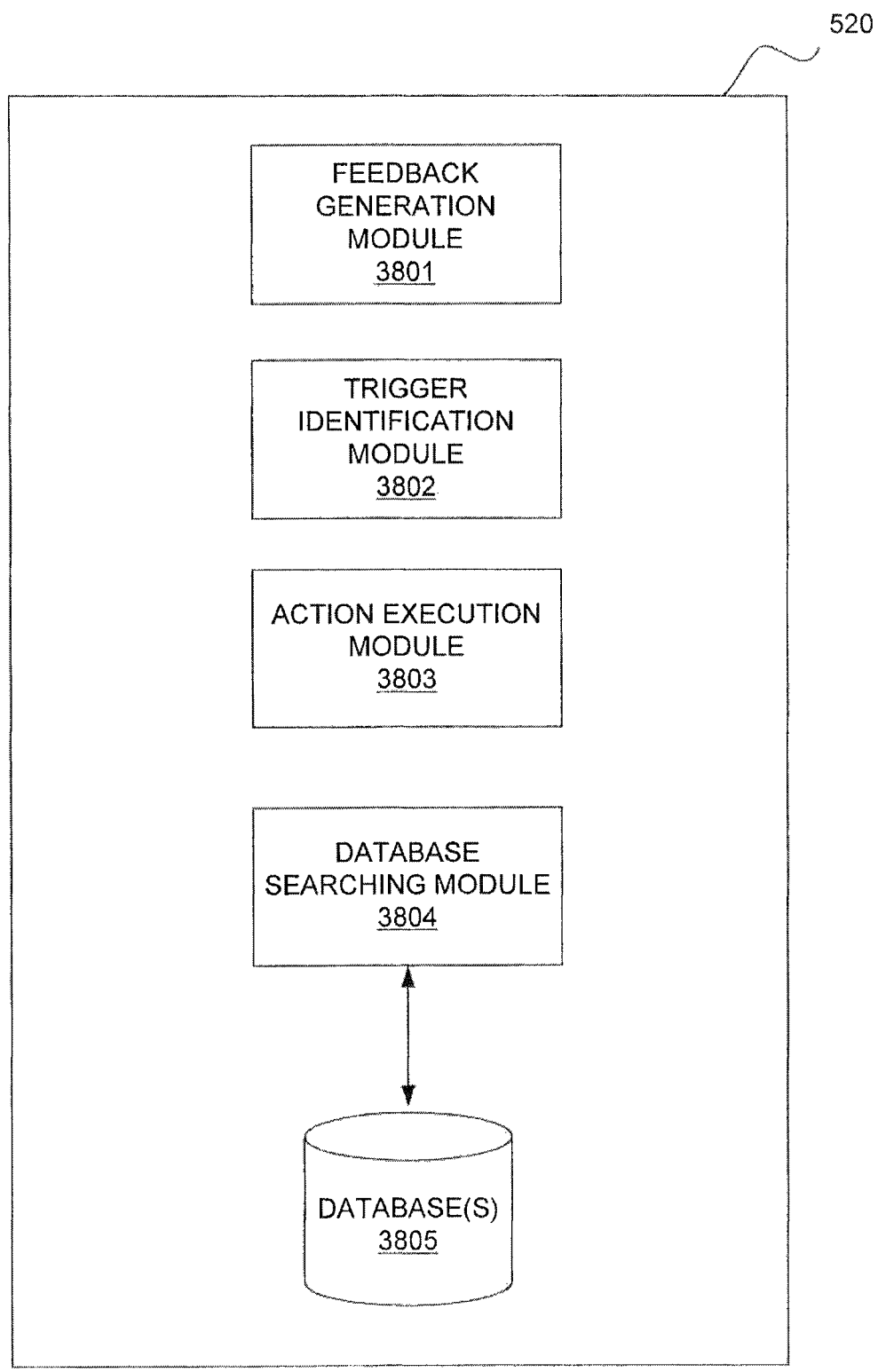
FIG. 38 is a block diagram illustrating an example of a memory contained within an apparatus for aiding persons who have low vision.

FIG. 38 is a block diagram illustrating memory 520 associated with apparatus 110 according to one embodiment. In the example shown in FIG. 38, memory 520 comprises a feedback generation module 3801, a trigger identification module 3802, an action execution module 3803, a database comparison module 3804, and one or more databases 3805.

Feedback generation module 3801 may provide functionality for apparatus 110 to generate and transmit information to user 100 in response to a query. Processor 540 may execute feedback generation module 3801 to generate and process feedback in a given context, then transmit the generated feedback to feedback-outputting unit 340 for output to user 100. In one embodiment, processor 540 and feedback-outputting unit 340 may be operatively connected via wire 130. In other embodiments, processor 540 and feedback-outputting unit 340 may be operatively connected via wireless transceiver(s) 530. As discussed above, in some embodiments, feedback generation module 3801 may generate audible feedback to user 100. In other embodiments, the feedback may be tactile in nature, such as a vibration.

Trigger identification module 3802 may provide functionality for apparatus 110 to identify in real-time audible or visual triggers that may precipitate a change in the operational status of apparatus 110. As used in this disclosure, a "trigger" may include, for example, the appearance of user 100's hand within the field of view of apparatus 110 while making a pre-defined gesture. Any external stimulus may constitute a trigger. In some embodiments, for example, user 100 may be able to audibly say words that serve as triggers, such as "Show," "When," "What," etc. It is understood that these are non-limiting examples. Trigger identification module 3802 may be configured to detect the presence of triggers, then cause processor 540 to execute software instructions that operate apparatus 110 in a manner associated with the trigger.

Action execution module 3803 may provide functionality for apparatus 110 to execute various functions in response to stimuli, be they triggers managed by user 100, appearance of objects within the field of view of apparatus 110, or other events occurring while apparatus 110 is in operation. Action execution module 3803 may, for example, coordinate the configuration and execution of one or more alternative actions that may be available to apparatus 110 upon positive identification of an object or a particular situation.

Database comparison module 3804 may provide functionality for apparatus 110 to compare objects detected in the user environment to objects and/or categories of said objects in a database, such as database(s) 3805, to be described in detail below. In some embodiments, database comparison module 3804 may derive information from real time image data received from image sensor 350. In other embodiments, other software elements or processors may derive the information and provide it to database comparison module 3804. Processor 540 may execute database comparison module 3804 to access one or more of the described databases, and compare the information derived from the received real time image data with information in the databases. If the derived information corresponds to information found in one or more of the databases, database comparison module 3804 may provide an indication to feedback generation module 3801 to that effect as discussed in further detail below in association with FIGS. 41-43.

Database(s) 3805 may comprise one or more databases that store information and are accessed and/or managed through memory 520. By way of example, databases 3805 may include document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 3805 may contain software code or macros that facilitate rapid searching and comparison by database comparison module 3804.

Feedback generation module 3801, trigger identification module 3802, action execution module 3803, and database searching module 3804 may be implemented in software, hardware, firmware, a mix of any of those, or the like. For example, if the modules are implemented in software, they may be stored in memory 520, as shown in FIG. 38. Other components of processing unit 140 and/or sensory unit 120 may be configured to perform processes to implement and facilitate operations of the modules. Thus, feedback generation module 3801, trigger identification module 3802, action execution module 3803, and database searching module 3804 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., feedback generation module 3801, trigger identification module 3802, action execution module 3803, and database searching module 3804) may each include dedicated sensors (e.g., IR, image sensors, etc.) and/or dedicated application processing devices to perform the functionality associated with each module.

As used herein, real-time image data may refer to image data captured in real-time or near real-time. For example, trigger identification detection module 3802 may monitor the field-of-view of apparatus 110 to detect inputs while action execution module 3803 may determine whether to execute a particular action based on a detected trigger. Accordingly, trigger identification detection module 3802 and action execution module 3803 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 39:
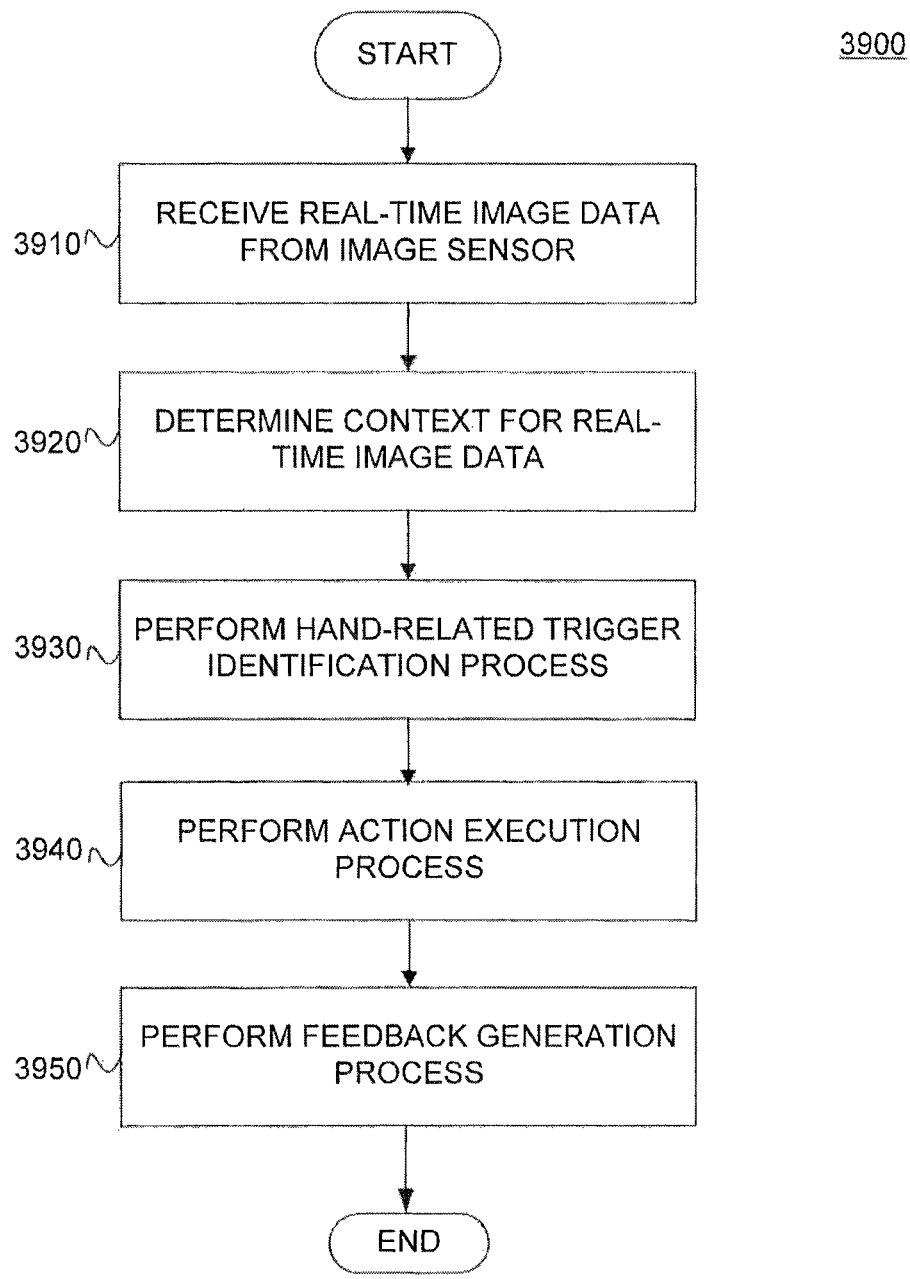
FIG. 39 is an example of a process for providing feedback to a person who has low vision, consistent with disclosed embodiments.

FIG. 39 illustrates an example of a process 3900 for providing feedback to a person who has low vision consistent with certain disclosed embodiments. Process 3900, as well as any or all of the individual steps therein, may be performed by various aspects of apparatus 110, such as sensory unit 120, processing unit 140, support 210, or any subcomponents therein. For exemplary purposes, FIG. 39 is described as being performed by processor 540, executing software instructions stored within memory 520.

Processor 540 may receive real-time image data from an image sensor, such as image sensor 350 (Step 3910). In other embodiments, processor 540 may receive the image data from an intermediate component associated with sensory unit 120. The intermediate unit may, for example, perform image processing operations on the real-time image data before transmitting it to processor 540. In some embodiments, the real-time image data may be received as a single streaming video file. In other embodiments, the real-time image data may be received as a series of still images. When the image data is received, processor 540 may store the data in memory 520 or database(s) 3805.

Processor 540 may determine a context for the received real-time image data based on stored information that facilitates the execution of one or more actions (Step 3920). In some embodiments, processor 540 may execute software instructions to process the representations of one or more objects in the real-time image data. In some embodiments, the processing may comprise image processing, such as image rotation, a change in the size of the image, image sharpening, cropping the image, enhancing the focus, etc. It is understood that these are non-limiting examples and that any manner of image processing may be applied to the real-time image data. In other embodiments, the processing may comprise optical character recognition (OCR), when the real-time image data comprises text. In these embodiments, the optical character recognition may facilitate recognition of the visualized text by processor 540, and facilitate formation of a search query for a database containing object information. Processor 540 may further derive or determine any other information contained in the received real-time image data relating to the context of the image, such as date, time, geographical location, etc.

In Step 3930 of process 3900, processor 540 may perform a hand-related trigger identification process (via trigger identification module 3802, for example), similar to the process described below in connection with FIG. 41. In brief, according to some embodiments, trigger identification module 3802 may configure components of apparatus 110, such as image sensor 350 and/or other components of sensory unit 120 and processing unit 140, to operate in a "ready mode" for trigger detection. Trigger identification module 3802 may determine if a user's hand is present in the real-time image data. If the user's hand is present, trigger identification module 3802 may determine the user hand trigger, if any, that is represented in the real-time image data. Trigger identification module 3802 may further determine one or more data categories associated with the determined hand trigger.

Processor 540, via action execution module 3803, may perform an action execution process, such as is described below in connection with FIG. 42 (Step 3940). In brief, according to some embodiments, action execution module 3803 may determine an object associated with a hand-related trigger identified in received real-time image data. Action execution module 3803 may also determine a context associated with the object. Based on the identified hand-related trigger and context, action execution module 3803, in conjunction with database comparison module 3804, may determine context-based alternative actions associated with the trigger and the identified object. Action execution module 3803 may select one or more of the determined context-based alternative actions, and then execute the selected action(s).

Processor 540, via feedback generation module 3801, may perform a feedback generation process, such as is described below in connection with FIG. 43 (Step 3950). In brief, according to some embodiments, feedback generation module 3801 may receive information associated with one or more objects identified in the real-time image data. Feedback generation module 3801 may determine audible feedback for output to user 100. Feedback generation module 3801 may configure the audible feedback, and then provide the audible feedback to feedback-outputting unit 430 for output to user 100.

Figure 40B:
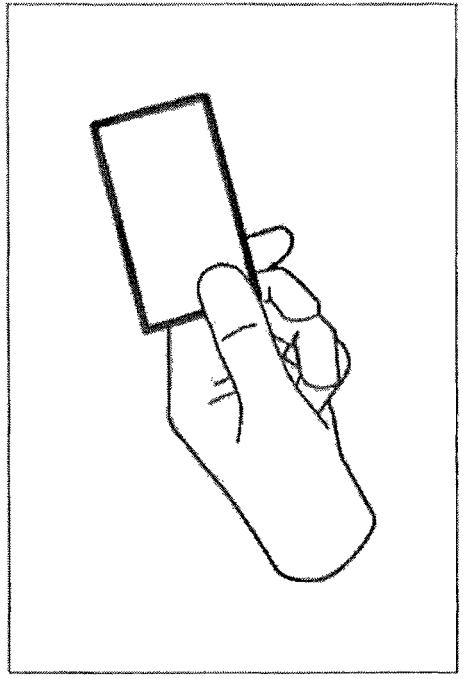
FIG. 40B is an example illustration of a hand-related trigger for an apparatus for aiding persons who have low vision, consistent with disclosed embodiments.
Figure 40D:
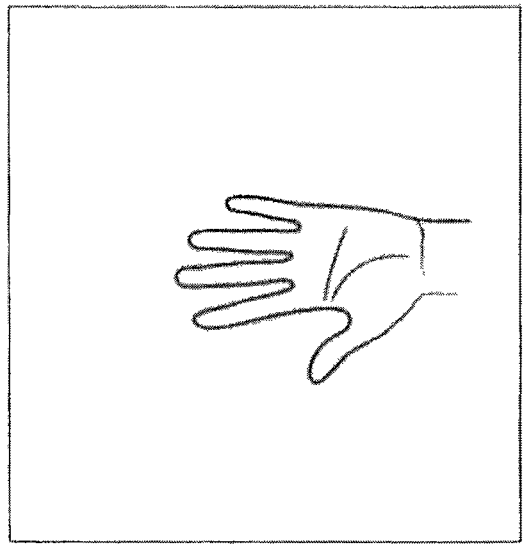
FIG. 40D is an example illustration of a hand-related trigger for an apparatus for aiding persons who have low vision, consistent with disclosed embodiments.
Figure 40A:
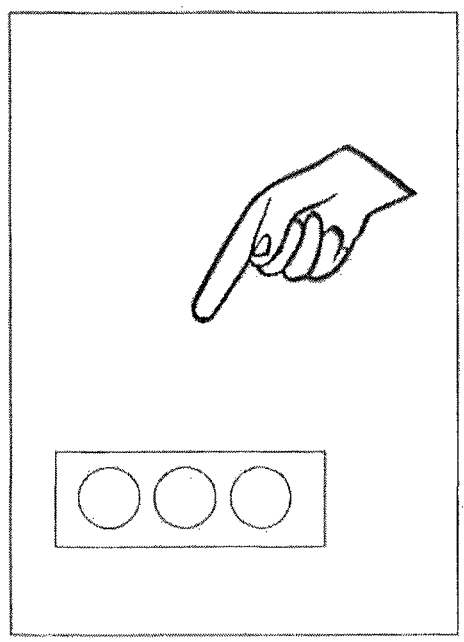
FIG. 40A is an example illustration of a hand-related trigger for an apparatus for aiding persons who have low vision, consistent with disclosed embodiments.

FIGS. 40A-40D illustrate examples of hand-related triggers, consistent with certain disclosed embodiments. FIG. 40A illustrates an example field of view of apparatus 110. In the example of FIG. 40A, a hand of a user, such as user 100, is present within the field of view, and is pointing at an object. In this example, the object is a stoplight, but the object can be any object that may be present in the environment surrounding user 100 while using apparatus 110. In some embodiments, a "pointing" hand trigger as illustrated in FIG. 40A may result in execution of one or more actions relating to the object being pointed at. For example, when user 100 points at a stoplight, as in FIG. 40A, apparatus 110 may detect the action (as will be described below), and audibly announce the status of the stoplight (i.e., "GREEN," "RED," etc.). In other embodiments, a pointing hand trigger may permit apparatus 110 to perform other actions, including, but not limited to, announcing the name of a familiar landscape or a familiar object, announcing route information for a public transportation vehicle, audibly reading text, or audibly recognizing a food item or a pharmaceutical. A pointing hand trigger may be used in disclosed embodiments for any action that provides more information about an object within the field of view of apparatus 110.

FIG. 40B illustrates another example field of view of apparatus 110. In the example of FIG. 40B, a hand of a user, such as user 100, is present within the field of view, and is holding an object. In this example, the object is a piece of paper containing text, but the object can be any object that may be present in the environment surrounding user 100 while utilizing apparatus 110. In some embodiments, a "holding" hand trigger as illustrated in FIG. 40B may result in execution of one or more actions relating to the object being held. For example, when user 100 holds a document or any other item containing text, as in FIG. 40B, apparatus 110 may detect the action (as will be described below), and audibly read the text on the document. In other embodiments, a holding hand trigger may permit apparatus 110 to perform other actions, including, but not limited to, announcing the name of a familiar object that is being held, managing database entries for objects (i.e. removing an item as being recognized, editing audible feedback for an item, etc.), or prompting the user to name an item if the held item is an unfamiliar item. A holding hand trigger may be used in disclosed embodiments for any action that provides more information about an object within the field of view of apparatus 110.

Figure 40C:
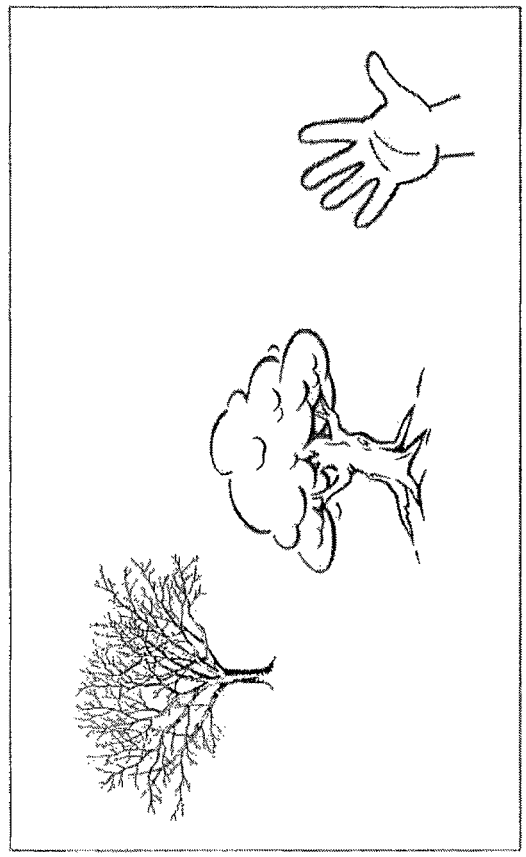
FIG. 40C is an example illustration of a hand-related trigger for an apparatus for aiding persons who have low vision, consistent with disclosed embodiments.

FIG. 40C illustrates another example field of view of apparatus 110. In the example of FIG. 40C, a hand of a user, such as user 100, is present within the field of view, and is waving. In this example, the hand of user 100 is waving in a landscape. In embodiments such as these, a "waving" hand trigger as illustrated in FIG. 40C may result in execution of one or more actions relating to an object or landscape in the field of view when user 100 waves. For example, when user 100 waves at a landscape that is familiar, apparatus 110 may detect elements of the familiar landscape (as will be described below), and audibly identify the location. In other embodiments, a waving hand trigger may permit apparatus 110 to perform other actions, such as prompting the user to identify an unfamiliar landscape when the user waves in an area that apparatus 110 is not familiar with. In some embodiments, waving hand triggers may be associated with pre-programmed landscapes, and landmarks from the landscapes may be stored in memory 520 or database(s) 3805. In these embodiments, for example, user 100 may be able to participate in a guided tour of a tourist attraction. In other embodiments, apparatus 110 may be configured to learn landscapes over time by prompting user 100 for information. A waving hand trigger may be used in disclosed embodiments for any action that provides more information about an object within the field of view of apparatus 110.

FIG. 40D illustrates another example field of view of apparatus 110. In the example of FIG. 40D, a hand of a user, such as user 100, is present within the field of view, and is outstretched in a "stop sign" position. In embodiments such as these, a "stop" hand trigger as illustrated in FIG. 40D may result in execution of one or more actions relating to an object or landscape in the field of view when user 100 presents their hand in this manner. For example, when user 100 presents a stop sign hand trigger during any ongoing operation or action associated with apparatus 110, the apparatus may be configured to immediately terminate the ongoing operation. In other embodiments, the stop sign hand trigger may serve as a "reset" for apparatus 110, or may be configured to help present user 100 with information about the status of the apparatus. In some embodiments, the stop sign hand trigger may serve to lock the user's home and/or turn on an alarm system.

Figure 41:
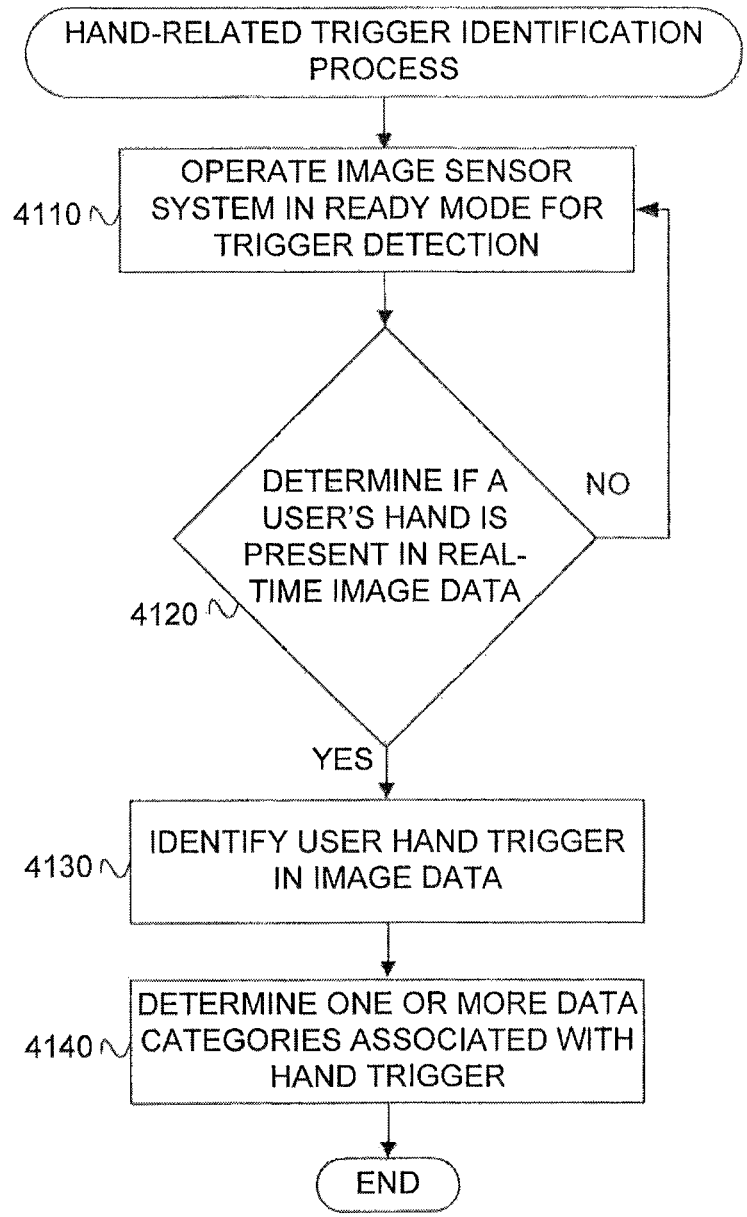
FIG. 41 is an example of a hand-related trigger identification process, consistent with disclosed embodiments.

FIG. 41 illustrates an example hand-related trigger identification process such as that described above in association with Step 3930 of process 3900 consistent with certain disclosed embodiments. Process 3930, as well as any or all of the individual steps therein, may be performed by various aspects of device 110, such as sensory unit 120, processing unit 140, support 210, or any subcomponents therein. For exemplary purposes, FIG. 41 is described as being performed by processor 540, executing software instructions stored within memory 520.

Processor 540, via trigger identification module 3802, may operate image sensor 350 in a normal manner, or "ready mode" while awaiting trigger detection (Step 4110). In some embodiments, apparatus 110 may be configured to always operate in a ready mode when no operations are active. In other embodiments, user 100 may be able to place apparatus 110 into a ready mode such that a hand trigger may be detected.

While in ready mode, trigger identification module 3802 may determine if at least a portion of a user's hand is present in the real-time image data (Step 4120). In some embodiments, trigger identification module 3802 may be configured to recognize the particular hand of the user 100 that is operating apparatus 110. In these embodiments, apparatus 110 may initially prompt user 100 to mime various hand triggers. Trigger identification module 3802 may capture images of the various hand triggers and store them in one or both of memory 520 or database(s) 3805 for ready recognition in the future. In alternative embodiments, trigger identification module 3802 may not be configured to recognize a particular hand, and may be pre-configured to recognize any hand, similar appendage, or equivalent substitute. In some embodiments, trigger identification module 3802 may be configured to recognize the hand of user 100 when it is covered in a glove, mitten, or other covering.

If no hand is detected as present in the real-time image data (Step 4120: NO), trigger identification module may configure image sensor 350 to continue to operate in ready mode, waiting for a future trigger. If a hand is determined to be present (Step 4120: YES), then trigger identification module 3802 may determine if the hand is performing a recognized hand trigger gesture (Step 4130). Examples of possible hand triggers are discussed above in association with FIGS. 40A-40D, but additional hand actions may be recognized by trigger identification module 3802. In some embodiments, as discussed above, a hand-related trigger may comprise an erratic or atypical movement of an object associated with the hand. For example, the hand of user 100 may point and track an erratic or atypically moving object, or may be holding an object, and waving it in an erratic or atypical manner. Trigger identification module 3802 may interact with database comparison module 3804 to search a database, such as database 3805, for recognized hand triggers.

Trigger identification module 3802 may determine one or more data categories associated with the determined hand trigger (Step 4140). For example, processor 540 may determine context information associated with the environment surrounding user 100, and may, along with the determined hand trigger, use the information to determine particular categories to search. For example, user 100 may be standing at an intersection desiring to cross the street. Apparatus 110 may detect this scenario as the current setting. Processor 540 may perform a variety of different alternative actions (via action execution module 3803) based on a particular hand trigger recognized by trigger identification module 3802. For example, one type of hand trigger may signal to trigger identification module 3802 that the category to search for is "warning of risks." As will be discussed further below, apparatus 110 may then scan the field of view for objects, then scan the database for matching objects that may represent risks to user 100. In some embodiments, multiple categories may be associated with a given hand trigger in a given context. For example, in the scenario just described, warning of risks may comprise a first category, and a second category may be "scene identification." Numerous combinations of categories are contemplated for various triggers and contexts. For example, in an alternative embodiment, "spatial guidance" may be the first category, and "warning of risks" may be the second category. Categories may be fluid based on current configuration of apparatus 110 at any given time. One skilled in the art may contemplate many possible categories of data and contexts in which they could be invoked or sorted.

Figure 42:
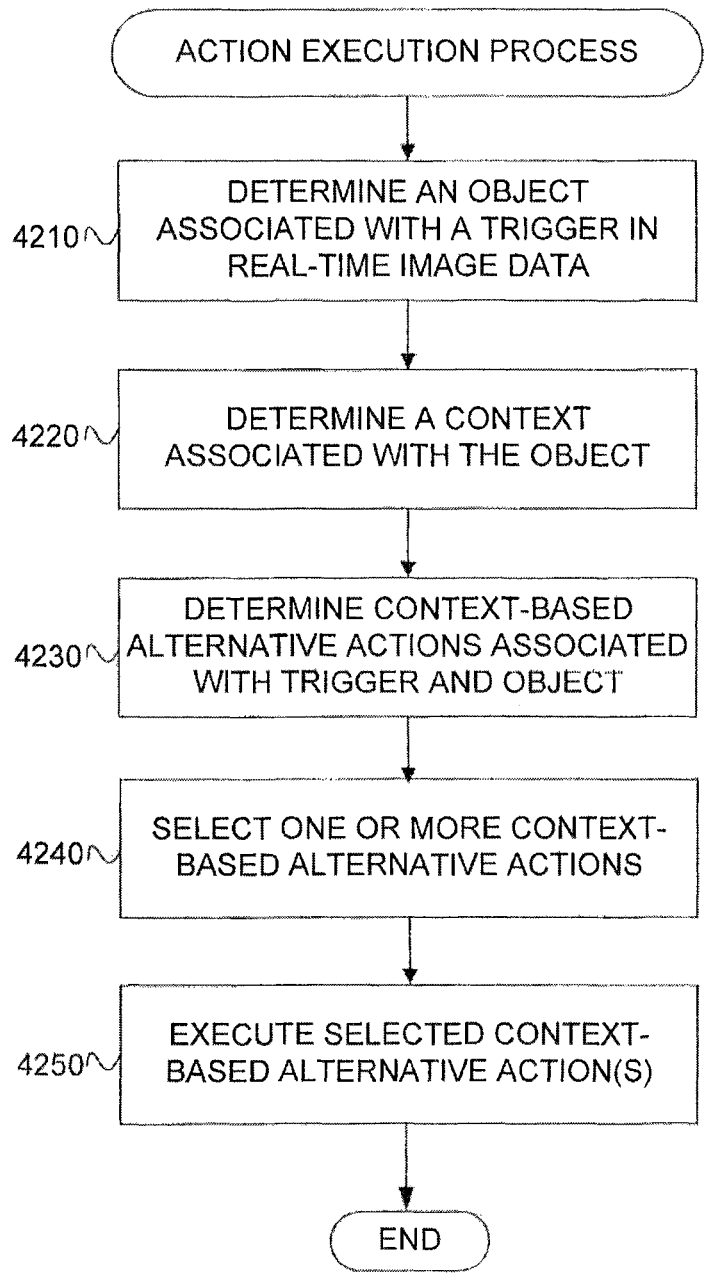
FIG. 42 is an example of an action execution process, consistent with disclosed embodiments.

FIG. 42 illustrates an example action execution process such as that described above in association with Step 3940 of process 3900 consistent with certain disclosed embodiments. Process 3940, as well as any or all of the individual steps therein, may be performed by various aspects of device 110, such as sensory unit 120, processing unit 140, support 210, or any subcomponents therein. For exemplary purposes, FIG. 42 is described as being performed by processor 540, executing software instructions stored within memory 520.

Processor 540, via trigger identification module 3802 and action execution module 3803, may determine an object associated with a trigger in real-time image data received from image sensor 350 (Step 4210). In some embodiments, the trigger may be a hand-related trigger that may be identified and processed using hand-related trigger identification process 3930 described above. In other embodiments, other triggers may be identified and processed by trigger identification module 3802, such as the appearance of a particular object into the field of view of apparatus 110. In these embodiments, trigger identification module 3802 may be configured to automatically identify and process the trigger when it appears. Alternatively, trigger identification module 3802 may be configured to identify and process the trigger when user 100 focuses on the object using apparatus 110. In some embodiments, trigger identification module 3802 may be configured to identify and process multiple triggers substantially simultaneously within the same field of view.

Once trigger identification module 3802 has identified and processed the relevant triggers present in the real-time image data, trigger identification module 3802 and database comparison module 3804 may determine one or more objects associated with the triggers. In some embodiments, database(s) 3805 may contain database entries linking particular objects to triggers, and database comparison module 3804 may be configured to search database(s) 3805 given the input of a particular trigger to find associated objects that are present in the received real-time image data. In other embodiments, database comparison module 3804 may take the reverse approach, and may identify one or more objects present in the received real-time image data, then search database(s) 3805 for matching triggers. Database comparison module 3804 may identify one or more trigger-object matches within database(s) 3805, and may extract data relating to those pairings for further analysis and processing consistent with disclosed embodiments.

Processor 540, via trigger identification module 3802, action execution module 3803, and database comparison module 3804, may determine a context associated with the identified objects (Step 4220). In some embodiments, processor 540 may determine object context based on real-time image data received from image sensor 350. In other embodiments, processor 540 may determine object context based on real-time audio data received from image sensor 350. In some embodiments, apparatus 110 may recognize a familiar context associated with the object based on prior experience, or based, for example, on context information pre-programmed into memory 520 or database(s) 3805. In these embodiments, database comparison module 3804 may identify known and familiar contexts associated with objects and triggers within database(s) 3805. Alternatively, the context determined from the image sensor data may not be recognized or familiar, and processor 540 may prompt user 100 to provide information relating to the context via an audio prompt or via a user interface visible to user 100 within the field of view of apparatus 100. Apparatus 110 may receive the context information in these embodiments from user 100, and then database comparison module 3804 may utilize the received information to search database(s) 3805 for relevant entries.

Additionally, processor 540 may call action execution module 3803 to determine one or more context-based alternative actions associated with the chosen category or categories, and their associated triggers and contexts (Step 4230). In some embodiments, action execution module performs such alternative actions in addition to any feedback generated by feedback generation module 3801. In other embodiments, the alternative actions are performed instead of the feedback generation.

One skilled in the art may contemplate a multitude of alternative actions that may be associated with a given object or objects in a given context. Alternative actions may include, but not be limited to, audibly reading text, sending an electronic message or instant message over the Internet; configuring settings for apparatus 110 or image sensor 350; activating a user interface, which may appear on the lens of the glasses within the vision of user 100 and provide additional interactivity options, announcing an identity of an inanimate object, announcing an identity of an individual, identifying a scene perceived within the field of view, summing money, monitoring a status of a traffic light (as illustrated, for example, in FIG. 40A), saving an individual's name, audibly reading a summary of text, monitoring an object expected to change, identifying a bus number, identifying currency, identifying a credit card, or identifying a pharmaceutical product, such as a pill.

Various alternative actions available for execution by action execution module 3803 may be stored in database entries within database(s) 3805 associated with various objects and triggers. In these embodiments, processor 540 may call database comparison module 3804 to access and extract possible alternative actions, then transmit the possible actions to action execution module 3803 for execution. When more than one object or trigger are visible, processor 540 may determine their relative locations to determine one or more possible alternative actions to execute.

Action execution module 3803 may select one or more of the context-based alternative actions presented for execution (Step 4240). In some embodiments, action execution module 3803 may select a single alternative action for execution based on the context. In other embodiments, action execution module 3803 may select multiple alternative actions. In these embodiments, one or more of the alternative actions may be sequential; for example, an alternative action may only be executed if another particular action is executed beforehand. Upon selecting one or more of the alternative actions, action execution module 3803 may execute various software instructions to perform the action (Step 4250). For example, if the action involves an audible output to user 100, action execution unit 3803 may employ feedback generation module 3801 and feedback-outputting unit 430 to generate, configure, and output the audible information, as will be discussed in further detail below. In some embodiments, processor 540 may be configured to rapidly adjust the alternative actions available to action execution module 3803 based in changes that may be identified in one or more of a trigger, an identified object, or a context related to the object. In these embodiments, as these elements change, processor 540 may call database comparison module 3804 to search database(s) 3805 for new alternative actions associated with the newly-changed trigger, object, or context.

As a non-limiting example of an automatic action selection process, such as that described above in association with FIG. 39, apparatus 110 may determine that a hand-related trigger is present, such as a portion of user 100's hand holding an object and waving it erratically to invoke detection of the trigger. Upon identification of the trigger, trigger identification module 3802 may further identify the object that user 100 is holding as a stack of currency. Database comparison module 3804 may then search database(s) 3805 for possible contexts involved with the particular trigger (hand-related; holding) and the object (currency). Database comparison module 3804 may determine possible contexts, such as needing to identify the type or amount of the currency to pay for a purchase. Database comparison module 3804 may then determine one or more alternative actions associated with the trigger, the object, and the context. Here, database comparison module may determine that alternative actions may include audibly announcing the face value of the currency, audibly announcing the type or national origin of the currency, or audibly summing the amount of the currency. The alternative actions may optionally be performed sequentially; for example, the currency might not be summed until apparatus 110 determines the type of currency first. Upon determining the possible alternative actions, database comparison module 3804 may pass the possible actions to action execution module 3803, which may select and execute one or more of the actions. Action execution module 3803 may execute software instructions to determine the type of currency, sum the currency, then generate, configure, and output audible announcements of the currency type and amount via feedback generation module 3801 and feedback-outputting unit 430. This process will now be described in further detail.

Figure 43:
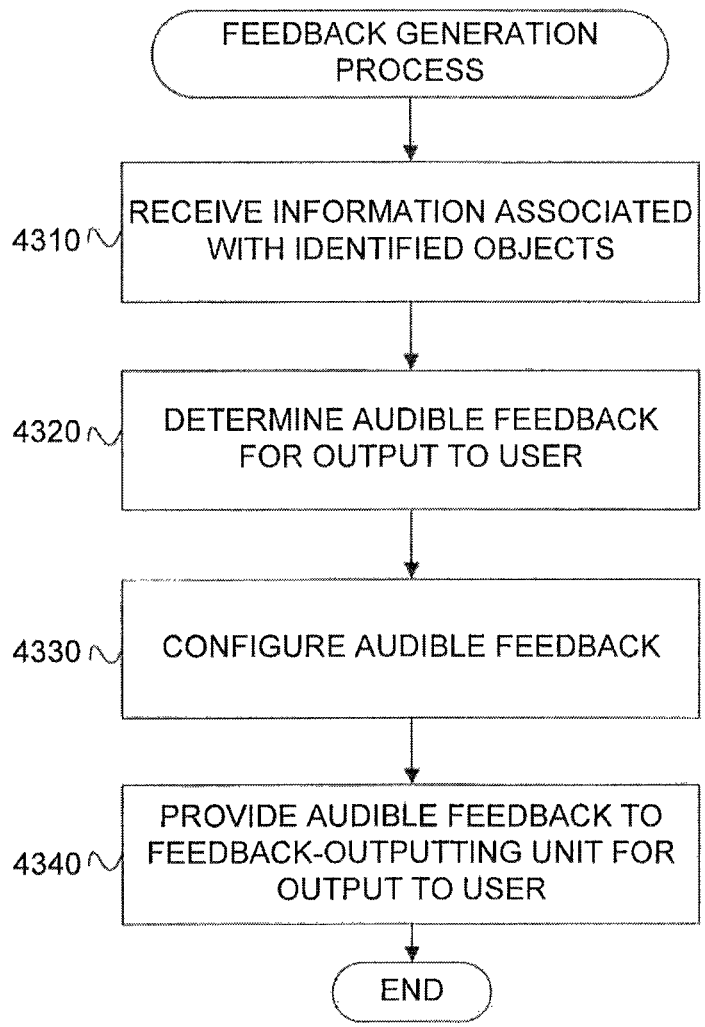
FIG. 43 is an example of a feedback generation process, consistent with disclosed embodiments.

FIG. 43 illustrates an example feedback generation process such as that described above in association with Step 3950 of process 3900 consistent with certain disclosed embodiments. Process 3950, as well as any or all of the individual steps therein, may be performed by various aspects of device 110, such as sensory unit 120, processing unit 140, support 210, or any subcomponents therein. For exemplary purposes, FIG. 43 is described as being performed by processor 540, executing software instructions stored within memory 520.

As discussed above, processor 540, via feedback generation module 3801, may receive information associated with one or more identified objects that have been determined to be present in the environment surrounding user 100 (Step 4310). The received information may further comprise information relating to a result of one or more executed alternative actions, as discussed above. Based on the received information, feedback generation module 3801 may determine audible feedback for output to user 100 (Step 4320). In some embodiments, the identified object or executed alternative action may each already be associated with an audible feedback file stored in memory 520 or database(s) 3805. In these embodiments, feedback generation module 3801 may simply access the existing associated audible feedback file and prepare it for transmission. In other embodiments, there may be multiple audible feedback files associated with the identified object(s) or actions, and feedback generation module may review the determined trigger and/or context information to determine the correct associated audible feedback to output to user 100. In still other embodiments, there may be no existing audible feedback associated with the identified object(s) or actions. In these embodiments, feedback generation module 3801 may determine content for audible feedback by prompting user 100 for the feedback, or may infer proper audible feedback, based on context and based on other objects within the category.

Upon determining the proper audible feedback to use, feedback generation module 3801 may configure the audible feedback into a readable format, if necessary (Step 4330), then provide the audible feedback to feedback-outputting unit 430 for output to user 100 (Step 4340). Feedback generation module 3801 may provide the feedback to feedback-outputting unit 430 via wire 130, or alternatively, via wireless transceiver(s) 530.

As is evident from the foregoing, apparatus 110 may provide a wide range of functionality. More specifically, one embodiment consistent with the present disclosure provides a triggered action function. As has been described, apparatus 110 may be configured to perform one or more actions based on an identification of a trigger, such as a trigger present in captured image data. The triggered action function of apparatus 110 may allow a user (e.g., a visually-impaired user) to provide input to apparatus 110 (e.g., a trigger) in order to cause apparatus 110 to perform a pre-defined action. Examples of pre-defined actions include providing feedback (e.g., an audible descriptor) associated with an object, and storing a captured representation of an object, such as for providing feedback during future use of apparatus 110.

Figure 44:
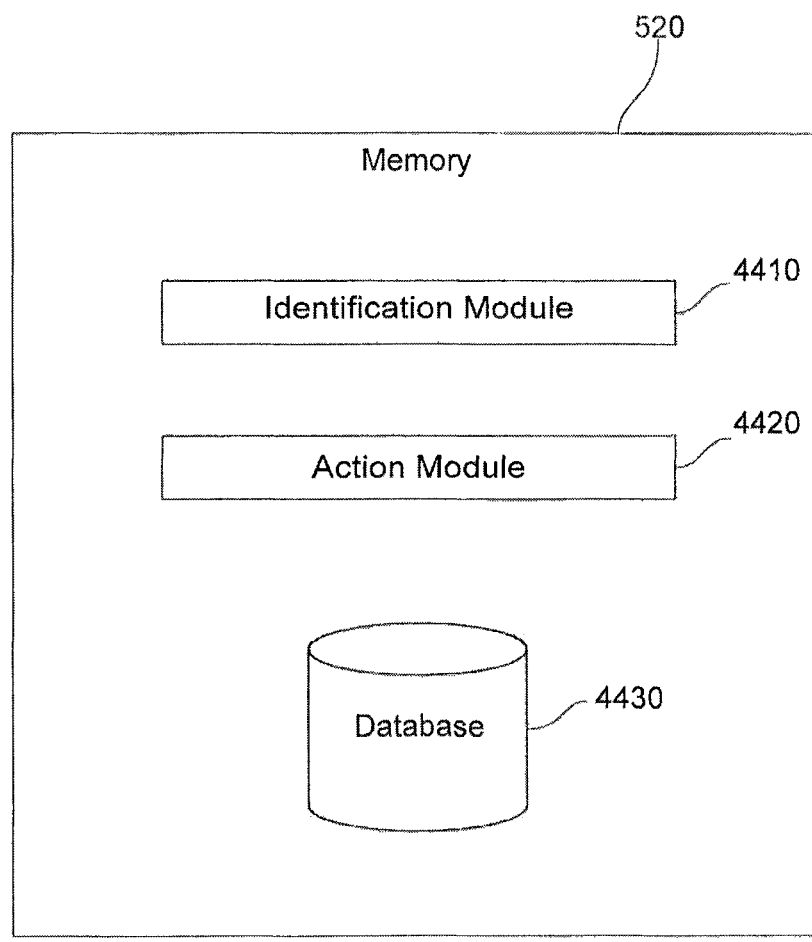
FIG. 44 is a block diagram illustrating an example of a memory configured to provide a triggered action function, consistent with disclosed embodiments.

In some embodiments, memory 520 may include components configured to provide the triggered action function. As shown in FIG. 44, memory 520 may include an identification module 4410, an action module 4420, and a database 4430. Identification module 4410 may be a component configured to identify a trigger based on image data captured by image sensor 350. Action module 4420 may be a component configured to perform and/or cause apparatus 110 to perform a pre-defined action (e.g., in response to a trigger). Database 4430 may be a component configured to store data associated with the triggered action function and provide particular data when requested.

Identification module 4410 and action module 4420 may be implemented in software, hardware, firmware, a mix of any of those, or the like. For example, if identification module 4410 and action module 4420 are implemented in software, they may be stored in memory 520, as shown in FIG. 44. Other components of processing unit 140 and/or sensory unit 120 may be configured to perform processes to implement and facilitate operations of identification module 4410 and action module 4420. Thus, identification module 4410 and action module 4420 may include software, hardware, or firmware instructions (or a combination thereof) executable by one or more processors (e.g., processor 540), alone or in various combinations with each other. For example, identification module 4410 and action module 4420 may be configured to interact with each other and/or other modules of apparatus 110 to perform functions consistent with disclosed embodiments. In some embodiments, any of the disclosed modules (e.g., identification module 4410 and action module 4420) may each include dedicated sensors (e.g., IR, image sensors, etc.) and/or dedicated application processing devices to perform the functionality associated with each module.

Database 4430 may include one or more memory devices that store information and are accessed and/or managed through a computing device, such as processing unit 140. In some embodiments, database 4430 may be located in memory 520, as shown in FIG. 44. In other embodiments, database 4430 may be located remotely from memory 520, and be accessible to other components of apparatus 110 (e.g., processing unit 140) via one or more wireless connections (e.g., a wireless network). While one database 4430 is shown, it should be understood that several separate and/or interconnected databases may make up database 4430. Database 4430 may include computing components (e.g., database management system, database server, etc.) configured to receive and process requests for data stored in memory devices associated with database 4430 and to provide data from database 4430.

In some embodiments, database 4430 may be configured to store data associated with the triggered action function of apparatus 110. For example, database 4430 may include recognized objects. In some embodiments, recognized objects may include captured representations of objects that were previously stored via apparatus 110. Recognized objects may be objects that apparatus 110 is configured to identify in real-time image data received by image sensor 350. Recognized objects may include any physical object, a person, an area, an environment, a background, and any combination and/or grouping of these. Recognized objects may include a particular aspect of an object (e.g., shape, color, text, etc.).

In some embodiments, database 4430 may retain a plurality of representations and a plurality of descriptors, each descriptor associated with at least one stored representation. Each of the plurality of descriptors may include an audible representation, which may be provided to a user of apparatus 110, such as by feedback-outputting unit 340. In certain examples, at least one descriptor may be associated with at least two stored representations.

In some embodiments, database 4430 may also be configured to store triggers, including triggers associated with the triggered action function of apparatus 110. Triggers may be any stored image or portion of an image that apparatus 110 may recognize as an input indicating a particular intention of the user of apparatus 110. For example, a pointing finger, a specific object, a particular hand motion, change in the field-of-view of apparatus 110, change in the user's area of focus, and the like, may be triggers. In some embodiments, triggers may include movements of objects. As has been described, an erratic movement of an object may be a trigger. In addition, other movements, such as a predefined movement sequence (e.g., a repetitive movement, a circular movement, a linear movement, etc.) may be stored as triggers. Apparatus 110 may be configured to identify movement of an object in image data to determine if the movement corresponds to a trigger.

After identifying a trigger in captured image data, apparatus 110 may perform a process to match the trigger to a trigger stored in database 4430, although other trigger identification processes are possible. For example, apparatus 110 may be configured to estimate the trajectory of a moving object and analyze the trajectory for a corresponding trigger. Regardless of how apparatus 110 identifies a trigger, apparatus 110 may be further configured to identify a captured representation of an object associated with the trigger. Further, apparatus 110 may be configured to perform a pre-defined action based on the trigger and/or the captured representation.

Identification module 4410 and action module 4420 may be configured to communicate with each other and with database 4430. For example, identification module 4410 may monitor real-time image data to identify objects and triggers associated with the objects (e.g., movement of the object). If an object and a trigger are detected, identification module 4410 may communicate with action module 4420 to determine a pre-defined action associated with the object and/or the trigger. Action module 4420 may communicate with components of apparatus 110 to cause apparatus 110 to perform the pre-defined action.

As used herein, real-time image data may refer to image data captured in real-time or near real-time. For example, identification module 4410 may monitor the field-of-view of apparatus 110 to detect inputs while action module 4420 may determine whether to initiate an action. Accordingly, identification module 4410 and action module 4420 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 45:
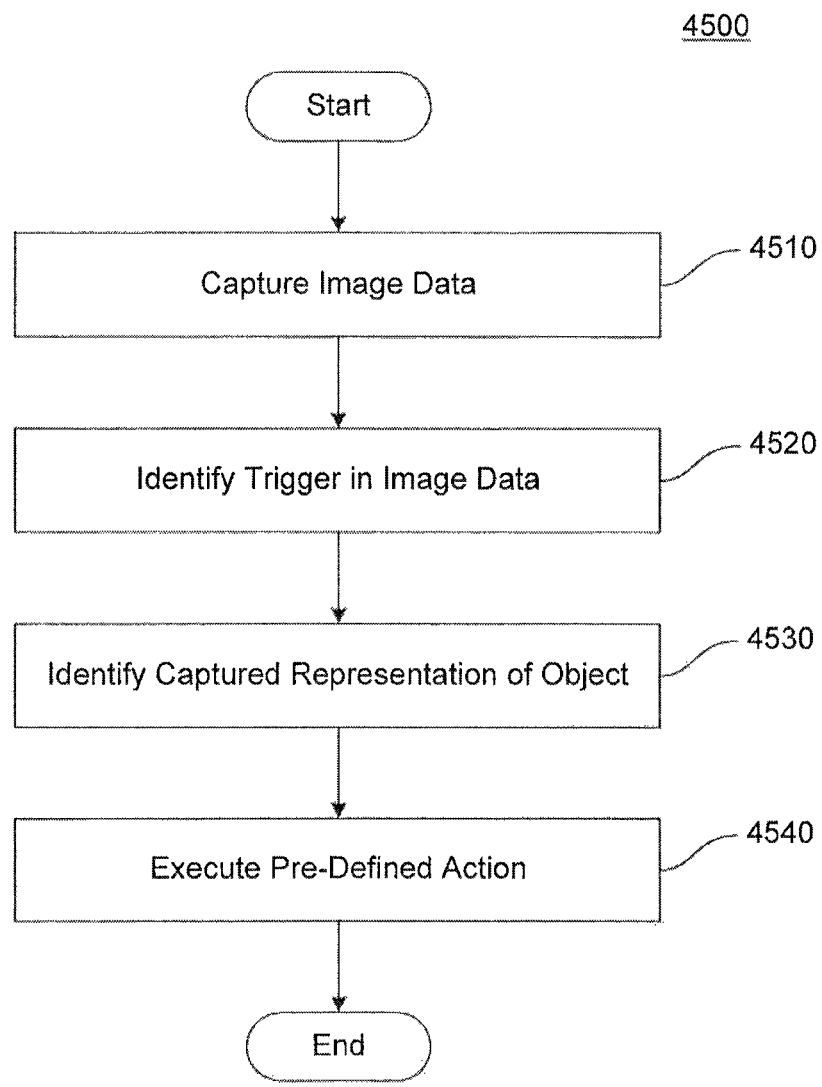
FIG. 45 is a flowchart of an example of a process for executing a pre-defined action in response to a trigger, consistent with disclosed embodiments.

FIG. 45 depicts a flowchart of an example process 4500 for executing a pre-defined action in response to identification of a trigger. In some embodiments, identification module 4410 and/or action module 4420 may be configured to perform at least a part of process 4500. Apparatus 110 may be arranged with image sensor 350 configured to capture image data from the environment of a user (e.g., a visually-impaired user of apparatus 110). In process 4500, image sensor 350 may capture image data (step 4510). In some embodiments, the image data may provide a plurality of sequential images of the user's environment. The images may include objects that are located within a field-of-view (e.g., a detectable area) of image sensor 350.

Identification module 4410 may be configured to analyze the captured image data to look for objects and/or triggers. Consistent with process 4500, identification module 4410 may identify a trigger using the captured image data (step 4520). In some aspects, the identified trigger may be associated with a desire of the user to cause at least one pre-defined action associated with an object (e.g., an object associated with the trigger). Identification module 4410 may be configured to perform a trigger identification process to identify the trigger. An example of a trigger identification process will be described in more detail in the description of FIG. 46. In some embodiments, only a portion of the image data (e.g., a portion associated with a center area of a plurality of sequential images) may be used to identify the trigger.

In some embodiments, the trigger may be a movement of the object. For example, a user may hold an object in the field-of-view of image sensor 350 and move the object in a way (an "object movement") that corresponds to a trigger that matches a particular action associated with the object that the user is attempting to cause apparatus 110 to perform (e.g., identify the object, store a representation of the object, etc.).

One example of an object movement that corresponds to a trigger is an erratic movement of the object. For example, a user may move an object through an unusual or irregular path within the field-of-view of image sensor 350. Identification module 4410 may be configured to identify the erratic movement of the object and determine that it matches a trigger. For example, identification module 4410 may be configured to identify a particular number of changes in the movement of an object, with a sufficient number of changes indicating an erratic movement. A change in movement of an object may correspond to a change in direction, a change in speed, and/or a rotation, for example. In one embodiment, an erratic movement may include at least one detected change in the movement of an object. In another embodiment, an erratic movement may include at least two detected changes in the movement of an object.

Another example of an object movement that corresponds to a trigger is a predefined movement sequence of the object. For example, a user may move an object through a particular sequential path within the field-of-view of image sensor 350. Examples of particular sequential paths may include linear paths and circular paths. In another example, repetitive movement may be a predefined movement sequence of the object (e.g., waving of the object back and forth). Predefined movement sequences, as with erratic movements, may be defined by a particular number of changes in the movement of an object. For example, a predefined movement sequence may include at least two detected changes in the movement of the object. Examples of processes by which identification module 4410 may identify a predefined movement sequence are described in more detail in the description of FIG. 46.

While identification module 4410 has been described as configured to identify triggers in the image data, it should be understood that identification module 4410 may additionally or alternatively be configured to identify a trigger without using the image data. For example, identification module 4410 may identify input from function button 410 as a trigger. In certain embodiments, identification module 4410 may be configured to identify a trigger without using the image data, in addition to a trigger, identified in the image data. In these embodiments, further processing to execute a pre-defined action may be initiated upon identification of both triggers.

In response to identification of the trigger, identification module 4410 may identify in the image data a captured representation of the object (step 4530). In some embodiments, the captured representation may include an image (or images) of the object. The image of the object may be cropped from an associated complete image, such that other objects, background information, etc., are removed from the image. In some embodiments, the captured representation of the object may be transmitted to action module 4420 for further processing.

Action module 4420 may receive notification of the trigger and/or the captured representation. Action module 4420 may determine a pre-defined action associated with the trigger and/or the captured representation of the object. In addition, action module 4420 may execute the pre-defined action (step 4540). The pre-defined action may include providing feedback to the user, matching the captured representation to a stored representation, storing the captured representation, and/or the like. An example of a process for executing a pre-defined action will be described in more detail in the description of FIG. 52.

Figure 46:
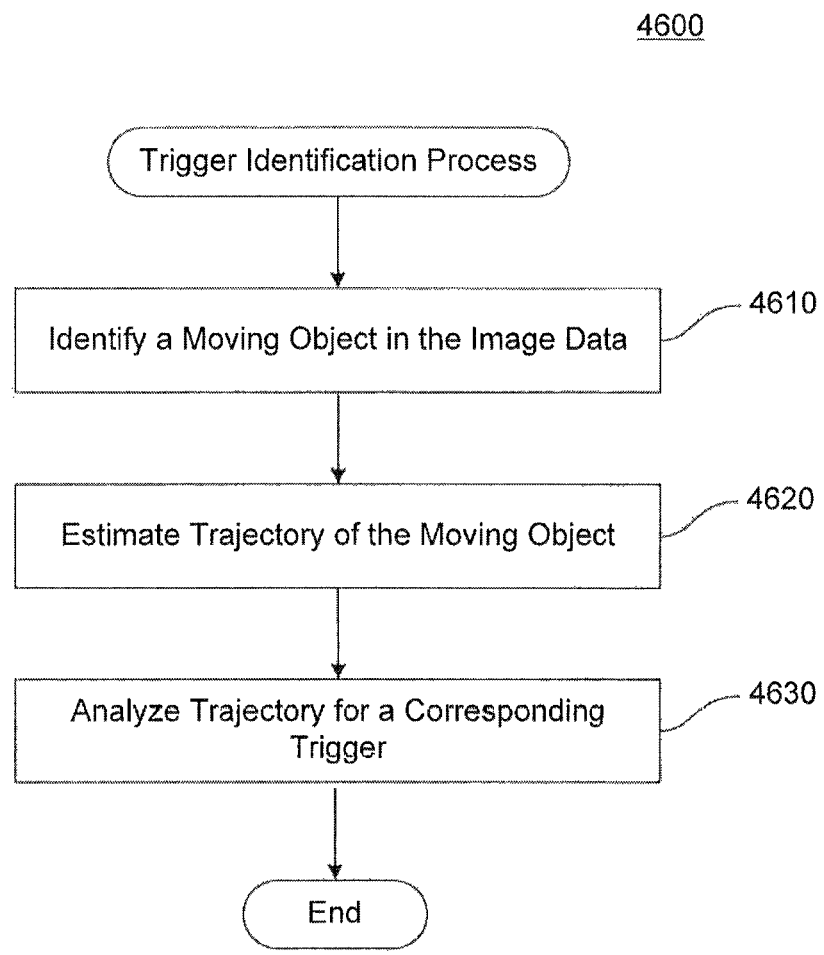
FIG. 46 is a flowchart of an example of a trigger identification process, which may be used conjunction with the process of FIG. 45.

FIG. 46 depicts a flowchart of an example trigger identification process 4600. In some aspects, process 4600 may correspond to step 4520 of process 4500. Identification module 4410 may be configured to perform process 4600 to identify a trigger in image data captured by image sensor 350. In some embodiments, identification module 4410 may use trigger identification process 4600 to isolate moving objects in a sequence of images captured by image sensor 350. In this way, identification module 4410 may be configured to compare the movement of each isolated object with stored movements that are associated with a trigger.

In process 4600, identification module 4410 may first identify a moving object in the image data (step 4610). In some embodiments, identification module 4410 may be configured to identify a moving object by analyzing a sequence of images that include the object. For example, identification module 4410 may be configured to recognize the same object at different locations within the sequential images, and therefore identify the object as a moving object. In some embodiments, identification module 4410 may be configured to determine a shape of the object, which may be based on differences in the plurality of sequential images.

Once a moving object is identified, identification module 4410 may be configured to estimate the trajectory of the moving object (step 4620). In order to estimate the trajectory of the moving object, identification module 4410 may use one or more algorithms to isolate the object within the sequence of images. For example, identification module 4410 may use a segmentation algorithm to supply a bounding box around the moving object, such that the object (and the bounding box) may be tracked throughout the sequence of images. The bounding box may be generated based on key points in the image, which may correspond to points on a boundary of the object.

In some embodiments, identification of at least a portion of a user's hand may be used to isolate the object (and/or place a bounding box). The presence of the user's hand in the image may indicate that the user is holding the object (e.g., to move the object erratically), and therefore possibly represents a boundary of the object.

These and other techniques may be used to isolate the object in the image data. The isolated object may be tracked between the sequence of frames to produce an estimated movement trajectory.

In some embodiments, identification module 4410 may analyze the estimated trajectory to determine if the estimated trajectory corresponds to a trigger (step 4630). For example, identification module 4410 may analyze an estimated trajectory of an object to determine if the movement of the object corresponds to an erratic movement trigger and/or a predefined movement sequence trigger. Identification module 4410 may analyze an estimated trajectory for an erratic movement trigger by determining the number of changes in direction the object undergoes, for example. Similarly, identification module 4410 may analyze an estimated trajectory for a predefined movement sequence by comparing the various locations of the object throughout the trajectory to the locations that may be expected for a particular predefined movement. If the estimated trajectory matches a particular trigger, the captured representation of the object (and/or the trigger) may be transmitted to action module 4420 for further processing and execution of a pre-defined action.

Figure 47:
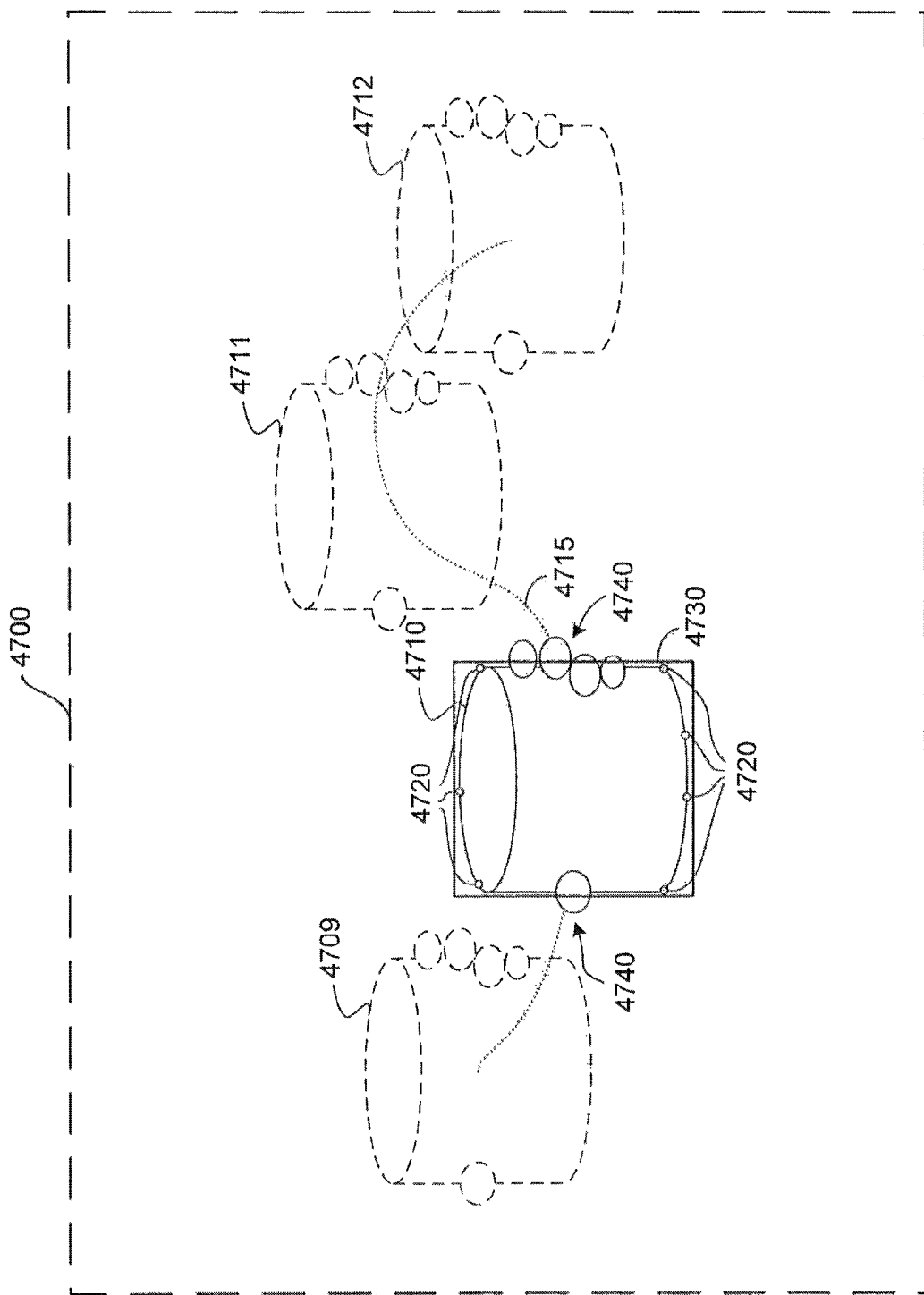
FIG. 47 is a schematic illustration of an image that includes an object, consistent with disclosed embodiments.

FIG. 47 depicts an example of an image 4700 that may be captured by image sensor 350, the image including an object 4710 that has been isolated by identification module 4410. Identification module 4410 may perform process 4600 to analyze image 4700, as well as any images that come before and/or after in a sequence of images captured by image sensor 350. For example, objects 4709, 4711, and 4712 may indicate the location of object 4710 in other images of the sequence, depicting object 4710 as it travels on a path 4715. Object 4710 may represent any object of any shape or size observable by user 100.

Identification module 4410 may use a segmentation algorithm to locate key points 4720 in the image. Key points 4720 may be points on or around the object that indicate a location of the object in the image. Key points 4720 may be identified, for example, based on local image gradients in image 4700, which may indicate a boundary of object 4710. A bounding box 930 may be placed around the key points 4720 in such a way that maximizes the density of the bounded key points 4720. Bounding box 4730 may be used as a constructive boundary of object 4710, such that tracking of bounding box 4730 through successive images may correspond to tracking of object 4710.

In some embodiments, identification module 4410 may be configured to look for a user's hand 4740 in the image. The user's hand 4740 may indicate that the object is being held by the user and may allow identification module 4410 to localize object 4710 within image 4700. Additionally or alternatively, the portion of the user's hand 4740 may be used to identify at least a portion of a boundary of object 4710 (e.g., used as key points 4720) and/or for placement of bounding box 4730.

Based on the key points 4720, bounding box 4730, and/or portion of the user's hand 4740, identification module 4410 may track object 4710 through a sequence of images to estimate the trajectory of the object (e.g., a path). As has been described, identification module 4410 may determine whether the estimated trajectory corresponds to an object movement trigger, such as an erratic movement or a predefined movement sequence. Based on the trigger and a captured representation of the object, action module 4420 may execute a pre-defined action, as described in the description of FIG. 45.

Figure 48:
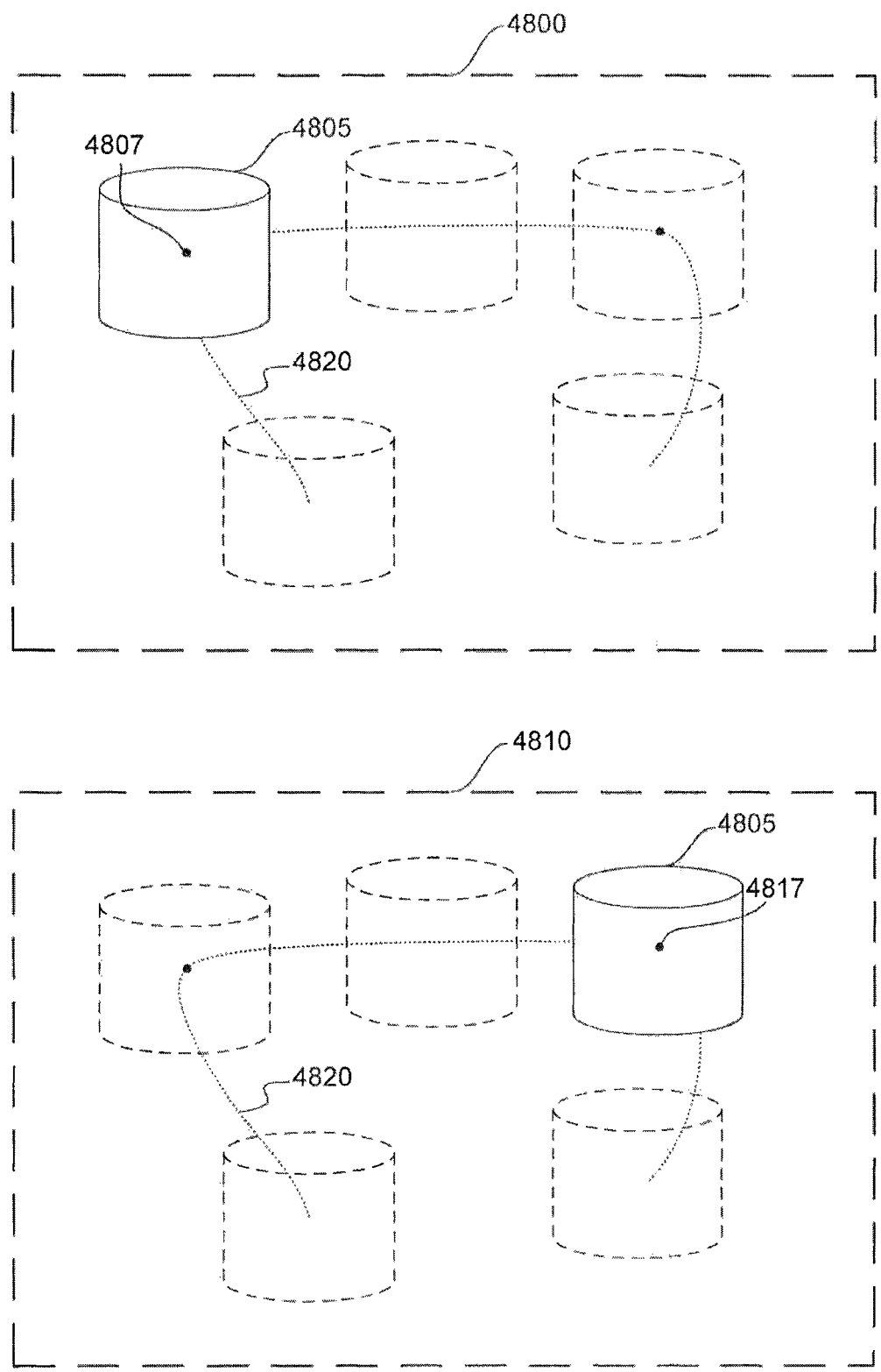
FIG. 48 is a schematic illustration of a sequence of images that depict an erratic movement of an object, consistent with disclosed embodiments.

FIG. 48 depicts an example of a sequence of images 4800 and 4810, each of which may be captured by image sensor 350 and which may include an object 4805. In one aspect, FIG. 48 may represent an example of an erratic movement trigger that identification module 4410 may be configured to identify. As shown in FIG. 48, object 4805 may move through a path 4820. While images 4800 and 4810 are depicted in a sequence, it should be understood that one or more images may be captured between the time images 4800 and 4810 are captured. However, for ease of discussion, only these images are shown.

Image 4800 depicts object 4805 at a location 4807 within the field-of-view of image sensor 350. Identification module 4410 may be configured to analyze image 4800 to isolate object 4805 at the location 4807. As shown by path 4850, location 4807 may indicate a first location along the path 4820 in which object 4805 changes movement (e.g., changes direction of movement). Identification module 4410 may identify the first change in movement of object 4805 based on the location of object 4805 in images preceding and following image 4800. While not shown, in some embodiments, location 4807 may be an initial location of object 4805 and identification module 4410 may be configured to identify a first change in movement based on a change in object 4805 from being stationary to being in-motion.

In some embodiments, identification module 4410 may determine that the first change in movement of object 4805 indicates an erratic movement trigger. In other embodiments, identification module 4410 may continue to look for additional changes in movement of object 4805 before an erratic movement is identified.

Image 4810 depicts image 4805 at a second location 4817 within the field-of-view of image sensor 350. As shown by path 4850, location 4817 may indicate a second location along the path in which object 4805 changes movement (e.g., changes direction of movement). Based on the identification of the second change in movement, identification module 4410 may determine that the movement of object 4805 corresponds to an erratic movement trigger. In other embodiments, identification module 4410 may continue to look for changes in movement of object 4805 before an erratic movement is identified (e.g., 3 or more changes in movement). Based on the identified erratic movement trigger, action module 4420 may execute a pre-defined action associated with object 4805.

Figure 49:
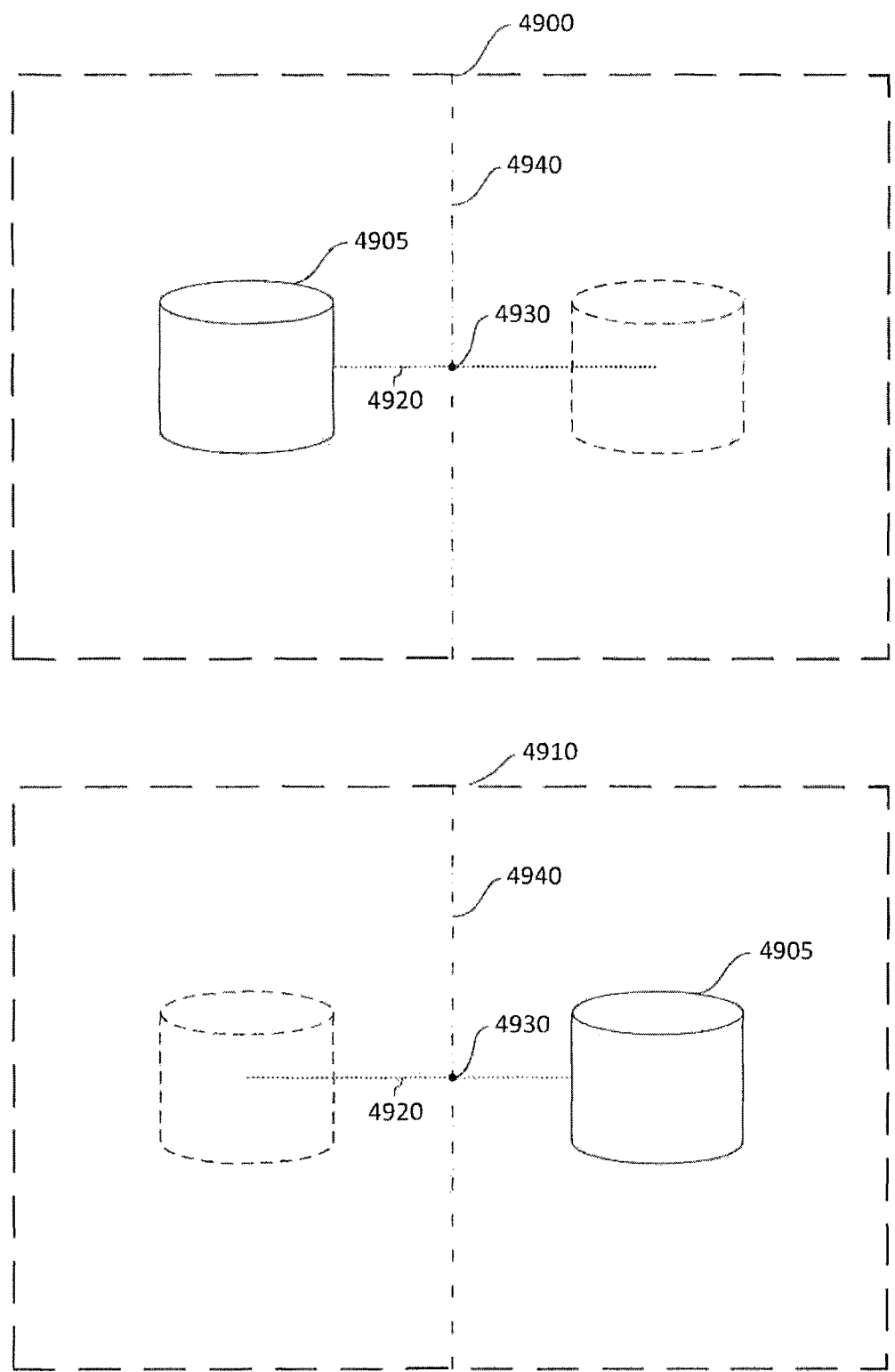
FIG. 49 is a schematic illustration of a sequence of images that depict various predefined movement sequences of an object, consistent with disclosed embodiments.

FIG. 49 depicts an example of a sequence of images 4900 and 4910, each of which may be captured by image sensor 350 and include an object 4905. In one aspect, FIG. 49 may represent an example of a predefined movement sequence trigger, corresponding to a repetitive movement of object 4905, that identification module 4410 may be configured to identify. Images 4900 and 4910 may be selected images from a sequence of images that depict object 4905 moving along path 4920.

In some embodiments, identification module 4410 may be configured to analyze the images of object 4905 moving along path 4920 to determine an average location 4930 of object 4905. Identification module 4410 may further identify a line 4940 that passes through the average location 4930. In certain embodiments, identification module 4410 may be configured to track the location of object 4905 throughout the sequence of images that include movement of object 4905 of path 4920 and compare the locations to the line 4940. Based on this comparison, identification module 4410 may be configured to determine the number of times the object 4905 crosses the line 4940 while on the path 4920.

For example, image 4900 may depict object 4905 on one side of the line 4940 and image 4910 may depict object 4905 on the opposite side of the line 4940. As the object is repetitively moved, identification module 4410 may identify the object 4905 as sequentially reaching the depicted positions on either side of line 4940, and determine that object 4905 is being moved in a predefined movement sequence that matches a trigger. In some embodiments, identification module 4410 may be configured to look for particular criteria before identifying the movement as a trigger. For example, identification module 4410 may determine the movement to be a repetitive movement associated with a trigger if it is determined that the object 4905 crosses the line 4940 a certain number of times (e.g., at least three times). Identification module 4410 may also determine if object 4905 moves far enough away from the line 4940 between any two sequential crossings before considering the movement as a sufficient crossing.

Figure 50:
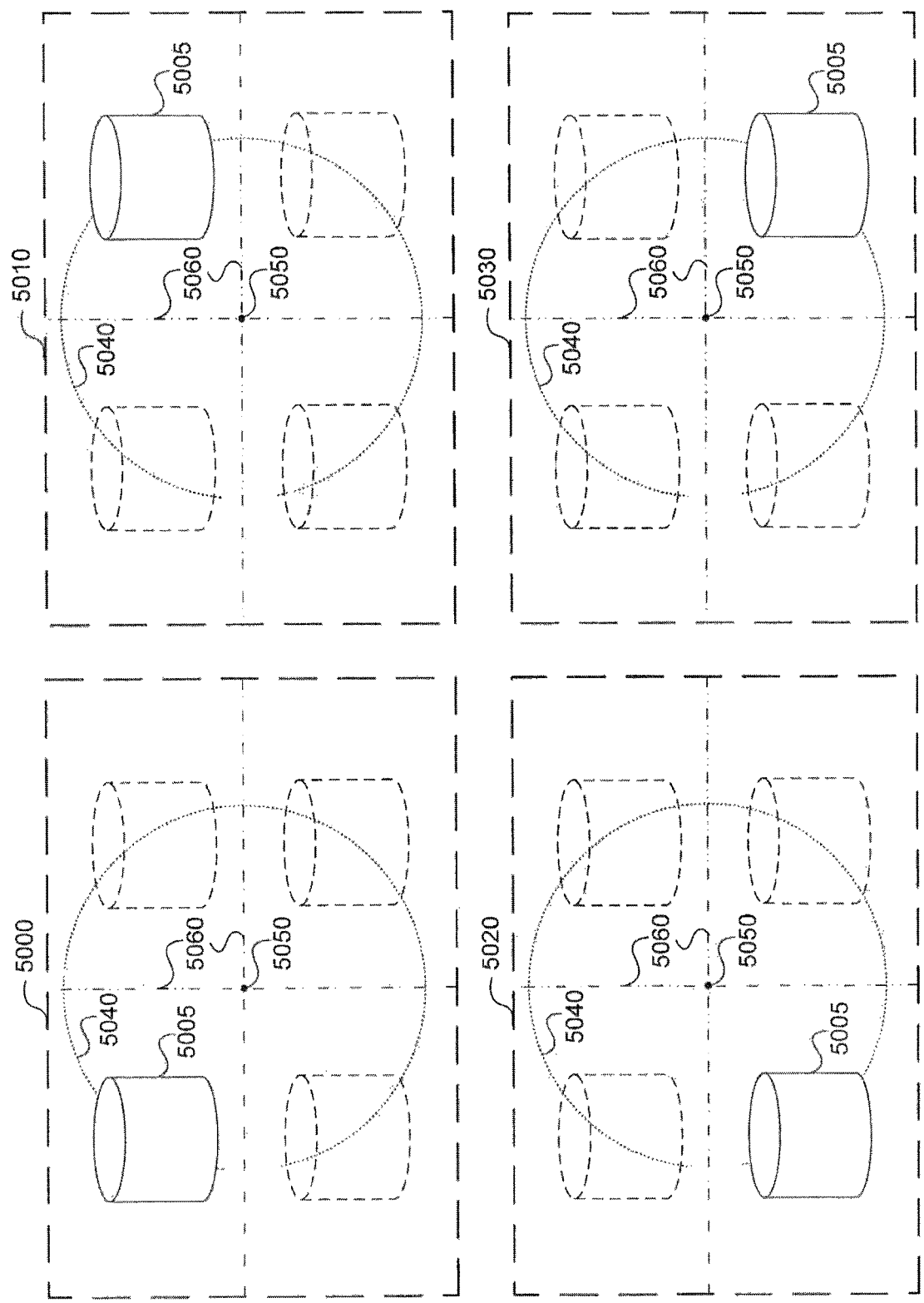
FIG. 50 is a schematic illustration of a sequence of images that depict various predefined movement sequences of an object, consistent with disclosed embodiments.

FIG. 50 depicts an example of a sequence of images 5000, 5010, 5020, and 5030, each of which may be captured by image sensor 350 and include object 5005. Similar to FIG. 49, FIG. 50 may represent another example of a predefined movement sequence that may be identified by identification module 4410 as a trigger. In the example of FIG. 50, the predefined movement sequence may correspond to a circular movement of object 5005 along a path 5040. Images 5000, 5010, 5020, and 5030 may be images selected from a sequence of images that include object 5005 moving along path 5040.

Identification module 4410 may analyze the images that include object 5005 moving along path 5040 to determine a center 5050 of the path 5040, which may be the center of a circle that correspond to path 5040. Identification module 4410 may identify a pair of perpendicular lines 5060 that intersect at center 5050, the perpendicular lines dividing each image into four regions. Identification module 4410 may track object 5005 throughout the images and compare the location of object 5005 in each image to the lines 5060. In some embodiments, identification module 4410 may determine that the object 5005 has moved in a circular movement by determining that the object 5005 is sequentially located in each region during its movement along path 5040. Based on this determination, identification module 4410 may be configured to identify the circular movement as a predefined movement sequence trigger. Images 5000, 5010, 5020, and 5030 depict examples of images that include object 5005 in one of each of the regions.

Figure 51:
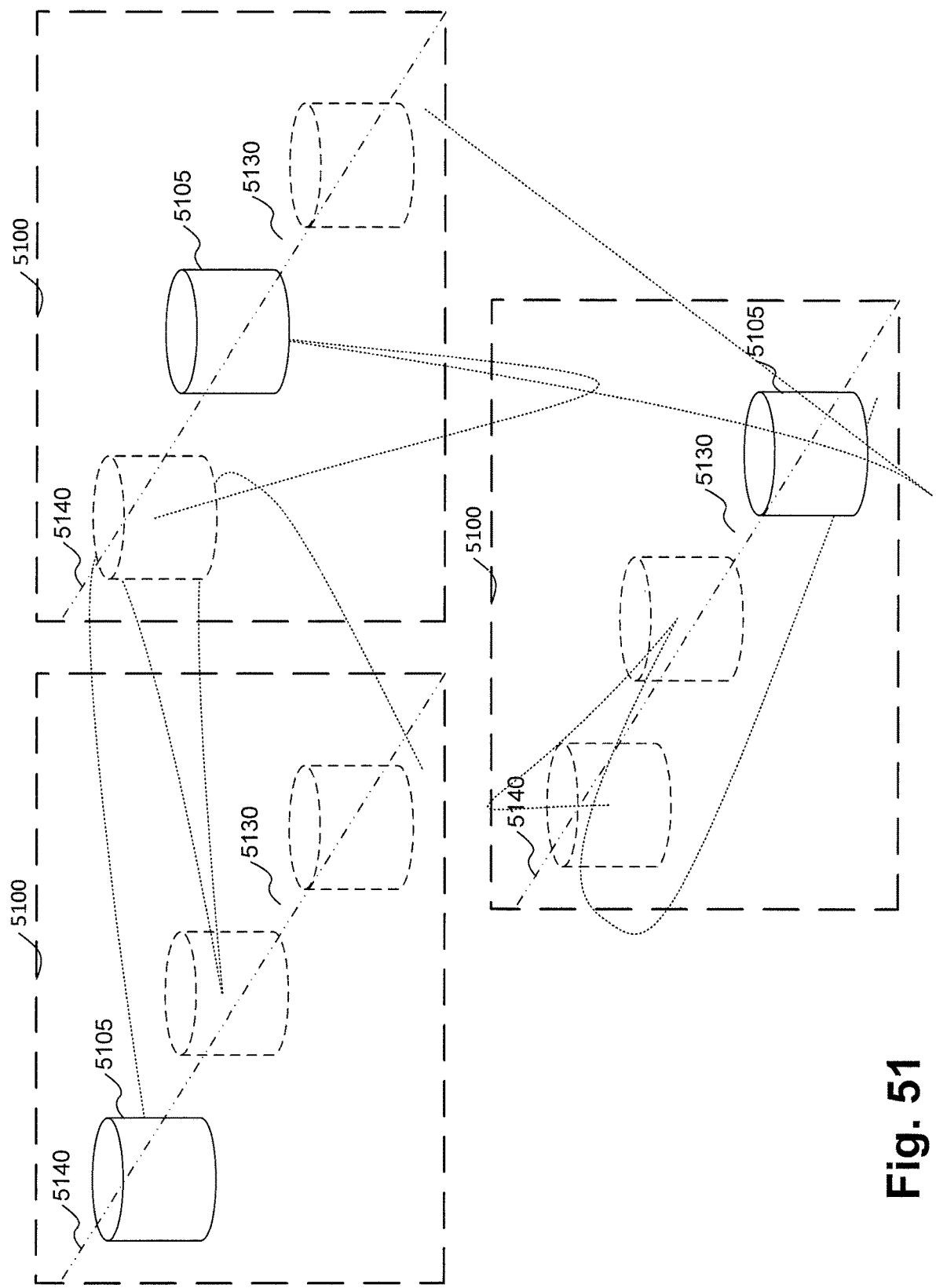
FIG. 51 is a schematic illustration of a sequence of images that depict various predefined movement sequences of an object, consistent with disclosed embodiments.

FIG. 51 depicts another example of a sequence of images 5100, 5110, and 5120, each of which may be captured by image sensor 350 and include an object 5105. Similar to FIGS. 49 and 50, FIG. 51 may represent yet another example of a predefined movement sequence that may be identified by identification module 4410 as a trigger. In the example of FIG. 51, the predefined movement sequence may correspond to a linear movement of object 5105 along a path 5130. Images 5100, 5110, and 5120 may be images selected from a sequence of images that include object 5105 moving along path 5130.

In some embodiments, identification module 4410 may be configured to analyze the images that include object 5105 moving along path 5130 to fit the points along the path 5130 (corresponding to the location of object 5105 in each of the images) to a two-dimensional line 5140, using a line equation (e.g., $a*x+b*y+c=0$). Identification module 4410 may be further configured to determine a distance of each point to the line 5140, using a distance equation, for example. In some embodiments, identification module 4410 may compare each distance to a threshold distance to determine if the points are sufficiently close to the line to constitute a predefined movement sequence. Based on this determination, identification module 4410 may be configured to identify the linear movement as a predefined movement sequence trigger. Images 5100, 5110, and 5120 depict examples of images that include object 5105 at various locations along path 5130.

FIGS. 48-51 depict examples of object movements that identification module 4410 may be configured to identify as triggers. It should be understood, however, that other processes for determining the object movements may be used. Similarly, other object movements may be used as triggers. As described in process 4500, once a trigger is identified, identification module 4410 may identify a captured representation of the object associated with the trigger. Based on the trigger and/or the captured representation of the object, action module 4420 may determine and execute an associated pre-defined action.

Figure 52:
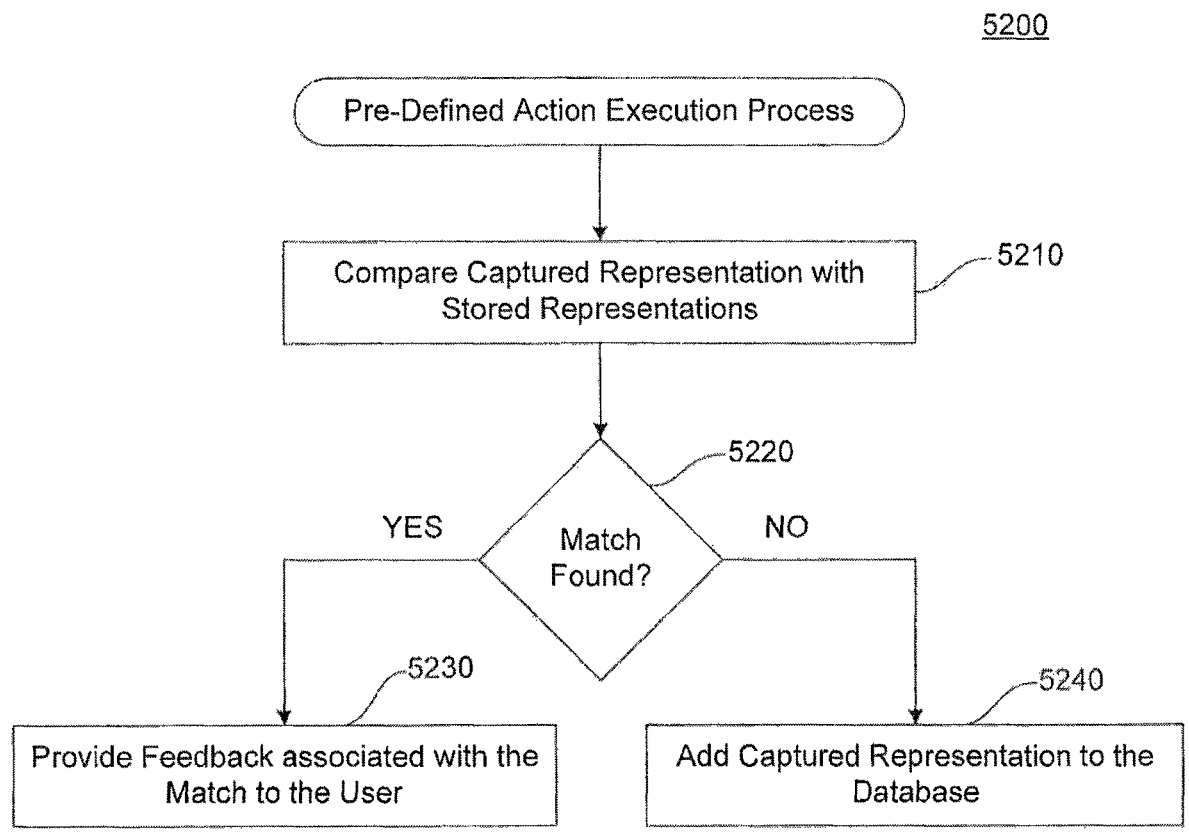
FIG. 52 is a flowchart of an example of a pre-defined action execution process, which may be used in conjunction with the process of FIG. 45.

FIG. 52 depicts a flowchart of an example of a pre-defined action execution process 5200. In some aspects, process 5200 may correspond to step 4540 of process 4500. That is, in some embodiments, action module 4420 may be configured to perform process 5200 to execute a pre-defined action in response to identification of a trigger and a captured representation of an object associated with the trigger.

In certain embodiments, execution of the pre-defined action may include comparing the captured representation of the object with a plurality of stored representations (step

5210). For example, action module 4420 may compare the captured representation with recognized objects stored in database 4430. In some embodiments, a determined shape of the object may be used in comparing the captured representation with the plurality of stored representations. Execution of the pre-defined action may also include determining whether there is a match between the captured representation and the stored representations (step 5220).

If a match is identified (step 5220—YES), action module 4420 may be configured to provide feedback to the user based on the match (step 5230). In some embodiments, the feedback may be an identification of the object, which may be based on a descriptor associated with the matched representation of the object. For example, in embodiments in which the plurality of stored representations are associated with a plurality of branded products, the feedback may include a descriptor of the branded product. The feedback may be provided to the user as audible feedback, for example, although other forms of feedback are possible.

If action module 4420 determines that no match is found between the captured representation and the stored representations (step 5220—NO), action module 4420 may be configured to add the captured representation of the object to a database (step 5240). For example, action module 4420 may store the captured representation in database 4430, along with additional information, such as a descriptor (e.g., an audible descriptor) of the object. In this way, future captured representations of the object may be matched to the stored representation to provide information (e.g., the audible descriptor) about the object. In some embodiments, action module 4420 may additionally or alternatively be configured to provide audible feedback indicating that no match was found when no match is found.

In certain embodiments, action module 4420 may be configured to additionally or alternatively perform other pre-defined actions. For example, in response to a trigger and a captured representation of an object, action module 4420 may be configured to store in a memory the captured representation of the object and an audible descriptor of the object (e.g., with or without attempting to match the captured representation to stored representation), which may include associating the captured representation with an audible descriptor. In another example, action module 4420 may be configured to execute a pre-defined action that includes detecting a barcode in the image data, decoding the barcode, and searching in a database (e.g., database 4430) for a product associated with the decoded barcode.

The disclosed embodiments may allow apparatus 110 to provide a triggered action function. The triggered action function may allow a user to interact with apparatus 110 such that feedback associated with objects is provided to the user. Further, the use of various triggers in causing apparatus 110 to execute a variety of pre-defined actions may allow for efficient and customized use of apparatus 110.

As is evident from the foregoing, apparatus 110 may provide a wide range of functionality. More specifically, in embodiments consistent with the present disclosure, apparatus 110 may capture image data that includes textual information and non-textual information disposed within a field-of-view of sensory unit 120, detect at least one trigger within the captured image data, identify a level break associated with the detected trigger within the textual information, and perform one or more actions that correspond to the detected trigger within a portion of the textual information associated with the level break.

In certain aspects, "textual information" consistent with the disclosed embodiments may include, but is not limited to, printed text, handwritten text, coded text, text projected onto a corresponding surface, text displayed to a user through a corresponding display screen or touchscreen, and any additional or alternate textual information appropriate to the user and to apparatus 110. Further, the "non-textual information" may include, but is not limited to, images of physical objects, images of persons, images of surroundings, and images of other non-textual objects disposed within the field-of-view of sensory unit 120.

In additional aspects, a "trigger" may include any information within the captured image data that causes apparatus 110 to perform the one or more actions on the corresponding portions of the textual information. For example, such a trigger may be associated with a desire of the user to hear textual information read aloud. In one embodiment, triggers consistent with the disclosed embodiments may include, but are not limited to images of a hand of the user, images of a finger of the user, images of an elongated object capable of being held and pointed by the user (e.g., a cane, a writing implement, a pointer, or a rod), and images of any additional or alternate object or appendage capable of being disposed within a field-of-view of sensory unit 120 by the user. In such instances, at least one of the triggers may correspond to a "pointing" trigger.

In additional embodiments, triggers consistent with the disclosed embodiments may also include images of pre-determined physical objects and individuals disposed within the captured image data. For example, apparatus 110 may be configured to perform one or more actions automatically upon detection of an image of an individual wearing a specific uniform (e.g., a firefighter, emergency medical technician (EMT), a police officer, a member of the military, or a flight attendant) within the captured image data.

Additionally or alternatively, triggers consistent with the disclosed embodiments may include one or images that collectively or individually identify an erratic movement of an object by the user of apparatus 110. For example, the detected trigger may represent one or more images that characterize a waving or shaking motion of a finger, hand, or other elongated object (e.g., a cane, a writing implement, a pointer, or a rod) by the user within a field-of-view of sensory unit 120.

In certain embodiments, at least one of the actions includes a text-based action performed on textual information located within the captured image data. By way of example, such test-based actions include, but are not limited to, optical character recognition (OCR) processes performed on portions of the textual information associated with the detected trigger, processes that generate audible representations of machine-readable text identified and retrieved from the textual information by the OCR processes, and various processes that summarize, process, translate, or store portions of the textual information and/or the machine-readable text.

In one embodiment, apparatus 110 may be configured to perform an action on a portion of the textual information associated with a trigger detected by apparatus 110 within captured image data. By way of example, the detected trigger may be associated with a position within the textual information, and as such, with an intermediate portion of the textual information disposed proximate to a "level break" within the textual information. In certain aspects, the term "level break" may refer to any discontinuity within the textual information, which includes, but is not limited to, a beginning or end of a sentence within the textual information, a beginning or end of a paragraph within the textual information, a beginning or end of a page of the textual information, and a beginning or end of a column of the textual information.

In such instances, the portion of the textual information associated with the detected trigger may be identified based on the level break. For example, the portion of the textual information associated with the detected trigger may corresponding to textual information disposed subsequent to the corresponding level break within the captured image data, prior to the corresponding level break within the captured image data, and/or disposed between the corresponding level break and one or more additional discontinuities within the textual data.

Figure 53:
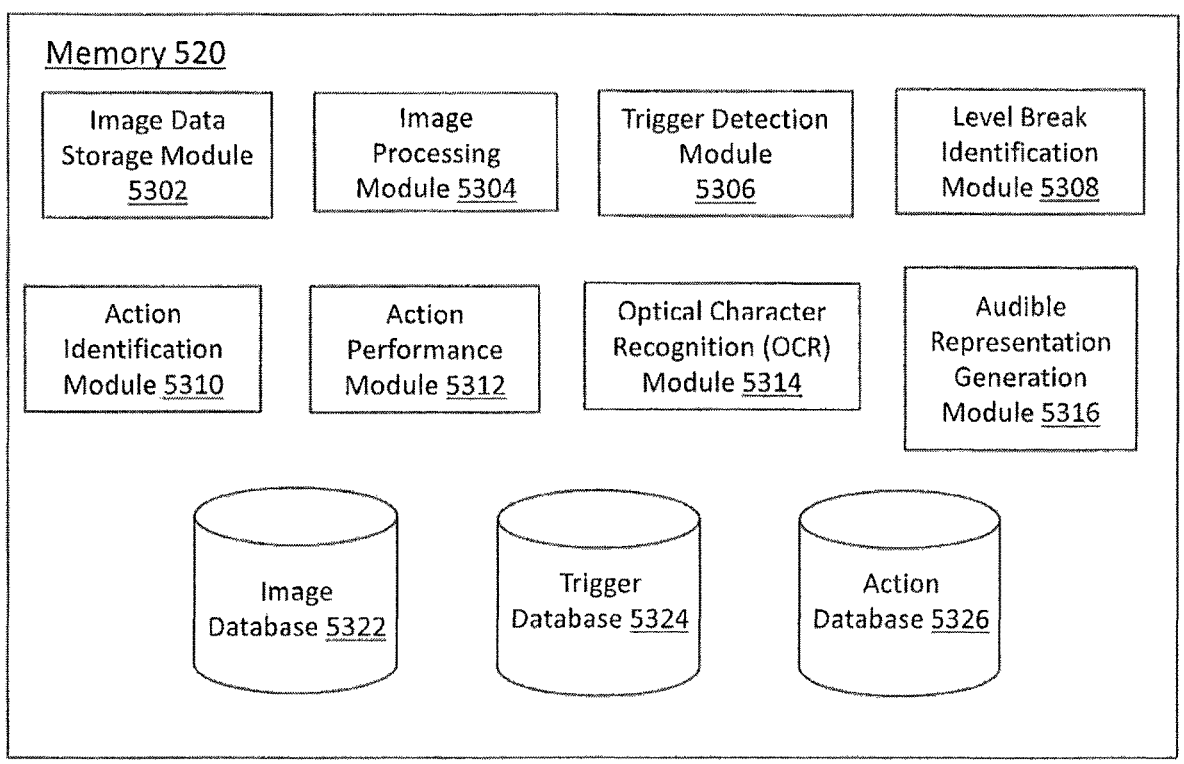
FIG. 53 illustrates an exemplary set of application modules and databases, according to disclosed embodiments.

In an embodiment, apparatus 110 may include a memory (e.g., memory 520) configured to store one or more applications and application modules that, when executed by a processor (e.g., processor 540), enable processor 540 to identify and perform at least one action based on a detection of one or more triggers within captured image data. In certain aspects, memory 520 may also be configured to store the captured image data and information associated with the captured image data. Additionally, memory 520 may store information that identifies one or more actions and further, information that links the one or more actions to corresponding triggers detectable by processor 540 within the captured image data. FIG. 53 illustrates an exemplary structure of memory 520, in accordance with disclosed embodiments.

In FIG. 53, memory 520 may be configured to store an image data storage module 5302, an image processing module 5304, and an image database 5322. In one embodiment, image data storage module 5302, upon execution by processor 540, may enable processor 540 to receive data corresponding to one or more images captured by sensory unit 120, and to store the captured image data within image database 5322. In some aspects, the captured image data may include textual information (e.g., printed, handwritten, coded, projected, and/or displayed text) and non-textual information (e.g., images of physical objects, persons, and/or triggers), and processor 540 may store the image data in image database 5322 with additional data specifying a time and/or date at which sensory unit 120 captured the image data. In additional embodiments, image data storage module 5302 may further enable processor 540 to configure wireless transceiver 530 to transmit the captured image data to one or more devices (e.g., an external data repository or a user's mobile device) in communication with apparatus 110 across a corresponding wired or wireless network.

In an embodiment, image processing module 5304, upon execution by processor 540, may enable processor 540 to process the captured image data and identify elements of textual information within the captured image data. In certain aspects, textual information consistent with the disclosed embodiments may include, but is not limited to, printed text (e.g., text disposed on a page of a newspaper, magazine, book), handwritten text, coded text, text displayed to a user through a display unit of a corresponding device (e.g., an electronic book, a television a web page, or an screen of a mobile application), text disposed on a flat or curved surface of an object within a field-of-view of apparatus 110 (e.g., a billboard sign, a street sign, text displayed on product packaging), text projected onto a corresponding screen (e.g., during presentation of a movie at a theater), and any additional or alternate text disposed within images captured by sensory unit 120.

In certain aspects, upon execution of image processing module 5304, processor 540 may perform a layout analysis of the image data to identify textual information within the captured image data. By way of example, processor 540 may perform a layout analysis to detect paragraphs of text, blocks of text, zones and/or regions that include text, logos, titles, captions, footnotes, and any additional or alternate portions of the image data that includes printed, handwritten, displayed, coded, and/or projected text.

Memory 540 may also be configured to store a trigger detection module 5306 and a trigger database 5324. In one embodiment, trigger detection module 5306 may, upon execution by processor 540, enable processor 540 to detect an existence of a trigger within the captured image data. In certain aspects, as described above, processor 540 may identify textual information within the captured data, and may execute trigger detection module 5306 to identify an existence of the trigger within the textual information. By way of example, processor 540 may access trigger database 5324 to obtain information identifying one or more candidate triggers, and processor 540 may leverage the candidate trigger information to detect the trigger within the captured image data.

In certain aspects, and as described above, the detected trigger may correspond to any information within the captured image data that causes apparatus 110 to perform one or more actions. By way of example, triggers consistent with the disclosed embodiments may include, but are not limited to, an image of a hand of the user, an image of a finger of the user, an image of an elongated object capable of being held and pointed by the user (e.g., a cane, a writing implement, a pointer, or a rod), and an image of any additional or alternate object or appendage capable of being disposed within a field-of-view of sensory unit 120 by the user.

Additionally or alternatively, triggers consistent with the disclosed embodiments may also include images of predetermined physical objects and specific individuals in uniform (e.g., a firefighter, emergency medical technician (EMT), a police officer, a member of the military, or a flight attendant). In additional aspects, triggers consistent with the disclosed embodiments may include one or more images that collectively or individually identify an erratic movement of an object by the user of apparatus 110. For example, the detected trigger may represent one or more images that characterize a waving or shaking motion of a finger, hand, or other elongated object (e.g., a cane, a writing implement, a pointer, or a rod) by the user within a field-of-view of sensory unit 120.

Referring back to FIG. 53, memory 520 may also be configured to store a level break identification module 5308. In an embodiment, level break identification module 5308 may, upon execution by processor 540, enable processor 540 to identify a level break that corresponds to the detected trigger. For example, a "level break" may represent any of a number of discontinuities within the textual information of the captured image data, which include, but are not limited to, a beginning or end of a sentence within the textual information, a beginning or end of a paragraph within the textual information, a beginning or end of a page of the textual information, and a beginning or end of a column of the textual information.

In certain aspects, the detected trigger may be associated with an intermediate portion of the textual information. By way of example, "intermediate portions" consistent with the disclosed embodiments may include, but are not limited to, a portion of a sentence disposed within the textual information, a portion of a paragraph disposed within the textual information, a portion of a page of the textual information, and a portion of a column of the textual information.

In certain embodiments, and upon execution of level break detection module 5308, processor 540 may assign a level break to the detected trigger based on the intermediate portion associated with the detected trigger. By way of example, if the determined intermediate portion falls within a particular paragraph of the textual information, processor 540 may identify a starting position of a successive paragraph as the level break for the detected trigger.

Additionally or alternatively, processor 540 may execute level break identification module 5308 to identify a discontinuity within the textual information disposed proximate to the intermediate portion as the level break for the detected trigger. For example, processor 540 may compute displacements between the identified level breaks and the intermediate portion of the detected trigger, and may assign the level break associated with a minimum of the displacements to the detected trigger.

Further, in an embodiment, the intermediate portion of the detected trigger may be disposed equidistant between two of the identified level breaks within the textual information. In such an instance, processor 540 may obtain contextual information associated with a user of apparatus 110 to determine which of the equidistant level breaks should be assigned to the detected trigger. By way of example, the contextual information may include information identifying a history of prior relationships between detected triggers and selected level breaks, prior documents browsed by the user, and any additional or alternate information appropriate to the user and to the captured image data.

Image data storage module 5302, image processing module 5304, trigger detection module 5306, level break identification module 5308, action identification module 5310, action performance module 5312, OCR module 5314, and audible representation module 5316 may be implemented in software, hardware, firmware, a mix of any of those, or the like. For example, if the modules are implemented in software, they may be stored in memory 520, as shown in FIG. 53. Other components of processing unit 140 and/or sensory unit 120 may be configured to perform processes to implement and facilitate operations of image data storage module 5302, image processing module 5304, trigger detection module 5306, level break identification module 5308, action identification module 5310, action performance module 5312, OCR module 5314, and audible representation module 5316. Thus, image data storage module 5302, image processing module 5304, trigger detection module 5306, level break identification module 5308, action identification module 5310, action performance module 5312, OCR module 5314, and audible representation module 5316 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., image data storage module 5302, image processing module 5304, trigger detection module 5306, level break identification module 5308, action identification module 5310, action performance module 5312, OCR module 5314, and audible representation module 5316) may each include dedicated sensors (e.g., IR, image sensors, etc.) and/or dedicated application processing devices to perform the functionality associated with each module.

Figure 54B:
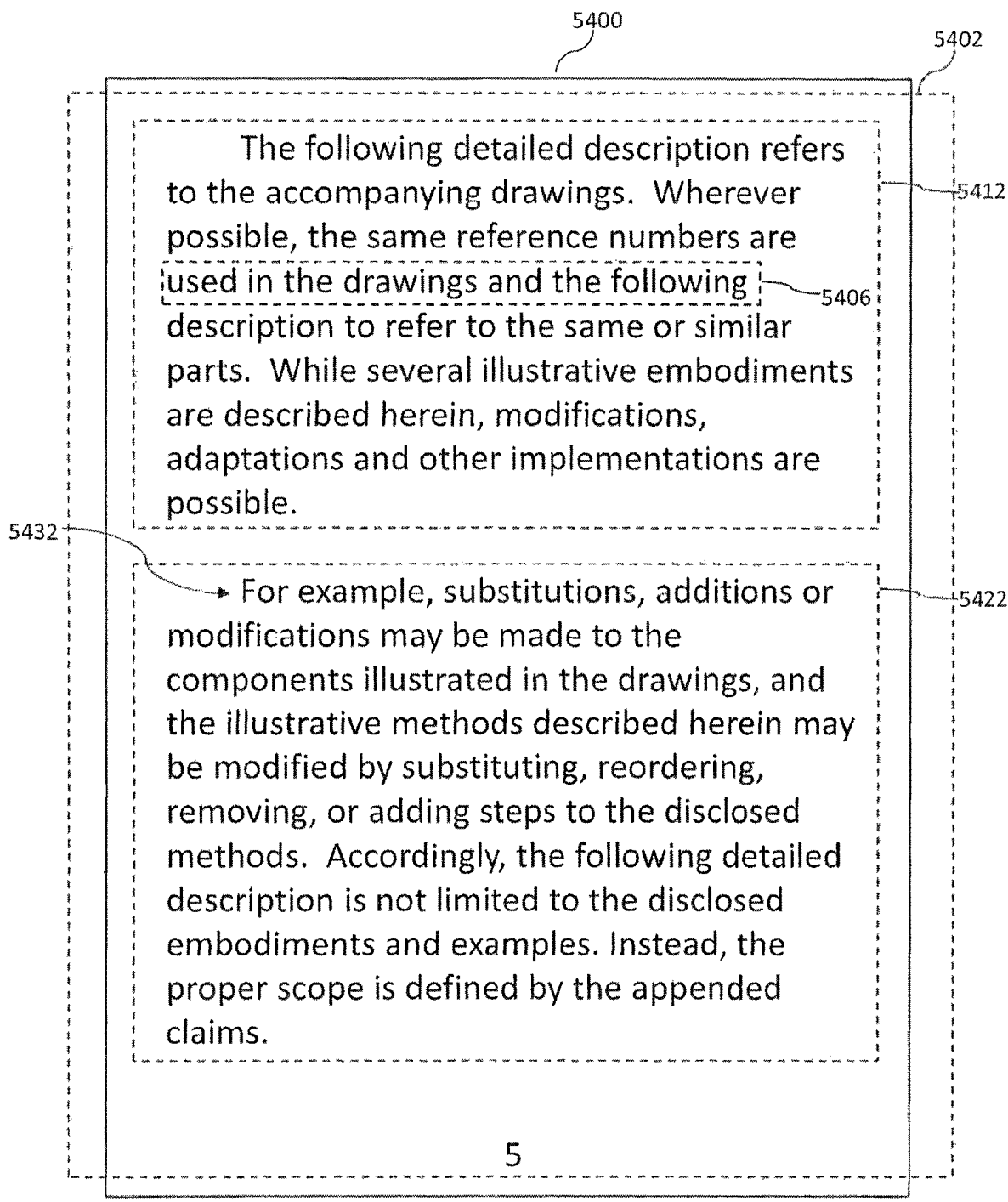

FIGS. 54A-54F illustrate exemplary level breaks disposed within corresponding textual information, according to disclosed embodiments. By way of example, as illustrated in FIG. 54A, a user of apparatus 110 may view a page 5400 of a printed newspaper, and may position a finger or other elongated object (e.g., a cane, a pointer, or a writing instrument) over a portion of the printed newspaper to serve as a trigger. Apparatus 110 may capture an image that includes a portion 5402 of page 5400 and an image 5404 of the finger or other elongated object.

As described above, processor 540 may execute image processor module 5304 to identify textual information within the captured image data, and further, may execute trigger detection module to detect an image of the trigger (e.g., image 5404) and identify an intermediate portion of the textual information that corresponds to image 5404. For example, as illustrated in FIG. 54B, the captured image data may include a single column of text that includes paragraphs 5412 and 5422, and the detected trigger (not shown) may be associated with an intermediate portion 5406 disposed within paragraph 5412. In one embodiment, processor 540 may, upon execution of level break identification module 5308, identify a discontinuity 5432 corresponding to a starting position of paragraph 5422, and select discontinuity 5432 as a level break associated with the detected trigger.

Figure 54C:
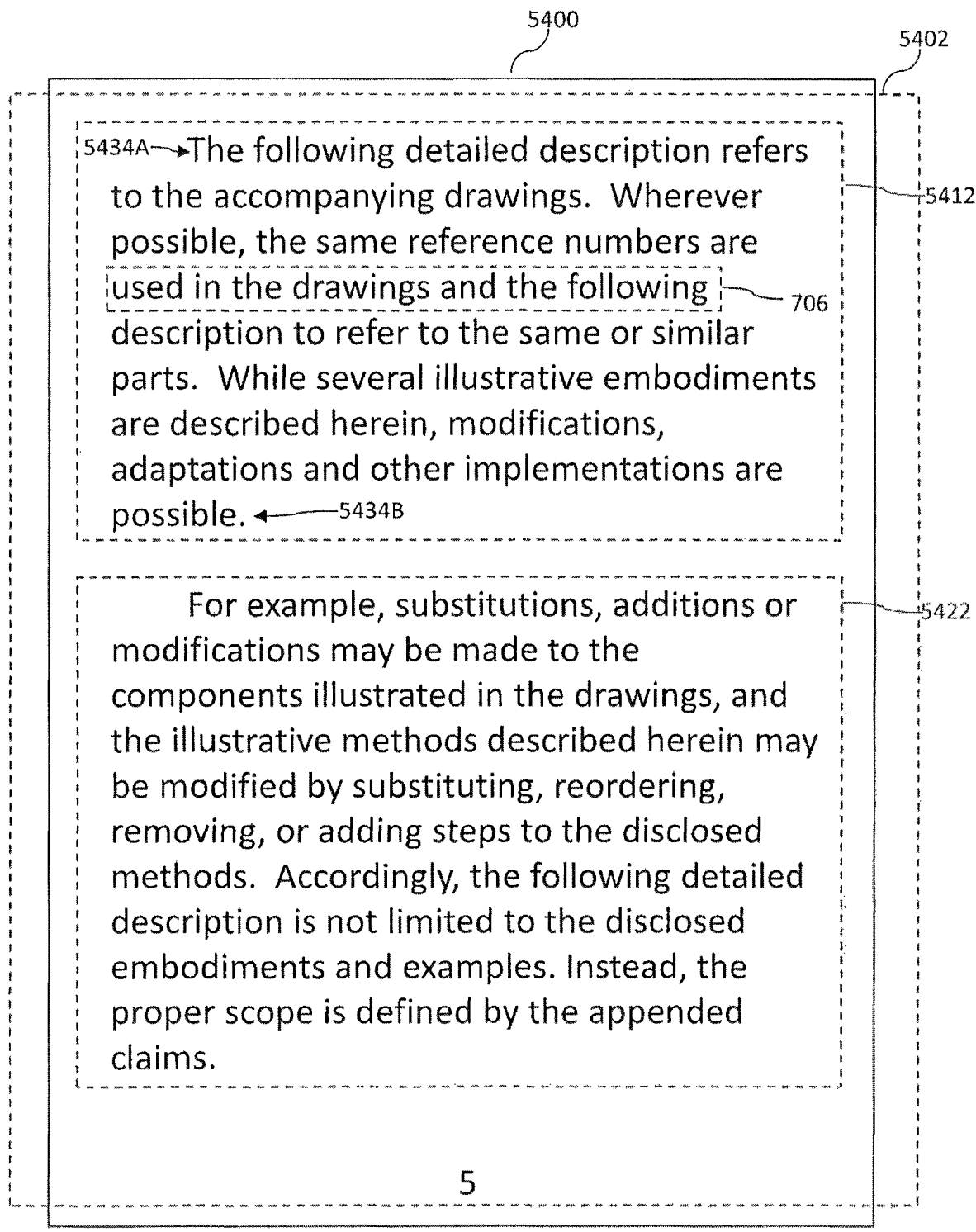

The disclosed embodiments are, however, not limited to the selection of level breaks that correspond to starting positions within subsequent paragraphs. For example, as illustrated in FIG. 54C, processor 540 may execute level break identification module 5308 to identify discontinuities 5434A and 5434B that correspond to a starting position and ending position of paragraph 5412. Depending on displacements between intermediate portion 5406 and corresponding ones of discontinuities 5434A and 5434B, processor 540 may select one of discontinuities 5434A and 5434B as the level break associated with the detected trigger. For example, processor 540 may select as the level break a corresponding one of discontinuities 5434A and 5434B associated with a minimum of the displacements.

Figure 54D:
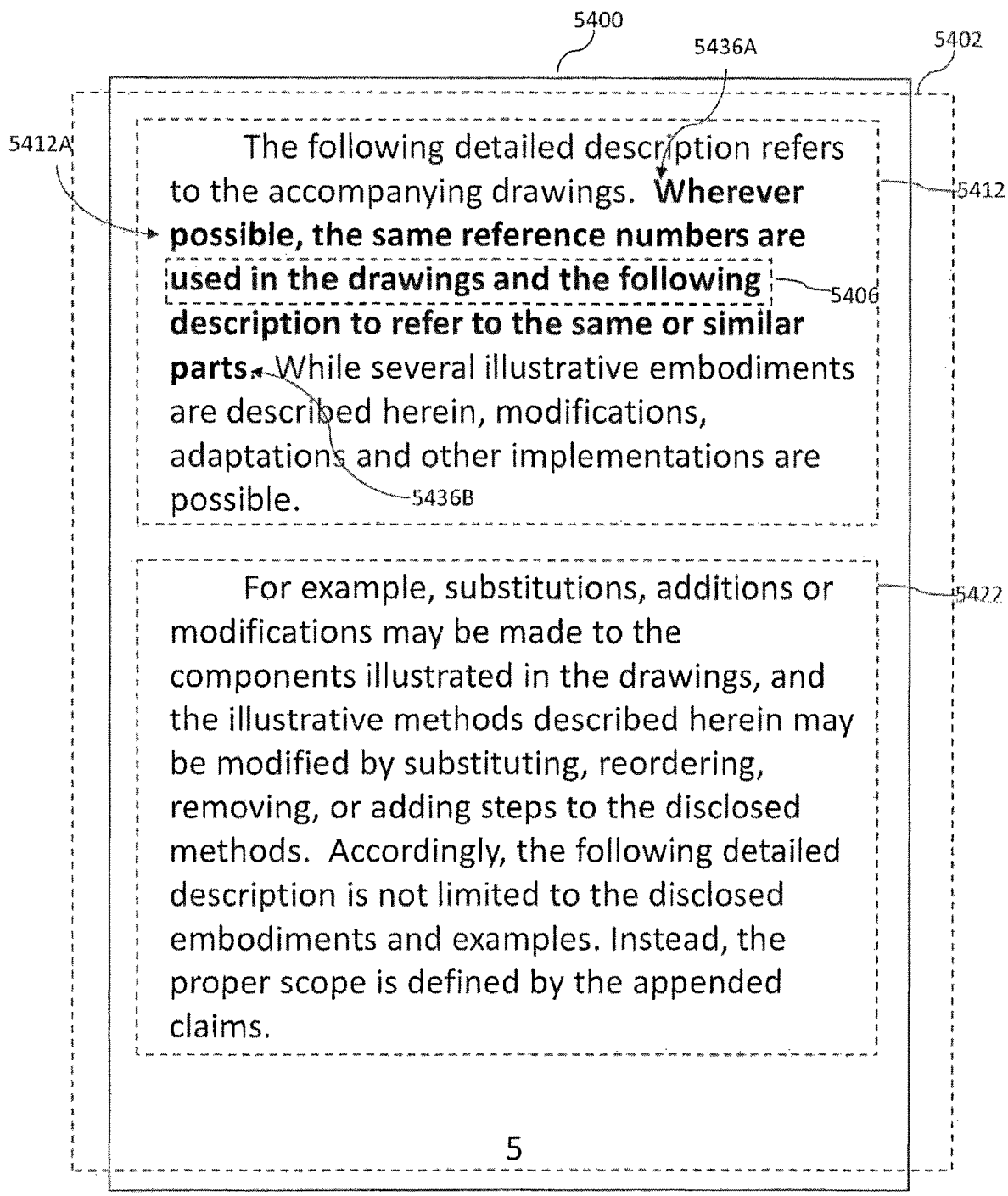

In other embodiments, illustrated in FIG. 54D, processor 540 may determine that intermediate portion 5406 is disposed within a sentence 5412A of paragraph 5412. Processor 540 may execute level break identification module 608 to identify discontinuities 5436A and 5436B that correspond to a starting position and ending position of sentence 5412A within paragraph 5412. As described above, processor 540 may select one of discontinuities 5436A and 5436B as the level break associated with the detected trigger.

Figure 54E:
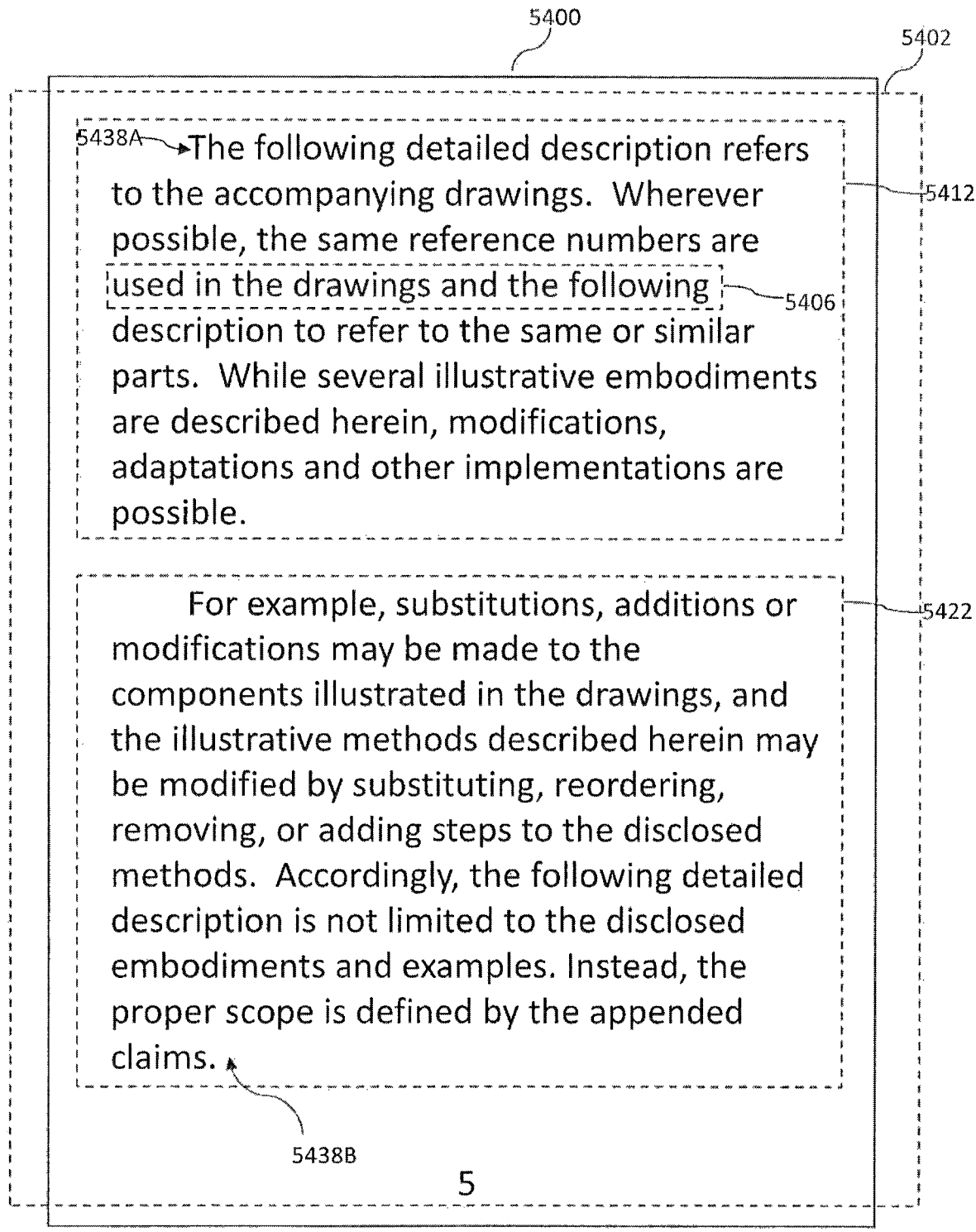

Further, in some embodiments, processor 540 may select level breaks that correspond to discontinuities located at a beginning or end of a page of the textual information. As illustrated in FIG. 54E, processor 540 may execute level break identification module 5308 to identify discontinuities 5438A and 5438B located at a beginning of page 5400 and at an end of page 5400. In such instances, processor 540 may select one or discontinuities 5438A and 5438B as the level break associated with the detected trigger.

Figure 54F:
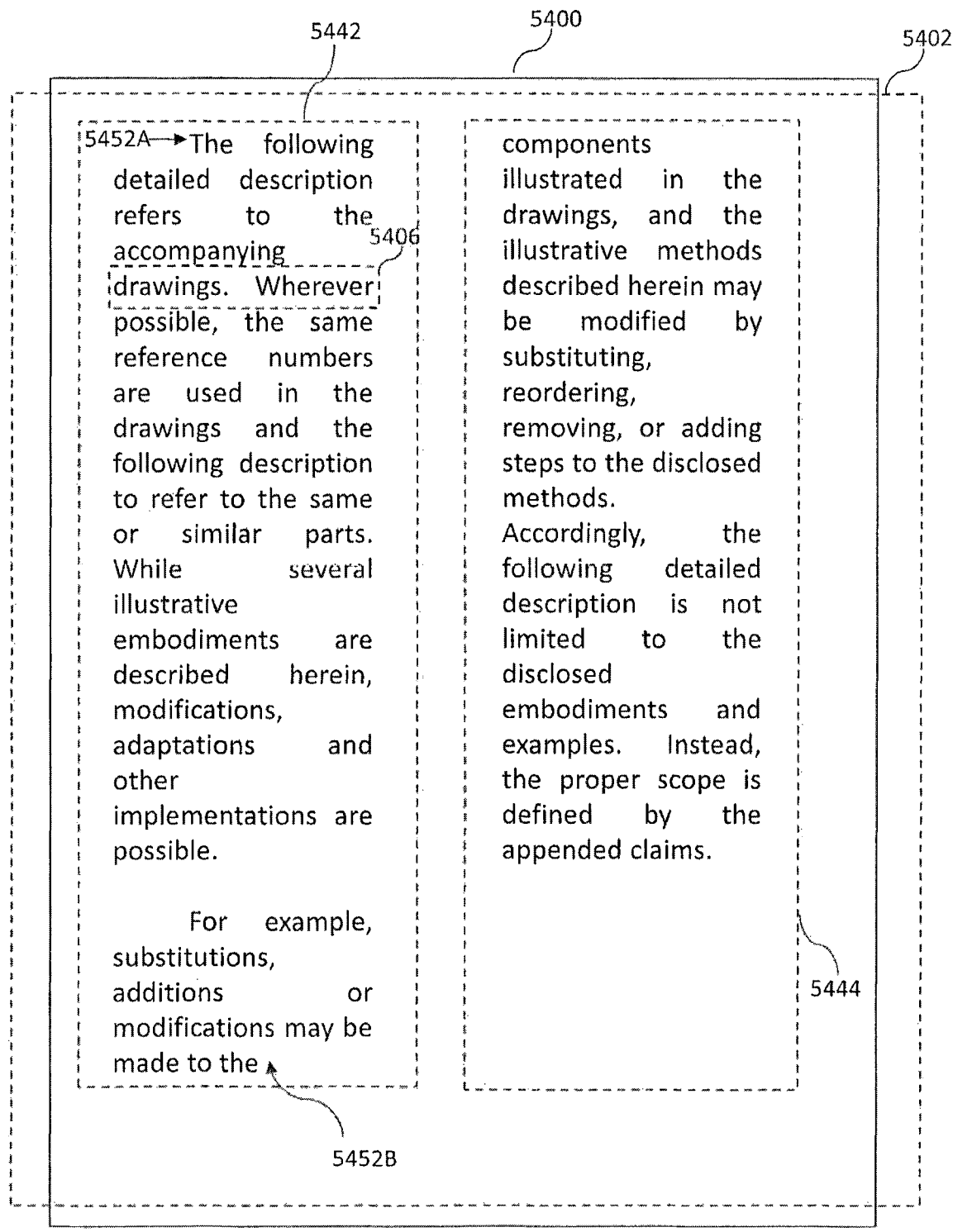

Further, in additional embodiments, the captured image data may include textual information disposed within two or more columns on page 5400. For example, as illustrated in FIG. 54F, the captured image data may include columns 5442 and 5444 of text disposed side-by-side along a longitudinal axis of page 5400, and the detected trigger (not shown) may be associated with intermediate portion 5406 disposed within column 5442. Processor 540 may execute level break identification module 5308 to identify discontinuities 5452A and 5452B located at a beginning of column 5442 and at an end of column 5442. In such instances, processor 540 may select one or discontinuities 5452A and 5452B as the level break associated with the detected trigger.

Referring back to FIG. 53, memory 520 may also be configured to store an action identification module 5310 and an action database 5326. In an embodiment, action database 5326 may be configured to store action information that identifies one or more actions, and further, links the actions to corresponding triggers. In one aspect, the action information may link a trigger to a single action to be performed by processor 540. In other aspects, however, the action information may link a plurality of discrete actions to a corresponding one of the triggers, and further, may identify a sequence in which processor 540 may perform the plurality of discrete actions in response to a detection of the corresponding trigger within the captured image data.

As described above, actions consistent with the disclosed embodiments may include text-based actions performed on textual information located within the captured image data. By way of example, such test-based actions include, but are not limited to, optical character recognition (OCR) processes performed on textual information associated with the detected trigger, processes that generate audible representations of machine-readable text identified and retrieved from the textual information by the OCR processes, and various processes that summarize, process, translate, or store portions of the textual information and/or the machine-readable text.

Further, upon execution of action identification module 5310, processor 540 may identify an action that corresponds to a trigger detected within the captured image date (e.g., as detected through the execution of trigger detection module 5306). In certain aspects, processor 540 may, upon execution of action identification module 5310, access action database 5326 and obtain action information linking the detected trigger to one or more corresponding actions. Based on the obtained action information, processor 540 may identify the action corresponding to the detected trigger.

Memory 520 may further be configured to store an action performance module 5312, an optical character recognition (OCR) module 5314, and an audible representation generation module 5316. As described above, processor 540 may execute level break identification module 5308 to identify a level break within the textual information, and may execute action identification module 5310 to identify one or more actions that correspond to the detected trigger. In an embodiment, action performance module 5312 may, upon execution by processor 540, enable processor 540 to initiate a performance of the one or more identified actions on a portion of the textual information located proximate to the identified level break. By way of example, and as described above, actions consistent with the disclosed embodiments include, but are not limited to, optical character recognition (OCR) processes that identify and retrieve machine-readable text from the textual information, processes that generate audible representations of machine-readable text, and various processes that summarize, process, translate, or store portions of the textual information and/or the machine-readable text.

In an embodiment, OCR module 5314 may, upon execution by processor 540, enable processor 540 to perform one or more OCR processes on the textual information. By way of example, processor 540 may execute OCR module 5306, either independently or in conjunction with action performance module 5312, to identify and retrieve machine-readable text from portions of the textual information disposed prior to or subsequent to the identified level break.

Audible representation generation module 5306 may, upon execution by processor 540, enable processor 540 to generate an audible representation of at least a portion of the machine-readable text, which apparatus 110 may present to the user through a speaker or a bone conduction headphone associated with processing unit 140. In an embodiment, processor 540 may execute OCR module 5314 and audible representation generation module 5316 sequentially such that processor 540 generates the audible representation of the machine-readable text upon completion of the OCR processes performed by OCR module 5314.

In additional embodiments, processor 540 may execute of audible representation generation module 5316 at a pre-determined time (e.g., one second, three second, or four seconds) after executing OCR module 5314. In such instances, processor 540 may be configured to generate and present to the user an audible representation of an initial portion of machine-readable text while concurrently executing OCR module 5314 to identify and retrieve subsequent portions of machine-readable text.

Further, in certain embodiments, processor 540 may selectively suspend and resume a performance of an action in response to more pre-determined actions taken by a user of apparatus 110. In one aspect, processor 540 may suspend the performance of the action on the textual information (e.g., an audible presentation of machine-readable text corresponding to the textual information) when the user looks away from the textual information. For example, during performance of the identified action, sensory unit 120 may continue to capture image data within a corresponding field-of-view, and may continuously provide the captured image data to processing unit 140 for storage within image database 5322.

In one aspect, and upon execution of action performance module 5312, processor 540 may monitor the newly-received captured image data to determine whether the user looks away from the textual information (e.g., through a corresponding change in the field-of-view of sensory unit 120). If processor 540 determines that the user no longer views at least a portion of the textual information, processor 540 may suspend the performance of the action (e.g., the audible presentation) and identify a position within the textual information that corresponds to the suspension (e.g., a stopping point). In certain embodiments, processor 540 may continue to monitor the captured image data to determine whether the user looks back to the textual information. If the user looks back to the textual information, processor 540 may resume the performance of the identified action (e.g., the presentation of the audible representation) from the identified stopping point.

In additional embodiments, processor 540 may suspend a performance of an identified action in response to a detection of an additional trigger within the captured image data. By way of example, as described above, processor 540 may execute various software modules to identify a first trigger within the captured image data, identify a first level break associated with the first trigger, and identify and perform a first action that corresponds to the first trigger on a portion of the textual information corresponding to the first level break. In certain aspects, processor 540 may continue to monitor image data captured by sensory unit 120 while performing the first action, and may detect an existence of a second trigger within the newly captured image data. Upon detection of the second trigger, processor 504 may suspend a performance of the first action, and may identify a second level break and a second action that corresponds to the second trigger. Processor 540 may perform the second action on a portion of the textual information corresponding to the second level break.

In other embodiments, image database 5322, trigger database 5324, and/or action database 5326 may be located remotely from memory 520, and be accessible to other components of apparatus 110 (e.g., processing unit 140) via one or more wireless connections (e.g., a wireless network). While multiple databases are shown, it should be understood that image database 5322, trigger database 5324, and action database 5326 may be combined and/or interconnected databases may make up the databases. Image database 5322, trigger database 5324, and/or action database 5326 may further include computing components (e.g., database management system, database server, etc.) configured to receive and process requests for data stored in associated memory devices.

Figure 55:
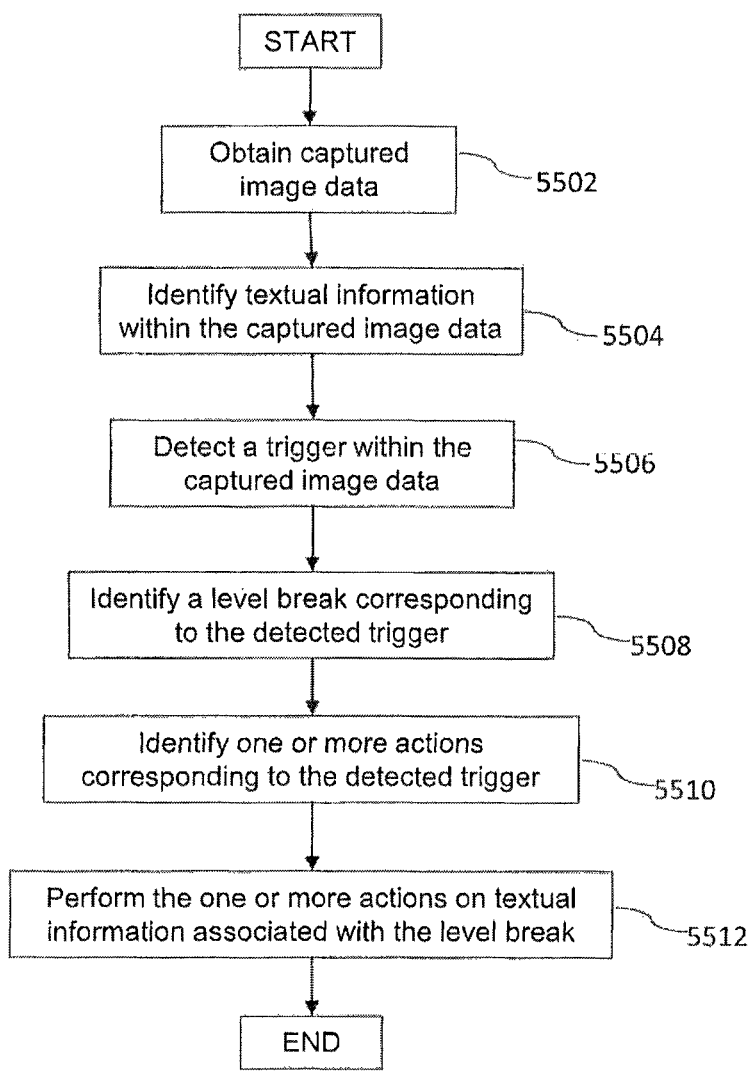
FIG. 55 is a flow diagram of an exemplary process for identifying and performing actions based on captured image data, according to disclosed embodiments.

FIG. 55 is a flow diagram of an exemplary process 5500 for identifying and performing actions on captured image data, according to disclosed embodiments. As described above, sensory unit 120 may capture image data that includes textual information and non-textual information disposed within a corresponding field-of-view. Processing unit 130 may receive the captured image data, and processor 540 may execute one or more application modules to detect a trigger within the captured data, identify one or more actions associated with the detected trigger, and initiate a performance of the one or more actions on the textual information within the captured image data. Process 5500 provides further details on how processor 540 identifies and performs one or more actions based on triggers included within the captured image data.

In step 5502, processor 540 may obtain captured image data. In some aspects, sensory unit 120 may capture one or more images, and the captured image data may be transmitted to processing unit 140 across wired or wireless communications link 130. Processor 540 may, in step 5502, obtain the captured image data directly from sensory module 120 across communications link 130, or alternatively, processor 540 may retrieve the captured image data from a corresponding data repository (e.g., image database 5322 of memory 540). By way of example, the captured image data may include one or more regions of printed, displayed, or projected information.

In step 5504, processor 540 may analyze the captured image data to identify the textual information. As described above, the textual information may include, but is not limited to, printed, handwritten, projected, coded, or displayed text, and processor 540 may perform a layout analysis to detect the textual information within the captured image data. By way of example, the detected textual information may include, but are not limited to, paragraphs of text, blocks of text, regions and/or zones that include text, logos, titles, captions, footnotes, and any additional or alternate portions of the captured image data that includes printed, handwritten, displayed, coded, and/or projected text.

In step 5506, processor 540 may leverage image processing techniques to detect an image of a trigger within the captured image data. In certain aspects, and as described above, the detected trigger may include, but is not limited to an image of a hand of a user of apparatus 110, an image of a finger of the user, an image of an elongated object capable of being held and pointed by the user (e.g., a cane, a writing implement, a pointer, or a rod), and images of any additional or alternate object or appendage capable of being disposed within a field-of-view of sensory unit 120 by the user. In additional aspects, triggers consistent with the disclosed embodiments may also include an image of a pre-determined physical object, an image of a specific individual in uniform (e.g., a firefighter, emergency medical technician (EMT), a police officer, a member of the military, or a flight attendant), and additionally or alternatively, a collection of images that identify an erratic movement of an object by the user.

Processor 540 may also identify an intermediate portion within the textual information that corresponds to the detected trigger in step 5506. In certain aspects, the intermediate portion may be disposed within a structured element of the textual information, such as a sentence, a paragraph, a page, or a column of textual information. Further, in some aspects, the intermediate portion corresponding to the detected trigger may be associated with a corresponding position within the captured image data.

Referring back to FIG. 55, in step 5508, processor 540 may identify a level break that corresponds to the detected trigger. As described above, the identified level break may represent any of a number of discontinuities within the identified textual information, which include, but are not limited to, a beginning or end of a sentence within the textual information, a beginning or end of a paragraph within the textual information, a beginning or end of a page of the textual information, and a beginning or end of a column of the textual information.

In one embodiment, processor 540 may analyze the identified textual information to identify a plurality of discontinuities, and may select one of the discontinuities as the level break in step 5508 based on a relationship between the selected discontinuity and the intermediate portion corresponding to the detected trigger. For example, processor 540 may select one of the identified discontinuities disposed proximate to the intermediate portion as the level break in step 5508. Additionally or alternatively, processor 540 may compute displacements between the identified discontinuities and the position associated with the intermediate portion in step 5508, and may select that discontinuity associated with a minimum of the displacements as the level break.

Additionally or alternatively, processor 540 may determine in step 5508 that the intermediate portion falls within a particular paragraph of the textual information. In such an instance, processor 540 may select a starting position of a subsequent paragraph as the level break associated with detected trigger. Further, processor 540 may determine in step 5508 that the intermediate portion falls within a particular sentence of the textual information, and may select a starting position of a subsequent sentence as the level break associated with detected trigger.

In some embodiments, processor 540 may determine that the intermediate portion falls equidistant between two discontinuities within the textual information. In certain embodiments, processor 540 may obtain contextual information related to one or more of the user of apparatus 110 or an object or document associated with the captured image data to infer the user's intentions and select a corresponding one of the discontinuities as the level break. By way of example, the contextual information may include information identifying a history of prior relationships between detected triggers and selected level breaks, prior documents browsed by the user, and any additional or alternate information appropriate to the user and to the captured image data.

Referring back to FIG. 55, processor 540 may identify one or more actions that correspond to the detected trigger in step 5510. In some aspects, as described above, processor 540 may access a corresponding data repository (e.g., action database 5326 of memory 520) to obtain action information that links the detected trigger to at least one predetermined action. Processor 540 may, in such instances, identify the one or more actions based on the obtained action information.

In an embodiment, the obtained information may link the detected trigger to a single action, which processor 540 may identify in step 5510. In other embodiments, the obtained action information may link the detected trigger to a plurality of discrete actions. By way of example, the obtained action information may link the detected trigger to a first process (e.g., an OCR process) and to a second process (e.g., a process that generates and presents an audible representation of machine-readable text to a user of apparatus 110). Further, the obtained action information may indicate an order in which processor 540 should execute the plurality of discrete actions. For example, in step 5510, processor 540 may determine that the detected trigger is associated with a first action and a second action that should be executed at a predetermined after an execution of the first action (e.g., a process that generates an audible representation should be executed by processor 540 at a predetermined time after executing an OCR process).

In certain aspects, actions consistent with the disclosed embodiments include various OCR processes, processes that generate an audible representation of portions of machine-readable text (e.g., as identified and retrieved by one or more of the OCR processes), and processes that present the audible representation to the user. In additional aspects, actions consistent with the disclosed embodiments may include other text-based actions, such as processes that summarize, process, translate, or store portions of the textual information and/or the machine-readable text.

In further embodiments, processor 540 may identify at least one action in step 5510 that corresponds to a manipulation of portions of machine-readable text. For example, a detected trigger may be associated with a first OCR process that retrieves text corresponding to denominations of paper currently, and a second process that computes a sum of the various denominations, which may be audibly presented to a user of apparatus 110.

In step 5512, processor 540 may identify a portion of the textual information associated with the identified level break (e.g., the level break associated with the detected trigger), and perform the one or more actions on the identified portion of the textual information. In an embodiment, the identified portion of the textual information may be disposed subsequent to the identified level break within the document or object associated with the captured image data. For example, the level break may correspond to a starting position of a paragraph within a page of textual information, and the portion of the textual information identified by processor 540 may include textual information disposed below the level break on the page. The disclosed embodiments are, however, not limited to portions of textual information disposed subsequent to a level break, and in additional embodiments, processor 540 may perform the one or more actions on portions of textual information disposed above the level break, or located at positions within the captured image data having any relation to the level break appropriate to the captured image data and the one or more actions. Upon performance of the one or more actions in step 5512, exemplary process 5500 is complete.

In some embodiments, as described above, processor 540 may identify a plurality of actions linked to the detected trigger. For example, processor 540 may determine in step 5510 that the detected trigger is linked to a first action that includes an OCR process, and a second action that includes a process for generating and presenting an audible representation of machine-readable text. In certain aspects, as described below in reference to FIG. 56, processor 540 may initiate and execution of the OCR process, and subsequently execute the process for generating and presenting the audible representation at a predetermined time after executing the OCR process, but prior to a completion of the OCR process. In such instances, processor 540 may cause apparatus 110 to present the audible representation of an initial portion of machine-readable text while the executed OCR process continues to identify and retrieve subsequent portions of machine-readable text.

Figure 56:
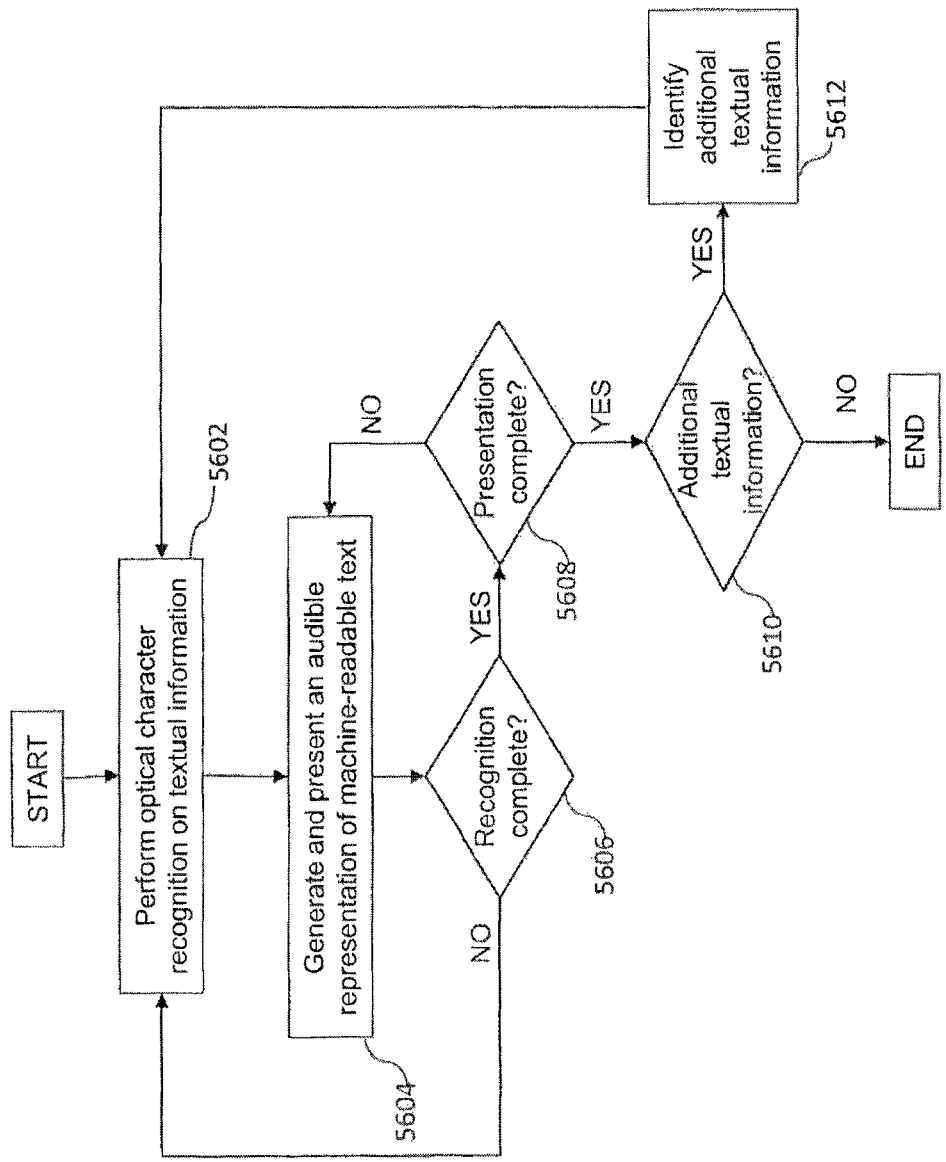
FIG. 56 is a flow diagram of an exemplary process for performing multiple actions based on captured image data, according to disclosed embodiments.

FIG. 56 is a flow diagram of an exemplary process 5600 for performing multiple actions based on captured image data, according to disclosed embodiments. As described above, processor 540 may detect a trigger within captured image data (e.g., step 5506 of FIG. 55), may identify a level break corresponding to the detected trigger (e.g., step 5508 of FIG. 55), and may identify and perform one or more actions that correspond to the detected trigger within a portion of textual information associated with the level break (e.g., steps 5508 and 5510 of FIG. 55). In certain embodiments, the one or more actions may include a first action corresponding to an OCR process and a second action corresponding to a process that generates and presents an audible representation of machine-readable text to a user of apparatus 110. Process 5600 provides further details on how processor 540 performs an OCR process, which identifies and retrieves machine-readable text from textual information, concurrently with a process that generates and presents an audible representation of the machine-readable text to the user.

In step 5602, processor 540 may perform an OCR process on textual information included within captured image data to identify and retrieve machine-readable text. As described above, sensory unit 120 may capture one or more images, and the captured image data may be transmitted to processing unit 140 across wired or wireless communications link 130. Processor 540 may obtain the captured image data (e.g., step 5502 of FIG. 55) may analyze the captured image data to identify portions of the captured image data that include the textual information (e.g., step 5504 of FIG. 55), may detect an image of a trigger within the captured image data (e.g., step 5506 of FIG. 55), and may identify a level break within the textual information that corresponds to the detected trigger (e.g., step 5508 of FIG. 55). In such embodiments, processor 540 may perform the OCR process on a portion of the textual information that is associated with the identified level break (e.g., textual information disposed below the level break within the captured image data).

In step 5604, processor 540 may generate an audible representation of at least a portion of the machine-readable text identified and retrieved by the executed OCR process, and configure apparatus 110 to present the generated audible representation to the user through a speaker or a bone conduction headphone associated with processing unit 140. In one embodiment, processor 540 may initiate the presentation of the audible representation in step 5604 prior to completing the OCR process initiated in step 5602. In such instances, processor 540 may identify and retrieve machine-readable text from a subset of the textual information associated with the identified level break before causing apparatus 110 to present the audible representation to the user.

In certain aspects, processor 540 may cause apparatus 110 to present the generated audible presentation in step 5604 within a predetermined time period after initiating the OCR process in step 5602. By way of example, predetermined time periods consistent with the disclosed embodiments may include, but are not to, one second, three second, and four seconds.

In step 5606, processor 540 may determine whether the OCR process initiated in step 5602 is complete (e.g., that processor 540 identified and retrieved machine-readable text from the entire identified portion of the textual information). If processor 504 determine that the OCR process is incomplete (e.g., step 5606; NO), then processor 540 may continue to perform the OCR process on the textual information associated with the identified level break. In such an instance, processor 540 may cause apparatus 110 to present an audible representation of an initial portion of machine-readable text while concurrently executing the OCR process to identify and retrieve addition portions of machine-readable text.

If, however, processor 540 determines that the OCR process is complete (e.g., step 5606; YES), processor 540 may determine in step 5608 whether apparatus 110 completes the audible presentation of the machine-readable text (e.g., that processor 540 caused apparatus 110 to present an audible representation of the machine-readable text in its entirety). If processor 540 determines that the audible presentation is incomplete (e.g., step 5608; NO), processor 540 may cause the processor to continue presenting the audible representation of the machine-readable text in step 5604.

Alternatively, if processor 540 determines that apparatus 110 completed the audible presentation of the machine-readable text (e.g., step 5608; YES), processor 540 determines in step 5610 whether additional textual information requires OCR processing. If processor 540 determines that no additional portions of the textual information require OCR processing (e.g., step 5610; NO), then exemplary process 5600 is complete.

If, however, processor 540 determines that additional textual information requires OCR processing (e.g., step 5610; YES), then processor 540 may identify one or more additional portions of the textual information for processing in step 5612. In some embodiments, processor 540 may select the additional portions of the textual information in step 5612 based on one or more portions of the previously retrieved machine-readable text.

In certain aspects, processor 540 may associate the identified level break with several paragraphs may be disposed below the level break within the textual information, and processor 540 may have performed the OCR processor on only a subset of the paragraphs in step 5602. In such an instance, processor 540 may determine that additional textual information require OCR processing in step 5610, and may select one or more of the remaining paragraphs associated with the level break for OCR processing in step 5612. Upon selection of the additional portions of the textual information in step 5612, exemplary process 5600 passes back to step 5602, and processor 540 performs the OCR process on the selected additional portions of the textual information, as described above.

Using the disclosed embodiments, processor 540 may detect a trigger within captured image data, identify textual information within the captured image data that is associated with the detected trigger, and automatically identify and perform one or more actions corresponding to the detected trigger on the identified textual information. For example, a user of apparatus 110 may point to a particular paragraph within a first newspaper article, and processor 540 may perform an OCR process to identify and retrieve machine-readable text within the first newspaper article, and cause apparatus 110 to present an audible representation of the machine-readable text to the user.

During the audible presentation of the machine-readable text, processor 540 may receive and analyze data corresponding to one or more additional images captured by sensory unit 120. At some point during the audible presentation, processor 540 may detect an additional trigger within the captured image data. For example, the user may look at an additional article within the newspaper, and may point to a headline associated with the additional article. In such instances, processor 540 may suspend the audible presentation, may initiate a second OCR process to identify and retrieve machine-readable text from the additional newspaper article, and may cause apparatus 110 to begin an audible presentation of the newly retrieved machine-readable text.

Figure 57:
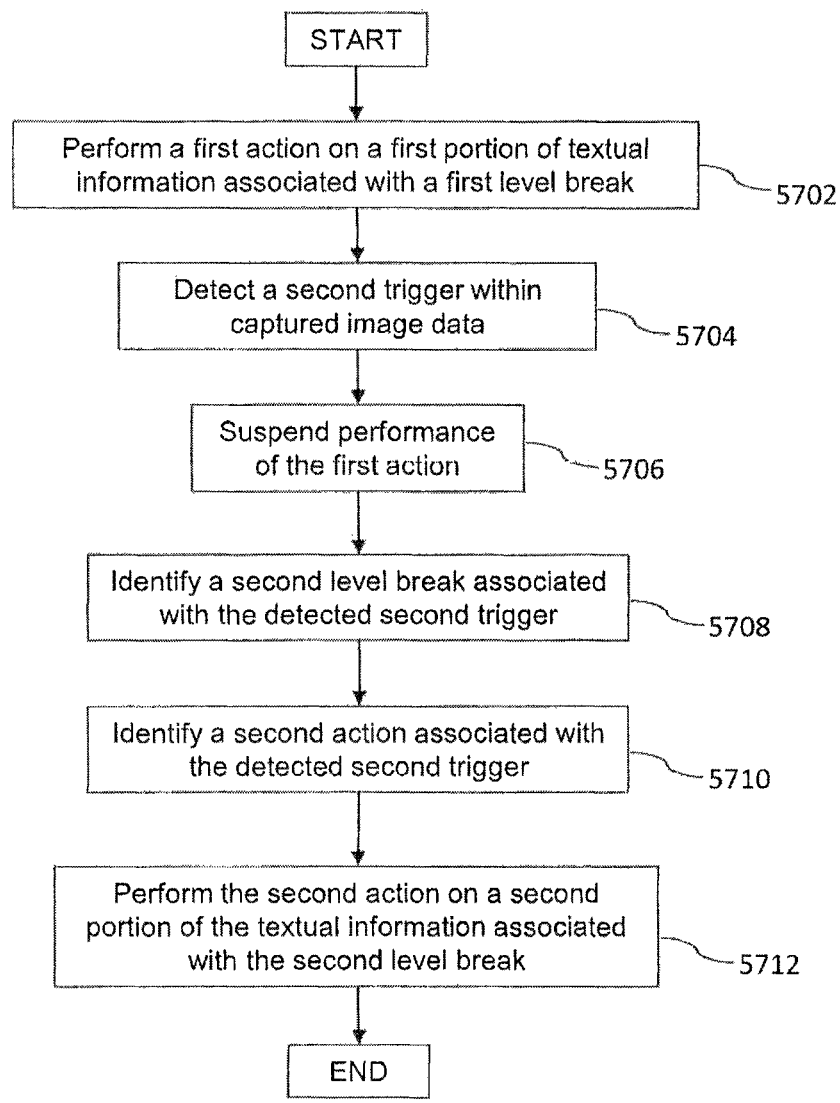
FIG. 57 is a flow diagram of an exemplary process for adaptively performing actions based on captured image data, according to disclosed embodiments.

FIG. 57 illustrates an exemplary process 5700 for adaptively performing actions on textual information within captured image data, according to disclosed embodiments. As described above, sensory unit 120 may capture image data that includes textual information and non-textual information disposed within a corresponding field-of-view. Processing unit 140 may receive the captured image data, and processor 540 may execute one or more application modules to identify textual information within the captured image data (e.g., step 5504 of FIG. 55), detect a first trigger within the captured image data (e.g., step 5506 of FIG. 55), identify a first level break within the textual information based on the detected trigger (e.g., step 5508 of FIG. 55), and perform one or more first actions that correspond to the detected trigger within a first portion of textual information associated with the first level break (e.g., steps 5510 and 5512 of FIG. 55). Process 5700 provides further details on how processor 540 identifies and performs one or more second actions on a second portion of the textual information in response to a detection of a second trigger within the captured image data.

In step 5702, processor 540 may perform the one or more first actions on the first portion of the textual information. As described above, processor 540 may detect an existence of the first trigger within the textual information of the captured image data. Based on a first intermediate portion of detected first trigger within the textual information, processor 540 may identify the first level break, which may be associated with the corresponding first portion of the textual information. Further, and as described above, processor 540 may access a corresponding data repository (e.g., action database 5326), and obtain action information that may enable processor 540 to identify the one or more first actions based on an association with the detected first trigger.

In an embodiment, the one or more first actions may include an OCR process performed on the first portion of the textual information to identify and retrieve machine-readable text, and a process that generates and causes apparatus 110 to present to a user an audible representation of at least a portion of the machine-readable text. The disclosed embodiments are, however, not limited to such exemplary actions, and in further embodiments, at least one of the first actions may include, but is not limited to, actions that summarize, process, translate, manipulate, or store portions of the machine-readable text.

As described above, processor 540 may receive and analyze additional image data captured by sensory unit 120 during a performance of the one or more first actions in step 5704. In step 5704, processor 540 may detect an existence of a second trigger within the additional captured image data, and further, may determine a second intermediate portion within textual information of the additional captured image data that corresponds to the detected second trigger.

In certain aspects, and as described above, the detected second trigger may include, but is not limited to an image of a hand of a user of apparatus 110, an image of a finger of the user, an image of an elongated object capable of being held and pointed by the user (e.g., a cane, a writing implement, a pointer, or a rod), and images of any additional or alternate object or appendage capable of being disposed within a field-of-view of sensory unit 120 by the user. In additional aspects, second triggers consistent with the disclosed embodiments may also include an image of a pre-determined physical object, an image of a specific individual in uniform (e.g., a firefighter, emergency medical technician (EMT), a police officer, a member of the military, or a flight attendant), and additionally or alternatively, a collection of images that identify an erratic movement of an object by the user.

In step 5708, and as similarly described above in reference to step 5508 of FIG. 55, processor 540 may identify a second level break within the textual information corresponding to the detected second trigger. As described above, the identified level break may represent any of a number of discontinuities within the identified textual information, which include, but are not limited to, a beginning or end of a sentence within the textual information, a beginning or end of a paragraph within the textual information, a beginning or end of a page of the textual information, and a beginning or end of a column of the textual information.

In step 5710, processor 540 may identify one or more second actions that correspond to the detected second trigger. By way of example, and as described above in reference step 5510 of FIG. 55, processor 540 may access a corresponding data repository (e.g., action database 5326 of memory 520), and obtain action information that links the detected second trigger to at least one predetermined actions. Processor 540 may then identify the one or more second actions based on the obtained action information.

In step 5712, processor 540 may perform the one or more second actions on a second portion of the textual information that corresponds to the identified second level break. As described above, the second portion of the textual information may be disposed subsequent to the identified second level break within the document or object associated with the captured image data. Upon completion of the one or more second actions, exemplary process 100 is complete.

In some aspects, the first and second actions may include actions that perform an OCR process on corresponding portions of textual information to identify and retrieve machine-readable text, actions that generate audible presentations of portions of the retrieved machine-readable text, and actions that cause processor 110 to present corresponding ones of the audible representation to a user. The disclosed embodiments are not limited to such exemplary actions, and in further embodiments, one or more of the first and second actions may include various processes that summarize, process, translate, manipulate, or store portions of the machine-readable text, as described above. For example, in one embodiment, processor 540 may select at least one of the second actions based on an output of at least one of the first actions (e.g., one or more portions of machine-readable text retrieved by an OCR process).

Further, in an embodiment, the one or more first actions may include a single first action associated with the detected first trigger, and the one or more second actions may include a single second action associated with the detected second trigger. In some aspects, the single first and second action may represent a common action, such as an OCR process that retrieves machine-readable text from corresponding portions of textual information. In alternate embodiments, the first and second actions may include different actions performed on different portions of the textual information within the captured image data. By way of example, the first action may include a process that presents an audible representation of machine-readable text from a first portion of textual information to a user, and the second action may include an OCR process that retrieves machine-readable text from a second portion of the textual information in anticipation of audible presentation.

Using the embodiments described above, processor 540 may suspend a performance of an action associated with a detected first trigger upon detection of a second trigger within the captured image data. The disclosed embodiments are, however, not limited to techniques that suspend a performance of an action in response to a detected trigger. In additional embodiments, described below in reference to FIG. 58, processor 540 may selectively suspend and resume a performance of an action based various activities of a user of apparatus 110.

Figure 58:
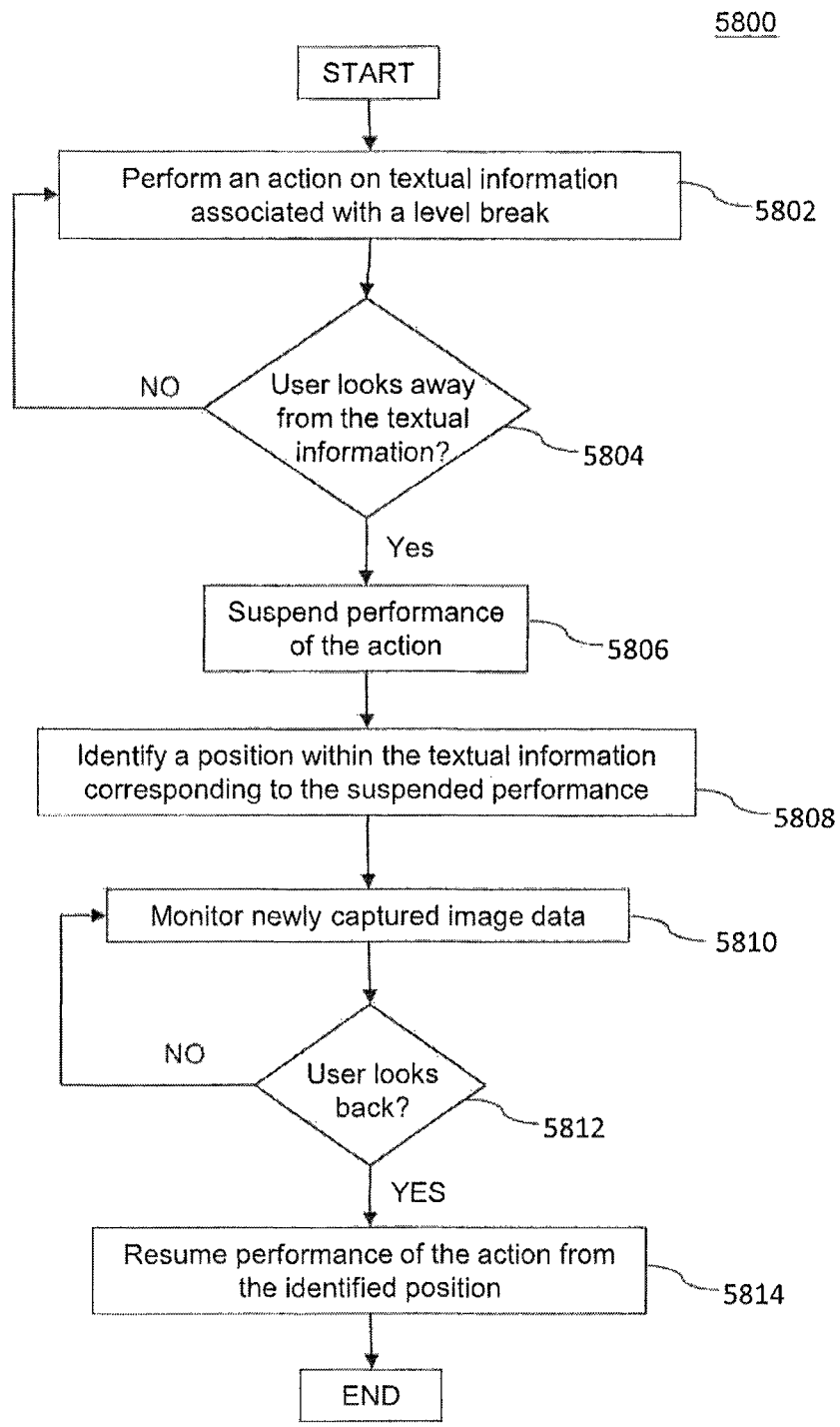
FIG. 58 is a flow diagram of an exemplary process for suspending a performance of actions based on detected user behavior, according to disclosed embodiments.

FIG. 58 illustrates an exemplary process 1100 for selectively suspending a performance of actions based on detected user behavior, according to disclosed embodiments. As described above, sensory unit 120 may capture image data that includes textual information and non-textual information disposed within a corresponding field-of-view. Processing unit 130 may receive the captured image data, and processor 540 may execute one or more application modules to identify textual information within the captured image data (e.g., step 5504 of FIG. 55), detect a trigger within the captured image data (e.g., step 5506 of FIG. 55), and identify a level break within the textual information based on the detected trigger (e.g., step 5508 of FIG. 55). Process 5800 provides further details on how processor 540 selectively suspends and resumes a performance of an action based on detected user activity.

In step 5802, processor 540 may perform an action that corresponds to the detected trigger within a portion of textual information associated with the level break. As described above, the level break may represent a discontinuity within the textual information, and processor 540 may identify the level break based on an associated with the detected trigger, and additionally or alternatively, a proximity of the level break to a position within the captured image data associated with the detected trigger.

In an embodiment, in step 5802, processor 540 may cause apparatus 110 to provide to a user an audible representation of machine-readable text retrieved from the portion of the textual information. In certain aspects, apparatus 110 may provide the audible representation to the user through a speaker or a bone conduction headphone associated with processing unit 140. The disclosed embodiments are, however, not limited to such exemplary actions, and in additional embodiments, the action performed by processor 540 in step 5802 may include, but is not limited to, an OCR process and various processes that summarize, process, translate, manipulate, or store portions of machine-readable text.

As described above, sensory unit 120 may continue to capture image data within a corresponding field-of-view during the audible presentation. In certain aspects, sensory unit 112 may continuously provide the captured image data to processing unit 140 for storage within image database 5322, and processor 540 may monitor the newly-received captured image data. For example, processor 540 may analyze the newly-captured image data upon receipt from sensory unit 120, or alternatively, may access image database 5322 to obtain and analyze portions of the newly-captured image data.

In step 5804, processor 540 may determine whether the user looks away from the portion of the textual information based on a corresponding change in the field-of-view of sensory unit 120. If processor 540 that the user continues to view the portion of the textual information (e.g., step 5804; NO), processor 540 may continue to perform the action on the portion of the textual information in step 5802. For example, processor 540 may continue to cause apparatus 110 to provide the audible representation to the user.

If, however, processor 540 determines that the user no longer views the portion of the textual information (e.g., step 5804; YES), processor 540 may suspend a performance of the action in step 5806, and may identify a position within the textual information that corresponds to suspension of the performance (e.g., a "stopping point") in step 5808. By way of example, if the user looks away from the textual information, processor 540 may suspend the audible presentation at a corresponding stopping point within the textual information.

In step 5810, processor 540 may continue to monitor the newly-captured image data, and in step 5812, processor 540 may determine whether the user resumes viewing the portion of the textual information. In certain aspects, processor 540 may determine that the user resumes viewing the portion of the textual information based on a change in the field-of-view of sensory unit 120.

If processor 540 determine that the user does not resume viewing the textual information (e.g., step 5812; NO), processor 540 may continue to monitor the newly captured image data in step 5810 for changes in the field-of-view of sensory unit 120. Alternatively, if processor 540 determines that the user resumed viewing the portion of the textual information (e.g., step 5812; YES), processor 540 may resume the performance of the suspended action from the identified stopping point. By way of example, in step 5812, processor 540 may resume the suspended audible presentation from the identified stopping point within the textual information. Exemplary process 5800 then ends.

As is evident from the foregoing, apparatus 110 may provide a wide range of functionality. More specifically, one embodiment consistent with the present disclosure provides a method for providing user 100, who may be visually impaired, with information about one or more objects or situations detected within the field of view of apparatus 110. Apparatus 110 may be configured to place detected objects or situations into categories, and may be operable to perform a hierarchical search of databases that contain information about objects and situations that user 100 may encounter. The hierarchical search capability may provide user 100 with more nuanced information about their surroundings and may enable faster, more topical reactions to environmental stimuli.

Figure 59:
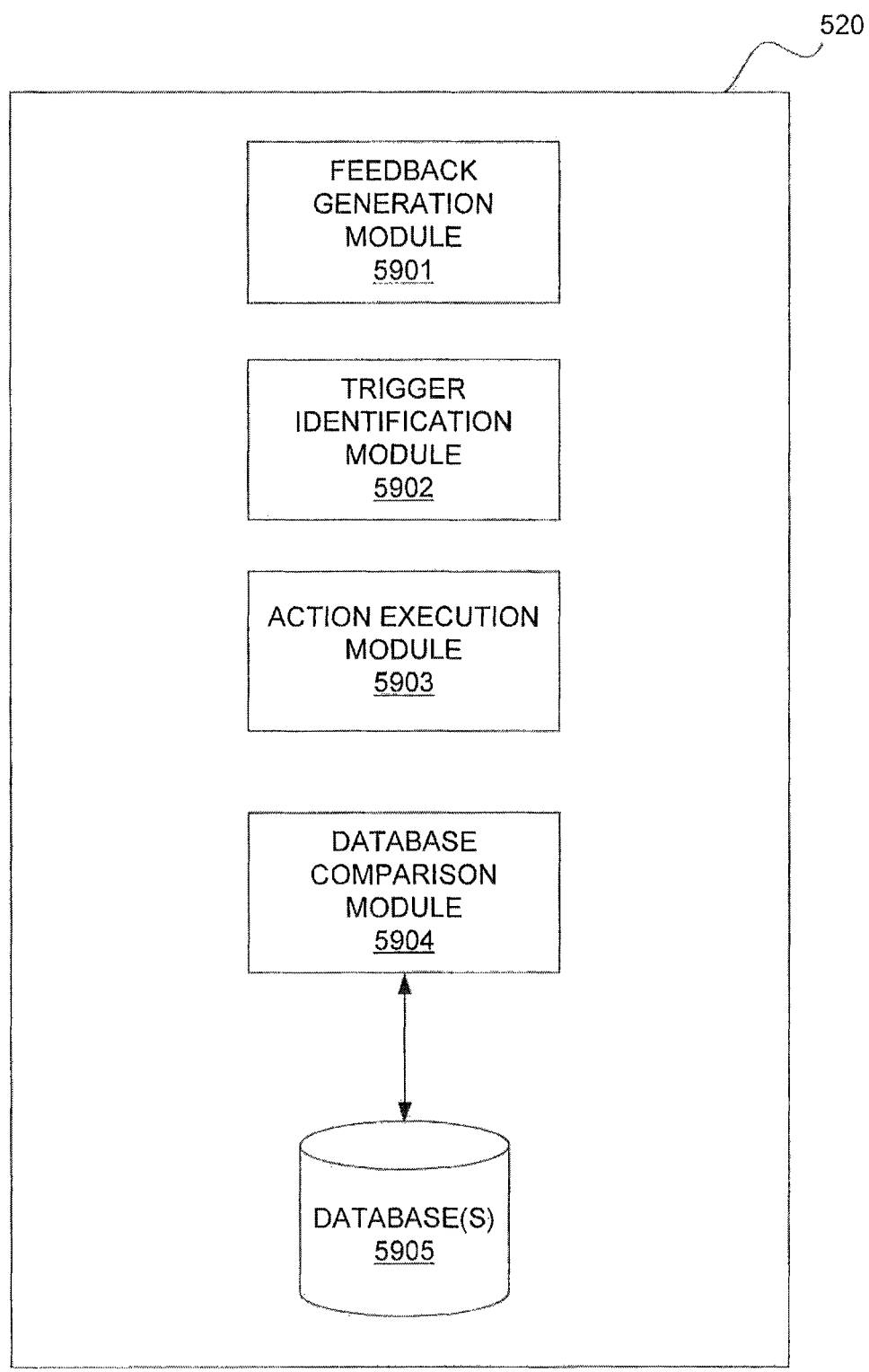
FIG. 59 is a block diagram illustrating an example of a memory contained within an apparatus for aiding persons who have low vision.

FIG. 59 is a block diagram illustrating memory 520 associated with apparatus 110 according to one embodiment. In the example shown in FIG. 59, memory 520 comprises a feedback generation module 5901, a trigger identification module 5902, an action execution module 5903, a database comparison module 5904, and one or more databases 5905.

Feedback generation module 5901 may provide functionality for apparatus 110 to generate and transmit information to user 100 in response to a query. Processor 540 may execute feedback generation module 5901 to generate and process feedback in a given context, then transmit the generated feedback to feedback-outputting unit 340 for output to user 100. In one embodiment, processor 540 and feedback-outputting unit 340 may be operatively connected via wire 130. In other embodiments, processor 540 and feedback-outputting unit 340 may be operatively connected via wireless transceiver(s) 530. As discussed above, in some embodiments, feedback generation module 5901 may generate audible feedback to user 100. In other embodiments, the feedback may be tactile in nature, such as a vibration.

Trigger identification module 5902 may provide functionality for apparatus 110 to identify in real-time audible or visual triggers that may precipitate a change in the operational status of apparatus 110. As used in this disclosure, a "trigger" may include, for example, the appearance of user 100's hand within the field of view of apparatus 100 while making a pre-defined gesture. Any external stimulus may constitute a trigger. In some embodiments, for example, user 100 may be able to audibly say words that serve as triggers, such as "Show," "When," "What," etc. It is understood that these are non-limiting examples. Trigger identification module 5902 may be configured to detect the presence of triggers, then cause processor 540 to execute software instructions that operate apparatus 110 in a manner associated with the trigger.

Action execution module 5903 may provide functionality for apparatus 110 to execute various functions in response to stimuli, be they triggers managed by user 100, appearance of objects within the field of view of apparatus 110, or other events occurring while apparatus 110 is in operation. Action execution module 5903 may, for example, coordinate the configuration and execution of one or more alternative actions that may be available to apparatus 110 upon positive identification of an object or a particular situation.

Database comparison module 5904 may provide functionality for apparatus 110 to compare objects detected in the user environment to objects and/or categories of said objects in a database, such as database(s) 5905, to be described in detail below. In some embodiments, database comparison module 5904 may derive information from real time image data received from image sensor 350. In other embodiments, other software elements or processors may derive the information and provide it to database comparison module 5904. Processor 540 may execute database comparison module 5904 to access one or more of the described databases, and compare the information derived from the received real time image data with information in the databases. If the derived information corresponds to information found in one or more of the databases, database comparison module 5904 may provide an indication to feedback generation module 5901 to that effect as discussed in further detail below in association with FIGS. 62-64.

Database(s) 5905 may comprise one or more databases that store information and are accessed and/or managed through memory 520. By way of example, databases 5905 may include document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 5905 may contain software code or macros that facilitate rapid searching and comparison by database comparison module 5904.

Feedback generation module 5901, trigger identification module 5902, action execution module 5903, and database comparison module 5904 may be implemented in software, hardware, firmware, a mix of any of those, or the like. For example, if the modules are implemented in software, they may be stored in memory 520, as shown in FIG. 59. Other components of processing unit 140 and/or sensory unit 120 may be configured to perform processes to implement and facilitate operations of the modules. Thus, feedback generation module 5901, trigger identification module 5902, action execution module 5903, and database comparison module 5904 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., feedback generation module 5901, trigger identification module 5902, action execution module 5903, and database comparison module 5904) may each include dedicated sensors (e.g., IR, image sensors, etc.) and/or dedicated application processing devices to perform the functionality associated with each module.

As used herein, real-time image data may refer to image data captured in real-time or near real-time. For example, trigger identification module 5902 may monitor the field-of-view of apparatus 110 to detect inputs while action execution module 5903 may determine whether to initiate an action. Accordingly, trigger identification module 5902 and action execution module 5903 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 60:
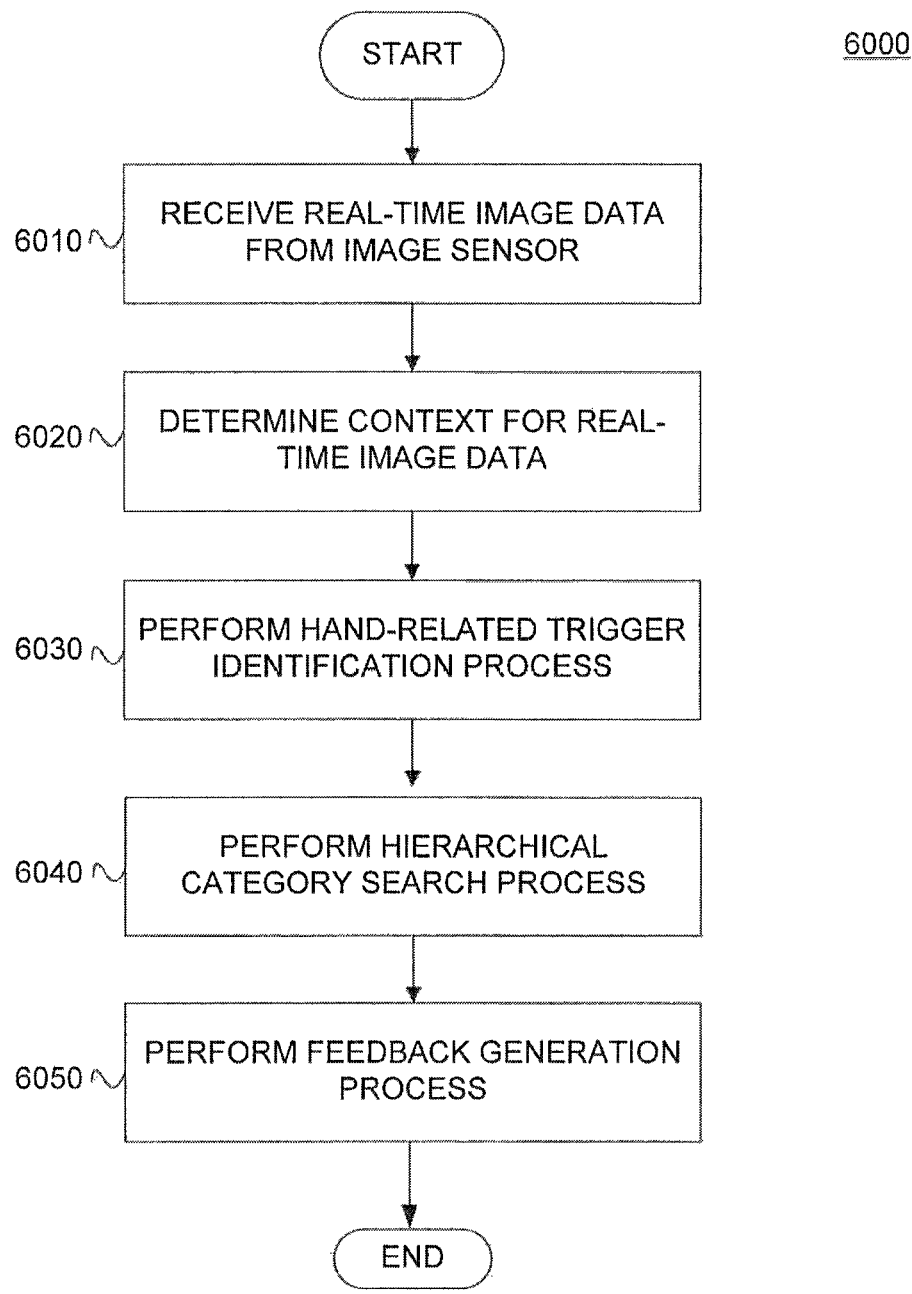
FIG. 60 is an example of a process for providing feedback to a person who has low vision, consistent with disclosed embodiments.

FIG. 60 illustrates an example process 6000 for providing feedback to a person who has low vision consistent with certain disclosed embodiments. Process 6000, as well as any or all of the individual steps therein, may be performed by various aspects of device 110, such as sensory unit 120, processing unit 140, support 210, or any subcomponents therein. For exemplary purposes, FIG. 6000 is described as being performed by processor 540, executing software instructions stored within memory 520.

Processor 540 may receive real-time image data from an image sensor, such as image sensor 350 (Step 6010). In other embodiments, processor 540 may receive the image data from an intermediate component associated with sensory unit 120. The intermediate unit may, for example, perform image processing operations on the real-time image data before transmitting it to processor 540. In some embodiments, the real-time image data may be received as a single streaming video file. In other embodiments, the real-time image data may be received as a series of still images. When the image data is received, processor 540 may store the data in memory 520 or database(s) 5905.

Processor 540 may determine a context for the received real-time image data based on stored information that facilitates the execution of one or more actions (Step 6020). In some embodiments, processor 540 may execute software instructions to process the representations of one or more objects in the real-time image data. In some embodiments, the processing may comprise image processing, such as image rotation, a change in the size of the image, image sharpening, cropping the image, enhancing the focus, etc. It is understood that these are non-limiting examples and that any manner of image processing may be applied to the real-time image data. In other embodiments, the processing may comprise optical character recognition (OCR), when the real-time image data comprises text. In these embodiments, the optical character recognition may facilitate recognition of the visualized text by processor 540, and facilitate formation of a search query for a database containing object information. Processor 540 may further derive or determine any other information contained in the received real-time image data relating to the context of the image, such as date, time, geographical location, etc.

In Step 6030 of process 6000, processor 540, via trigger identification module 5902, may perform a hand-related trigger identification process, such as is described below in connection with FIG. 62. In brief, according to some embodiments, trigger identification module 5902 may configure components of apparatus 110, such as image sensor 350 and/or other components of sensory unit 120 and processing unit 140, to operate in a "ready mode" for trigger detection. Trigger identification module 5902 may determine if a user's hand is present in the real-time image data. If the user's hand is present, trigger identification module 5902 may determine the user hand trigger, if any, that is represented in the real-time image data. Trigger identification module 5902 may further determine one or more data categories associated with the determined hand trigger.

Processor 540, via database comparison module 5904, may perform a hierarchical search process, such as is described below in connection with FIG. 63 (Step 6040). In brief, according to some embodiments, database comparison module 5904 may determine objects associated with each data category. Database comparison module 5904 may further determine a category with the highest priority based on the determined context for the real-time image data. Processor 540, via database comparison module 5904, may search the real-time image data for objects associated with the category. The processor may determine if additional categories are to be searched. If so, database comparison module 5904 may determine the category with the next highest priority, and repeat the search process. Once it is determined that no additional categories should be searched, processor 540 may provide information about the identified objects to feedback generation module 5901.

Processor 540, via feedback generation module 5901, may perform a feedback generation process, such as is described below in connection with FIG. 64 (Step 6050). In brief, according to some embodiments, feedback generation module 5901 may receive information associated with one or more objects identified in the real-time image data. Feedback generation module 5901 may determine audible feedback for output to user 100. Feedback generation module 5901 may configure the audible feedback, and then provide the audible feedback to feedback-outputting unit 430 for output to user 100.

Figure 61B:
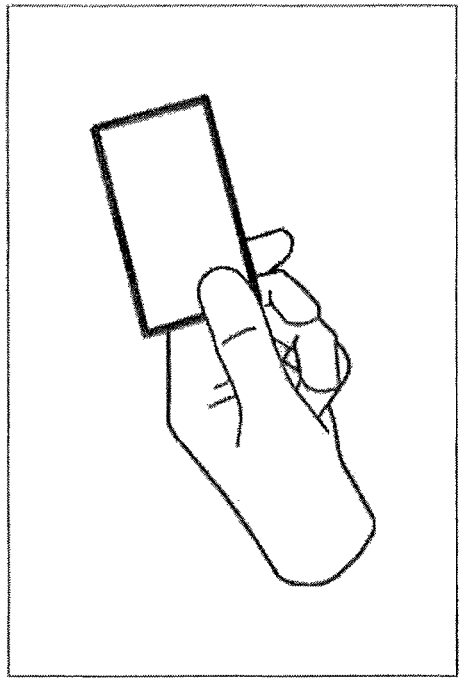
FIG. 61B is an example illustration of a hand-related trigger for an apparatus for aiding persons who have low vision, consistent with disclosed embodiments.
Figure 61D:
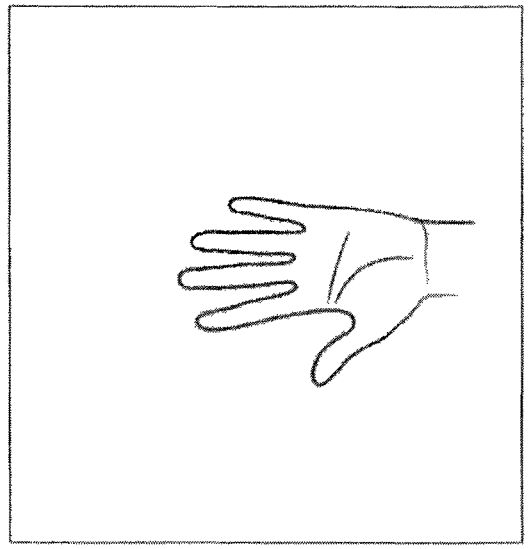
FIG. 61D is an example illustration of a hand-related trigger for an apparatus for aiding persons who have low vision, consistent with disclosed embodiments.
Figure 61A:
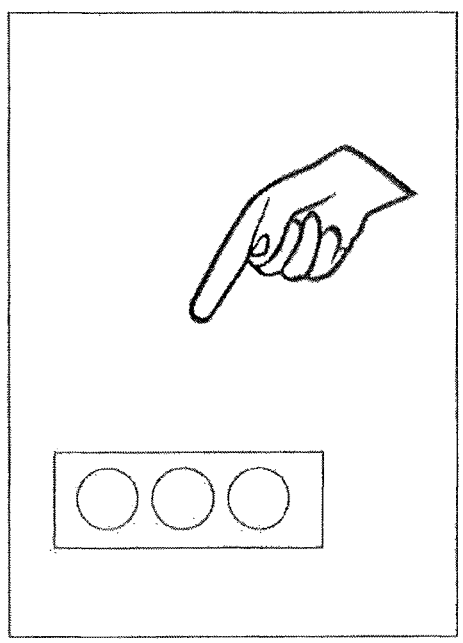
FIG. 61A is an example illustration of a hand-related trigger for an apparatus for aiding persons who have low vision, consistent with disclosed embodiments.

FIGS. 61A-61D illustrate examples of hand-related triggers, consistent with certain disclosed embodiments. FIG. 61A illustrates an example field of view of apparatus 110. In the example of FIG. 61A, a hand of a user, such as user 100, is present within the field of view, and is pointing at an object. In this example, the object is a stoplight, but the object can be any object that may be present in the environment surrounding user 100 while using apparatus 110. In some embodiments, a "pointing" hand trigger as illustrated in FIG. 61A may result in execution of one or more actions relating to the object being pointed at. For example, when user 100 points at a stoplight, as in FIG. 61A, apparatus 110 may detect the action (as will be described below), and audibly announce the status of the stoplight (i.e., "GREEN,"

"RED," etc.). In other embodiments, a pointing hand trigger may permit apparatus 110 to perform other actions, including, but not limited to, announcing the name of a familiar landscape or a familiar object, announcing route information for a public transportation vehicle, audibly reading text, or audibly recognizing a food item or a pharmaceutical. A pointing hand trigger may be used in disclosed embodiments for any action that provides more information about an object within the field of view of apparatus 110.

FIG. 61B illustrates another example field of view of apparatus 110. In the example of FIG. 61B, a hand of a user, such as user 100, is present within the field of view, and is holding an object. In this example, the object is a piece of paper containing text, but the object can be any object that may be present in the environment surrounding user 100 while using apparatus 110. In some embodiments, a "holding" hand trigger as illustrated in FIG. 61B may result in execution of one or more actions relating to the object being held. For example, when user 100 holds a document or any other item containing text, as in FIG. 61B, apparatus 110 may detect the action (as will be described below), and audibly read the text on the document. In other embodiments, a holding hand trigger may permit apparatus 110 to perform other actions, including, but not limited to, announcing the name of a familiar object that is being held, managing database entries for objects (i.e. removing an item as being recognized, editing audible feedback for an item, etc.), or prompting the user to name an item if the held item is an unfamiliar item. A holding hand trigger may be used in disclosed embodiments for any action that provides more information about an object within the field of view of apparatus 110.

Figure 61C:
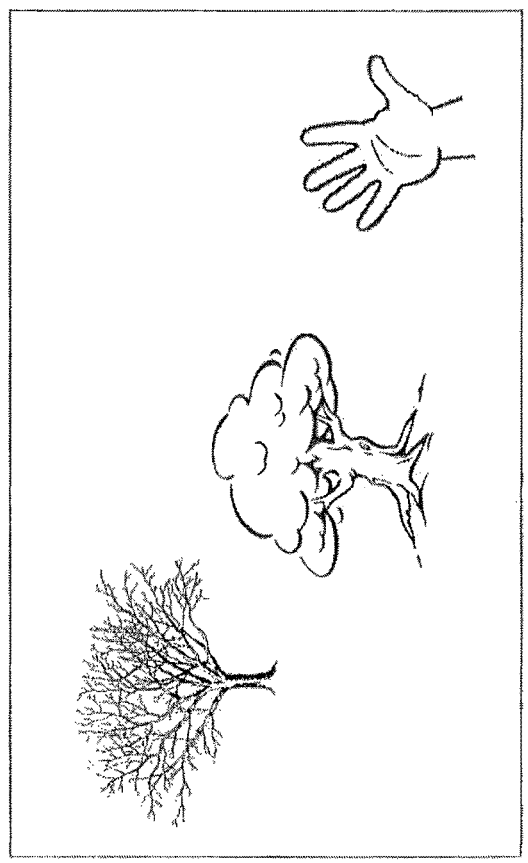
FIG. 61C is an example illustration of a hand-related trigger for an apparatus for aiding persons who have low vision, consistent with disclosed embodiments.

FIG. 61C illustrates another example field of view of apparatus 110. In the example of FIG. 61C, a hand of a user, such as user 100, is present within the field of view, and is waving. In this example, the hand of user 100 is waving in a landscape. In embodiments such as these, a "waving" hand trigger as illustrated in FIG. 61C may result in execution of one or more actions relating to an object or landscape in the field of view when user 100 waves. For example, when user 100 waves at a landscape that is familiar, apparatus 110 may detect elements of the familiar landscape (as will be described below), and audibly identify the location. In other embodiments, a waving hand trigger may permit apparatus 110 to perform other actions, such as prompting the user to identify an unfamiliar landscape when the user waves in an area that is not identifiable by apparatus 110. In some embodiments, waving hand triggers may be associated with pre-programmed landscapes, and landmarks from the landscapes may be stored in memory 520 or database(s) 5905. In these embodiments, for example, user 100 may be able to participate in a guided tour of a tourist attraction. In other embodiments, apparatus 110 may be configured to learn landscapes over time by prompting user 100 for information. A waving hand trigger may be used in disclosed embodiments for any action that provides more information about an object within the field of view of apparatus 110.

FIG. 61D illustrates another example field of view of apparatus 110. In the example of FIG. 61D, a hand of a user, such as user 100, is present within the field of view, and is outstretched in a "stop" gesture. In embodiments such as these, a "stop" hand trigger as illustrated in FIG. 61D may result in execution of one or more actions relating to an object or landscape in the field of view when user 100 presents their hand in this manner. For example, when user 100 presents a stop hand trigger during any ongoing operation or action associated with apparatus 110, the apparatus may be configured to immediately terminate the ongoing operation. In other embodiments, the stop hand trigger may serve as a "reset" for apparatus 110, or may be configured to help present user 100 with information about the status of the apparatus.

Figure 62:
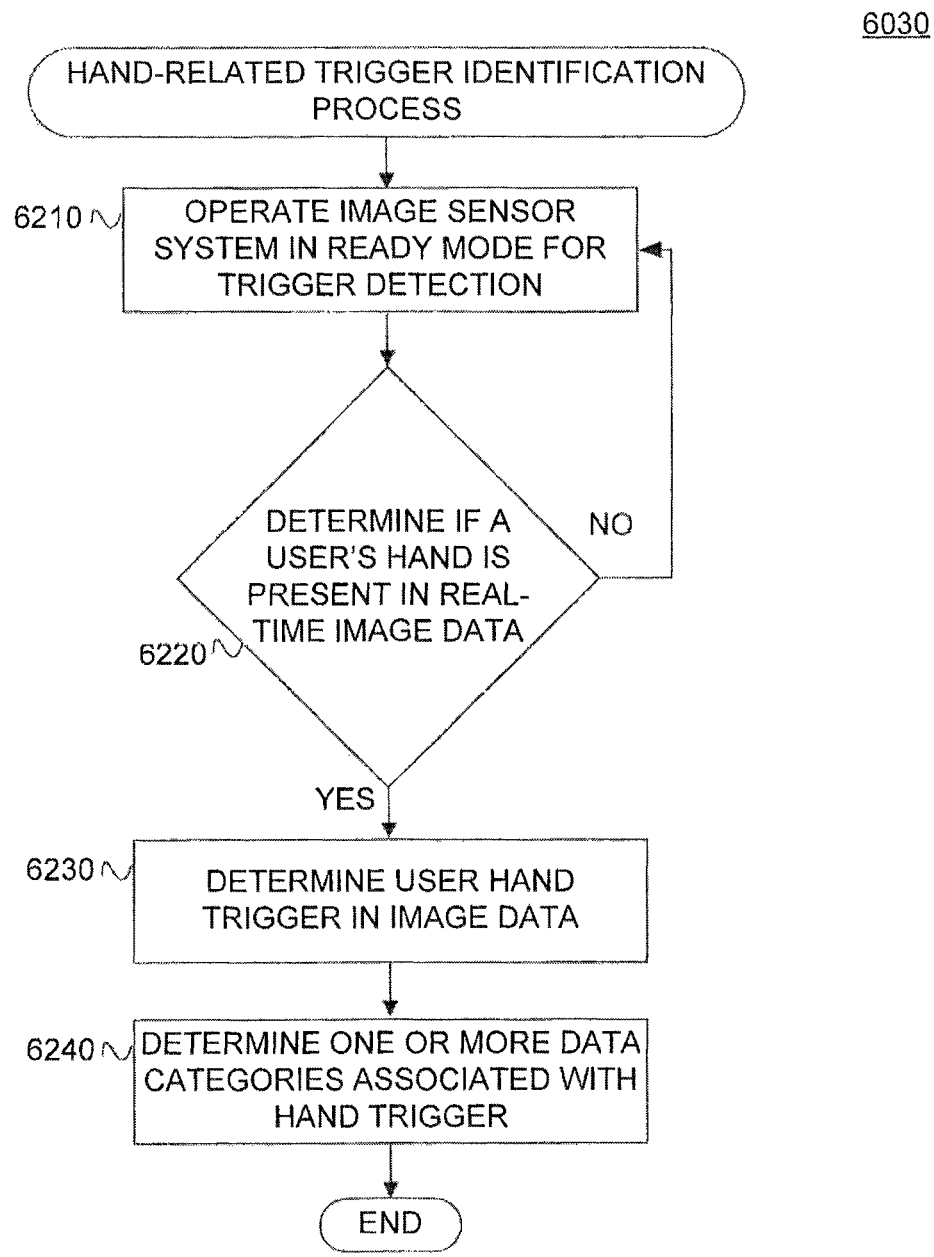
FIG. 62 is an example of a hand-related trigger identification process, consistent with disclosed embodiments.

FIG. 62 illustrates an example of a hand-related trigger identification process, such as that described above in association with Step 6030 of process 6000 consistent with certain disclosed embodiments. Process 6030, as well as any or all of the individual steps therein, may be performed by various aspects of device 110, such as sensory unit 120, processing unit 140, support 210, or any subcomponents therein. For exemplary purposes, FIG. 62 is described as being performed by processor 540, executing software instructions stored within memory 520.

Processor 540, via trigger identification module 5902, may operate image sensor 350 in a normal manner, or "ready mode" while awaiting trigger detection (Step 6210). In some embodiments, apparatus 110 may be configured to always operate in a ready mode when no operations are active. In other embodiments, user 100 may be able to place apparatus 110 into a ready mode such that a hand trigger may be detected.

While in ready mode, trigger identification module 5902 may determine if a user's hand is present in the real-time image data (Step 6220). In some embodiments, trigger identification module 5902 may be configured to recognize the particular hand of the user 100 that is operating apparatus 110. In these embodiments, apparatus 110 may initially prompt user 100 to mime various hand triggers. Trigger identification module 5902 may capture images of the various hand triggers and store them in one or both of memory 520 or database(s) 5905 for ready recognition in the future. In alternative embodiments, trigger identification module 5902 may not be configured to recognize a particular hand, and may be pre-configured to recognize any hand, similar appendage, or equivalent substitute. In some embodiments, trigger identification module 5902 may be configured to recognize the hand of user 100 when it is covered in a glove, mitten, or other covering.

If no hand is detected as present in the real-time image data (Step 6220: NO), trigger identification module may configure image sensor 350 to continue to operate in ready mode, waiting for a future trigger. If a hand is determined to be present (Step 6220: YES), then trigger identification module 5902 may determine if the hand is performing a recognized hand trigger gesture (Step 6230). Examples of possible hand triggers are discussed above in association with FIGS. 61A-61D, but additional hand actions may be recognized by trigger identification module 5902. Trigger identification module 5902 may interact with database comparison module 5904 to search a database, such as database 5905, for recognized hand triggers.

Trigger identification module 5902 may determine one or more data categories associated with the determined hand trigger (Step 6240). For example, processor 540 may determine context information associated with the environment surrounding user 100, and may, along with the determined hand trigger, use the information to determine particular categories to search. For example, user 100 may be standing at an intersection desiring to cross the street. Apparatus 110 may detect this scenario as the current setting. Processor 540 may perform a variety of different alternative actions (via action execution module 5903) based on a particular hand trigger recognized by trigger identification module 5902. For example, one type of hand trigger may signal to trigger identification module 5902 that the category to search for is "warning of risks." As will be discussed further below, apparatus 110 may then scan the field of view for objects, then scan the database for matching objects that may represent risks to user 100. In some embodiments, multiple categories may be associated with a given hand trigger in a given context. For example, in the scenario just described, warning of risks may comprise a first category, and a second category may be "scene identification." Numerous combinations of categories are contemplated for various triggers and contexts. For example, in an alternative embodiment, "spatial guidance" may be the first category, and "warning of risks" may be the second category. Categories may be fluid based on current configuration of apparatus 110 at any given time. One skilled in the art may contemplate many possible categories of data and contexts in which they could be invoked or sorted.

Figure 63:
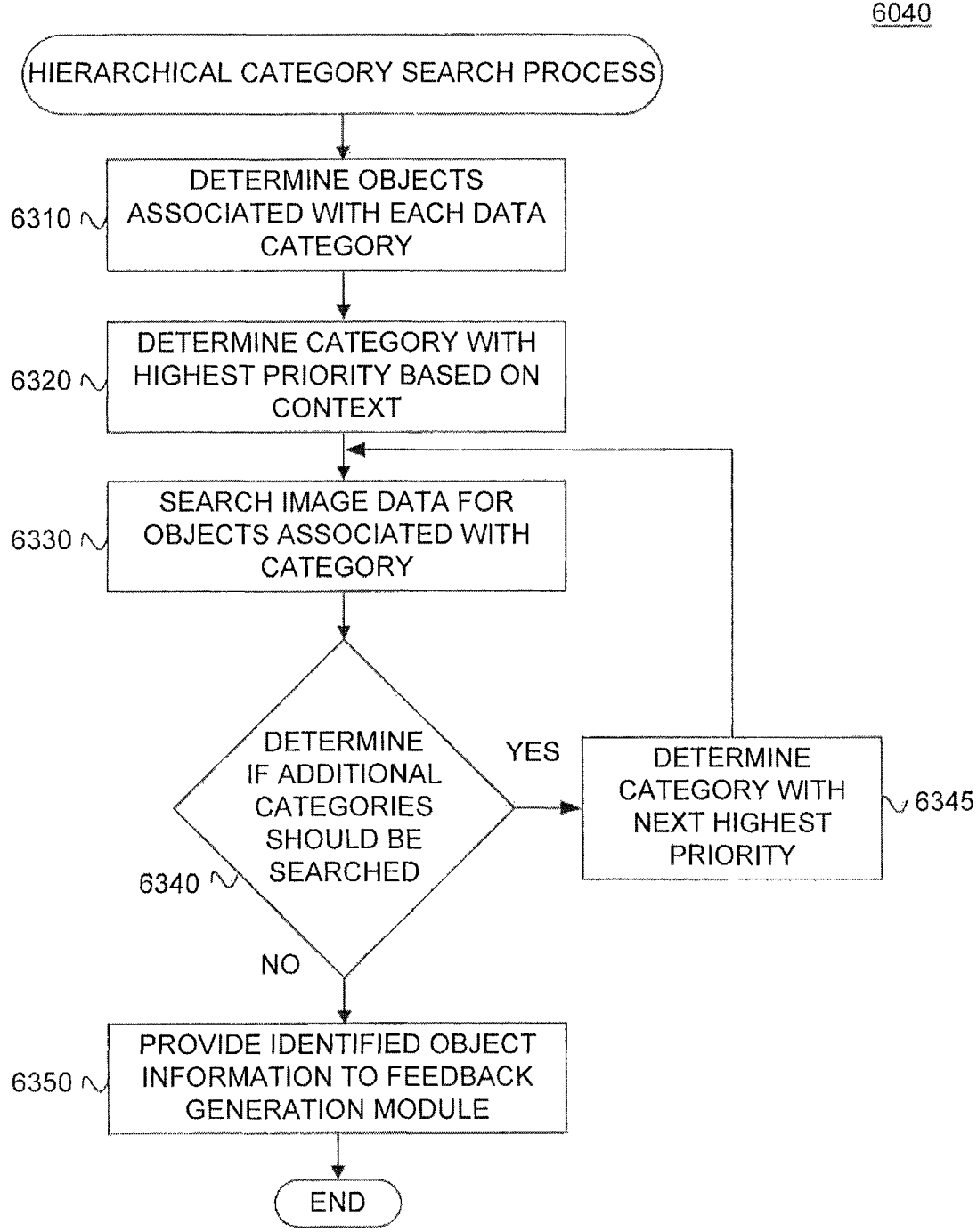
FIG. 63 is an example of a hierarchical category search process, consistent with disclosed embodiments.

FIG. 63 illustrates an example hierarchical category search process, such as that described above in association with Step 6040 of process 6000 consistent with certain disclosed embodiments. Process 6040, as well as any or all of the individual steps therein, may be performed by various aspects of device 110, such as sensory unit 120, processing unit 140, support 210, or any subcomponents therein. For exemplary purposes, FIG. 63 is described as being performed by processor 540, executing software instructions stored within memory 520.

Processor 540 may determine one or more objects associated with each category recognized by trigger identification module 5902 (Step 6310). In some embodiments, the determination may be made initially when apparatus 110 is first configured. In other embodiments, apparatus 110 may prompt user 100 to determine the objects associated with each category. Some objects may be associated with a single category, such as, for example, public transportation vehicles. Other objects may be associated with multiple categories.

Based on the particular context, processor 540 may determine the category of data with the highest priority (Step 6320). For example, in the "crossing the street" scenario presented previously, the "warning of risks" category may be ranked highest due to the risks posed to user 100. In other embodiments, other categories may be given the highest priority. For example, if user 100 is operating apparatus 110 at a train station, and apparatus 110 recognizes the landscape as such, a category involving "public transit vehicles" may be given the highest priority to assist user 100 in identifying the correct train to board.

Processor 540 may search the received real-time image data for known objects associated with the chosen category (Step 6330). Processor 540 may call database comparison module 5904 to search database(s) 5905 for the desired objects. In some embodiments, database comparison module 5904 may be configured to search the chosen category until all objects associated with the category have been exhausted. In other embodiments, database comparison module 5904 may be configured to search the chosen category for a pre-determined period of time. Further, database comparison module 5904 may also be configured to search the category until any item in the environment is identified.

After either the chosen category is exhausted or the pre-determined period of time has elapsed, database comparison module 5904 may determine if additional categories should be searched (Step 6340). Additional searching may be necessary if the previous category did not result in any matches with objects in the received real-time image data. In these embodiments, database comparison module 5904 may be configured to execute a second search. In some embodiments, an object may be identified that is associated with the first category, but apparatus 110 may be configured to identify more than one object in the environment, or may want to search a secondary category to clarify and confirm context of the identification. In these embodiments, processor 540, via database comparison module 5904, may be configured to execute the second search in the second category only after an object from the first category is identified during the first search. In some embodiments, processor 540 may be configured to execute the first search and the second search sequentially.

If additional categories are determined to need searching by database comparison module 5904 (Step 6340: YES), then processor 540 may determine the category of data with the next highest priority for the given hand trigger information and context information associated with the current system status (Step 6345). Once the next category to be searched is determined, processor 540 may repeat Steps 6330 and 6340 as many times as is necessary or desired. For example, after initiating the first search of the first category, database comparison module 5904 may execute a second search in the image data to identify at least a second object from the second category. In some embodiments, the first and second categories are overlapping or otherwise related. In other embodiments, the first and second categories are different. In some embodiments, the processor may be configured to repetitively execute the first search and the second search until at least one object from one or both of the categories is identified. In some embodiments, third and even fourth categories may be searched. Depending on context, these categories may include, for example, lists of branded products (to assist with identification), text to be read, spatial guidance, text in the wild (i.e. not on an item held or otherwise controlled by user 100), or scene identification.

Alternatively, processor 540 may determine that all proper objects are identified, and that no further categories require search (Step 6340: NO). In these embodiments, processor 540 may provide information about the identified object or objects to feedback generation module 5901 (Step 6350). The information may include, as non-limiting examples, the identity of the object, the location of the object, the size of the object, the "status" of the object (e.g., what color is a stoplight), and so on. Upon receipt of the identified object information, feedback generation module 5901 may generate feedback to user 100, in a process that will be described below in further detail.

Additionally, processor 540 may call action execution module 5903 to execute one or more category-based alternative actions associated with the chosen category or categories, and their associated triggers and contexts. In some embodiments, action execution module performs such alternative actions in addition to the audible feedback generated by feedback generation module 5901. In other embodiments, the alternative actions are performed instead of the feedback generation. Alternative actions may include, but not be limited to, reading text, sending an electronic message or instant message over the Internet; configuring settings for apparatus 110 or image sensor 350; activating a user interface, which may appear within the field of view of user 100 and provide additional interactivity options, etc.

Figure 64:
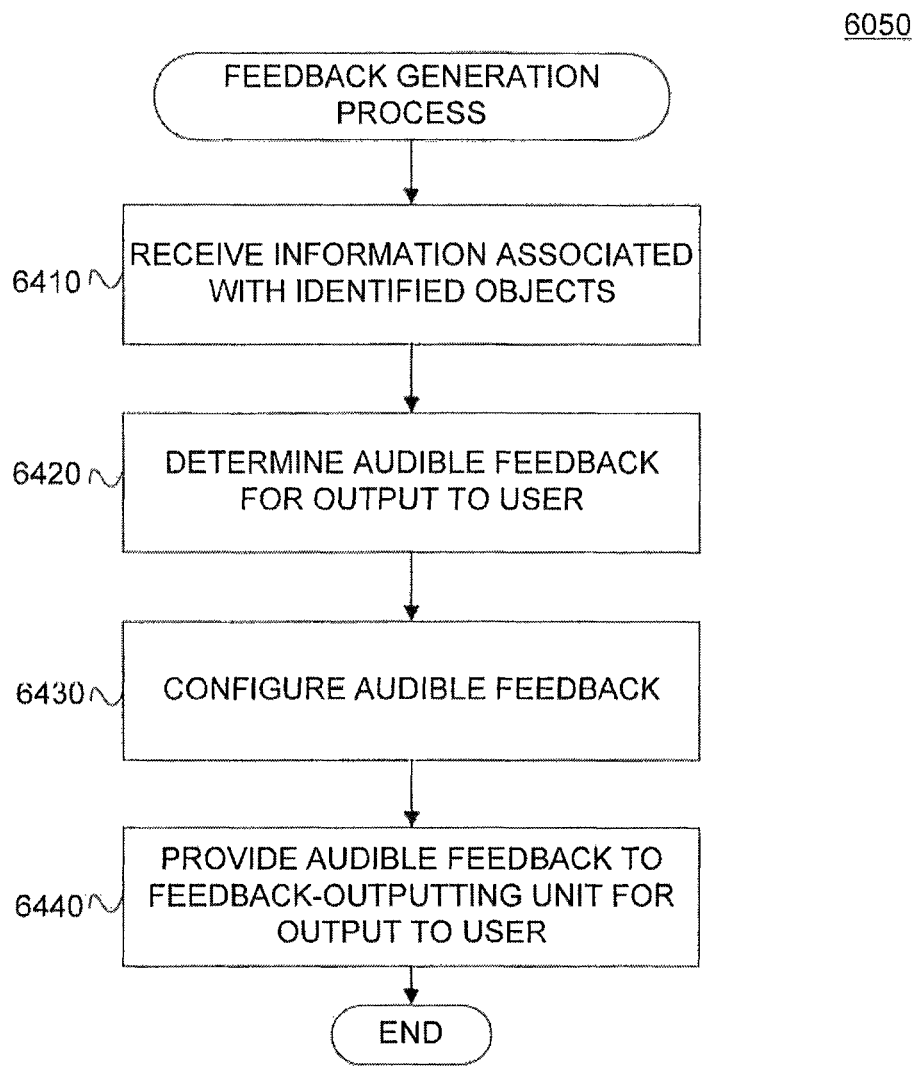
FIG. 64 is an example of a feedback generation process, consistent with disclosed embodiments.

FIG. 64 illustrates an example of a feedback generation process, such as that described above in association with Step 6050 of process 6000 consistent with certain disclosed embodiments. Process 6050, as well as any or all of the individual steps therein, may be performed by various aspects of device 110, such as sensory unit 120, processing unit 140, support 210, or any subcomponents therein. For exemplary purposes, FIG. 64 is described as being performed by processor 540, executing software instructions stored within memory 520.

As discussed above, processor 540, via feedback generation module 5901, may receive information associated with one or more identified objects that have been determined to be present in the environment surrounding user 100 (Step 6410). Based on the received information, feedback generation module 5901 may determine audible feedback for output to user 100 (Step 6420). In some embodiments, the identified object may already be associated with an audible feedback file stored in memory 520 or database(s) 5905. In these embodiments, feedback generation module 5901 may simply access the existing associated audible feedback file and prepare it for transmission. In other embodiments, there may be multiple audible feedback files associated with the identified object(s), and feedback generation module may review the determined trigger and/or context information to determine the correct associated audible feedback to output to user 100. In still other embodiments, there may be no existing audible feedback associated with the identified object or objects. In these embodiments, feedback generation module 5901 may determine content for audible feedback by prompting user 100 for the feedback, or may infer proper audible feedback, based on context and based on other objects within the category.

Upon determining the proper audible feedback to use, feedback generation module 5901 may configure the audible feedback into a readable format, if necessary (Step 6430), then provide the audible feedback to feedback-outputting unit 430 for output to user 100 (Step 6440). Feedback generation module 5901 may provide the feedback to feedback-outputting unit 430 via wire 130, or alternatively, via wireless transceiver(s) 530.

As is evident from the foregoing, apparatus 110 may provide a wide range of functionality. More specifically, one embodiment consistent with the present disclosure provides an image capturing and processing function that may assist a person with low vision to recognize objects. Apparatus 110 may use the image capturing and processing function to identify objects near the user of apparatus 110. In this way, in situations in which a visually-impaired user of apparatus 110 cannot identify or is unsure of the identity of an object nearby, apparatus 110 may be configured to recognize the object or to process and present the processed image to the user, which may be easier for the visually-impaired user to recognize.

Figure 65:
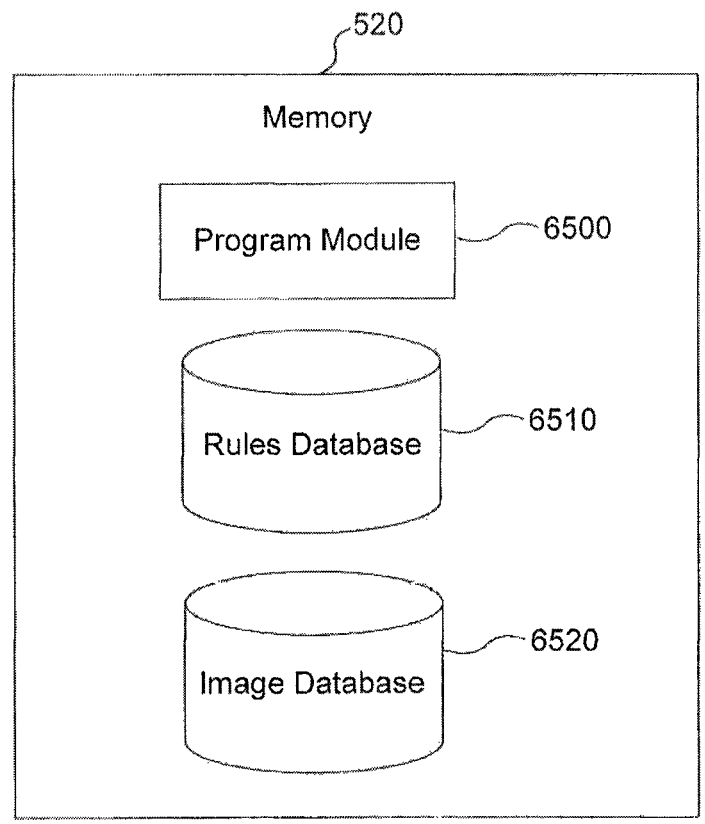
FIG. 65 is a block diagram of a memory that may be used in conjunction with an apparatus for aiding persons who have low vision.

FIG. 65 is a block diagram of memory 520. Memory 520 may include components configured to store various types of data that may be used in image capturing or processing. For example, memory 520 may include at least one program module 6500 configured to store program code or instructions that may be executed by processor 540 to perform methods and operations to identify objects near the user of apparatus 110. Memory 520 may also include a rules database 6510 configured to store data, such as rules that associate image contexts with image capture resolutions and rules that associate image contexts with image capture frame rates. Memory 520 may also include an image database 6520 configured to store data, such as captured images, and information associated with captured images, such as time, place, identification of objects, sizes of images, etc.

Program module 6500, rules database 6510, and image database 6520 may be implemented in software, hardware, firmware, a mix of any of those, or the like. Other components of processing unit 140 and/or sensory unit 120 may be configured to perform processes to implement and facilitate operations of program module 6500, rules database 6510, and/or image database 6520. For example, program module 6500, rules database 6510, and/or image database 6520 may include software, hardware, or firmware instructions (or a combination thereof) executable by one or more processors (e.g., processor 540), alone or in various combinations with each other. Program module 6500, rules database 6510, and/or image database 6520 may be configured to interact with each other and/or other components of apparatus 110 to perform functions consistent with disclosed embodiments. In some embodiments, any of the disclosed modules (e.g., program module 6500) may each include dedicated sensors (e.g., IR, image sensors, etc.) and/or dedicated application processing devices to perform the functionality associated with each module.

Rules database 6510 and/or image database 6520 may include one or more memory devices that store information and are accessed and/or managed through a computing device, such as processing unit 140. In some embodiments, rules database 6510 and/or image database 6520 may be located in memory 520, as shown in FIG. 65. In other embodiments, database 6530 may be located remotely from memory 520, and may be accessible to other components of apparatus 110 (e.g., processing unit 140) via one or more wireless connections (e.g., a wireless network). While one rules database 6510 and one image database 6520 are shown, it should be understood that several separate and/or interconnected databases may make up rules database 6510 and/or image database 6520. Rules database 6510 and/or image database 6520 may include computing components (e.g., database management system, database server, etc.) configured to receive and process requests for data stored in memory devices associated with rules database 6510 and/or image database 6520 and to provide data from rules database 6510 and/or image database 6520.

Figure 66:
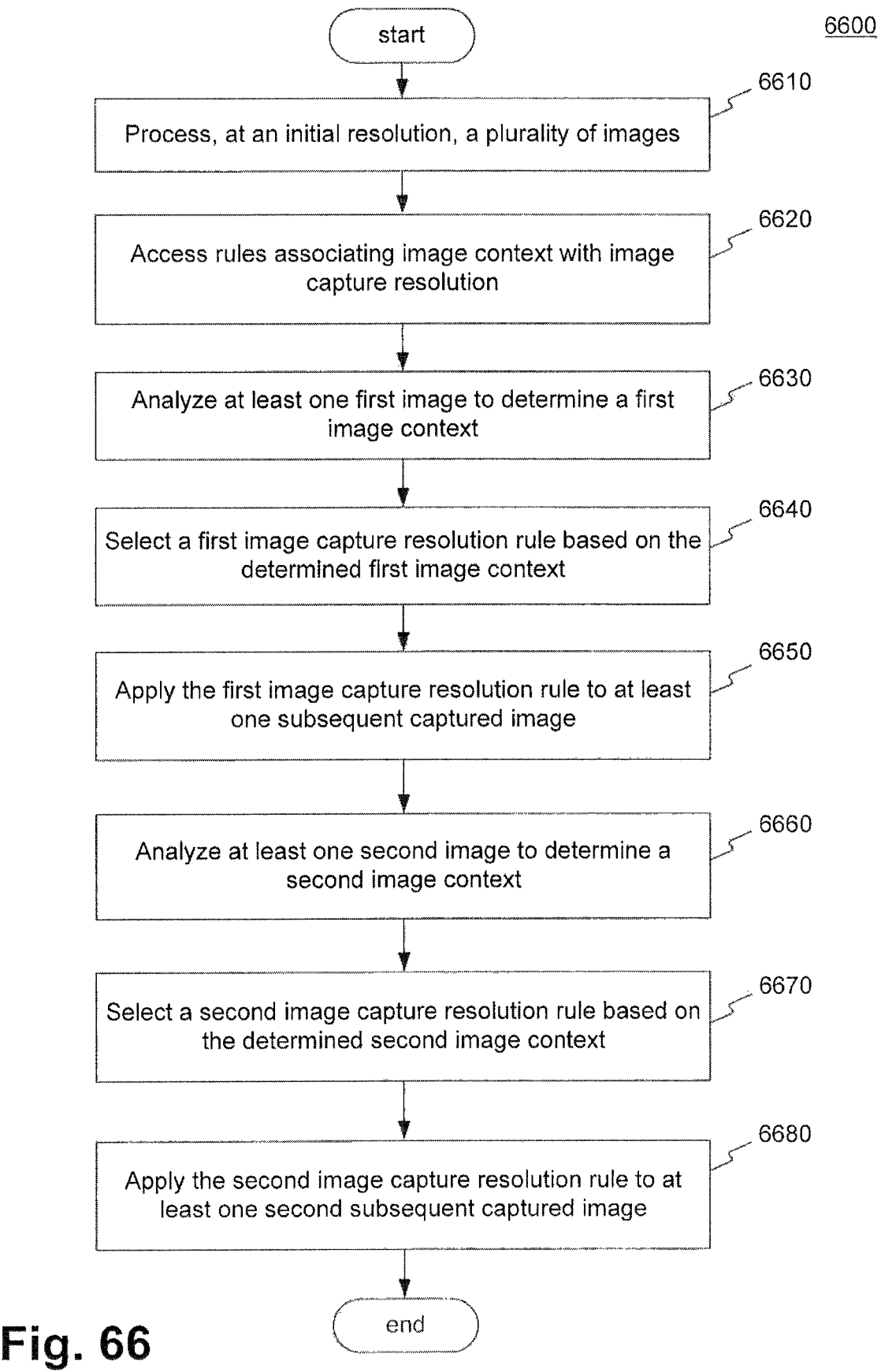
FIG. 66 is a flowchart showing an example of a method for processing images.

FIG. 66 shows an example of a method 6600 for processing images, consistent with a disclosed embodiment. Method 6600 may include one or more operations that may be performed by processor 540. As shown in FIG. 66, processor 540 may be configured to process, at an initial resolution, a plurality of images from image sensor 350 to determine existence of a trigger (Step 6610). The initial resolution may vary depending on specific applications. For example, in one embodiment, the initial resolution may be lower than or higher than 5 megapixels. In another embodiment, the initial resolution may be lower than or higher than 80,000 pixels. The plurality of images may be captured by image sensor 350, and may be received by processor 540 from image sensor 350 for processing. Alternatively or additionally, images captured by image sensor 350 may be stored in memory 520, such as image database 6520, and processor 540 may retrieve images from memory 520 for processing. The trigger that is determined in step 6610 may be, for example, a gesture made by a user who at least partially appears in the images.

Processor 540 may access rules associating image contexts with image capture resolutions to enable images of a first context to be processed at a lower capture resolution than images of a second context (Step 6620). The rules may be referred to as image capture resolution rules. The rules may define resolutions to be used for capturing and/or processing images associated with different image contexts. The image capture resolution rules may be stored in rules database 6510 included in memory 520. The term resolution means the fidelity at which the image data is captured. For example, this includes the number of picture elements ("pixels"), the frequency of taking images, zoom configuration, and sensor sensitivity parameters (such as gain and aperture), and other operational aspects of sensory unit 120.

An image context may provide information associated with the context of a particular image. For example, an image context may be related to the time and/or place that an image of an object and/or an environment was captured. As other examples, an image context may be related to the meaning of text written on an object that appears in an image. As another example, context may be related to a particular arrangement of objects in the image. Certain image contexts may be associated with different rules. For example, the rules may specify a low image capture resolution for images associated with certain image contexts. Processor 540 may analyze the scene to determine that an object was inserted into the field of view and optimize the capture parameters to capture that object, possibly at the expense of other objects. The image capture resolution rules may specify a high capture resolution for images associated with other image contexts.

Processor 540 may analyze at least one first image to determine a first image context (Step 6630). For example, processor 540 may analyze at least one first image to determine the time and/or place that the first image was captured. Processor 540 may select a first capture resolution rule based on the determined first image context (Step 6640). The first capture resolution rule may define a relatively lower resolution for capturing images associated with the first image context. For example, the first image capture resolution rule may define a first resolution of, e.g., 80,000 pixels, 1 megapixel, 5 megapixels, 10 megapixels, etc. The first resolution may be greater than, lower than, or substantially equal to the initial resolution. For example, in some embodiments, the first resolution may be greater than 300,000 pixels, and the initial resolution may be equal to the first resolution. In some embodiments, the first resolution may be greater than 10 megapixels, and the initial resolution may be less than 1 megapixel. In other embodiments, the first resolution may be 1 megapixel, and the initial resolution may be 2 megapixels. Furthermore, in some embodiments, the first image capture resolution rule may include zoom information. Zoom information may include, for example, 1×, 2×, 8×, or 16× zoom, which was used in capturing the images, or which will be used in capturing subsequent images.

Processor 540 may apply the first image capture resolution rule to at least one subsequent captured image (Step 6650). For example, processor 540 may apply a first resolution of 10 megapixels to one or more images captured following the first image (e.g., the third and fourth subsequent captured images). In some embodiments, the first image capture resolution rule may further define a plurality of image portions. Each image portion may be associated with a different resolution to be captured in the at least one subsequent captured image. For example, the first image capture resolution rule may define a first image portion, a second image portion, and a third image portion. The first image portion may be captured at a resolution of 1 megapixel in a first subsequent captured image. The second image portion may be captured at a resolution of 1.5 megapixels in a second subsequent captured image. The third image portion may be captured at a resolution of 2 megapixels in a third subsequent captured image.

The first, second, and third image portions may be portions of the same image. Alternatively, the first, second, and third image portions may be portions of different images. For example, the first image portion may be a portion of a first subsequent captured image, and the second and third image portions may be portions of a second subsequent captured image. In some embodiments, at least one image portion defined by the first image capture resolution rule may not be part of the at least one subsequent captured image. For example, the first image portion may be a portion of the first image (which is not one of the subsequent captured images), and other image portions may be portions of a separate image, such as one of the subsequent captured images. Thus, processor 540 may process portions of images across multiple images.

Processor 540 may analyze at least one second image to determine a second image context (Step 6660). For example, the second image context may be related to the meaning of text written on an object captured in an image. Processor 540 may select a second image capture resolution rule based on the determined second image context (Step 6670). For example, the second image capture resolution rule may define a second resolution of, e.g., 80,000 pixels, 1 megapixel, 5 megapixels, 10 megapixels, or 15 megapixels, etc., for capturing images. The second resolution may be greater than, lower than, or substantially equal to the first resolution. For example, the second resolution may be 2 megapixels, and the first resolution may be 2 megapixels, less than 2 megapixels, or greater than 2 megapixels. Processor 540 may apply the second image capture resolution rule to at least one second subsequent captured image (Step 6680). For example, processor 540 may apply a 2 megapixels resolution to one or more images captured following the second image, such as the fourth and fifth images captured following the second image.

Processor 540 may be further configured to perform other operations that may be included in method 6600. For example, processor 540 may be further configured to execute an action selected from multiple context-based actions. The multiple context-based actions may include at least one action associated with a first resolution and at least one additional action associated with a second resolution. For example, the at least one action associated with the first resolution may include an action of recognizing a place in which the image was captured using the first resolution. The at least one additional action associated with the second resolution may include an action of recognizing the meaning of text written on an object using the second resolution. Thus, an action selected from the multiple context-based actions may be an action that includes both recognizing a place and recognizing the meaning of text, for example, from the same image. Processor 540 may be further configured to identify objects in images that were captured in the second resolution. For example, processor 540 may identify buildings, vehicles, landmarks, human beings from images captured in the second resolution. Processor 540 may be further configured to execute an optical character recognition operation on images captured in the second resolution, for example, to identify text written on a surface.

Figure 67:
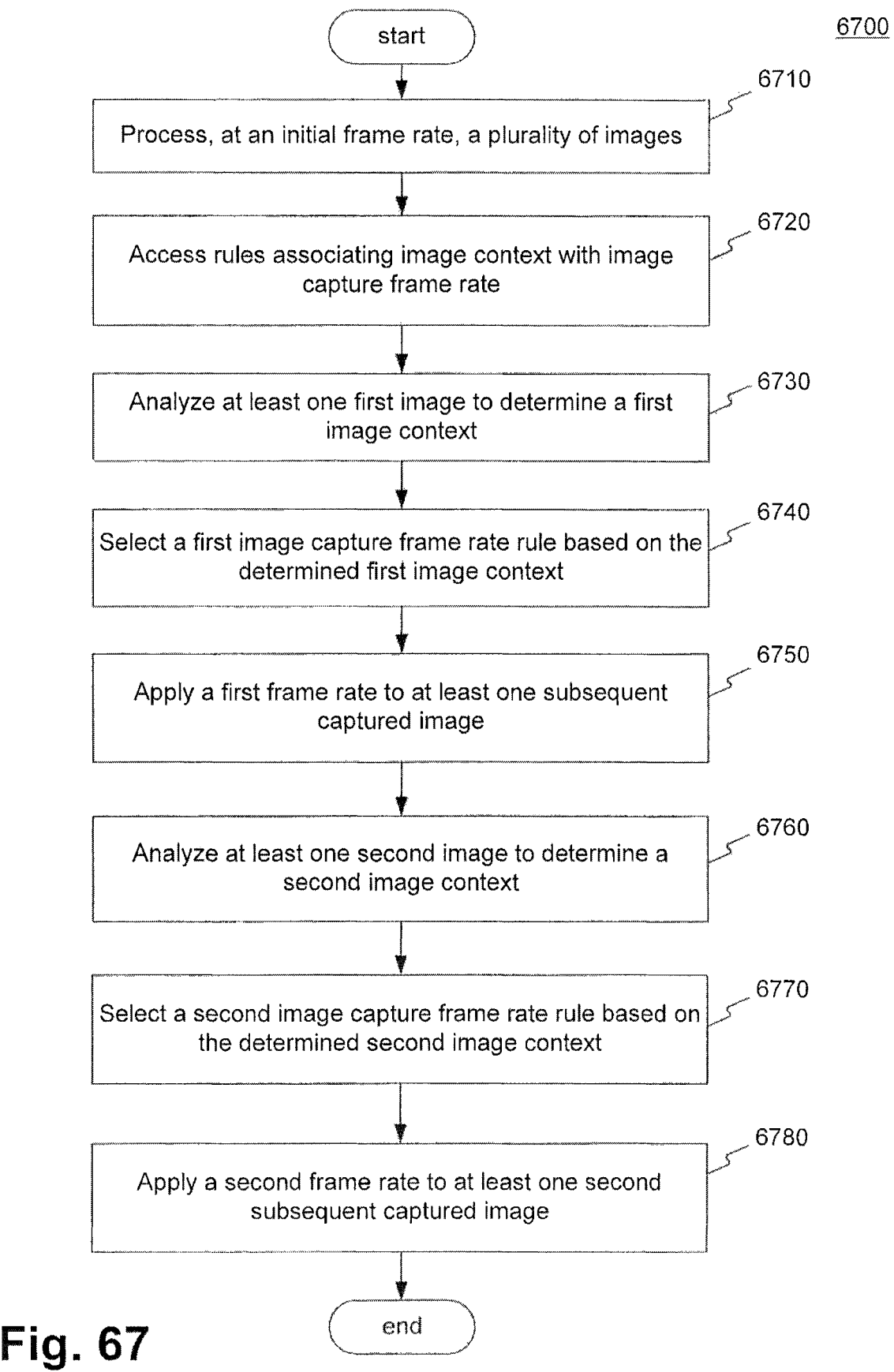
FIG. 67 is a flowchart showing another example of a method for processing images.

FIG. 67 is a flowchart showing an example of a method 6700 for processing images, consistent with a disclosed embodiment. Method 6700 may include a plurality of operations that may be performed by processor 540. Processor 540 may be configured to process, at an initial frame rate, a plurality of images from image sensor 350 to determine existence of a trigger (Step 6710). Processor 540 may access rules associating image context with image capture frame rates to enable images of a first context to be processed at a lower frame rate than images of a second context (Step 6720). The rules may define frame rates to be used for capturing images. Processor 540 may analyze at least one first image to determine a first image context (Step 6730). For example, the first image context may be related to the time and/or place that an image of an object was captured.

Processor 540 may select a first image capture frame rate rule based on the determined image context (Step 6740). The first image capture frame rate rule may define a first frame rate (e.g., 1 frame-per-second). Processor 540 may apply the first frame rate to at least one subsequent captured image (Step 6750). For example, processor may apply a 1 frame-per-second frame rate to the second, third, and fourth subsequent captured images. Processor 540 may analyze at least one second image to determine a second image context (Step 6760). For example, the second image context may be related to the meaning of text written on an object in the at least one second image. Processor 540 may select a second image capture frame rate rule based on the determined second image context (Step 6770). The second image capture frame rate rule may define a second frame rate, for example, 2 frames-per-second. Processor 540 may apply the second frame rate to at least one second subsequent captured image (Step 6780). For example, processor 540 may apply the 2-frames-per-second frame rate to the fifth, sixth, and seventh subsequent captured images. The second frame rate may be higher than, lower than, or equal to the first frame rate. For example, the second frame rate may be 2-frames-per-second, and the first frame rate may be 2-frames-per-second, higher than 2-frames-per-second, or lower than 2-frames-per-second.

The initial frame rate may be associated with an image resolution, and the second frame rate may be associated with a different image resolution. For example, the initial frame rate may be associated with an image resolution of 1 megapixel, and the second frame rate may be associated with an image resolution of 2 megapixels. The first frame rate may be higher than, lower than, or substantially equal to the initial frame rate. For example, the initial frame rate may be less than 10 frames-per-second, and the first frame rate may be higher than 9 frames-per-second, lower than 10-frames-per-second, or equal to the initial frame rate. In some embodiments, the first frame rate may be higher than 29 frames-per-second.

Figure 68:
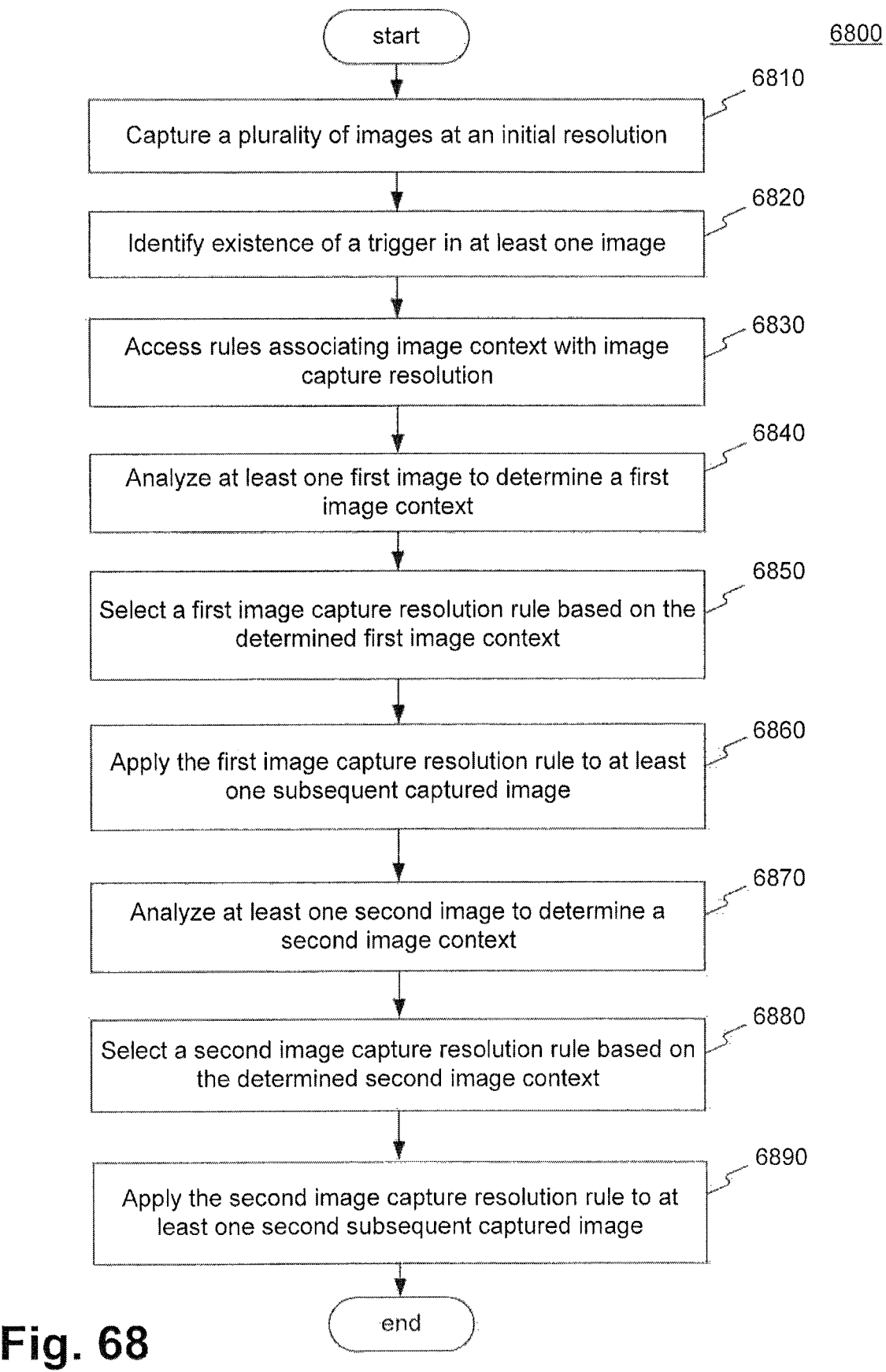
FIG. 68 is a flowchart showing yet another example of a method for processing images.

FIG. 68 is a flowchart showing a method 6800 for processing images, consistent with a disclosed embodiment. Method 6800 may include a plurality of operations that may be performed by processor 540. For example, processor 540 may capture a plurality of images at an initial resolution from an environment of a user (Step 6810). In one embodiment, processor 540 may control image sensor 350 to capture the images. Processor 540 may identify the existence of a trigger in at least one image (Step 6820). For example, processor 540 may identify as a trigger a gesture made by a user who appears in a captured image. Processor 540 may access rules associating image contexts with image capture resolutions to enable images of a first context to be processed at a lower capture resolution than images of a second context (Step 6830). For example, processor 540 may access rules that define a lower capture resolution of 80,000 pixels for processing images of a first context, and a higher capture resolution of 2 megapixels for processing images of a second context. Processor 540 may analyze at least one first image to determine a first image context (Step 6840). For example, processor 540 may analyze the first captured image to determine the place the first image was captured. Processor 540 may be configured to select a first image capture resolution rule based on the determined first image context (Step 6850). The first rule may define a first resolution; for example, 1 megapixel for processing images.

Processor 540 may apply the first image capture resolution rule to at least one subsequent captured image (Step 6860). For example, processor 540 may apply a first image capture resolution rule that defines a resolution of 80,000 pixels to process a first subsequent captured image. Processor 540 may analyze at least one second image to determine a second image context (Step 6870). For example, processor 540 may analyze a second image to determine the meaning of text written on a surface that appears in the second image. Processor 540 may select a second image capture resolution rule based on the determined second image context (Step 6880). The second image capture resolution rule may define a second resolution, for example, 2 megapixels. Processor 540 may further apply the second image capture resolution rule to at least one second subsequent captured image (Step 6890). For example, processor 540 may apply a resolution of 2 megapixels to the third, fourth, and fifth subsequent captured images. The second resolution may be greater than, lower than, or equal to the first resolution. For example, the second resolution may be 2 megapixels, and the first resolution may be 2 megapixels, greater than 2 megapixels, or lower than 2 megapixels.

As is evident from the foregoing, apparatus 110 may provide a wide range of functionality. More specifically, one embodiment consistent with the present disclosure provides an object information function. The object information function may allow apparatus 110 to provide feedback to a user based on an identified object and information associated with the object. In this way, the user may receive information related to the object.

As has been described, apparatus 110 may be configured to identify objects from real-time images captured (e.g., by image sensor 350) from an environment of a user of apparatus 110. Many objects may provide information that people may use to understand their environment and make decisions. For example, a road sign (e.g., a speed-limit sign) includes information (e.g., the speed-limit of a road) observable by individuals who view the road sign. In some embodiments, apparatus 110 may be configured to identify an object and provide feedback to a user such that the user understands information provided by or associated with the object.

Further, many objects change state over time, where each state may represent different information to people who view the object. For example, a traffic light may change colors and/or signals over time (e.g., red to green, walk to don't walk, etc.), with each color and/or signal conveying different information (e.g., safe or unsafe to go/walk). In some embodiments, apparatus 110 may be configured to identify and monitor an object, and use information associated with an object to provide appropriate feedback to a user, such as feedback indicating that the object is capable of changing states, is likely to change states, has changed its state, etc. As used herein, an object has "changed its state" when any aspect of the object is different from a previous point in time. For example, an object may change its state when the object, or any part, portion, and/or component of the object, changes its appearance, moves locations, changes properties (e.g., temperature), receives another object, has a portion or component thereof removed, etc.

Figure 69:
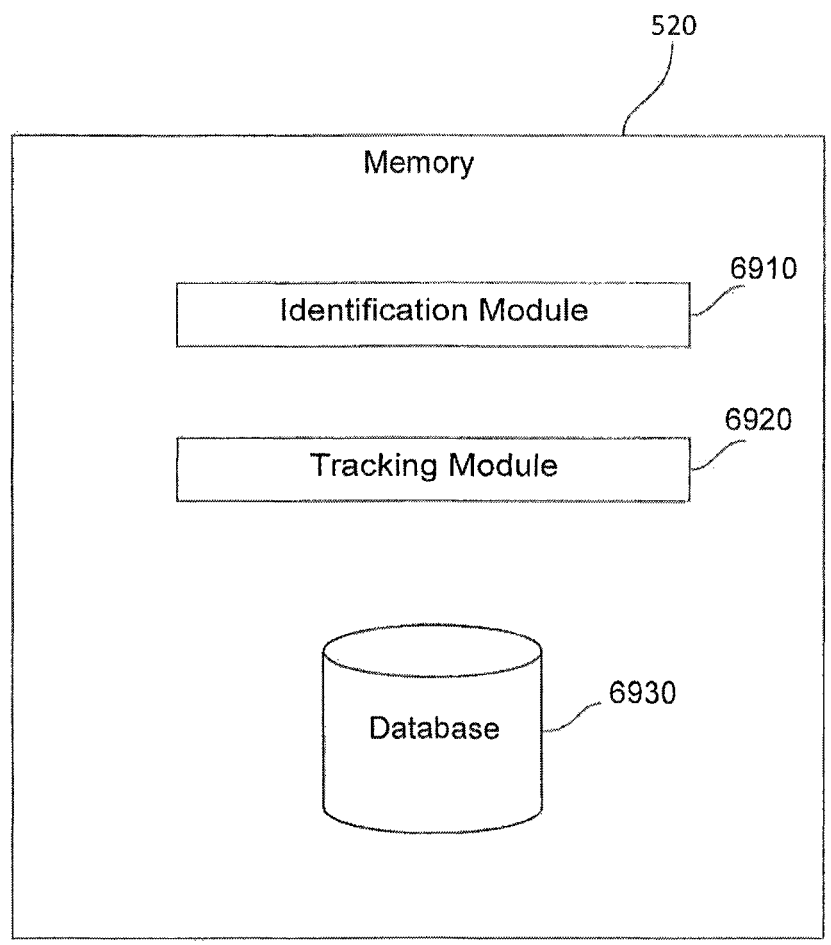
FIG. 69 is a block diagram illustrating an example of a memory configured to provide an object information function, consistent with disclosed embodiments.

In some embodiments, memory 520 may include components configured to provide the object information function. As shown in FIG. 69, memory 520 may include an identification module 6910, a tracking module 6920, and a database 6930. Identification module 6910 may be a component configured to identify an object in real-time images captured by apparatus 110. Tracking module 6920 may be a component configured to track an identified object in the captured real-time images over time. Database 6930 may be a component configured to store data associated with the object information function and provide particular data when requested.

Identification module 6910 and tracking module 6920 may be implemented in software, hardware, firmware, a mix of any of those, or the like. For example, if identification module 6910 and tracking module 6920 are implemented in software, they may be stored in memory 520, as shown in FIG. 69. Other components of processing unit 140 and/or sensory unit 120 may be configured to perform processes to implement and facilitate operations of identification module 6910 and tracking module 6920. Thus, identification module 6910 and tracking module 6920 may include software, hardware, or firmware instructions (or a combination thereof) executable by one or more processors (e.g., processor 540), alone or in various combinations with each other. For example, identification module 6910 and tracking module 6920 may be configured to interact with each other and/or other modules of apparatus 110 to perform functions consistent with disclosed embodiments.

Database 6930 may include one or more memory devices that store information and are accessed and/or managed through a computing device, such as processing unit 140. In some embodiments, database 6930 may be located in memory 520, as shown in FIG. 69. In other embodiments, database 6930 may be located remotely from memory 520, and be accessible to other components of apparatus 110 (e.g., processing unit 140) via one or more wireless connections (e.g., a wireless network). While one database 6930 is shown, it should be understood that several separate and/or interconnected databases may make up database 6930. Database 6930 may include computing components (e.g., database management system, database server, etc.) configured to receive and process requests for data stored in memory devices associated with database 6930 and to provide data from database 6930.

In some embodiments, database 6930 may be configured to store data associated with the object information function of apparatus 110. For example, database 6930 may include recognized objects. In some embodiments, recognized objects may include images of objects that were previously stored via apparatus 110. Recognized objects may be objects that apparatus 110 is configured to identify in real-time image data received by image sensor 350. Recognized objects may include any physical object, a person, an area, an environment, a background, and any combination and/or grouping of these. Recognized objects may include a particular aspect of an object (e.g., shape, color, text, etc.). In some embodiments, database 6930 may also store information indicating whether a recognized object is associated with an object that is likely to change its state, as will be described in more detail below.

In some embodiments, recognized objects may include triggers, including triggers associated with the object information function of apparatus 110. In some embodiments, triggers may be any stored image or portion of an image that apparatus 110 may recognize as an input indicating a particular intention of the user of apparatus 110. For example, a pointing finger, a specific object, a particular hand motion, change in the field-of-view of apparatus 110, change in the user's area of focus, and the like, may be triggers. In some embodiments, apparatus 110 may be configured to perform a process to match a trigger in real-time image data to a trigger stored in database 6930 and perform additional processing to determine whether an object is likely to change states, a state of an object, etc.

In some embodiments, apparatus 110 may be configured to use the object information function to provide information associated with an object to a user. In one example, apparatus 110 may identify an object, determine information associated with the object, and provide feedback to the user based on the determined information, such as audible feedback through feedback-outputting unit 340. In some embodiments, apparatus 110 may also be configured to perform additional processing to determine if an object is likely to change its state and provide feedback based on the results of the determination. In instances in which apparatus 110 determines that an object is likely to change its state, apparatus 110 may be configured to perform additional processing to track the object and provide feedback based on the state of the object, including feedback before and after an object changes states.

Identification module 610 and tracking module 6920 may be implemented in software, hardware, firmware, a mix of any of those, or the like. For example, if the modules are implemented in software, they may be stored in memory 520, as shown in FIG. 69. Other components of processing unit 140 and/or sensory unit 120 may be configured to perform processes to implement and facilitate operations of the modules. Thus, identification module 6910 and tracking module 6920 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., identification module 6910 and tracking module 6920) may each include dedicated sensors (e.g., IR, image sensors, etc.) and/or dedicated application processing devices to perform the functionality associated with each module.

As used herein, real-time image data may refer to image data captured in real-time or near real-time. For example, identification module 6910 may monitor the field-of-view of apparatus 110 to detect inputs while tracking module 6920 may track objects. Accordingly, identification module 6910 and tracking module 6920 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 70:
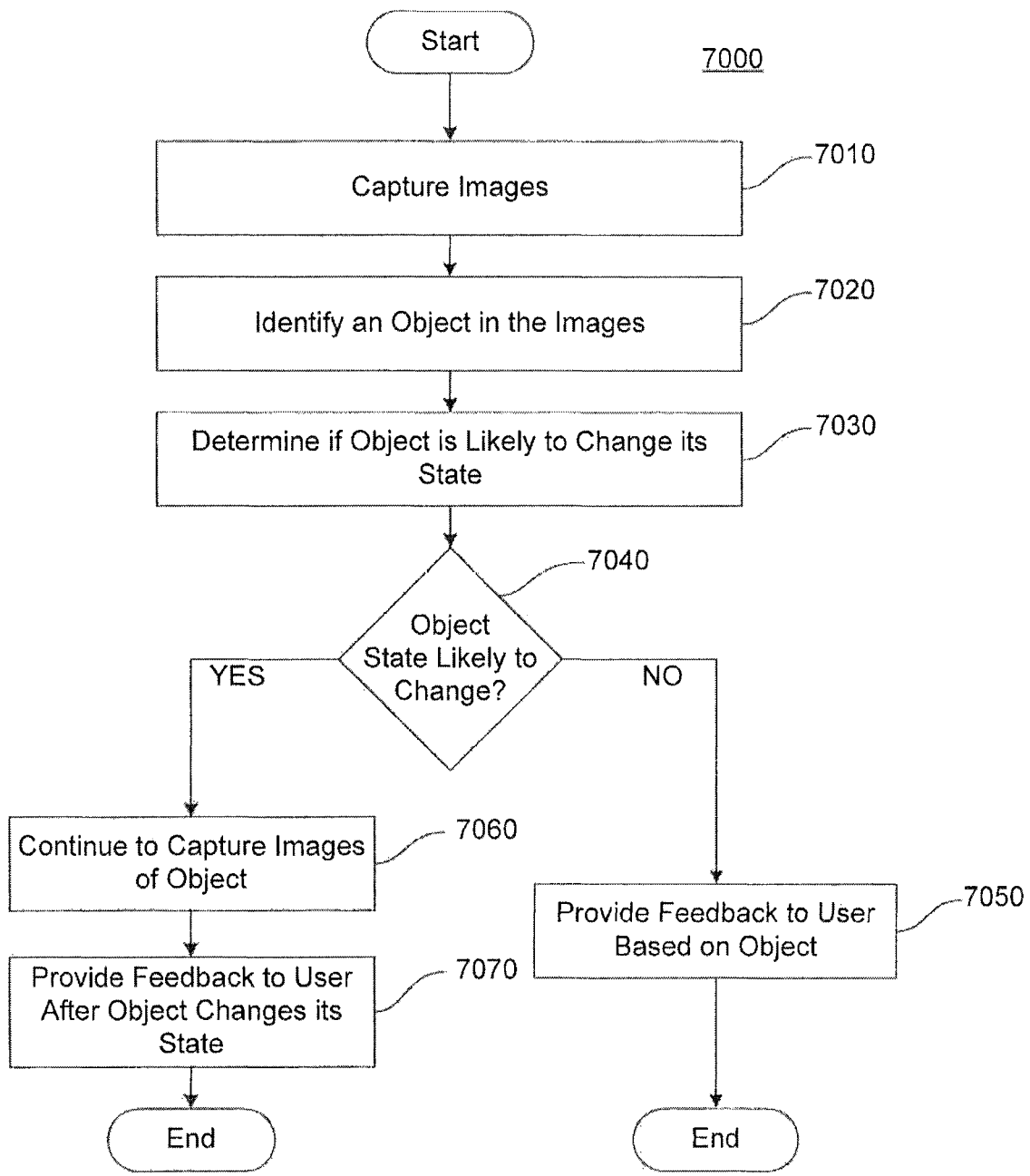
FIG. 70 is a flowchart of an example of a process for providing feedback to a user as part of an object information function, consistent with disclosed embodiments.

FIG. 70 depicts an example of a process 7000 for providing feedback to a user as part of an object information function of apparatus 110. In one embodiment, apparatus 110 may be configured to perform process 7000 to provide information associated with an object to a user, the information depending on a determination of whether the object is likely to change states and, if it is likely to change states, the state of the object.

As apparatus 110 operates, image sensor 350 may capture real time images from an environment of the user (step 7010). Image sensor 350 may capture the images as image data. In some embodiments, identification module 6910 may be configured to process the received image data. For example, identification module 6910 may be configured to process image data to determine if one or more of the images contain an object, such as by matching image data associated with an object to a recognized object stored in database 6930. Based on the determination, identification module 6910 may identify an object in the real-time image(s) (step 7020).

In some embodiments, apparatus 110 may be configured to initially process at least one image captured by image sensor 350 to determine whether an object in the environment of the user is likely to change its state. For example, identification module 6910 may be configured to process received image data to determine whether an identified object is an object that is likely to change its state (step 7030). As used herein an object is "likely to change its state" when the object is capable of changing its state and information associated with the object indicates that the change in state may occur while the object remains in the environment of the user. Examples of changes in state of an object may include a change in color, position, operation, or display of information associated with an object.

The information associated with the object indicating that the object is likely to change states may include any type or form of information. In one example, the information may include stored information associated with the object. For example, the information may include a type of the object identified in the image(s). The type of the object may be stored as information associated with recognized objects in database 6930. Types of objects may include, for example, readily-movable objects (e.g., people, vehicles, hand-held objects, etc.), signals (e.g., stop lights), and displays (e.g., electronic signs, computer screens, televisions, etc.). In some embodiments, an object may only be "likely to change its state" when the object matches a recognized object stored in database 6930 that is associated with information that indicates that the object is a type of object that is likely to change its state. For example, a pedestrian gate in a subway, which may be at an open or closed position.

In another example, the information associated with the object indicating that the object is likely to change states may include additional information that is determined from the image data. Identification module 6910 may be configured to, in addition to identifying objects, identify additional information from at least one of the captured images, which may include additional objects, contextual information, etc. For example, identification module 6910 may be configured to identify a portion of a user's hand in the captured image(s). The portion of the user's hand may be placed in relation to an identified object in such a way that identification module 6910 may make a determination that the user is holding the identified object. For example, identification module 6910 may process an image that includes a portion or portions of a user's hand (e.g., fingers) around the sides of an object. The identification of at least a portion of the user's hand may indicate that the user is holding the object and therefore the object may be readily movable. Movement of the object may constitute a change in state. In this way, identification module 6910 may determine that an object is likely to change its state. In some embodiments, the portion of a user's hand holding the object may act as a trigger that indicates an object is likely to change its state. Identification module 6910 may be configured to identify other triggers that indicate that an object is likely to change states in the image data. For example, identification module 6910 may identify triggers such as a user pointing at an object, a head movement of a user, erratic movement of an object, among others. Similarly, identification module 6910 may be configured to identify a background of an object, and use a particular context of the background of the object as information that indicates that an object is likely to change states.

It should be understood that identification module 6910 may also be configured to determine if an object is unlikely to change its state. An object may be "unlikely to change its state" when the object is incapable of changing its state and/or information associated with the object indicates that the object will not change its state. In some embodiments, identification module 6910 may use the same information to determine if an object is unlikely to change its state as was described with respect to determining that the object is likely to change its state. For example, identification module 6910 may be configured to determine that an object is unlikely to change its state based on a type of an object identified in the image data, an identification of at least a portion of a user's hand, identification of a trigger, a particular context of a background of an object, etc. In some embodiments, identification module 6910 may determine that an object is unlikely change its state in any instance in which a determination that an object is likely to change its state is not made. For example, if no information indicates that the object may change its state while the object remains in the environment of the user, then identification module 6910 may assume that the object is unlikely to change its state. Similarly, identification module 6910 may determine if information associated with an object indicates that the object is unlikely to change its state, and if no information provides such an indication, assume that the object is likely to change its state.

Regardless of the manner in which apparatus 110 determines whether an object is likely (and/or unlikely) to change its state, apparatus 110 may be configured to provide feedback to the user based on the object (e.g., as part of the object information function). In instances in which identification module 610 determines that the object is unlikely to change its state (step 7040—NO), apparatus 110 (via identification module 6910 or some other component), may be configured to provide feedback to the user. For example, if, during initial processing, a determination is made that the object is unlikely to change its state, apparatus 110 may be configured to additionally process the image data (e.g., at least one image in which the object was identified) and provide feedback to the user based on the information in the image data (step 7050). For example, apparatus 110 may be configured to provide feedback (e.g., audible feedback), such as an identification of the object. In another example, apparatus 110 may determine that a traffic light isn't operational since neither of the "walk" or "don't walk" lights are on for a period of time, after which apparatus 110 may notify the user.

In instances in which identification module 6910 determines that an object is likely to change its state (step 7040—yes), apparatus 110 may be configured to perform additional processing to provide appropriate feedback to the user. For example, if, during initial processing, a determination is made that the object is likely to change its state, apparatus 110 may be configured to capture images of the object (step 7060) and alert the user with feedback after a change in state of the object occurs (step 7070). For example, tracking module 6920 may be configured to track an object throughout one or more additional images of the object, and identification module 6910 may be configured to continue to process image data associated with the tracked object and determine that the object has changed its state. After this type of identification is made, apparatus 110 may be configured to provide feedback (e.g., audible feedback) to the user, such as an indication that the state of the object has changed and/or an indication of the state of the object. In some embodiments, apparatus 110 may also be configured to provide feedback (e.g., audible feedback) to the user based on the initial state of the object (e.g., before the object changes states), such as an indication that an identified object is likely to change states and/or an indication of the state of the object at that time.

Apparatus 110 may perform process 7000 to provide a user with information about an object, including an object that is likely to change its state. The information may include an initial state of an object and a subsequent state of an object (e.g., after a change in state). Apparatus 110 may provide information associated with each state of an object to a user, such that the user may understand what information the object is conveying at the time, and make appropriate decisions based on the information. In this way, a visually-impaired user of apparatus 110 may be able to interact with objects in their environment, even though they may be unable to visually identify information associated with an object.

Figure 71:
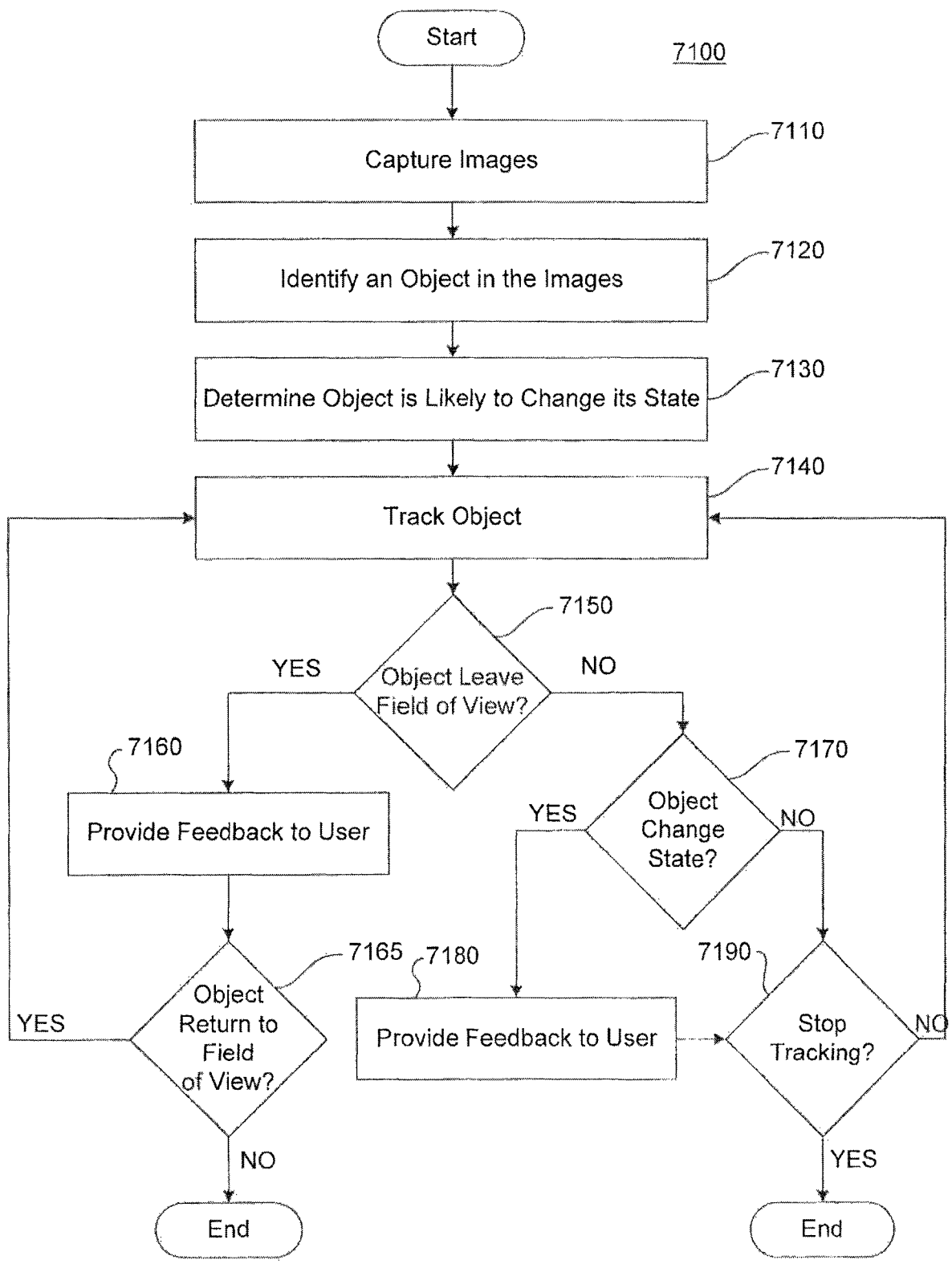
FIG. 71 is a flowchart of another example of a process for providing feedback to a user as part of an object information function.

FIG. 71 depicts another example of a process 7100 for providing feedback to a user as part of the object information function of apparatus 110. In one aspect, process 7100 may be performed by apparatus 110 in instances in which an identified object is determined to be likely to change its state. In some embodiments, identification module 6910 and tracking module 6920 may be configured to perform process 7100 to provide a user with feedback about an object that is likely to change its state. To perform process 7100, apparatus 110 may be arranged with image sensor 350 configured to capture real-time images from an environment of a user (step 7110). In some embodiments, image sensor 350 may also be configured to be worn by a user such that a field-of-view of image sensor 350 (e.g., the detectable area) substantially coincides with a field-of-view of the user (e.g., the area a visually-unimpaired user may be configured to see).

As has been described in relation to other disclosed processes, apparatus 110 may be configured to process real-time images to determine an existence of an object in the field-of-view of image sensor 350 (step 7120). For example, identification module 6910 may process received image data to match a portion of an image to a recognized object stored in database 6930.

Apparatus 110 may be further configured to determine whether a state of the object is likely to change. Identification module 6910 may determine whether a state of the object is likely to change in a manner that is the same or similar to the determination process described in step 7040 of process 7000. In the example of process 7100, identification module 6910 may determine that an identified object is likely to change its state (step 7130).

In some embodiments, apparatus 110 may be configured to track the identified object (step 7140). In some aspects, apparatus 110 may track the object, while the object remains within the field-of-view of the image sensor, to determine when the change of state occurs. For example, after an object has been identified in an image, tracking module 6920 may be configured to monitor subsequent images for existence of the object and any change in state of the object.

During tracking of an object, tracking module 6920 may determine if the object leaves the field-of-view of image sensor 350 (step 7150). An object may leave the field-of-view of image sensor 350, for example, when the user moves his or her head in such a way that image sensor 350 is directed away from the object, when the object moves to a location outside the field-of-view of image sensor 350, when another object blocks the tracked object from being captured in an image, etc.

In instances in which tracking module 6920 determines that the object has left the field-of-view of image sensor 350 (step 7150—YES), apparatus 110 (e.g., through tracking module 6920) may be provide feedback to the user of apparatus 110 (step 7160). For example, apparatus 110 may provide an indication, such as an audible indication, when the object exits the field-of-view of image sensor 350. The feedback may serve as an indication that an object that was being tracked is no longer in the images being captured by apparatus 110, and, therefore, apparatus 110 may not be able to provide additional feedback if the object changes states.

Tracking module 6920 (and/or identification module 6910) may be configured to determine if the object returns to the field-of-view of image sensor 350 (step 7165). If and when the object returns to the field-of-view of image sensor 350 (e.g., it reappears in the image data) (step 7165—YES), tracking module 6920 may automatically resume following (e.g., tracking) the object (e.g., at step 7140). In some embodiments, tracking module 6920 may be configured to resume following the object if the object reappears in the field-of-view of image sensor 350 with a predetermined period of time. If the object does not return to the field-of-view of image sensor (step 7165—NO), in a predetermined period of time, for example, apparatus 110 may stop performing processes associated with the object and process 7100 may end.

While tracking module 6920 continues to track an object that remains in the field-of-view of image sensor 350 (step 7150—NO), identification module 6910 (and/or tracking module 6920) may be configured to determine if the object has changed its state (step 7170). For example, identification module 6910 may monitor image data to determine if an object in an image (e.g., a tracked object) is in a state that is different from previous images of the object.

In some embodiments, in instances when apparatus 110 determines that a state of an object has changed (step 7170—YES), apparatus 110 (e.g., through identification module 6910) may provide feedback to the user (step 7180). For example, apparatus 110 may be configured to provide audible feedback to the user. The audible feedback may include information such as an indication that the object changed states, an indication of the state to which the object changed, information that is intended to be conveyed by the state of the object, etc. In some embodiments, apparatus 110 may be configured to provide a plurality of audible feedbacks, each audible feedback being associated with a specific change in the state of an object.

Tracking module 6920 may be further configured to determine whether to stop tracking an object (step 7190). In instances in which a determination that a tracked object has changed states has not yet been made (step 7170—NO), tracking module 6920 may be configured to determine whether the object should continue to be tracked. Even in instances in which an object did change its state and feedback was provided to the user, tracking module 6920 may determine whether the object should continue to be tracked, such as to identify subsequent changes in a state of the object.

If tracking module 6920 determines that the object should continue to be tracked (step 7190—NO), process 7100 may return to step 7140, where tracking module 6920 may continue to monitor real-time images to follow the object. In this way, if the object changes states (for the first time and/or a subsequent time), apparatus 110 may provide feedback to the user. Process 7100 may continue through iterations of tracking an object and providing feedback each time it leaves a field-of-view and/or changes states, as long as tracking module 6920 determines that the object should continue to be tracked. However, if tracking module 6920 determines that tracking of the object should stop (step 7190—YES), apparatus 110 may stop performing processes associated with the object and process 7100 may end. For example, apparatus 110 may be configured to stop tracking an object after a predetermined number of changes in the state of the object has occurred, after a predetermined period of time, after a predetermined period of time without any change to the state of an object, etc.

Through example processes 7000 and 7100, apparatus 110 may identify an object and alert a user to the state of the object. For example, apparatus 110 may be configured to identify an object as a traffic light. A traffic light may include multiple lights, each which illuminate in a different color (e.g., red, yellow, green) to indicate different information to a viewer of the traffic light (e.g., stop, slow, go). As applied to the disclosed embodiments, a change of a state of the traffic light may include a change in color of the traffic light (e.g., red to green, green to yellow, yellow to red, etc.). Apparatus 110 may be configured to perform processes 7000 and/or 7100 to identify the traffic light, track the traffic light, and alert a user when the traffic light changes states (e.g., turns to red, turns to green, etc.).

Figure 72B:
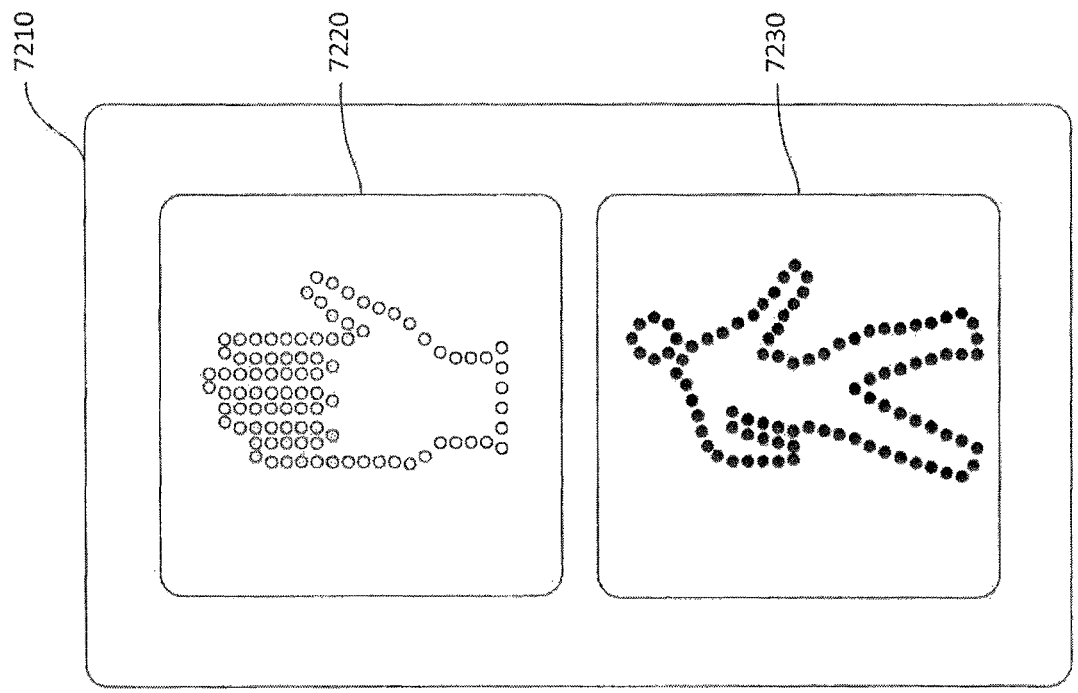
FIGS. 72A and 72B illustrate an example of a pedestrian stoplight that changes state.
Figure 72A:
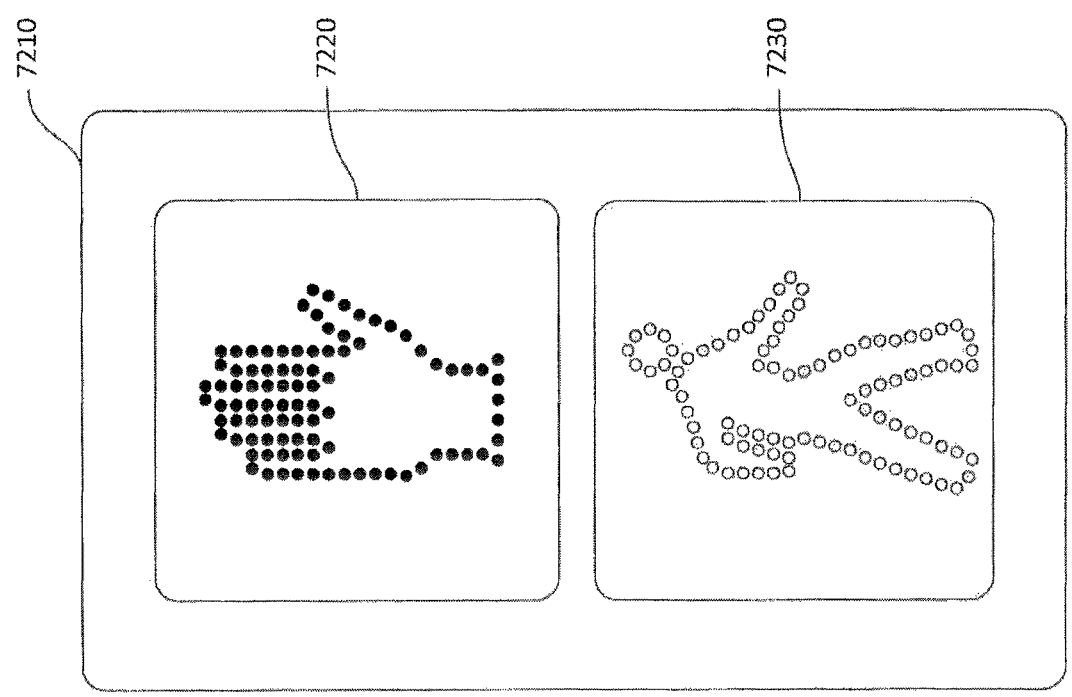

FIGS. 72A and 72B depict an example of an object that changes its state, and that may be identified by apparatus 110. As shown in FIGS. 72A and 72B, the object is a pedestrian stoplight 7210 that includes a first electronic signal 7220 and a second electronic signal 7230. First electronic signal 7220 may be a stop signal configured to be illuminated to indicate to individuals not to enter a particular crosswalk, for example. Second electronic signal 7230 may be a walk signal configured to be illuminated to indicate to individuals that it may be safe to enter the crosswalk, for example.

FIG. 72A depicts an example of a first state of pedestrian stoplight 7210. In the first state, first electronic signal 7220 may be illuminated (e.g., with red light) and second electronic signal 7230 may be dark (e.g., not illuminated). FIG. 72B depicts an example of a second state of pedestrian stoplight 7210. In the second state, first electronic signal 7220 may be dark (e.g., not illuminated) and second electronic signal 7230 may be illuminated (e.g., with green light).

In providing an object information function, apparatus 110 may identify pedestrian stoplight 7210 in at least one image captured by image sensor 350, when pedestrian stoplight 7210 is in the field-of-view of image sensor 350. In addition, apparatus 110 may be configured to determine that pedestrian stoplight 7210 is an object that is likely to change its state (e.g., based on the type of the object, a background of the object, a trigger, etc.). Apparatus 110 may be further configured to provide feedback to the user (e.g., an audible indicator), such as an indication of the first state of pedestrian stoplight 7210 and/or associated information (e.g., "the stoplight is red," "do not walk," etc.).

Apparatus 110 may also be configured to track pedestrian stoplight 7210, while it remains in the field-of-view of image sensor 350. If the pedestrian stoplight 7210 leaves the field-of-view of image sensor 350, apparatus 110 may provide feedback to the user to indicate that the user should return stoplight 7210 to the field-of-view (e.g., "lost view of the stoplight," "please look at the stoplight," etc.). When the pedestrian stoplight 7210 changes from the first state (FIG. 72A) to the second state (FIG. 72B), apparatus 110 may provide feedback to the user, such as an indication of the second state of stoplight 7210 and/or associated information (e.g., "the stoplight is green," "safe to cross," etc.).

Figure 73A:
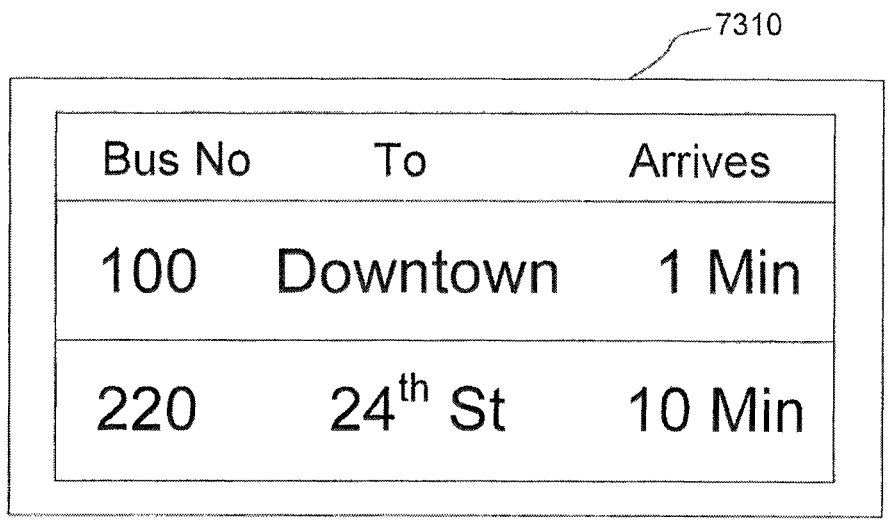
FIGS. 73A and 73B illustrate an example of an electronic display that changes state.
Figure 73B:
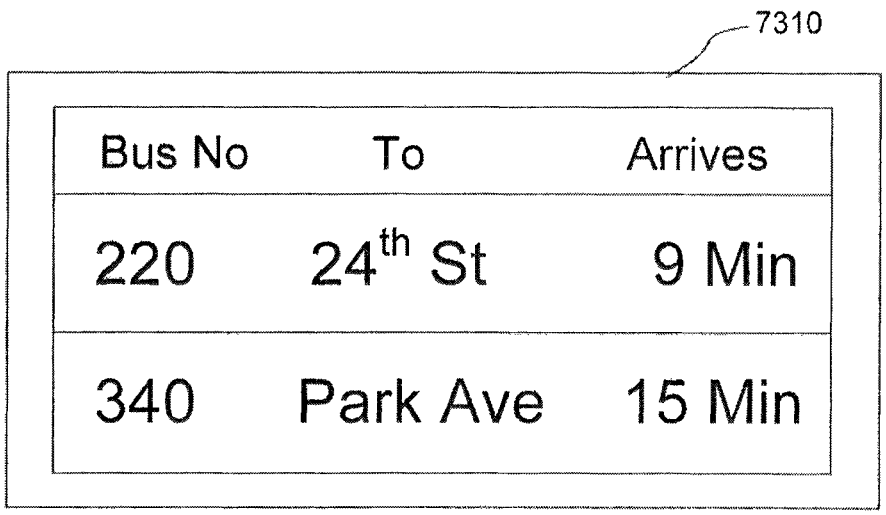

It should be understood that the disclosed embodiments may be used to apply the object information function to many different objects that may change states in a variety of ways. For example, apparatus 110 may use similar processing to identify an electronic display and provide feedback to a user to identify a change in state of the electronic display, including an update to the text of an electronic display. In this way, a user may be alerted to a change in information on a sign. FIGS. 73A and 73B illustrate an example of an electronic display 7310 that includes textual information identifying the arrival time of a public transportation vehicle. FIG. 73A may depict a first state of electronic display 7310 and FIG. 73B may depict a second state of electronic display 7310. Apparatus 110 may be configured to provide feedback associated with the first state of electronic display 7310 (e.g., audibly read the text). Consistent with disclosed embodiments, apparatus 110 may also be configured to determine that electronic display 7310 is likely to change its state and track electronic display 7310 in captured image data. After electronic display changes from the first state to the second state, apparatus 110 may determine that state has changed, and provide additional feedback to the user, such as an indication that electronic sign 7310 has changed states and/or information associated with the second state (e.g., audibly read the text).

In another example, apparatus 110 may be configured to identify a person as an object and provide feedback to the user based on a change in state of the person. For example, apparatus 110 may be configured to monitor a facial expression of the person and provide feedback when a facial expression of the person changes (e.g., the person smiles, frowns, etc.). In this way, the user may be alerted to a visual characteristic of a person that may communicate particular information about the person (e.g., the person is happy, sad, angry, etc.). For example, a visually-impaired user may want to know if a person (e.g., a store clerk) in front of them is looking at them (and is awaiting a reply, for example).

In another example of the object information function, apparatus 110 may be configured to identify readily-movable objects and provide feedback based on the movement of the object. For example, apparatus 110 may be configured to identify a vehicle (including stationary vehicles and moving vehicles), which may also be determined to be an object that is likely to change its state.

For example, apparatus 110 may identify a public transportation vehicle in the image data. Apparatus 110 may be configured to identify an appearance of the public transportation vehicle in the environment of the user as a change in state of the object. In this way, apparatus 110 may be configured to provide feedback to a user to indicate that a public transportation vehicle has arrived (e.g., and/or is ready to be boarded). Similarly, apparatus 110 may be configured to identify a change in direction or speed of a moving vehicle as a change in state of an object. In this way, the user may be alerted to the movement of vehicles in their environment.

Another example of a change in state of a readily-movable object may include the appearance of a portion of the object in the image data. For example, an object may include text on at least a portion of the object. Apparatus 110 may identify an appearance of the text on the object in the environment of the user as a change in state of the object and provide feedback to the user based on this change (e.g., audibly read the text to the user). In some instances, apparatus 110 may identify an object that includes text at least a part of which is not viewable by the image sensor, where the change in state of the object may include an appearance of at least a part of the text to image sensor 350. Further, it should be understood that movement of the user to bring an object, or a portion of an object, into the field-of-view of image sensor 350 may constitute a similar change in state of an object, causing apparatus 110 to provide appropriate feedback.

As is evident from the foregoing, apparatus 110 may provide a wide range of functionality. More specifically, one embodiment consistent with the present disclosure provides a method for providing user 100, who may be visually impaired, with information about one or more objects or situations detected within the field of view of apparatus 110. Apparatus 110 may be configured to monitor real-time image data to determine relative motion between portions of scenes captured within the image data. If one portion of the scene moves less than at least one other portion of the scene, apparatus 110 may be configured to obtain contextual information from that portion of the scene. In some embodiments, apparatus 110 may further provide feedback to the user based on at least part of the contextual information. In other embodiments, apparatus 110 may further adjust one or more parameters associated with image sensor 350 or an associated camera based on at least part of the contextual information.

Figure 74:
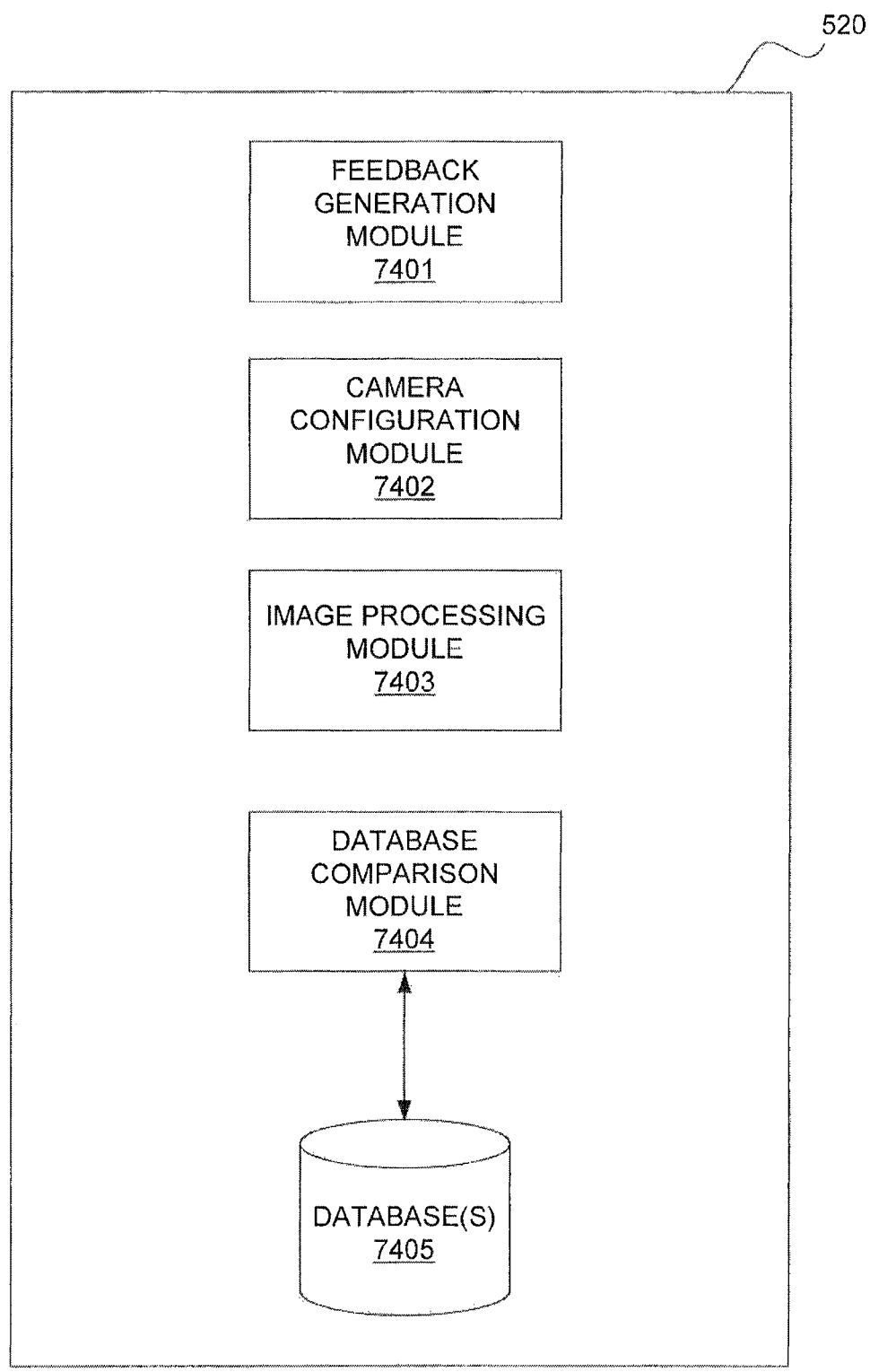
FIG. 74 is a block diagram illustrating an example of a memory contained within an apparatus for aiding persons who have low vision.

FIG. 74 is a block diagram illustrating memory 520 associated with apparatus 110 according to one embodiment. In the example shown in FIG. 74, memory 520 comprises a feedback generation module 7401, a camera configuration module 7402, an image processing module 7403, a database comparison module 7404, and one or more databases 7405.

Feedback generation module 7401 may provide functionality for apparatus 110 to generate and transmit information to user 100 in response to a query. Processor 540 may execute feedback generation module 7401 to generate and process feedback in a given context, then transmit the generated feedback to feedback-outputting unit 340 for output to user 100. In one embodiment, processor 540 and feedback-outputting unit 340 may be operatively connected via wire 130. In other embodiments, processor 540 and feedback-outputting unit 340 may be operatively connected via wireless transceiver(s) 530. As discussed above, in some embodiments, feedback generation module 601 may generate audible feedback to user 100. In other embodiments, the feedback may be tactile in nature, such as a vibration.

Camera configuration module 7402 may provide functionality for apparatus 110 to capture real-time image data via image sensor 350. Processor 540 may execute camera configuration module 7402 to acquire the images, and may additionally use camera configuration module 7402 to adjust one or more parameters associated with image sensor 350 and an associated camera. In one embodiment, processor 540 and image sensor 350 may be operatively connected via wire 130. In other embodiments, processor 540 and image sensor 350 may be operatively connected via wireless transceiver(s) 530.

Image processing module 7403 may provide functionality for apparatus 110 to analyze sets of real-time image data captured by image sensor 350. Processor 540 may execute image processing module 7403, for example, to determine the positions of objects in one or more sets of image data over time, and determine the relative motion of those objects. As discussed above, image processing module 7403 may be configured to execute software instructions to perform actions to assist user 100, such as performing optical character recognition on text that is detected within the captured sets of real-time image data.

Database comparison module 7404 may provide functionality for apparatus 110 to compare objects detected in the user environment to objects and/or categories of said objects in a database, such as database(s) 7405, to be described in detail below. In some embodiments, database comparison module 7404 may derive information from real time image data received from image sensor 350. In other embodiments, other software elements or processors may derive the information and provide it to database comparison module 7404. Processor 540 may execute database comparison module 7404 to access one or more of the described databases, and compare the information derived from the received real time image data with information in the databases. If the derived information corresponds to information found in one or more of the databases, database comparison module 604 may provide an indication to feedback generation module 7401 to that effect as discussed in further detail below in association with FIGS. 79-80.

Database(s) 7405 may comprise one or more databases that store information and are accessed and/or managed through memory 520. By way of example, databases 7405 may include document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 7405 may contain software code or macros that facilitate rapid searching and comparison by database comparison module 7404.

Feedback generation module 7401, camera configuration module 7402, image processing module 7403, and database comparison module 7404 may be implemented in software, hardware, firmware, a mix of any of those, or the like. For example, if the modules are implemented in software, they may be stored in memory 520, as shown in FIG. 74. Other components of processing unit 140 and/or sensory unit 120 may be configured to perform processes to implement and facilitate operations of the modules. Thus, feedback generation module 7401, camera configuration module 7402, image processing module 7403, and database comparison module 7404 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., feedback generation module 7401, camera configuration module 7402, image processing module 7403, and database comparison module 7404) may each include dedicated sensors (e.g., IR, image sensors, etc.) and/or dedicated application processing devices to perform the functionality associated with each module.

As used herein, real-time image data may refer to image data captured in real-time or near real-time. For example, image processing module 7401 may monitor the field-of-view of apparatus 110 to detect inputs while database comparison module 7404 may compare captured image data to stored images. Accordingly, image processing module 7401 and while database comparison module 7404 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 75:
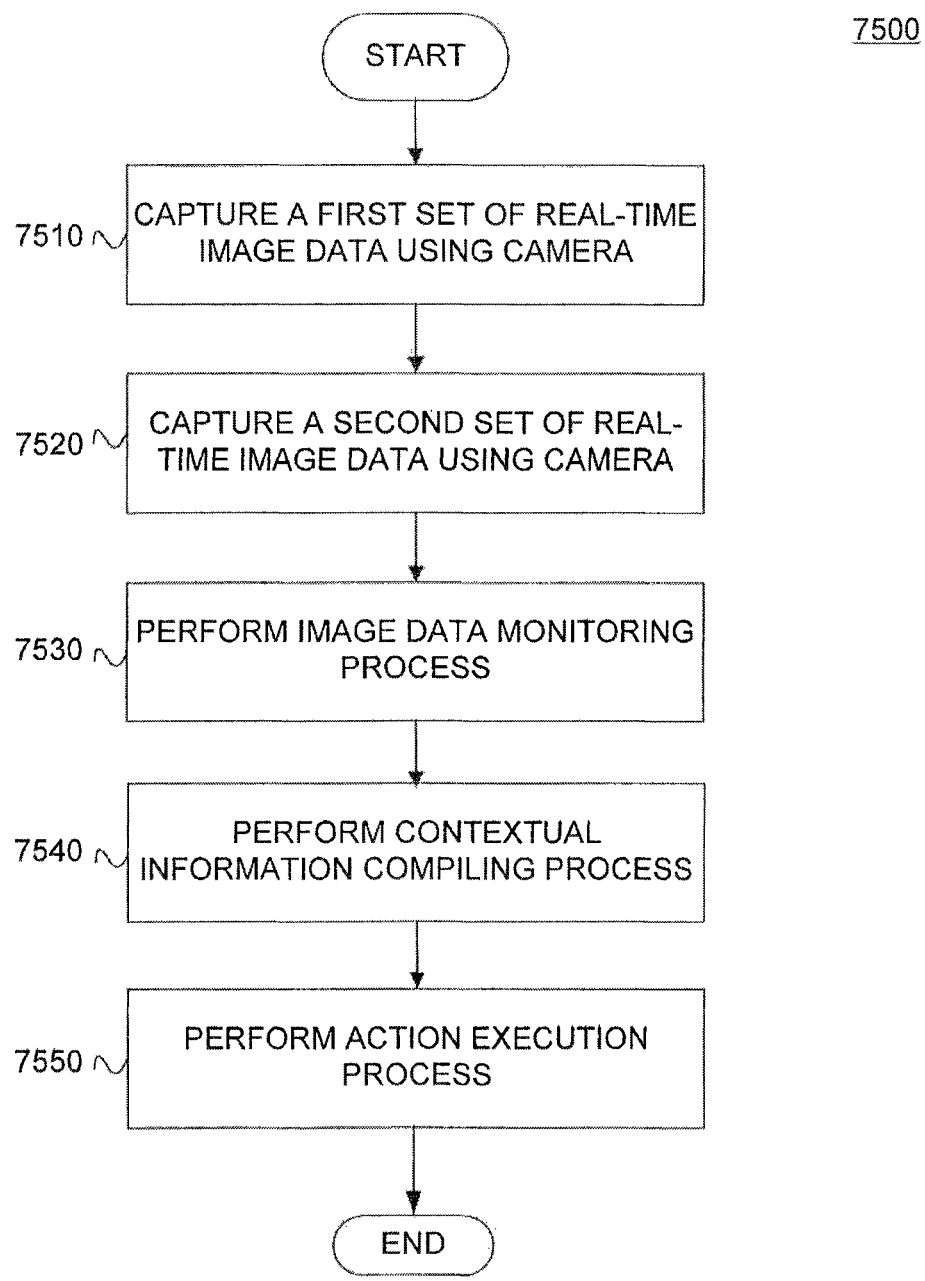
FIG. 75 is an example of a process for providing feedback to a person who has low vision, consistent with disclosed embodiments.

FIG. 75 illustrates an example of a process 7500 for providing feedback to a person who has low vision consistent with certain disclosed embodiments. Process 7500, as well as any or all of the individual steps therein, may be performed by various aspects of device 110, such as sensory unit 120, processing unit 140, support 210, or any subcomponents therein. For exemplary purposes, FIG. 75 is described as being performed by processor 540, executing software instructions stored within memory 520.

Processor 540 may execute software instructions via camera configuration module 7402 that enable apparatus 110 to capture a first set of real-time image data using a camera associated with an image sensor, such as image sensor 350 (Step 7510). In some embodiments, processor 540 may receive the captured first set of image data directly from image sensor 350. In other embodiments, processor 540 may receive the captured first set of image data from an intermediate component associated with sensory unit 120. The intermediate unit may, for example, perform image processing operations on the real-time image data before transmitting it to processor 540, as will be discussed in further detail below. In some embodiments, the captured first set of real-time image data may be received as a single streaming video file. In other embodiments, the real-time image data may be received as a series of still images. When the captured image data is received, processor 540 may store the data in memory 520 or database(s) 7405.

Processor 540 may execute software instructions via camera configuration module 7402 that enable apparatus 110 to capture a second set of real-time image data using a camera associated with an image sensor, such as image sensor 350 (Step 7520). The second set of real-time image data may be captured, processed, and received in substantially the same manner as the first set of image data described above. In some embodiments, the captured first set of real-time image data may be received as a single streaming video file. In other embodiments, the real-time image data may be received as a series of still images. When the captured image data is received, processor 540 may store the data in memory 520 or database(s) 7405.

In Step 7530 of process 7500, processor 540, via image processing module 7403, may perform an image data monitoring process, such as is described below in connection with FIG. 77. In brief, according to some embodiments, image processing module 7403 may load the first and second captured sets of real-time image data. Image processing module 7403 may determine positions of one or more objects in the first set of captured real-time image data, and may also do so for the second set of data. Image processing module 7403 may determine which of the detected objects are in the foreground of the images within the image data sets, and which of the detected objects are in the background. Image processing module 7403 may then determine the relative motion, if any, of the detected objects across the first and second sets of captured image data.

Processor 540 may perform a contextual information compiling process, such as is described below in connection with FIG. 78 (Step 7540). In brief, according to some embodiments, processor 540, via image processing module 7403, may determine one or more objects across the first and second sets of captured real-time image data that are relatively stationary based on image data monitoring. Processor 540 may also determine one or more moving objects across the two sets of data based on the monitoring. Additionally, processor 540 may determine one or more "lingering" objects of interest across the two sets of data based on the monitoring. Based on the identified images, image processing module 7403 may select objects requiring compilation of contextual information. Processor 540 may then compile contextual information on the selected objects.

Processor 540 may perform an action execution process, such as is described below in connection with FIG. 79 (Step 7550). In brief, according to some embodiments, processor 540 may select one or more system processing schemes based on compiled contextual information. Based on the selected system processing scheme, processor 540, in conjunction with database comparison module 7404, may determine one or more context-based actions associated with the processing scheme. Processor 540 may select one or more of the determined context-based actions, and then execute the selected action(s). Finally, processor 540 may perform a feedback generation process.

Figure 76B:
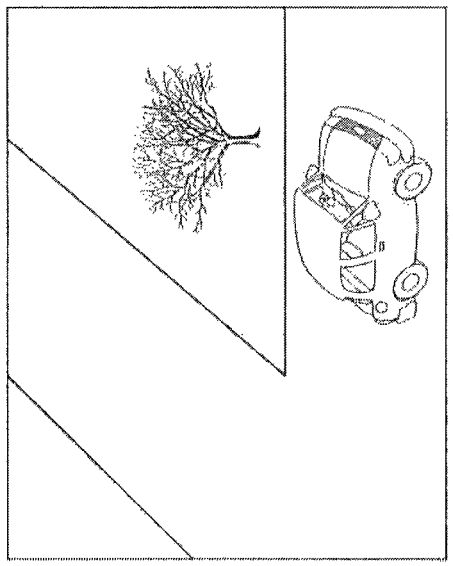
FIGS. 76A and 76B are example illustrations of an object moving through the field of view of an apparatus while the background remains stationary, consistent with disclosed embodiments.
Figure 76D:
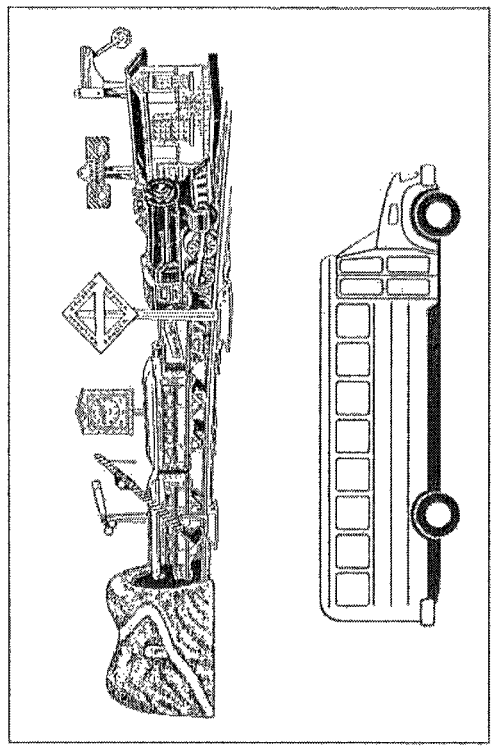
FIGS. 76C and 76D are example illustrations of an object moving through the field of view of an apparatus and being tracked by the head of a user, consistent with disclosed embodiments.
Figure 76A:
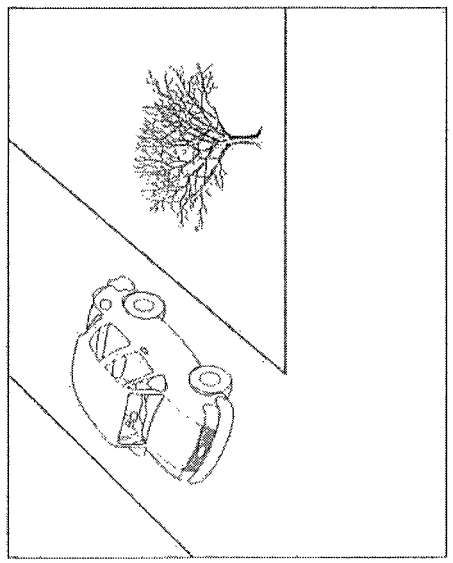

FIGS. 76A-76G illustrate examples of fields of view of apparatus 110, consistent with certain disclosed embodiments. FIGS. 76A-76B illustrate an example field of view of apparatus 110 in which an object is seen to move in the foreground of the field of view while the background remains stationary. In the example of FIG. 76A, a car can be seen approaching an intersection. In FIG. 76B, the car has turned onto the cross street of the intersection. In these embodiments, processor 540 may be configured to obtain contextual information relating to either the moving object (the car) or the stationary background. Apparatus 110 may then perform one or more context-based actions relating to the recognized scene elements.

Figure 76C:
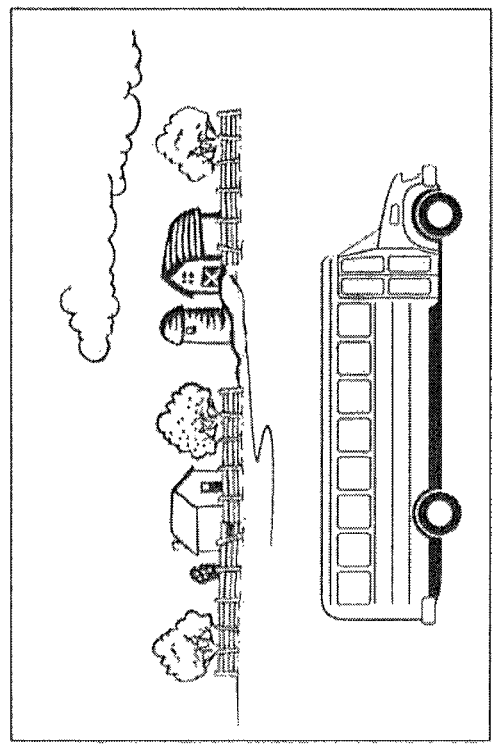

FIGS. 76C-76D illustrate an example field of view of apparatus 110 in which user 100 tracks an object as it moves. Therefore, the tracked object appears to be stationary while the background moves. In the example of FIG. 76C, a bus can be seen passing one background scene. In FIG. 76D, the bus remains in the center of the field of view of apparatus 110 as user 100 tracks its motion with their head, but the background scene behind it has changed. In these embodiments, processor 540 may be configured to obtain contextual information relating to either the object being tracked (e.g., the bus) or the various background fields. Apparatus 110 may then perform one or more context-based actions relating to the recognized scene elements.

Figure 76E:
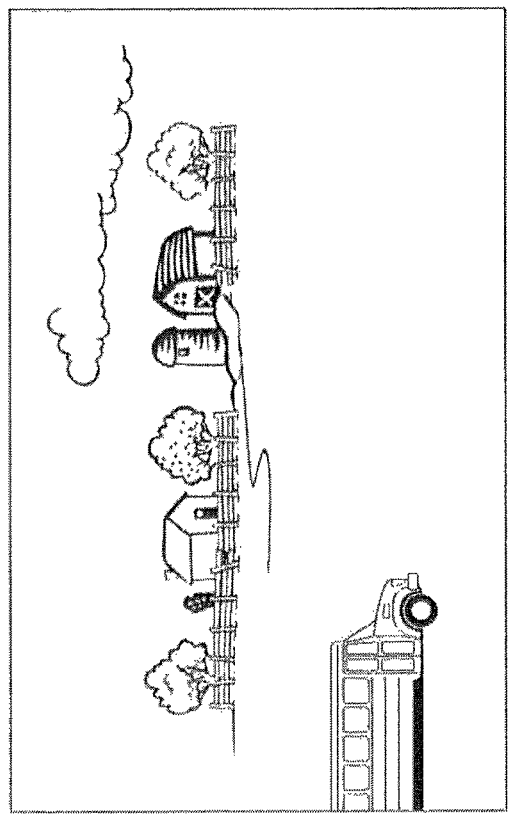
FIGS. 76E, 76F, and 76G are example illustrations of an object lingering in the field of view of an apparatus, consistent with disclosed embodiments.
Figure 76F:
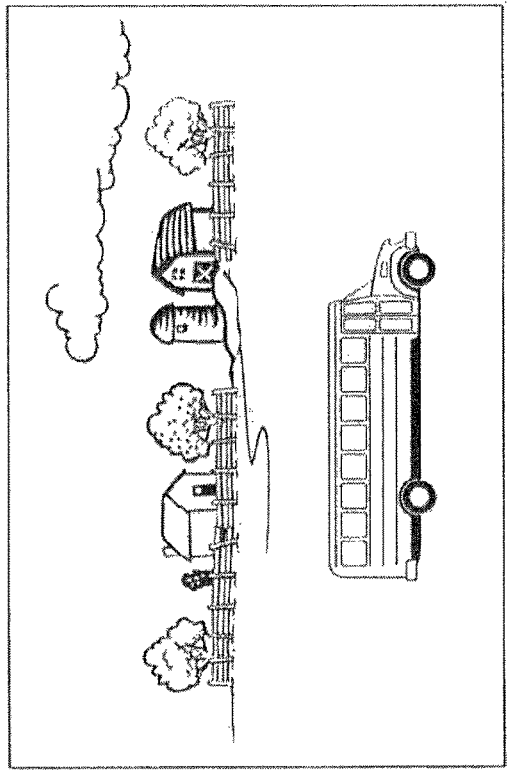
Figure 76G:
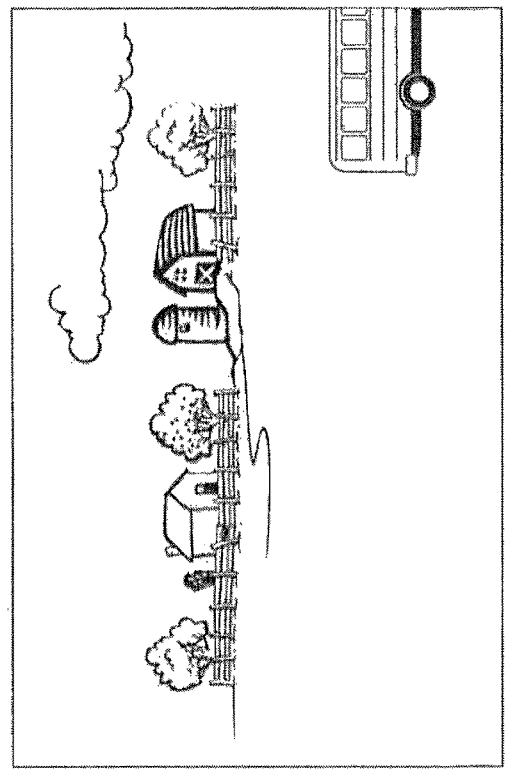

FIGS. 76E, 76F, and 76G illustrate an example field of view of apparatus 110 in which an object enters the field of view, lingers temporarily, then leaves. Therefore, the lingering object moves, then stops, then moves again, while the background remains stationary. In the example of FIG. 76E, a bus can be seen entering the left side of the field of view. In FIG. 76F, the bus is lingering temporarily, and remains in the center of the field of view of apparatus. In FIG. 76G, the bus is moving again, and leaves the field of view to the right. In these embodiments, processor 540 may be configured to obtain contextual information relating to either the lingering object (the bus) or the background. Apparatus 110 may then perform one or more context-based actions relating to the recognized scene elements.

Figure 77:
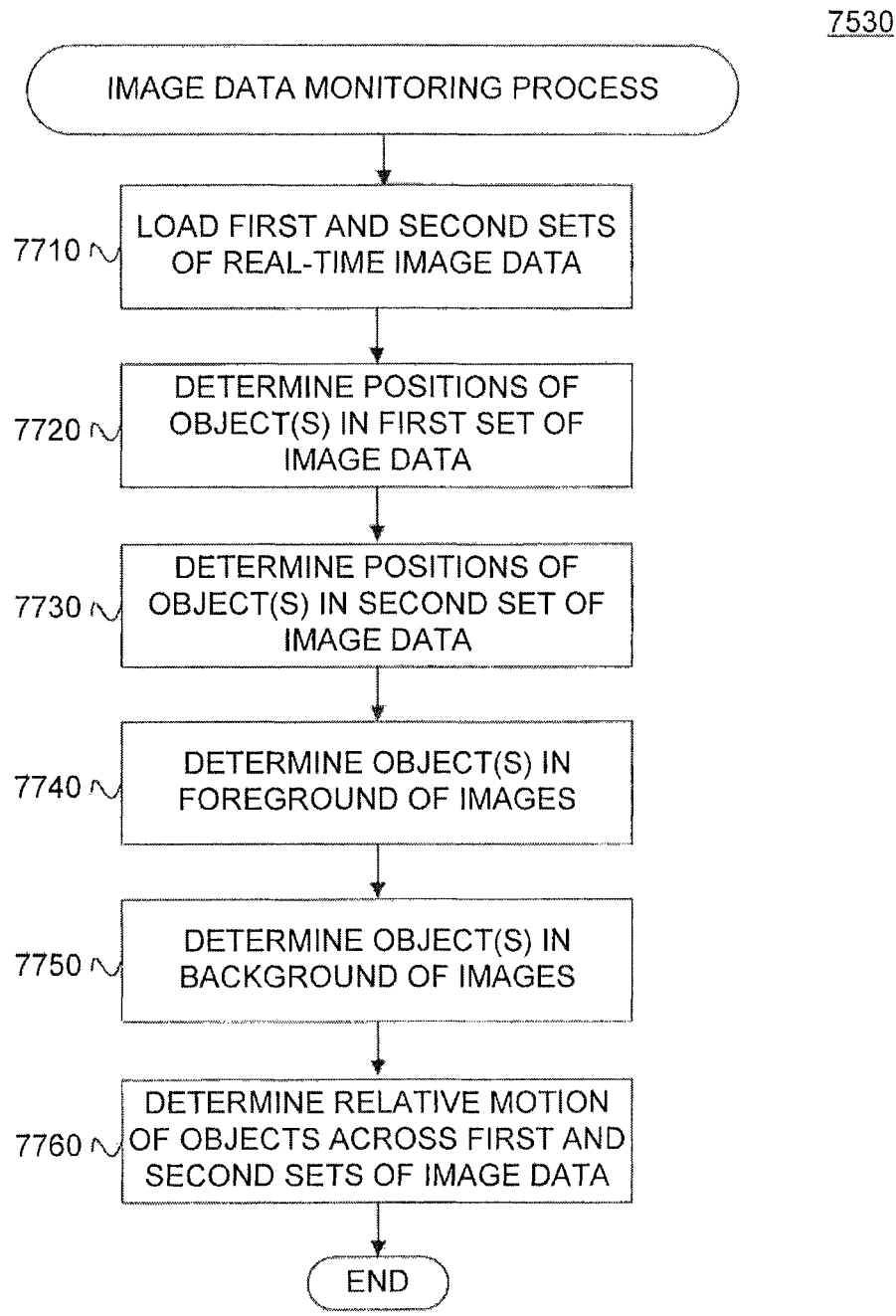
FIG. 77 is an example of an image data monitoring process, consistent with disclosed embodiments.

FIG. 77 illustrates an example image data monitoring process such as that described above in association with Step 7530 of process 7500, consistent with certain disclosed embodiments. Process 7530, as well as any or all of the individual steps therein, may be performed by various aspects of device 110, such as sensory unit 120, processing unit 140, support 210, or any subcomponents therein. For exemplary purposes, FIG. 77 is described as being performed by processor 540, executing software instructions stored within memory 520.

Processor 540, via image processing module 7403, may load first and second sets of captured real-time image data (Step 7710). Image processing module 7403 may determine positions of one or more objects in the first set of captured image data (Step 7720). In some embodiments, image processing module 7403 may determine the positions of particular objects within the first set of captured image data. In other embodiments, image processing module 7403 may instead divide the frames of image data into portions, for example, halves, quadrants, etc. Image processing module 7403 may determine the positions of objects or the location of portions by a coordinate system or similar system of referential location. In other embodiments, image processing module 7403 may determine the positions of objects or location of portions by relative distance from one or more edges of the field of view of apparatus 110; for example, image processing module 7403 may register the position of an object or the location of a portion by the number of pixels the object is away from the top and left sides of the field of view. Positions of objects may be determined by their edges, their centers/centroids, or by any method known to those skilled in the art of image processing. Image processing module 7403 may repeat Step 7720 for the second captured set of image data, and for any subsequent sets of captured image data (Step 7730).

Image processing module 7403 may determine one or more objects in the foreground of the images captured in one or both of the first and second sets of captured real-time image data (Step 7740). In some embodiments, image processing module 7403 may determine that an object is in the foreground based on the focus of the image. In these embodiments, processor 540 may additionally call camera configuration module 7402 in order to determine the center of focus of the image, the focal length of the lens of image sensor 350, or any other parameter of image sensor 350 and any associated camera(s) that may assist in determining the depth of field of the image data. In some embodiments, image processing module 7403 may determine that an object is in the foreground of an image based on its proximity to a known, recognized object that is detected within the image data. For example, if information about a bus stop has been previously stored within database(s) 7405, processor 540 may detect that the bus stop appears in the field of view of apparatus 110, by way of image processing module 7403 and database comparison module 7404. If a second, novel object of interest such as a bus is determined to be between user 100 and the known bus stop, image processing module 7403 may determine that the bus is in the "foreground" of the image. Image processing module 7403 may determine that objects are in the "background" of the image by similar methods (Step 7750). It is to be understood that "foreground" and "background" as used in this specification are relative terms, and that the terms are not tied to any specific dimensional meaning or distance measurement.

Image processing module 7403 may determine relative motion of one or more of the determined objects across the first and second captured sets of image data (Step 7760). In some embodiments, camera configuration module 7402 and/or image processing module 7403 may determine that the position of an object changed from the time that the first set of image data was captured to the time that the second set of images was captured. As an example, in the illustration described above with respect to FIGS. 76A-76B, the car in FIG. 76A made a left turn at the intersection shown in FIG. 76A, and is therefore in a different position in FIG. 76B. In that example, FIG. 76A may comprise a first set of captured image data, and FIG. 76B may comprise a second set of such data. Image processing module 7403 may determine that the object in question changed position by detecting that an edge of the object or a determined center/centroid of the object is not at the same position in the second set of captured image data as it was in the first set of such data. In embodiments where image processing module 7403 is configured to use a coordinate system for position determination, image processing module 7403 may determine that the edge or center/centroid of the object of interest is at a different coordinate position in the second set of captured image data versus the first set of such data. Alternatively, in embodiments where image processing module 7403 divides the field of view of apparatus 110 into portions, image processing module 7403 may gauge relative motion of objects within the individual portions, or may focus on the field of view as a whole to determine whether relative motion occurs between a first portion of a scene and other portions of the scene captured in the plurality of images comprising the first and second sets of image data.

Figure 78:
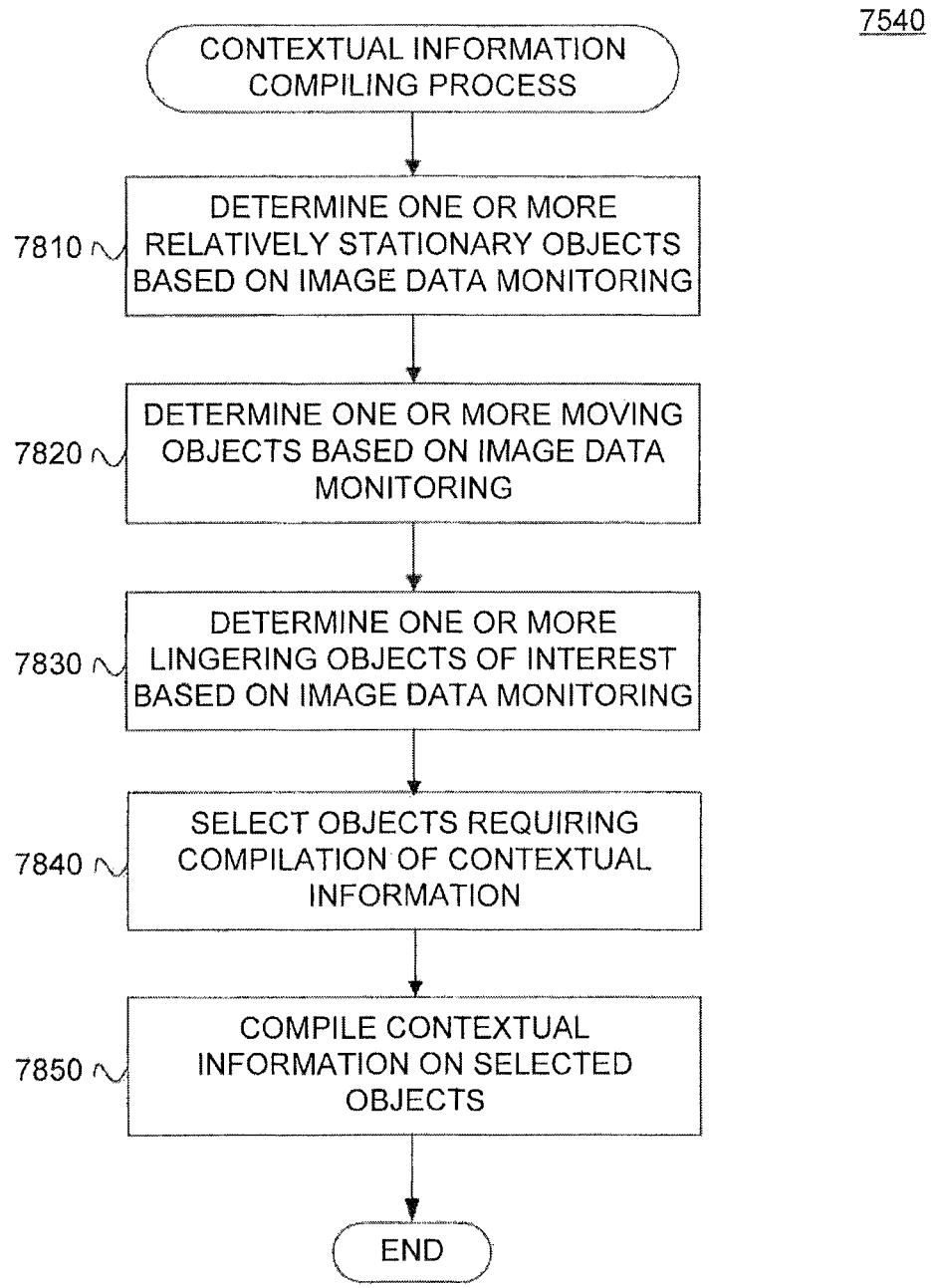
FIG. 78 is an example of a contextual information compiling process, consistent with disclosed embodiments.

FIG. 78 illustrates an example contextual information compiling process such as that described above in association with Step 7540 of process 7500 consistent with certain disclosed embodiments. Process 7540, as well as any or all of the individual steps therein, may be performed by various aspects of device 110, such as sensory unit 120, processing unit 140, support 210, or any subcomponents therein. For exemplary purposes, FIG. 78 is described as being performed by processor 540, executing software instructions stored within memory 520.

Based on the relative motion determinations described above in association with FIG. 77 and example image data monitoring process 7530, processor 540, via image processing module 7403, may determine and evaluate a motion status of various objects identified within the field of view of apparatus 110. For example, image processing module 7403 may determine that one or more objects were stationary in the scene based on the image data monitoring (Step 7810). Image processing module 7403 may determine that an object was relatively stationary based on a determination that there was little to no relative motion of the object between a first and second set of captured image data. In some embodiments, a stationary object may be determined to be an object in the background of the image, as discussed above. These stationary objects may be permanent elements of a scene. For example, in the illustration of FIGS. 76A-76B described above, stationary objects might include the two streets comprising the intersection. In other embodiments, an object may appear relatively stationary even though in reality it is moving. This may occur because user 100's head is tracking the object as it moves. For example, in the illustration of FIGS. 76C-76D described above, the bus appears relatively stationary as the background changes behind it because user 100 is tracking the bus.

Similarly, image processing module 7403 may determine one or more moving objects in the scene based on the image data monitoring (Step 7820). Image processing module 7403 may determine that an object was moving based on a determination that there was detectable relative motion of the object between a first and second set of captured image data. For example, in the illustration of FIGS. 76A-76B described above, the car would be determined to be a moving object because in FIG. 76A the car is traveling down one cross street comprising an intersection, and in FIG. 76B the car has turned and is traveling down the other cross street. In other embodiments, an object may appear to be moving even though in reality it is relatively stationary. This may occur because user 100's head is tracking another moving object as it moves. For example, in the illustration of FIGS. 76C-76D described above, the scenery behind the bus appears to be moving because user 100 is tracking the bus.

In another embodiment, image processing module 7403 may determine one or more "lingering" objects of interest within the first and second sets of captured image data based on the image data monitoring (Step 7830). Image processing module 7403 may determine that an object is lingering based on a determination that there were one or more periods of relative motion of the object between a first and second set of captured image data, and also one or more periods when the object was relatively stationary. For example, in the illustration of FIGS. 76E-76G described above, the bus enters the field of view in FIG. 76E, lingers in FIG. 76F, and then departs in FIG. 76G.

Image processing module 7403 may select one or more objects in the first and/or second sets of captured image data that require compilation of information relating to context (Step 7840). In some embodiments, processor 540 and image processing module 7403 may determine that contextual information about an object in the background of the image data is needed to identify an item in the foreground of the image data, or vice versa. In some embodiments, processor 540 and image processing module 7403 may determine that contextual information about a moving object in the image data is needed to identify a stationary object in the image data, or vice versa. In some embodiments, as discussed above, image processing apparatus may determine that an object identified in the image data is a branded product, and that contextual information is needed about the brand or the particular product. In some embodiments, processor 540 and image processing module 7403 may determine that contextual information is needed about a moving object that appears relatively stationary because the head of user 100 wearing apparatus 110 is tracking it. It is to be understood that these are non-limiting examples, and that any particular situation may present a need for apparatus 110 to compile contextual information on a particular object, scene, or other element captured in real-time image data via image sensor 350.

Processor 540, via image processing module 7403 and database comparison module 7404, may compile contextual information on the selected objects (Step 7850). In some embodiments, apparatus 110 may recognize a familiar context associated with the object based on prior experience, or based, for example, on context information pre-programmed into memory 520 or database(s) 7405. In these embodiments, database comparison module 7404 may identify known and familiar contexts associated with objects and triggers within database(s) 7405. Alternatively, the context determined from the image sensor data may not be recognized or familiar, and processor 540 may prompt user 100 to provide information relating to the context via an audio prompt or via a user interface visible to user 100 within the field of view of apparatus 110. Apparatus 110 may receive the context information in these embodiments from user 100, and then database comparison module 7404 may use the received information to search database(s) 7405 for relevant entries. Alternatively, as described above, database comparison module 7404 may determine that an object also appearing in the image data has a known context, and may use that contextual information to compile the same information for any objects with unknown or unfamiliar contexts. In some embodiments, compiling the contextual information may include comparing a portion of a scene captured in the first or second sets of image data to stored image data. In other embodiments, compiling the contextual information may include performing additional image processing on one or more areas of the images comprising the first or second sets of image data. For example, image processing module 7403 may determine that text is present in the image data, and may perform optical character recognition on an area of at least one of the images within the image data sets. These descriptions are intended as non-limiting examples; processor 540 may undertake any operable means of compiling contextual data.

Figure 79:
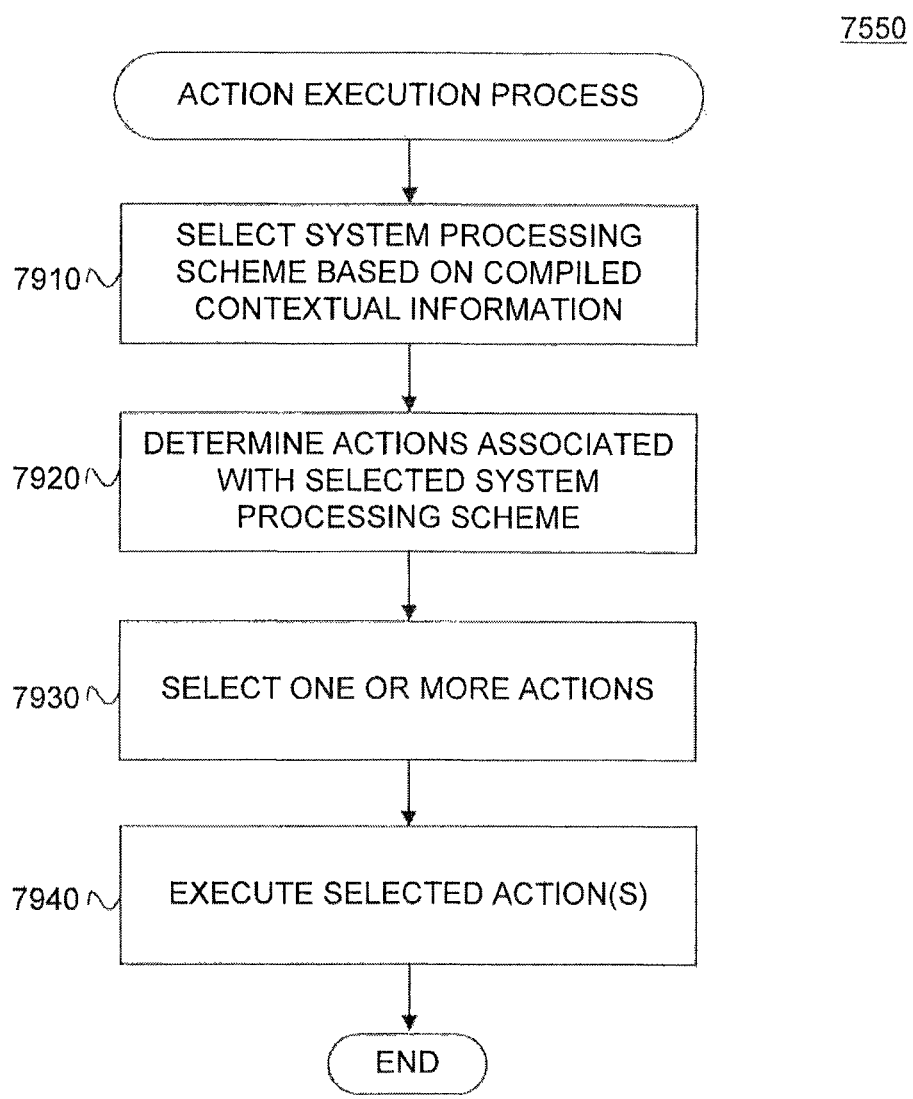
FIG. 79 is an example of an action execution process, consistent with disclosed embodiments.

FIG. 79 illustrates an example action execution process such as that described above in association with Step 7550 of process 7500 consistent with certain disclosed embodiments. Process 7550, as well as any or all of the individual steps therein, may be performed by various aspects of device 110, such as sensory unit 120, processing unit 140, support 210, or any subcomponents therein. For exemplary purposes, FIG. 79 is described as being performed by processor 540, executing software instructions stored within memory 520.

In some embodiments, processor 540 may select a system processing scheme for apparatus 110 based on the compiled contextual information (Step 7910). As discussed above, processor 540 may determine object context in a contextual information compiling process based on real-time image data received from image sensor 350. In other embodiments, processor 540 may determine object context based on real-time audio data received from image sensor 350. In some embodiments, apparatus 110 may recognize a familiar context associated with the object based on prior experience, or based, for example, on context information pre-programmed into memory 520 or database(s) 7405. In these embodiments, database comparison module 7404 may identify known and familiar processing schemes for processor 540 and apparatus 110 associated with the identified objects, backgrounds, and contextual information within database(s) 7405. Alternatively, if the objects, backgrounds, or contexts are not recognized or familiar, processor 540 may prompt user 100 to provide information relating to the context via an audio prompt or via a user interface visible to user 100 within the field of view of apparatus 100. Apparatus 110 may receive the context information in these embodiments from user 100, and then database comparison module 7404 may use the received information to search database(s) 7405 for relevant entries. For example, in some embodiments, the selected processing scheme may identify an object. In some embodiments, the selected processing scheme may identify an individual. In other embodiments, the processing scheme may audibly read text, or may continuously monitor an object.

Additionally, processor 540 may determine one or more context-based actions associated with the selected system processing scheme (Step 7920). In some embodiments, processor 540 performs such actions in addition to any feedback generated by feedback generation module 7401. In other embodiments, the actions are performed instead of the feedback generation.

One skilled in the art may contemplate a multitude of actions that may be associated with a given processing scheme. As discussed above, actions may include, but not be limited to, audibly reading text, sending an electronic message or instant message over the Internet; configuring settings for apparatus 110 or image sensor 350; activating a user interface, which may appear on the lens of the glasses within the vision of user 100 and provide additional interactivity options, announcing an identity of an inanimate object, announcing an identity of an individual, identifying a scene perceived within the field of view, tracking an object, summing money, monitoring a status of a traffic light, saving an individual's name, audibly reading a summary of text, monitoring an object expected to change, identifying a bus number, identifying currency, identifying a credit card, or identifying a pharmaceutical product, such as a pill.

Various actions available for execution by processor 540 may be stored in database entries within database(s) 7405 associated with various objects and triggers. In these embodiments, processor 540 may call database comparison module 604 to access and extract possible alternative actions, then transmit the possible actions to processor 540 for execution.

Processor 540 may select one or more of the context-based actions presented for execution (Step 7930). In some embodiments, processor 540 may select a single action for execution based on the context. In other embodiments, processor 540 may select multiple actions. In these embodiments, one or more of the actions may be sequential; for example, an action may only be executed if another particular action is executed beforehand.

Upon selecting one or more of the actions, processor 540 may execute various software instructions to perform the action (Step 7940). For example, in some embodiments, the context-based action may comprise providing feedback to the user based on at least part of the contextual information. In these embodiments, processor 540 may employ feedback generation module 7401 and feedback-outputting unit 430 to generate, configure, and output the feedback, as will be discussed in further detail below. In some embodiments, the feedback may comprise audible feedback; in other embodiments, the feedback may be of a tactile nature.

In other embodiments, processor 540 may call camera configuration module 7402 to perform a context-based action associated with the configuration of apparatus 110 itself. In these embodiments, image sensor 350 may comprise a camera, and camera configuration module 7402 may, based on at least part of the contextual information, adjust at least one parameter associated with the camera. The camera-associated parameter may include at least one of a focus point, an exposure time, an aperture size, light sensitivity, an image resolution, and a frame rate. This list of parameters is intended to be exemplary, and any other parameter or setting associated with cameras may be altered as part of the execution of the context-based action. Adjusting the camera settings in this manner may permit apparatus 110 to adjust to changing circumstances in the environment of user 100, such as availability of light at a particular time of day or in particular weather conditions. Additionally, processor 540 may use camera configuration module 7402 to check and verify the operational status of image sensor 350, and if needed, may assist with maintenance of apparatus 110.

In some embodiments, processor 540 may be configured to rapidly adjust the alternative actions available to processor 540 based in changes that may be identified in one or more of a trigger, an identified object, or a context related to the object. In these embodiments, as these elements change, processor 540 may call database comparison module 7404 to search database(s) 7405 for new alternative actions associated with the newly-changed trigger, object, or context.

As a non-limiting example of process for providing information to a user (such as user 100) who may be visually-impaired, such as that described above in association with FIG. 75, apparatus 110 may determine that user 100 is visually tracking an object, such as the bus illustrated in FIGS. 76C-76D, and needs to identify it. Via camera configuration module 7402, processor 540 may execute software instructions enabling apparatus 110 (via image sensor 350) to capture at least two sets of real-time image data across a period of time. Via image processing module 7403, processor 540 may monitor the image data, and determine various objects in the background that the bus passes, as well as their relative motion over time. Via database comparison module 7404, processor 540 may compile contextual information from the background objects to help determine the identity of the bus. Database comparison module 7404 may compare the compiled contextual information to existing information in database(s) 7405, and determine the identity of the bus. Finally, processor 540 may execute software instructions to provide feedback to user 100 via feedback generation module 7401 and feedback-outputting unit 430 identifying the bus to user 100. This feedback generation process will now be described in further detail.

Figure 80:
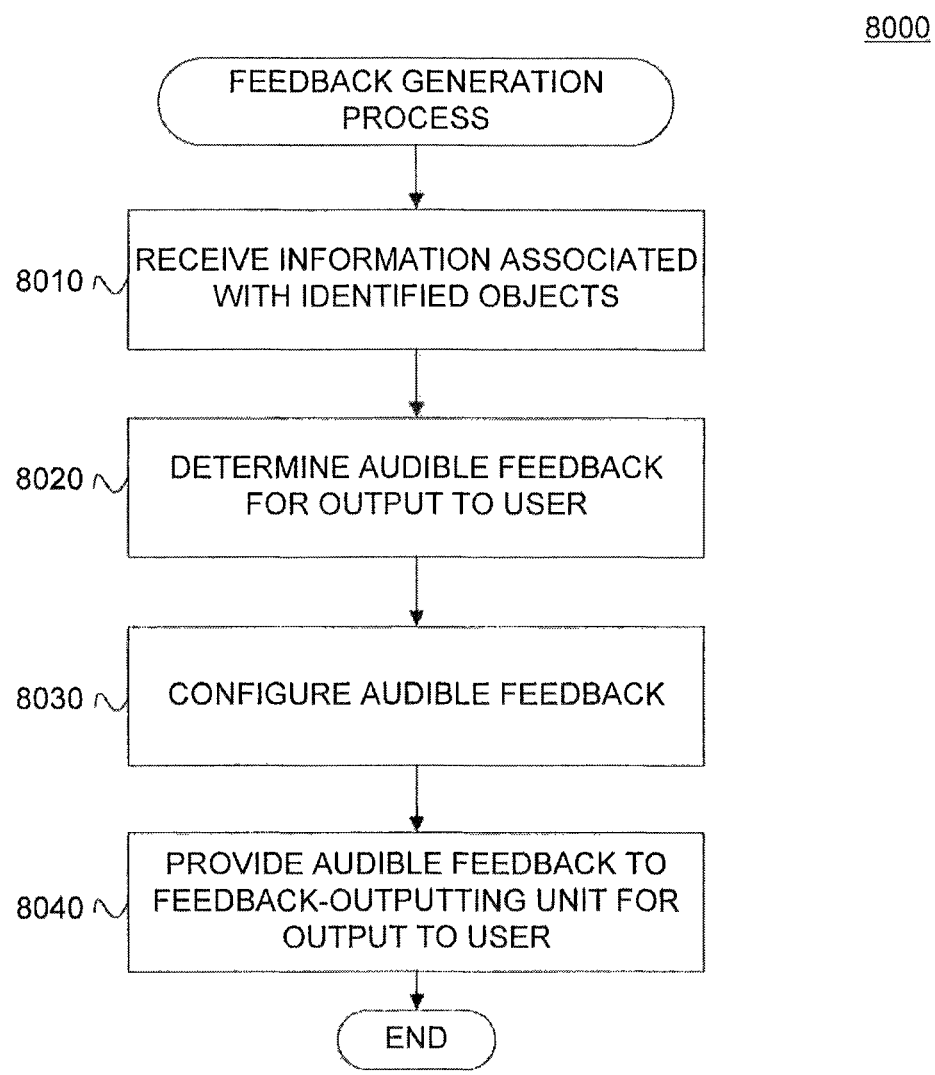
FIG. 80 is an example of a feedback generation process, consistent with disclosed embodiments.

FIG. 80 illustrates an example feedback generation process 8000 consistent with certain disclosed embodiments. Process 8000, as well as any or all of the individual steps therein, may be performed by various aspects of device 110, such as sensory unit 120, processing unit 140, support 210, or any subcomponents therein. For exemplary purposes, FIG. 80 is described as being performed by processor 540, executing software instructions stored within memory 520.

As discussed above, in some embodiments, processor 540 may perform a context-based action (for example, in Step 7940 of action execution process 7550 discussed above) after analyzing real-time image data and using changes in relative motion in different portions of the image to determine context. In some embodiments, the context-based action may comprise providing feedback to user 100 via apparatus 110. Process 8000 is an example feedback generation process describing how processor 540 may execute such an action. Processor 540, via feedback generation module 7401, may receive information associated with one or more identified objects that have been determined to be present in the environment surrounding user 100 (Step 8010). The received information may further comprise information relating to a result of one or more executed alternative actions, as discussed above. Based on the received information, feedback generation module 7401 may determine audible feedback for output to user 100 (Step 8020). In some embodiments, the identified object or executed alternative action may each already be associated with an audible feedback file stored in memory 520 or database(s) 7405. In these embodiments, feedback generation module 7401 may simply access the existing associated audible feedback file and prepare it for transmission. In other embodiments, there may be multiple audible feedback files associated with the identified object(s) or actions, and feedback generation module may review the determined trigger and/or context information to determine the correct associated audible feedback to output to user 100. In still other embodiments, there may be no existing audible feedback associated with the identified object(s) or actions. In these embodiments, feedback generation module 7401 may determine content for audible feedback by prompting user 100 for the feedback, or may infer proper audible feedback, based on context and based on other objects within the category.

Upon determining the proper audible feedback to use, feedback generation module 7401 may configure the audible feedback into a readable format, if necessary (Step 8030), then provide the audible feedback to feedback-outputting unit 430 for output to user 100 (Step 8040). Feedback generation module 7401 may provide the feedback to feedback-outputting unit 430 via wire 130, or alternatively, via wireless transceiver(s) 530.

As is evident from the foregoing, apparatus 110 may provide a wide range of functionality. More specifically, embodiments consistent with the present disclosure may provide an apparatus, a method, and a software product stored on a non-transitory computer readable medium for recognizing text on a curved surface.

Figure 81:
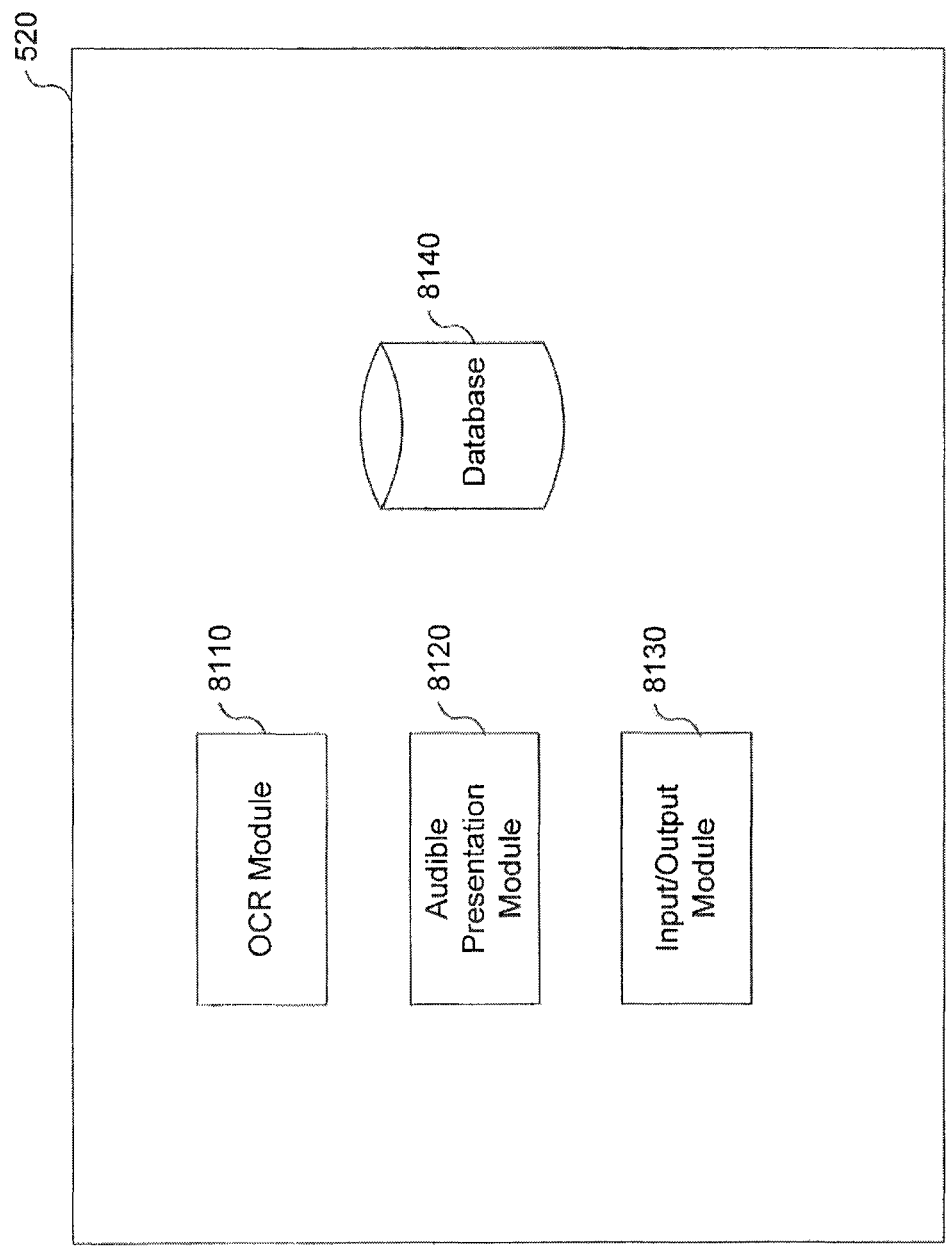
FIG. 81 is a block diagram illustrating an example of a memory storing software modules.

In some embodiments, recognizing text on a curved surface may be implemented using apparatus 110 with software instructions loaded into memory 520. The software instructions, when executed by processor 540, may perform various functions related to text recognition. FIG. 81 is a block diagram illustrating an example of a set of software instructions, organized in different functional modules, which can be loaded into memory 520 for recognizing text on a curved surface.

Referring to FIG. 81, memory 520 may store an OCR module 8110, which may include software instructions for perform OCR processing. OCR module 8110 can generate a recognized representation of a text based on an image that includes the text. The recognized representation of the text may include a collection of letters, words, phrases, sentences, or any other suitable semantic symbols. In some embodiments, the recognized representation of the text may include audible reading of the text. The image containing the text may include a static image, a frame of a video stream, or any other graphical forms that contain at least a part of the text.

Memory 520 may store an audible presentation module 8120, which may include software instructions for performing an audible presentation, such as reading aloud, of the recognized representation of the text generated by the OCR module 8110. Audible presentation module 8120 may execute the software instructions to perform an audible presentation after at least a part of the text has been recognized by OCR module 8110. In some embodiments, audible presentation module 8120 may simultaneously perform an audible presentation of the first part of the text while OCR module 8110 is recognizing the second part of the text.

Memory 520 may store an input/output (I/O) module 8130, which may include software instructions for performing image capture, audio output, user selection, or similar functions. For example, I/O module 8130 may perform image capture from image sensor 350. In another example, I/O module 8130 may perform audible feedback through feedback-outputting unit 340.

Memory 520 may store a database 8140. Database 8140 may contain data related to OCR, audible presentation, and/or input/output functions. For example, database 8140 may store data of images or frames captured by image sensor 350 to be recognized by OCR module 8110. Database 8140 may store recognized representation generated by OCR module 8110. Database 8140 may store audible data to be presented to the user through feedback-outputting unit 340. Other forms of data related to the functions performed by modules 8110, 8120, and 8130, including transitional or temporary data, may also be stored in database 8140.

In other embodiments, database 8140 may be located remotely from memory 520, and be accessible to other components of apparatus 110 (e.g., processing unit 140) via one or more wireless connections (e.g., a wireless network). While one database is shown, it should be understood that several separate and/or interconnected databases may make up database 8140. Database 8140 may include computing components (e.g., database management system, database server, etc.) configured to receive and process requests for data stored in memory devices associated with database 8140 and to provide data from database 8140.

OCR module 8110, audible presentation module 8120, and input/output module 8130 may be implemented in software, hardware, firmware, a mix of any of those, or the like. For example, if the modules are implemented in software, they may be stored in memory 520, as shown in FIG. 81. Other components of processing unit 140 and/or sensory unit 120 may be configured to perform processes to implement and facilitate operations of the modules. Thus, OCR module 8110, audible presentation module 8120, and input/output module 8130 may include software, hardware, or firmware instructions (or a combination thereof) executable by one or more processors (e.g., processor 540), alone or in various combinations with each other. For example, OCR module 8110, audible presentation module 8120, and input/output module 8130 may be configured to interact with each other and/or other modules of apparatus 110 to perform functions consistent with disclosed embodiments. In some embodiments, any of the disclosed modules (e.g., OCR module 8110, audible presentation module 8120, and input/output module 8130) may each include dedicated sensors (e.g., IR, image sensors, etc.) and/or dedicated application processing devices to perform the functionality associated with each module.

Figure 82:
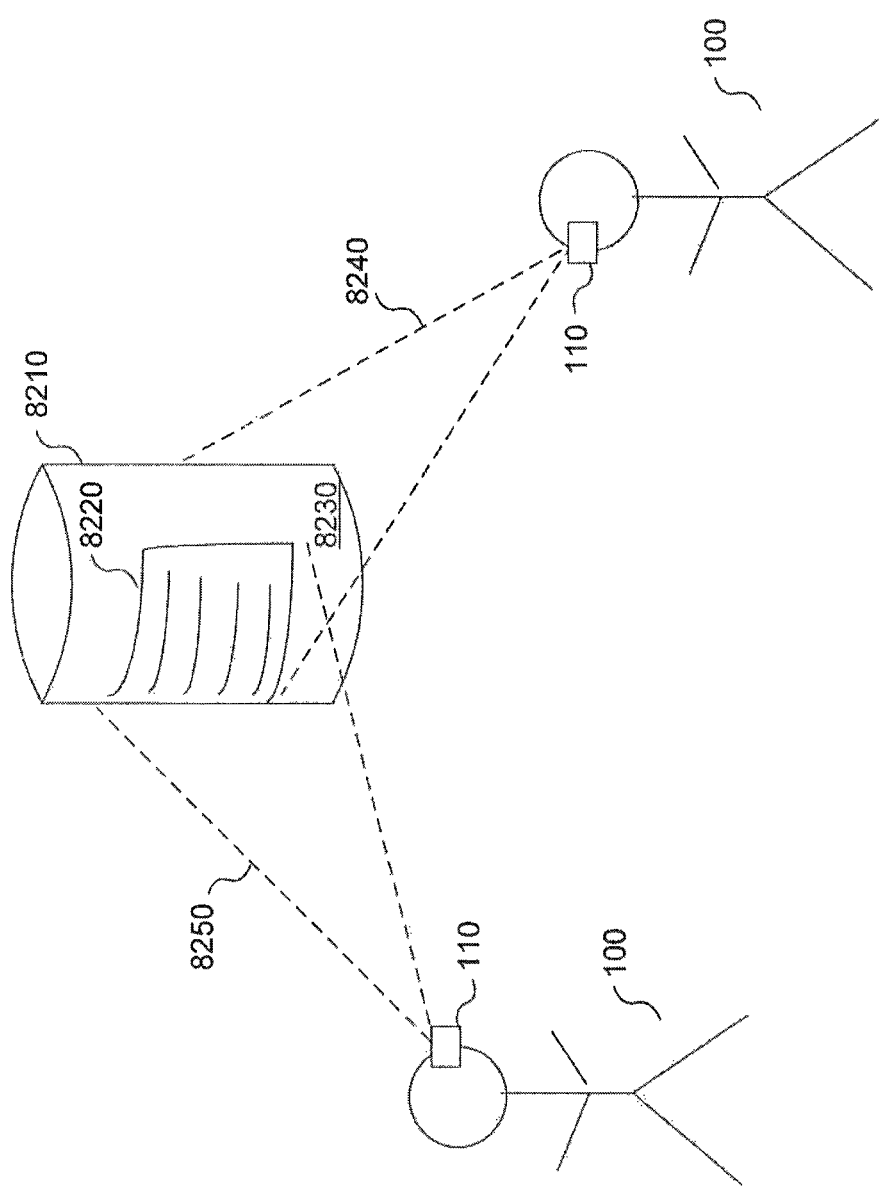
FIG. 82 is a schematic illustration of an example of a user using an apparatus to recognize text on a curved surface from two perspectives.

FIG. 82 is a schematic illustration of an example of a user 100 using apparatus 110 to recognize text 8220 on a curve surface 8230 from two perspectives. In FIG. 82, an object 8210 has curved surface 8230. As used herein, a curved surface includes any surface containing at least one bend, arc, round, or any other non-straight structure. For example, the outer surfaces of a bottle, a can, a tin, and a cathode ray tube (CRT) screen are all examples of a curved surface. For simplicity, an object having a curved surface is herein referred to as a curved object. Referring back to FIG. 82, curved object 8210 may include a display of an electric device, such as a television screen or a computer monitor, and text 8220 may include text shown on the display. In other embodiments, curved object 8210 may include a food product (e.g., a food product with a can or a tin package), a beverage (e.g., a bottle or a can), a pharmaceutical drug (e.g., a drug with a drug bottle), etc., and text 8220 may include text on a label associated with curved object 8210.

As shown in FIG. 82, user 100 may be equipped with apparatus 110. As described above, apparatus 110 may include image sensor 350. Image sensor 350 may be connected to glasses 105 worn by user 100, to enable image sensor 350 to move with the head of user 100. Image sensor 350 may be configured to be movable with the head of user 100 in such a manner that an aiming direction of image sensor 350 substantially coincides with a field of view of user 100. For example, as described above, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

Apparatus 110 may capture images of different perspectives of text 8220. As used herein, a perspective of text may include the text viewed from a certain angle, an image of the text having a certain resolution, a frame in a video stream of the text, or other forms of graphical representation of the text.

For example, user 100 may use apparatus 110 to capture a first image of text 8220 at a first position (right hand side) or at a first angle towards curved object 8210, with a field of view 8240 covering a first portion of curved surface 8230. The first image contains a first perspective of text 8220. User 100 may also use apparatus 100 to capture a second image of text 8220 at a second position (left hand side) or at a second angle towards curved object 8210, with a field of view 8250 covering a second portion of curved surface 8230. The second image contains a second perspective of text 8220. It is noted that when capturing images of text 8220, user 100 may also slightly move her head to change the coverage or direction of her field of view, without physically moving her body from one position to another position.

In another example, user 100 may use apparatus 110 to capture a video stream while moving from the first position to the second position (or moving from the first angle to the second angle towards curved object 8210). As used herein, a video stream may include a series of pictures collectively forming a motion picture of a scene. Each picture in the video stream may also be referred to as a frame. In some embodiments, each frame may contain image data with full resolution (e.g., in case of progressive scan). In other embodiments, each frame may contain image data with half resolution (e.g., in case of interlaced scan). Regardless of which scanning technique is used, user 100 may capture a video stream of text 8220, which includes multiple frames of text 8220 captured at different time. Each frame of the captured video stream contains one perspective of text 8220. It is noted that when capturing a video stream, user 100 may also slightly move her head to change the coverage or direction of her field of view, without physically moving from one position to another position.

In yet another example, user 100 may stay substantially stationary when capturing images or video stream, e.g., without substantially changing the coverage or direction of her field of view, but capture images or video stream of text 8220 with different resolutions. As used herein, a resolution of an image or a video stream may be defined by the number of pixels composing the image or the video stream. For example, an image may have a resolution of 800×600, 1024×768, etc. A video stream may have a resolution of 640×480, 1280×720, 1920×1080, etc. (each resolution may also contain variations of progressive scan, such as 480p, 720p, 1080p; and interlaced scan, such as 480i, 720i, 1080i). For video streams, teams such as standard resolution (or "SD", e.g., 480i and 480p), high resolution (or "HD", e.g., 720i/720p, 1080i/1080p, etc.), and ultra-high resolution (or UHD, e.g., 4K resolution: 3840×2160 or other variations having horizontal pixel count on the order of 4000) are also used to define resolution. Resolution can also be defined by the total number of pixels of an image sensor used to product an image or a video stream. For example, an image or a video stream may have a resolution of 3M, 5M, 8M, 16M, 27M, etc., where "M" refers to megapixels. Resolution may also be defined by pixel density, such as dots per inch (DPI), pixels per inch (PPI), lines per inch (LPI), pixels per centimeter, etc. For example, an image or a video stream may have a resolution of 120 DPI, 160 DPI, 240 DPI, 320 DPI, 480 DPI, 640 DPI, etc.

Referring back to FIG. 82, user 100 may capture multiple images, multiple video streams, or a video steam with multiple frames, where the multiple images/video streams/frames have different resolutions. User 100 may conduct the image/video capture without substantially changing the coverage or direction of her field of view. For example, user 100 may capture multiple images having different resolutions with her field of view 8240 substantially unchanged. A first image having a first resolution contains a first perspective of text 8220. A second image having a second resolution contains a second perspective of text 8220. In another example, user 100 may capture multiple video streams having different resolutions. A first video stream having a first resolution contains a first perspective of text 8220. A second video stream having a second resolution contains a second perspective of text 8220. In yet another example, user 100 may capture one video stream contains multiple frames, where the multiple frames have different resolutions. A first frame having a first resolution contains a first perspective of text 8220. A second frame having a second resolution contains a second perspective of text 8220.

Figure 83C:
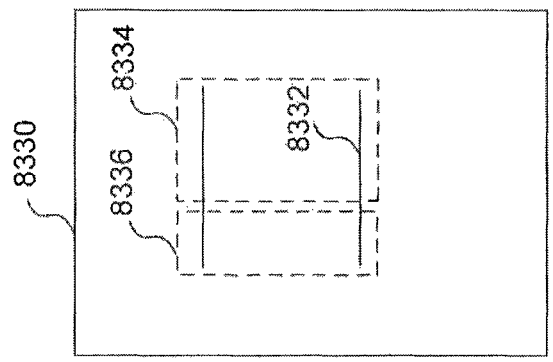
FIGS. 83A-83C are schematic illustrations of examples of text viewed from different perspectives.
Figure 83B:
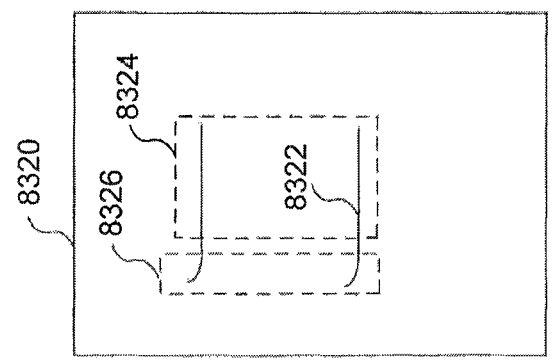
Figure 83A:
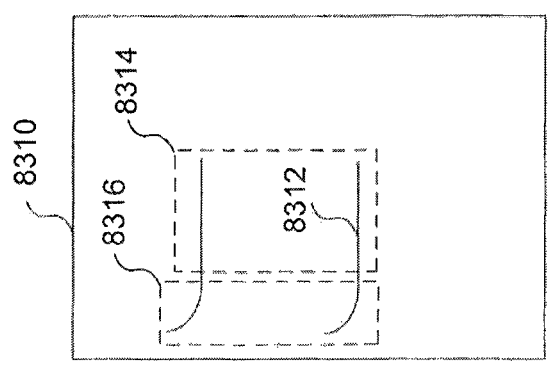

FIGS. 83A-83C are schematic illustrations of examples of text from different perspectives. FIG. 83A shows an image or frame 8310 (herein after image 8310 for simplicity) captured when, for example, user 100 is at the first position (e.g., the right hand side in FIG. 82) with field of view 8240. In image 8310, text 8220 on curved surface 8230 is captured as text section 8312. Text section 8312 may constitute a first perspective of text 8220. Because of the limited coverage of field of view 8240 and/or the nature of curved surface 8230, a portion of text section 8312, for example portion 8316, is unrecognizable in an OCR process. For example, portion 8316 may contain skewed text. Text section 8312 may also contain a portion of text, for example portion 8314, which can be recognized in an OCR process.

FIG. 83B shows an image or frame 8320 (herein after image 8320 for simplicity) captured when, for example, user 100 is at a position (not shown in FIG. 82) between the first (right hand side in FIG. 82) and second (left hand side in FIG. 82) positions. In this intermediate position, text 8220 on curved surface 8230 is captured as text section 8322. As user 100 moves to the left, her field of view may align better with text 8220. As a result, text section 8322 may shift towards the center of image 8320 and a portion of text unrecognizable by an OCR process, such as portion 8326, may become smaller. Accordingly, a portion of text that can be recognized by an OCR process, such as portion 8324, becomes larger.

FIG. 83C shows an image or frame 8330 (herein after image 8330 for simplicity) captured when, for example, user 100 is at the second position (e.g., the left hand side in FIG. 82) with field of view 8250. In the second position, text 8220 on curved surface 8230 is captured as text section 8332. Text section 8332 may constitute a second perspective of text 8220. When the user moves to the second position, her field of view 8250 may cover the entire portion of text 8220 and may align with text 8220. As a result, text section 8332 may further shift towards the center of image 8330. Previously unrecognizable portion 8316 in image 8310 may now become recognizable portion 8336. In other words, while portion 8316 and 8336 correspond to substantially the same portion of text in text 8220, in image 8310 portion 8316 is not recognizable due to, for example, skewed text, but in image 8330 portion 8336 is recognizable because the text is no longer skewed when captured from field of view 8250. Image 8330 may also contain a portion 8334 corresponding to other portion of text 8220 captured in image 8330.

In some embodiments, when FIGS. 83A-83C represents frames of a video stream, frame 8320 may be captured subsequent to frame 8310, and frame 8330 may be captured subsequent to frame 8320. In one example, frames 8310, 8320, and 8330 may be captured consecutively. In an OCR process, frame 8330, rather than frame 8320, may be used to recognize text portion 8336 that is unrecognizable in portion 8316.

Figure 84B:
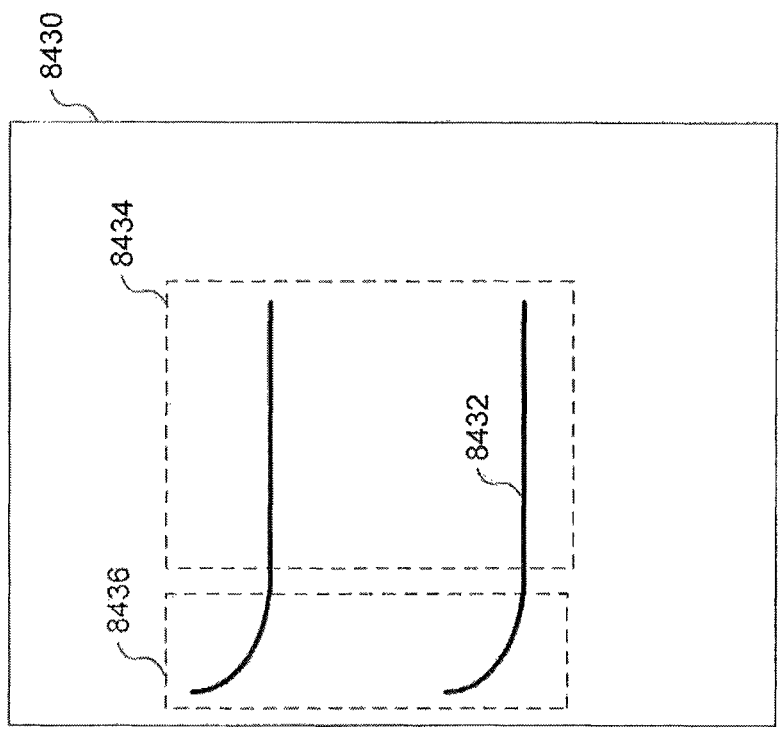
FIGS. 84A-84B are schematic illustrations of additional examples of text viewed from different perspectives.
Figure 84A:
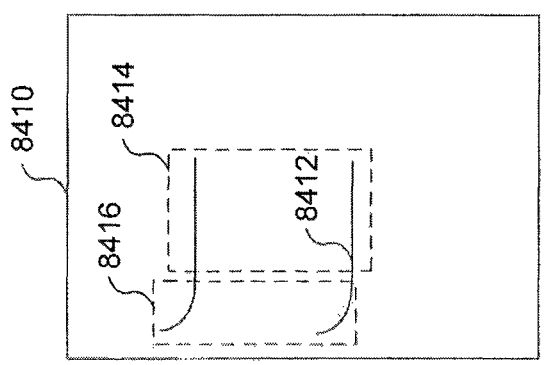

FIGS. 84A and 84B are schematic illustrations of additional examples of text viewed from different perspectives. FIG. 84A is similar to FIG. 83A, showing an image or frame 8410 (herein after image 8410 for simplicity) captured when, for example, user 100 is at the first position (e.g., the right hand side in FIG. 82) with field of view 8240. In image 8410, text 8220 on curved surface 8230 is captured as text section 8412. Text section 8412 may constitute a first perspective of text 8220. Because of the limited coverage of field of view 8240 and/or the nature of curved surface 8230, a portion of text section 8412, for example portion 8416, is unrecognizable in an OCR process. For example, portion 8416 may contain skewed text. Text section 8412 may also contain a portion of text, for example portion 8414, which can be recognized in an OCR process.

FIG. 84B shows an image or frame 8430 (herein after image 8410 for simplicity) captured with a higher resolution. User 100 may or may not need to move to a new position or change her field of view to capture image 8430. Image 8430 contains more pixels than image 8410. Therefore, image 8430 is shown in FIG. 84B in a larger size assuming the pixel density is unchanged. Alternatively, image 8430 may also be shown in the same size as image 8410 but with a higher pixel density. Text section 8432 may constitute a second perspective of text 8220. Because of the increased pixel count, previously unrecognizable portion 8416 may now become recognizable portion 8436. Image 8430 may also contain a portion 8434 corresponding to other portion of text 8220 captured in image 8430.

Figure 85:
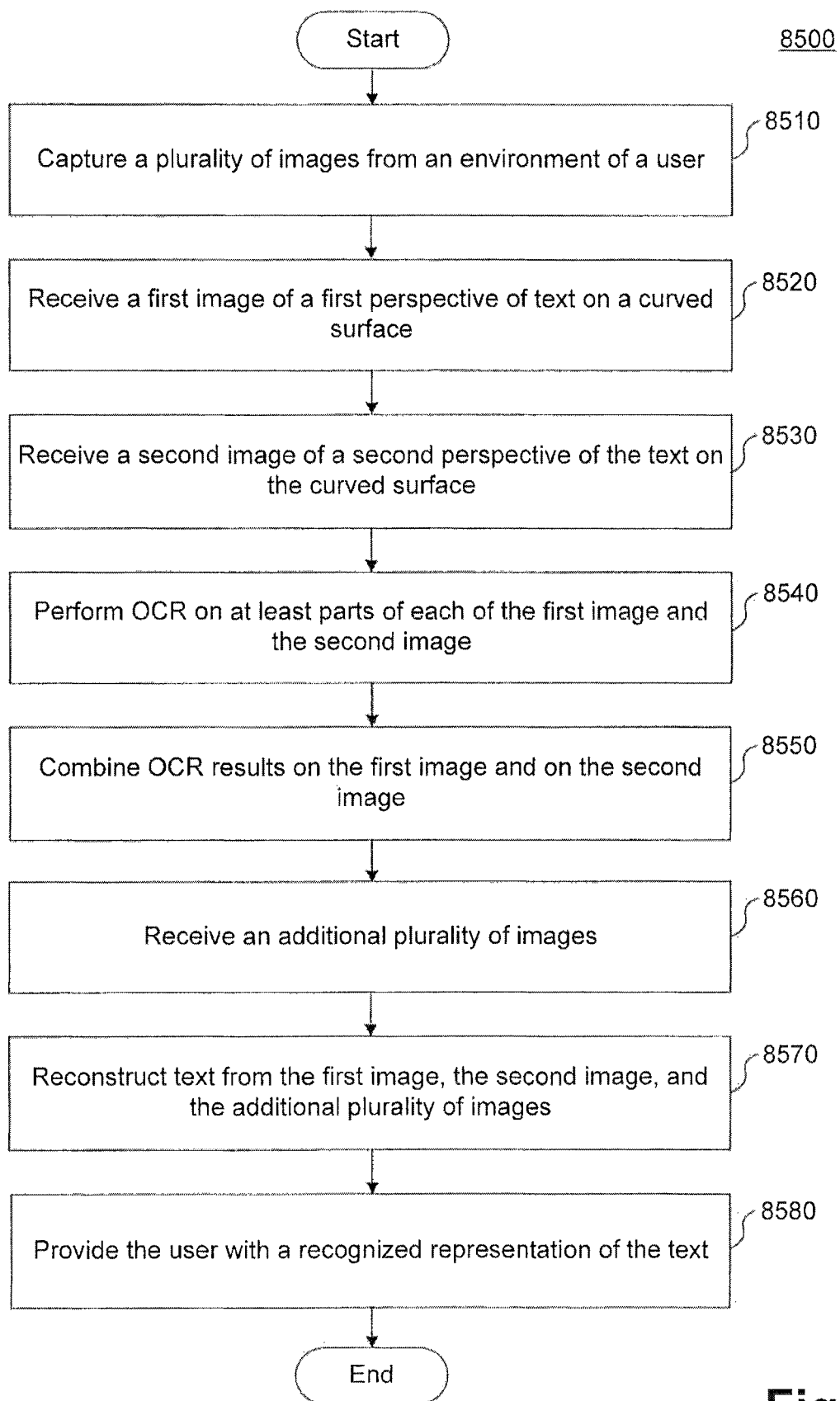
FIG. 85 is a flow chart of an exemplary process for recognizing text on a curved surface.

In some embodiments, apparatus 110 may be used to recognize text on a curved surface. FIG. 85 is a flow chart of an exemplary process 8500 performed by apparatus 110 to implement text recognition. For example, apparatus 110 may include at least one processor device (e.g., processor 540) to execute one or more steps of process 8500. It is noted that process 8500 may be executed before or after another process, or can be embedded into other processes.

Apparatus 100 may comprise an image sensor such as image sensor 350. In step 8510, image sensor 350 may capture from an environment of user 100 a plurality of images (e.g., images 8310, 8320, 8330 or images 8410 and 8430) of text (e.g., text 8220) on a curved surface (e.g., surface 8230). The environment may include object 8210 having the curved surface 8230. The captured images may be saved in memory 520 (e.g., in database 8140).

In step 8520, processor 540 may receive a first image (e.g., image 8310) of a first perspective of text (e.g., text section 8312) on the curved surface. The first image may include a first portion of text unrecognizable in an optical character recognition process. For example, processor 540 may receive the first image 8310 by executing program instructions stored in I/O module 8130 to retrieve image 8310 captured by image sensor 350 and saved in database 8140. Text section 8312 may include a portion 8316 that is unrecognizable in an OCR process due to, for example, skewed text caused by limited coverage of field of view and/or curved surface 8230.

In step 8530, processor 540 may receive a second image (e.g., image 8330) of a second perspective of the text (e.g., text section 8332) on the curved surface. The second image may include the first portion of text in a form capable of recognition in the optical character recognition process. For example, text section 8332 may include portion 8336 that is capable of recognition in an OCR process.

In step 8540, processor 540 may perform optical character recognition on at least parts of each of the first image and the second image. For example, processor 540 may execute program instructions stored in OCR module 8110 to perform the OCR process. Processor 540 may perform OCR on text portion 8314 (e.g., recognizable) of the first image 8310 and text portion 8336 (e.g., recognizable) of the second image 8330.

In step 8550, processor 540 may combine results of the optical character recognition of the first image and the second image. For example, processor 540 may combine the OCR results of text portion 8314 in the first image 8310 and text portion 8336 in the second image 8330 to form a combined OCR result of text 8220 on curved surface 8230. Text portions 8316 and 8334 may collectively cover the content of text 8220.

In some cases, the combination of text portions 8316 and 8334 may not cover the entire content of text 8220 or the combined OCR results may not be satisfactory. In such cases, apparatus 110 may perform an OCR sub process to reconstruct text on the curved surface based on additional images (e.g., images in addition to images 8310 and 8330). Steps 8560 and 8570 show an example of such sub process.

In step 8560, processor 540 may receive an additional plurality of images. For example, processor 540 may execute program instructions stored in I/O module 8130 to receive a plurality of images in addition to images 8310 and 8330. The additional plurality of images may be captured by image sensor 350 before, between, or after images 8310 and 8330 are captured. For example, user 100 may use apparatus 110 to capture a series of images while moving around curved object 8210, and two of the series of images may be used to perform initial OCR to reconstruct text on curved surface 8230, as described in steps 8520-8550. When additional images are needed, processor 540 may choose the additional images from the rest of the series of images, and images captured before, between, or after images 8310 and 8330 may be chosen as candidates. In another example, when additional images are needed, processor 540 may prompt user 100 to capture additional images of, for example, different perspectives from those of previously captured.

In step 8570, processor 540 may perform OCR on the additional images to reconstruct text from the first image (e.g., image 8310), the second image (e.g., image 8330), and the additional plurality of images. For example, processor may perform OCR on the additional images and combine the OCR results of the additional images with the OCR results of images 8310 and 8330. In this case, OCR is performed on individual images and the OCR results are combined afterwards. In another example, the image data of one or more images may be combined first and OCR process may be performed on the combined image data. These two approaches will be described in greater detail later with respect to FIGS. 86 and 87.

In step 8580, processor 540 may provide user 100 with a recognized representation of the text, including a recognized representation of the first portion of text. For example, processor 540 may execute program instructions stored in audible presentation module 8120 to perform audible reading of recognized text (e.g., combined text portions 8316 and 8334 or the reconstructed text from image 8310, image 8330, and additional images generated in step 8570 if the results of step 8550 is not satisfactory) to user 100.

The above description of process 8500 is described in connection with the exemplary images shown in FIGS. 83A and 83C. It is noted that process 8500 may also be implemented using other images. For example, the first and second images may be images 8410 and 8430 shown in FIGS. 84A and 84B, respectively. Accordingly, the first perspective of text may be text section 8412, and the second perspective of text may be text section 8432. As described above, image 8430 has a higher resolution than image 8410. Therefore, even if images 8410 and 8430 are captured with substantially the same field of view (e.g., direction and/or coverage), text portion 8436 may be recognizable while text portion 8416 is not. By combining recognizable portion 8414 in image 8410 and recognizable portion 8436 in image 8430, processor 540 may reconstruct text 8220 on curved surface 8230 for audible presentation to user 100.

In some embodiments, process 8500 may be implemented based on a video stream instead of, or in addition to, static images. When process 8500 is implemented based on a video stream, the first and second images may be first and second frames of the video stream. Steps to recognize and combine video frames are similar to those for processing static images, as discussed above.

Figure 86:
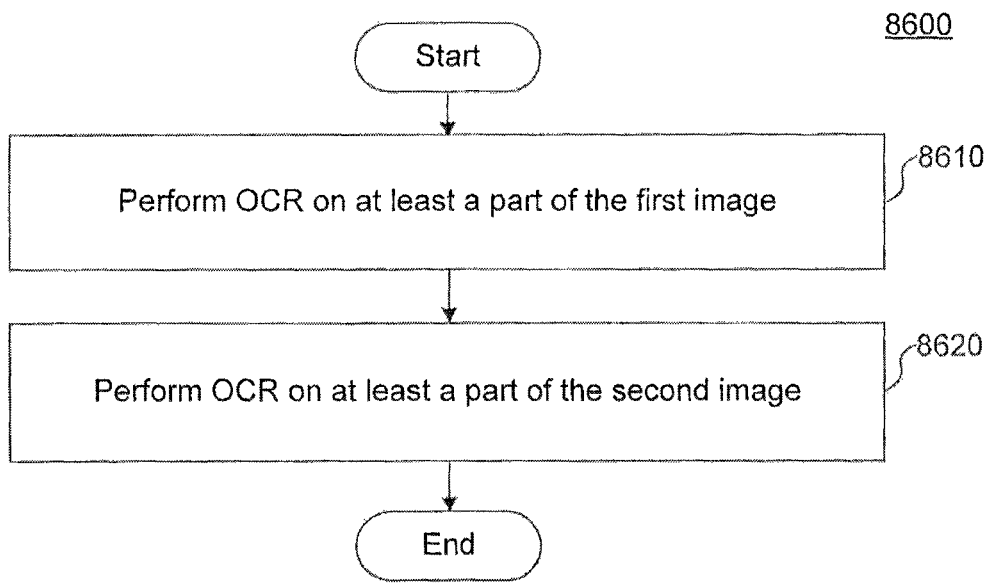
FIG. 86 is a flow chart of an exemplary process for performing optical character recognition.
Figure 87:
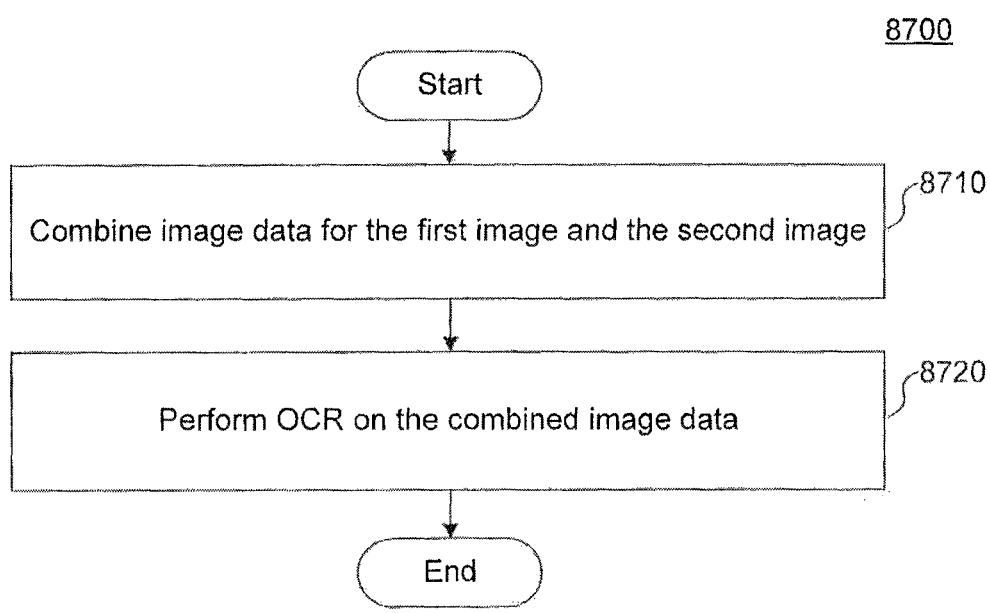
FIG. 87 is a flow chart of another exemplary process for performing optical character recognition.

Different approaches can be adopted to recognize and combine text images. FIGS. 86 and 87 show two exemplary processes 8600 and 8700, respectively, to perform the OCR step (e.g., step 8540 in FIG. 85) and/or combination step (e.g., step 8550 in FIG. 85).

FIG. 86 shows an exemplary process 8600 for performing OCR on the first and second images, which may be a sub process of step 8540 in FIG. 85. In process 8600, processor 540 performs OCR separately on the first image and the second image. For example, in step 8610, processor 540 performs OCR on at least a part of the first image, e.g., portion 8314 of image 8310. In step 8620, processor 540 separately performs OCR on at least a part of the second image, e.g., portion 8334 of image 8330. After the parts of the first and second images are separately recognized, processor 540 may continue the process according to step 8550 in FIG. 85 to combine the OCR results.

FIG. 87 shows another exemplary process 8700 for performing OCR on the first and second images. In process 8700, processor 540 first combines image data for the first image and the second image and, thereafter, performs OCR on the combined image data. For example, in step 8710, processor 540 may combine image data of portion 8314 of image 8310 and portion 8336 of image 8330 to form a combined image. Then, in step 8720, processor 540 may perform OCR on the combined image data to recognize text.

Figure 88:
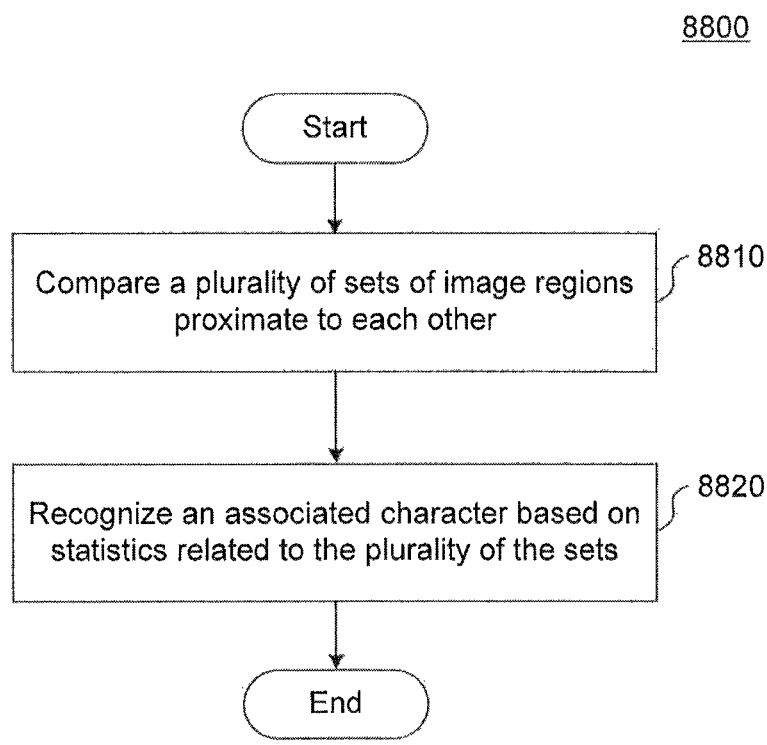
FIG. 88 is a flow chart of yet another exemplary process for performing optical character recognition.

FIG. 88 shows an exemplary process 8800 for performing OCR. Process 8800 may be a sub process of step 8540 in FIG. 85. In step 8810, processor 540 may compare a plurality of sets of image regions that are proximate to each other. For example, processor 540 may compare text regions of image to be recognized with a set of candidate image regions that have already been associated with text characters or representations. The candidate image regions and associated text characters or representations may be stored, for example, in database 8140. The comparison may yield likelihoods that the to-be-recognized image regions match one or more candidate image regions that have already established text association. In step 8820, processor 540 may recognize an associated character based on statistics related to the plurality of sets of image regions. For example, processor 540 may recognize a text character based on statistical results, e.g., the likelihoods of matching between the to-be-recognized image regions and the candidate image regions.

Figure 89:
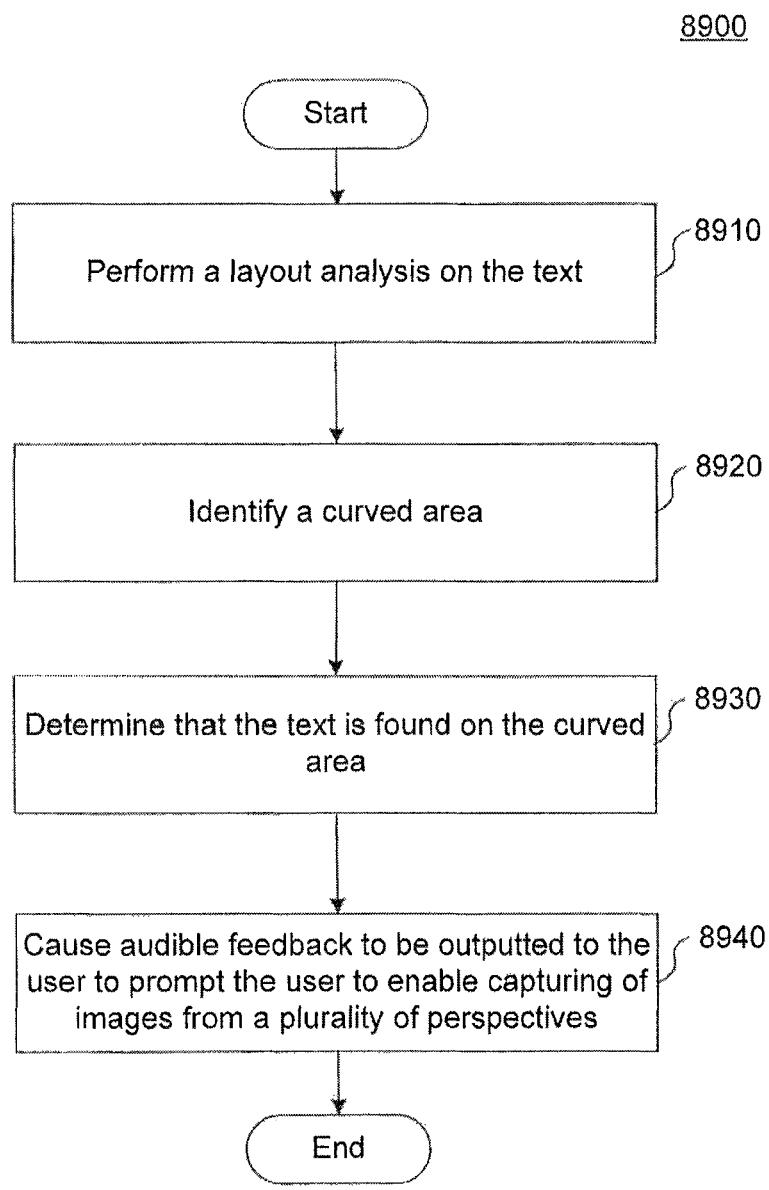
FIG. 89 is a flow chart of an exemplary process for identifying a curved area and determining whether text is found on the curved area.

In some embodiments, apparatus 110 may identify a curved area and/or determine that text if found on a curved area before performing image capture/recognition using different perspectives. FIG. 89 shows an exemplary process 8900 for identifying a curved area and determining whether text is found on the curved area. It is noted that process 8900 may be performed before step 8510 or before step 8520 in FIG. 85. Process 8900 may be initiated when one or more text images are captured by apparatus 110 (e.g., using image sensor 350). In step 8910, processor 540 may perform a layout analysis on the text. For example, after image 8310 is captured, processor 540 may analyze the layout of text section 8312, such as starting/ending point, start/end of a line, line direction, change of line direction, etc. In step 8920, processor 540 may identify one or more curved areas based on the layout analysis. For example, processor 540 may identify area 8316 as a curved area base on, for example, the direction of text lines changes beyond a threshold. Other criteria may also be used to identify curved areas.

In some embodiments, processor 540 may identify a curved area using other methods. For example, processor 540 may analyze the shade pattern, light distribution, image distortion, of other characteristics of an image to identify a curved area. After a curved area is identified, process 8900 may proceed to step 8930 to determine whether text is found in the curved area. For example, processor 540 determine that text is found in the curved area if the curved area contains any shape resembling text characters (e.g., even skewed characters), or if the curved area is close to any non-curved area that contains text, or by other suitable means. Once processor 540 determines that text is found in a curved area, or identifies that a text area is curved, process 8900 may proceed to step 8940. In step 8940, processor 540 may cause audible feedback to be outputted to user 100 to prompt user 100 to enable capturing of images from a plurality of perspectives. For example, processor 540 may execute program instructions stored in I/O module 8130 to output audible feedback to user 100 to instruct user 100 to capture images using higher resolution, from different angles, with different field of views, etc.

Figure 90:
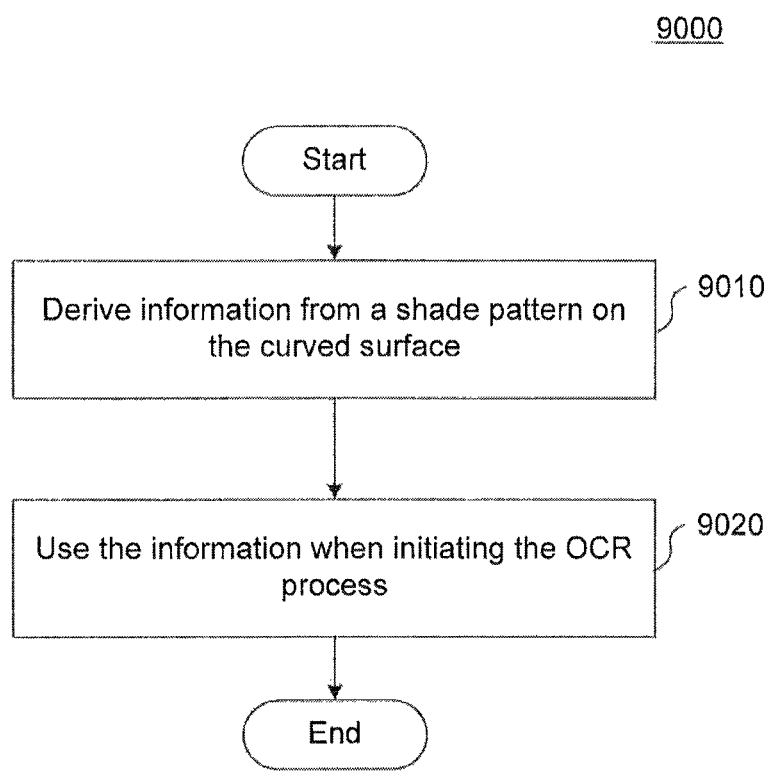
FIG. 90 is a flow chart of an exemplary process for performing optical character recognition.

In some embodiments, information other than text in a curved area may be used to perform an OCR process. FIG. 90 shows a process 9000 for performing OCR using information derived from a shade pattern. Process 9000 may be a sub process of step 8540 in FIG. 85. In step 9010, processor 540 may derive information from a shade pattern on a curved surface. For example, processor 540 may analyze the shade pattern on surface 8230 or from image 8310. Due to the curvature of surface 8230, certain areas of surface 8230 may exhibit a different shade pattern (e.g., the image may be darker at the curved areas). In step 9020, processor 540 may use the derived information when initiating the optical character recognition. For example, processor 540 may use the derived information to aid the OCR process. In some embodiments, processor 540 may identify a curved area based on the shade pattern information. In other embodiments, processor 540 may perform image enhancement on the image based on the shad pattern information, e.g., brightening the darker areas such that text in these darker areas are easier to recognize.

Figure 91:
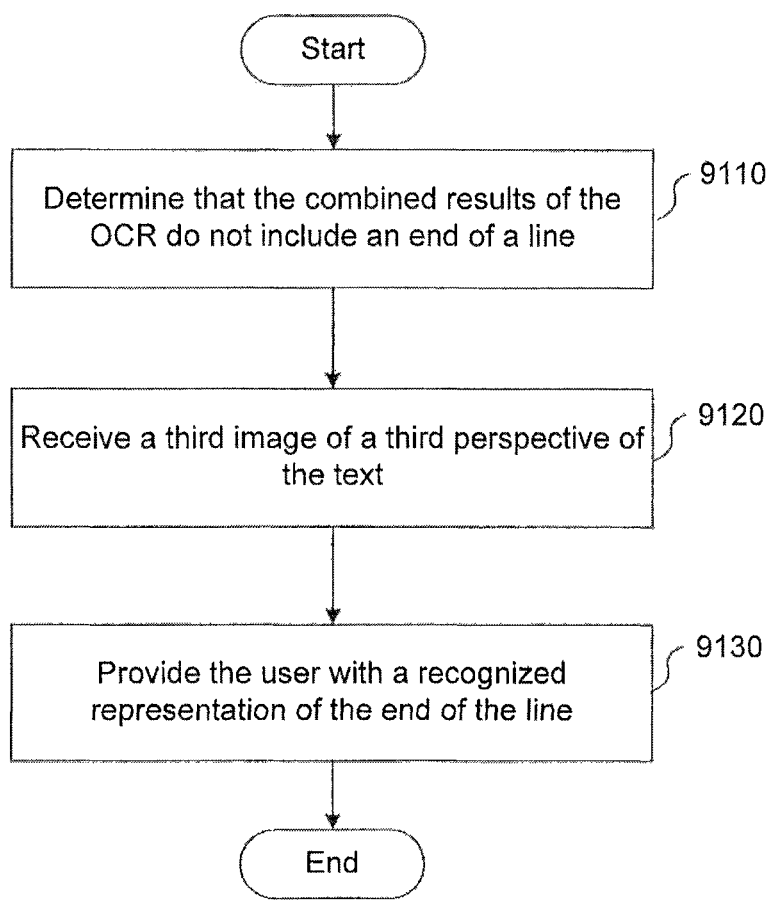
FIG. 91 is a flow chart of an exemplary process for providing a user with a recognized representation of an end of line.

FIG. 91 shows a process 9100 for providing user 100 with a recognized representation (e.g., an audible reading) of an end of a line. An end of line may include an end of a sentence, an end of a row/column of text, an end of a passage or paragraph, an end of a page, etc. To provide user 100 with an audible reading of an end of line may help user 100 to realize that a certain section of text (e.g., a sentence, a row or column, a passage or paragraph, a page, etc.) has been recognized and presented. Examples of recognized representations of an end of line may include a termination phrase such as "end," "over," "finished," "completed," etc.; an audible tone; a short period of stop or silence; a vibration; or other recognizable forms of notification.

Process 9100 may be performed after step 8580 in FIG. 85. In step 9110, processor 540 may determine that the combined results of the optical character recognition process (e.g., combined OCR results from step 8550 or results from step 8570 that takes into account information from additional images) do not include an end of a line. For example, text sections 8312 and 8332 may not cover an entire sentence, row/column, passage/paragraph, etc. Processor 540 may determine such a situation exists through, for example, analyzing the layout, punctuation, etc. of the text. In step 9120, processor 540 may receive a third image (e.g., a different image from the first and second images received in steps 8520 and 8530) of a third perspective of the text (e.g., a different perspective from the first and second perspectives described in steps 8520 and 8530). For example, processor 540 may instruct user 100 to take one or more additional images having a different perspective (e.g., the one or more additional images cover the end of line of the text) from those of images 8310 and 8330 and save the one or more additional images in memory 520 (e.g., database 8140). These additional images may be retrieved by processor 540 from memory 520 to recognize the text portion related to the end of the line. In step 9130, processor 540 may provide user 100 with a recognized representation of the end of the line. For example, processor 540 may provide user 100 with audible reading of a termination phrase, an audible tone; a short period of stop or silence; a vibration; or other recognizable forms of notification, as described above.

As is evident from the foregoing, apparatus 110 may provide a wide range of functionality. More specifically, in embodiments consistent with the present disclosure, apparatus 110 may capture image data that includes textual information and non-textual information disposed within a field-of-view of sensory unit 120, and identify portions of the textual information for audible presentation based on contextual information and one or more contextual rules. Apparatus 110 may use the one or more contextual rules to associate the contextual information with portions of the textual information to include and/or exclude from the audible presentation.

In certain aspects, "textual information" consistent with the disclosed embodiments may include, but is not limited to, printed text, handwritten text, coded text, text projected onto a corresponding surface, text displayed to the user through a corresponding display screen or touchscreen, and any additional or alternate textual information appropriate to the user and to apparatus 110. Further, the "non-textual information" may include, but is not limited to, images of various triggers (e.g., a human appendage, a cane, or a pointer), images of physical objects, images of persons, images of surroundings, and images of other non-textual objects disposed within the field-of-view of sensory unit 120.

Further, in some aspects, "portions" of textual information consistent with the disclosed embodiments may represent one or more linguistic elements capable of conveying literal or practical meaning to the user of apparatus 110. By way of example, such linguistic elements may include, but are not limited to, words, phrases, sentences, paragraphs, and other linguistic elements appropriate to the user and the textual information. The disclosed embodiments are, however, not limited such exemplary linguistic elements, and in further embodiments, portions of textual information consistent with the disclosed embodiments may include numbers, alpha-numeric character strings (e.g., acronyms, license plate numbers, road numbers, etc.), and other structured, non-linguistic elements capable of conveying meaning to the user of apparatus 110.

In certain embodiments, the portions of textual information may be disposed within discrete regions of the captured image data. By of example, the discrete regions may correspond to "zones" within an object associated with the captured image data (e.g., a document or physical object disposed within a field-of-view of sensory unit 120). In certain aspects, textual information disposed within a corresponding one of the zones may be associated with a particular logical role or purpose within the underlying object. For example, sensory unit 120 may capture an image of a train schedule, and the captured image data may include textual information disposed within discrete zones that inform the user of apparatus 110 of departing trains, arriving trains, and general announcements.

In some aspects, "contextual information" may include any information having a direct or indirect relationship with textual or non-textual information disposed within a field-of-view of sensory unit 120 of apparatus 110. By way of example, contextual information consistent with the disclosed embodiments may include, but is not limited to, a time or a location at which apparatus 110 captured a portion of textual and/or non-textual information, information identifying a type of document associated with captured image data (e.g., a newspaper, magazine, or web page), information indicative of one or more user preferences for an audible presentation of textual information, a location of a user, and any additional or alternate contextual information appropriate to the user, the textual information, and apparatus 110.

Further, in some aspects, "contextual rules" consistent with the disclosed embodiments may associate elements of contextual information with elements of textual information to be excluded from an audible presentation of the textual information. By way of example, apparatus 110 may capture image data corresponding to a newspaper article, and the textual information may include text associated with a body of the article, a title of the article, and further, an author, publication date, and page number associated with the article. In such an instance, a contextual rule consistent with the disclosed embodiments may specify that apparatus 110 exclude text corresponding to the author, the publication date, and/or the page number from an audible presentation of the newspaper article.

The disclosed embodiments are, however, not limited to contextual rules that exclude certain portions of textual information from audible presentation. In certain aspects, at least one of the contextual rules may associate elements of the contextual information with one of more of the portions that should be included within the audible presentation. Additionally or alternatively, contextual rules consistent with the disclosed embodiments may specify a presentation order for corresponding portions of textual information, and additionally or alternatively, may specify that one or more portions of the textual information are prioritized during audible presentation.

By way of example, apparatus 110 may capture image data corresponding to a product displayed for sale in a grocery store, and the textual information may include a list of ingredients. In such instances, contextual information associated with the ingredients may identify a food allergy of a corresponding user (e.g., an allergy to peanuts and products processed in proximity to peanuts), and contextual rules consistent with the disclosed embodiments may specify that apparatus 110 prioritize the audible presentation of any ingredients within the list that correspond to the user's food allergy.

Figure 92:
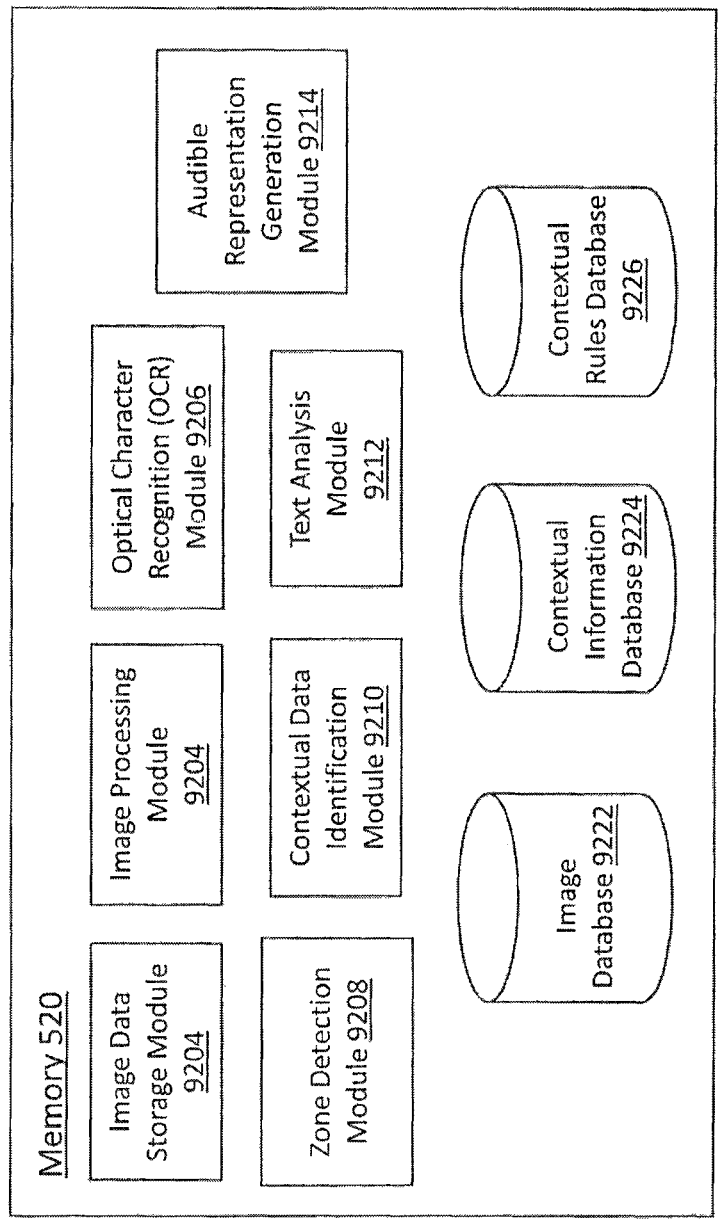
FIG. 92 illustrates an exemplary set of application modules and databases, according to disclosed embodiments.

In an embodiment, apparatus 110 may include a memory (e.g., memory 520) configured to store one or more applications and application modules that, when executed by a processor (e.g., processor 540), enable processor 540 to identify and audible present portions of captured textual data based on corresponding contextual information and one or more contextual rules that associate the contextual information with excluded, included, ordered, or prioritized portions of the textual information. In certain aspects, memory 520 may also be configured to store information that identifies one or more elements of contextual information associated with the captured image data and/or textual information disposed within the captured data. Additionally, memory 520 may store information that identifies one or more contextual rules that associate elements of the contextual information with corresponding portions of the textual information to be excluded, included, ordered, or prioritized within the audible presentation. FIG. 92 illustrates an exemplary structure of memory 520, in accordance with disclosed embodiments.

In FIG. 92, memory 520 may be configured to store an image data storage module 9202 and an image database 9222. In one embodiment, image data storage module 9202, upon execution by processor 540, may enable processor 540 to receive data corresponding to one or more images captured by sensory unit 120, and to store the captured image data within image database 9222. In some aspects, the captured image data may include textual information (e.g., printed, handwritten, coded, projected, and/or displayed text) and non-textual information (e.g., images of physical objects, persons, and/or triggers), and processor 540 may store the image data in image database 9222 with additional data specifying a time and/or date at which sensory unit 120 captured the image data. In additional embodiments, image data storage module 9202 may further enable processor 540 to configure wireless transceiver 530 to transmit the captured image data to one or more devices (e.g., an external data repository or a user's mobile device) in communication with apparatus 110 across a corresponding wired or wireless network.

Memory 520 may also be configured to store an image processing module 9204, optical character recognition (OCR) module 9206, and a zone detection module 9208. In an embodiment, image processing module 9204, upon execution by processor 540, may enable processor 540 to process the captured image data and identify textual information within the captured image data. In certain aspects, textual information consistent with the disclosed embodiments may include, but is not limited to, printed text (e.g., text disposed on a page of a newspaper, magazine, book), handwritten text, coded text, text displayed to a user through a display unit of a corresponding device (e.g., an electronic book, a television a web page, or an screen of a mobile application), text disposed on a flat or curved surface of an object within a field-of-view of apparatus 110 (e.g., a billboard sign, a street sign, text displayed on product packaging), text projected onto a corresponding screen (e.g., during presentation of a movie at a theater), and any additional or alternate text disposed within images captured by sensory unit 120.

In an embodiment, OCR module 9206 may, upon execution by processor 540, enable processor 540 to perform one or more OCR processes on textual information disposed within the captured image data. By way of example, processor 540 may execute image processing module 9204 to identify portions of the captured image data that include textual information, and further, may execute OCR module 9206 to retrieve machine-readable text from the textual information. In certain aspects, processor 540 may execute OCR module 9206 to identify and retrieve machine-readable text from textual information that includes characters defined by 10 or less pixels, and additionally or alternatively characters defined by 6 or less pixels In further embodiments, zone detection module 9208 may, upon execution by processor 540, enable processor 540 to analyze textual information within the captured data to detect one or more "zones" of textual information. In certain aspects, and as described above, the textual information within each of the detected zones may have a corresponding logical role and/or purpose within a document or object associated with the captured image data.

By way of example, apparatus 110 may capture an image of a train schedule for a local rail station that includes, among other things, information identifying arriving trains, departing trains, and various general announcements. In some embodiments, processor 540 may execute image processing module 9204 to identify portions of the captured image data that include textual information, and further, may execute zone detection module 9208 to detect zones of the identified textual information that inform the user of apparatus 110 of the arriving trains, the departing trains, and the general announcements. In additional embodiments, processor 540 may execute zone detection module 9208 in conjunction with OCR module 9206 to detect one or more zones within the textual information, and to subsequently identify and retrieve machine-readable text from the textual information disposed within the zones.

Referring back to FIG. 92, memory 520 may also be configured to store a contextual data identification module 9210, a contextual information database 9224, and a contextual rule database 9226. In an embodiment, processor 540 may, upon execution of contextual data identification module 9210, access contextual information database 9224 and obtain contextual information having a direct or indirect relationship with the identified textual information and/or the captured image data. By way of example, contextual information consistent with the disclosed embodiments may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

Further, processor 540 may also access contextual rule database 9226 upon execution of contextual data identification module 9210, and may obtain one or more contextual rules that associate elements of the contextual information with corresponding portions of textual information within the captured image data. In some aspects, the contextual rules may associate an element of contextual information with one or more of the portions that should be excluded from an audible presentation. Additionally or alternatively, the contextual rules may associate elements of the contextual information with one of more of the portions that should be included within the audible presentation. Further, in other embodiments, the contextual rules may identify an order in which processor 540 presents the portions to the user during the audible presentation, and/or may specify that processor 540 should prioritize one or more of the portions during the audible presentation.

As illustrated in FIG. 92, memory 520 may also be configured to store a text analysis module 9212 and an audible representation generation module 9214. In one embodiment, processor 540 may execute text analysis module 9214 to identify portions of the textual information for audible presentation to the user. In certain aspects, upon execution of text analysis module, processor 540 may leverage contextual information associated with the captured image data and one or more corresponding contextual rules to identify portions of the textual information that should be included within an audible presentation. As described above, the identified portions of textual information may include portions of machine-readable text identified and retrieved using a corresponding OCR process, and further, may also include textual information disposed within corresponding zones having specific logical roles or purposes within a document or object associated with the captured image data.

In certain aspects, processor 540 may leverage the contextual information and corresponding contextual rules to identify at least one first portion of the textual information for inclusion in an audible presentation of the textual information, and at least one second portion of the textual information to be excluded from the audible presentation. By way of example, the excluded second portion may include at least one pre-defined word, one or more pre-defined types of textual information (e.g., an author of the textual information, a page number, and/or a publication date). Further, in other aspects, the included first portion and the excluded second portion may be drawn from a single linguistic element of the textual information (e.g., a single sentence or a single paragraph).

In an embodiment, and upon execution of audible representation generation module 9214, processor 540 may generate the audible representation of the textual information, which apparatus 110 may present to the user through a speaker or a bone conduction headphone associated with processing unit 140. In some aspects, processor 540 may generate discrete audible representations corresponding to one or more portions of textual information selected for audible presentation (e.g., in accordance with contextual information and corresponding contextual rules), and may concatenate, combine, or order the discrete audible presentations to generate the audible representation of the textual information. For example, as described above, the generated audible representation of the textual information may include the at least one first portion of the textual information, and exclude the at least one second portion of the textual information.

In some aspects, processor 540 may generate and cause apparatus 110 to present the audible representation of the textual information in response to an existence of a "trigger" within the captured image data. By way of example, triggers consistent with the disclosed embodiments include, but are not limited to, an image of a human appendage (e.g., a finger) within the captured image data, an image of a cane or other pointer, or a particular movement of a human appendage, cane, or other pointer within the field-of-view of sensor unit 120. In such instances, processor 540 may detect the existence of the trigger within the captured image data, and may execute audible representation generation module 9214 in response to the detected trigger.

In other embodiments, processor 540 may execute audible representation generation module 9214 in response to an audible input provided by the user (e.g., an audible input spoken by the user into a microphone associated with apparatus 110), a tactile input provided by the user (e.g., the user may tap a sensor or other input device disposed on a surface of apparatus 110). Further, in some embodiments, processor 540 may execute audible representation generation module 9214 automatically upon receipt of the captured image data, or within a pre-determined time period after receipt of the captured image data.

Further, in certain embodiments, apparatus 110 may selectively pause and restart the audible presentation of the textual information in response to one or more pre-determined actions by the user. For example, and as described above, processor 540 may execute audible representation generation module 9214 to generate the audible representation of the textual information, which apparatus 110 may present to the user. During presentation of the audible representation, sensory unit 120 may continue to capture image data within a corresponding field-of-view of sensory unit 120, and may continuously provide the captured image data to processing unit 140 for storage within image database 9222.

In one aspect, and upon execution of audible representation generation module 9214, processor 540 may monitor the newly-received captured image data to determine whether the user looks away from the textual information (e.g., through a corresponding change in the field-of-view of sensory unit 120). If processor 540 determines that the user no longer views at least a portion of the textual information, processor 540 may pause the audible presentation and identify a stopping point within the textual information. In certain embodiments, processor 540 may continue to monitor the captured image data to determine whether the user again views at least a portion of the textual information. If the user again views the presented textual information, processor 540 may cause apparatus 110 to present the audible representation of the textual information from the identified stopping point.

In other embodiments, image database 9222, contextual information data 9224, and/or contextual rule database 9226 may be located remotely from memory 520, and be accessible to other components of apparatus 110 (e.g., processing unit 140) via one or more wireless connections (e.g., a wireless network). While three databases are shown, it should be understood that one or more of image database 9222, contextual information data 9224, and contextual rule database 9226 may be combined and/or interconnected databases may make up the databases. Image database 9222, contextual information data 9224, and/or contextual rule database 9226 may further include computing components (e.g., database management system, database server, etc.) configured to receive and process requests for data stored in associated memory devices.

Image data storage module 9202, image processing module 9204, OCR module 9206, zone detection module 9208, contextual data identification module 9210, text analysis module 9212, and audible representation generation module 9214 may be implemented in software, hardware, firmware, a mix of any of those, or the like. For example, if the modules are implemented in software, they may be stored in memory 520, as shown in FIG. 92. Other components of processing unit 140 and/or sensory unit 120 may be configured to perform processes to implement and facilitate operations of the modules. Thus, image data storage module 9202, image processing module 9204. OCR module 9206, zone detection module 9208, contextual data identification module 9210, text analysis module 9212, and audible representation generation module 9214 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., image data storage module 9202, image processing module 9204, OCR module 9206, zone detection module 9208, contextual data identification module 9210, text analysis module 9212, and audible representation generation module 9214) may each include dedicated sensors (e.g., IR, image sensors, etc.) and/or dedicated application processing devices to perform the functionality associated with each module.

Figure 93:
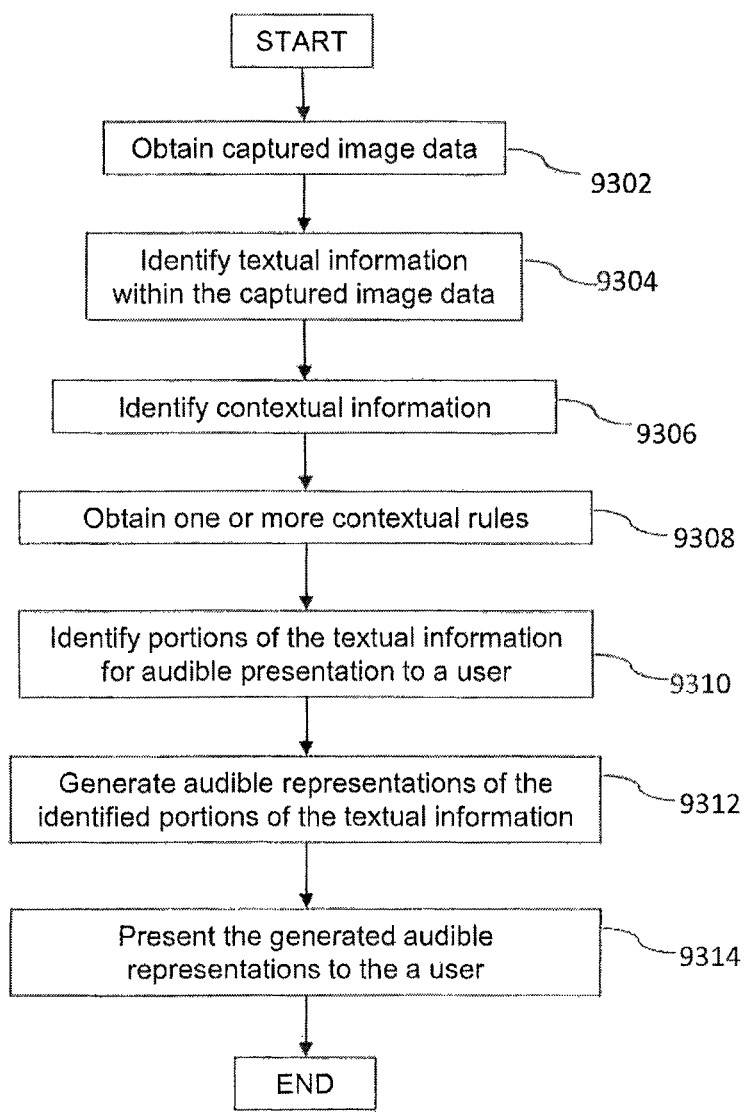

FIG. 93 is a flow diagram of an exemplary process 9300 for generating audible representations of textual data within captured image data, in accordance with disclosed embodiments. As described above, sensory unit 120 may capture image data that includes textual information and non-textual information disposed within a corresponding field-of-view. Processing unit 130 may receive the captured image data, and processor 540 may execute one or more application modules to identify portions of textual information for audible presentation based on contextual information and one or more corresponding contextual rules. Process 9300 provides further details on how processor 540 identifies portions of textual information for audible representation based on contextual information and contextual rules that associate elements of the contextual information with corresponding ones of the portions.

In step 9302, processor 540 may obtain captured image data. In some aspects, sensory unit 120 may capture one or more images, and the captured image data may be transmitted to processing unit 140 across wired or wireless communications link 130. Processor 540 may, in step 9302, obtain the captured image data directly from sensory module 120 across communications link 130, or alternatively, processor 540 may retrieve the captured image data from a corresponding data repository (e.g., image database 9222 of memory 540). By way of example, the captured image data may include one or more regions of printed, displayed, or projected information.

In step 9304, processor 540 may analyze the captured image data to identify textual information. As described above, the textual information may include, but is not limited to, printed, handwritten, projected, coded, or displayed text, and processor 540 may perform a layout analysis to detect the textual information within the captured image data. By way of example, the detected textual information may include, but are not limited to, paragraphs of text, blocks of text, regions that include text, logos, titles, captions, footnotes, and any additional or alternate portions of the captured image data that includes printed, handwritten, displayed, coded, and/or projected text.

In step 9306, processor 540 may identify contextual information associated with the identified textual data and/or the captured image. By way of example, in step 9306, processor 540 may access a corresponding data repository (e.g., contextual information database 9224 of memory 540) to identify and obtain the contextual information. In some aspects, as described above, the contextual information may include any information having a direct or indirect relationship with the identified textual information and/or the captured image data. For example, the contextual information may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

In step 9308, processor 540 may obtain one or more contextual rules associated with the identified contextual information. By way of example, in step 9308, processor 540 may access a corresponding data repository (e.g., contextual rules database 9226) to identify and obtain the one or more contextual rules. In some aspects, at least one of the contextual rules may associate an element of the contextual information with a corresponding portion of the textual information that should be excluded from an audible presentation of the textual information. In other aspects, at least one of the contextual rules may associate an element of the contextual information with a corresponding portion of the textual information that should be included within the audible presentation. Additionally or alternatively, the contextual rules may specify an order in which processor 540 should audibly present corresponding portions of the textual information, and further may specify that one or more portions the textual information are prioritized during the audible presentation.

In step 9310, processor 540 may leverage the contextual information and the contextual rules to identify portions of the textual information that should be included within the audible presentation of the textual information. As described above, processor 540 may identify portions of textual information in step 9310 that include portions of machine-readable text identified and retrieved using a corresponding OCR process. Further, in some aspects, processor 540 may identify portions of the textual information disclosed within at least one zone having a specific logical role or purpose within a document or object associated with the captured image data.

In one embodiment, in step 9310, processor 540 may leverage the contextual information and corresponding contextual rules to identify at least one first portion of the textual information for inclusion in the audible presentation, and at least one second portion of the textual information to be excluded from the audible presentation. By way of example, the excluded second portion may include at least one pre-defined word, one or more pre-defined types of textual information (e.g., an author of the textual information, a page number, and/or a publication date). Further, in other aspects, the included first portion and the excluded second portion may be drawn from a single linguistic element of the textual information (e.g., a single sentence or a single paragraph).

In step 9312, processor 540 may generate audible representations of the one or more identified portions of the textual information (e.g., the portions identified in step 9310), and in step 9314, processor 540 may configure apparatus 110 to present the generated audible representations to the user through a speaker or a bone conduction headphone associated with processing unit 140. In one embodiment, processor 540 may order (e.g., as specified within a corresponding one of the contextual rules), concatenate, or otherwise combine the generated audible representation to form a collective audible representation of the textual information within the captured data, which may be present to the user of apparatus 110 in step 9314.

By way of example, as described above in reference to step 9310, processor 540 may identify a first portion of the textual information that will be included within the audible representation of the textual information, and further, may identify a second portion of the textual information that will be excluded from the audible presentation. In such an instance, processor 540 may generate an audible representation of the first portion of the textual information in step 9312, and may cause apparatus 110 to present the generated audible representation to the user in step 9314. Upon presentation of the audible representation of the textual information to the user, exemplary routine 9300 is complete.

In some aspects, processor 540 may generate and cause apparatus 110 to present the audible representations in response to an existence of a "trigger" within the captured image data. By way of example, triggers consistent with the disclosed embodiments include, but are not limited to, an image of a human appendage within the captured image data, an image of a cane or other pointer, or a particular movement of a human appendage, cane, or other pointer within the field-of-view of sensor unit 120. In such instances, processor 540 may detect the existence of the trigger within the captured image data, and in response to the detected trigger, may generate the audible representations of the identified portions of the textual information in step 9312.

In other embodiments, processor 540 may cause apparatus 110 to present the generated audible representation in response to an audible input provided by the user (e.g., an audible input spoken by the user into a microphone associated with apparatus 110), a tactile input provided by the user (e.g., the user may tap a sensor or other input device disposed on a surface of apparatus 110).

Further, in certain embodiments, apparatus 110 may adaptively pause and restart the audible presentation of the textual document in response to pre-determined actions of the user. For example, and as described above, processor 540 may generate the audible representation of the textual information, which apparatus 110 may present to the user in step 9314. During presentation of the audible representation, sensory unit 120 may continue to capture image data within a corresponding field-of-view of sensory unit 120, and may continuously provide the captured image data to processing unit 140 for storage within image database 9222.

In one aspect, processor 540 may monitor the newly-received captured image data to determine whether the user glances away from the textual information (e.g., through a corresponding change in the field-of-view of sensory unit 120). If processor 540 determines that the user no longer views at least a portion of the textual information, processor 540 may cause apparatus 110 to pause the audible presentation of the textual information in step 9314, and may identify a stopping point within the textual information that corresponds to the paused audible presentation. In certain embodiments, processor 540 may continue to monitor the captured image data to determine whether the user again views at least a portion of the textual information. If the user again views the textual information, processor 540 may cause apparatus 110 to re-start a presentation of the audible representation from the identified stopping point.

Using the embodiments described above, processor 540 may identify textual information within captured image data (e.g., step 9304 of FIG. 93), identify and obtain contextual information and corresponding contextual rules (e.g., steps 9306 and 9308 of FIG. 93), and identify one or more portions of the textual information for audible presentation based on the contextual information and the corresponding contextual rules (e.g., step 9310 of FIG. 93). In some embodiments, described below in reference to FIG. 94, processor 540 may identify at least one of the textual information portions based on an analysis of machine-readable text retrieved from the textual information by a corresponding OCR process.

Figure 94:
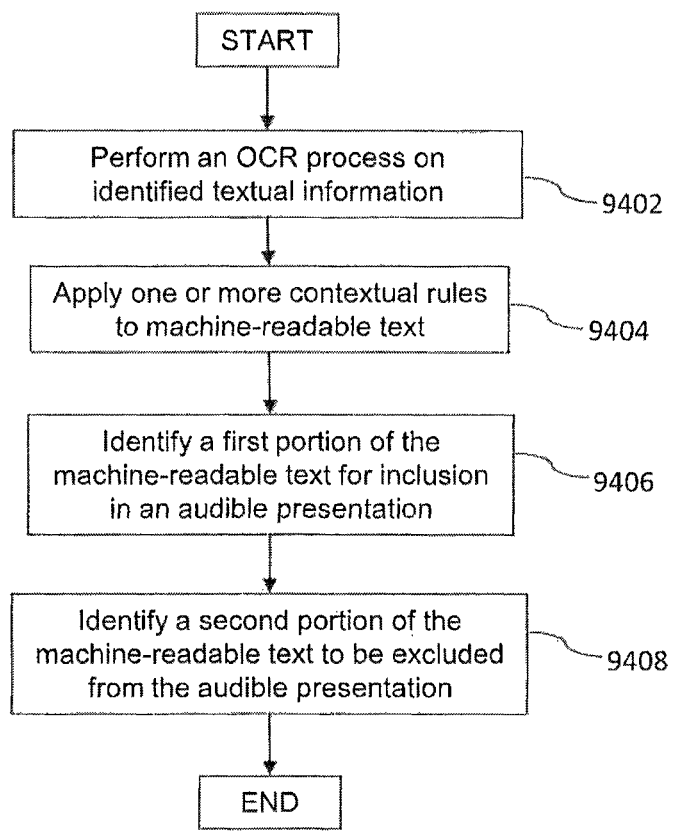

FIG. 94 is a flow diagram of an exemplary process 9400 that identifies portions of machine-readable text for audible presentation to a user, according to disclosed embodiments. As described above, processor 540 may leverage contextual information and corresponding contextual rules to identify a first portion of textual information to be included within an audible representation of the textual information, and further, a second portion of the textual information to be excluded from the audible representation. In some embodiments, the first and second portions of the textual information may include machine-readable text retrieved from the textual information through a corresponding OCR process. Process 9400 provides further details on how processor 540 performs an OCR process to retrieved machine-readable text from textual information within captured image data, and leverages contextual information and one or more contextual rules to identify portions of the machine-readable text for audible presentation to a user.

In step 9402, processor 540 may perform an OCR process on at least a portion of textual information included within captured image data to identify and retrieve machine-readable text. As described above, sensory unit 120 may capture one or more images, and the captured image data may be transmitted to processing unit 140 across wired or wireless communications link 130. Processor 540 may obtain the captured image data (e.g., step 9302 of FIG. 93) and may analyze the captured image data to identify portions of the captured image data that include the textual information (e.g., step 9304 of FIG. 93). By way of example, the textual information may include, but is not limited to, paragraphs of text, blocks of text, regions that include text, logos, titles, captions, footnotes, and any additional or alternate portions of the image data that includes printed, handwritten, displayed, coded, and/or projected text.

In step 9404, processor 540 may apply one or more contextual rules to the retrieved machine-readable text. In certain aspects, at least one of the contextual rules may associate contextual information with a specific portion of the machine-readable text that will be excluded from an audible presentation of the textual information. Additionally or alternatively, at least one of the contextual rules may associate the contextual information with a specific portion of the machine-readable text that will be included within the audible presentation. Further, in additional aspects, contextual rules consistent with the disclosed embodiments may specify an order in which processor 540 may audibly present specific portions of the machine-readable text to the user. By way of example, the specified ordering may prioritize one or more portions of the machine-readable text that may be of particular importance to the user, such as information relevant to the user's health, safety, and well-being (e.g., portions of machine-readable text within a menu that correspond to an allergy of the user).

In some aspects, as described above, processor 540 may obtain the contextual information and the contextual rules from corresponding data repositories (e.g., contextual information database 9224 and contextual rules database 9226 of memory 520). As described above, the contextual information may include any information having a direct or indirect relationship with the textual information. For example, the obtained contextual information may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

In step 9408, processor 540 may identify at least one first portion of the machine-readable text that will be included within the audible representation, and in step 9408, processor 540 may identify at least one second portion of the machine readable text that will be excluded from the audible representation. As described above, processor 540 may identify the first and second portions based on an application of one or more contextual rules to the machine-readable text.

In certain aspects, in step 9408, processor 540 may identify a plurality of first portions of the machine-readable text for inclusion within the audible presentation, and further, may identify an order in which the audible representation presents the identified first portions to the user. Additionally, in some aspects, the excluded second portion may include at least one pre-defined word or pre-defined types of machine-readable text (e.g., an author of the textual information, a page number, and/or a publication date). Further, in other aspects, the included first portion and the excluded second portion may be drawn from a single sentence or a single paragraph within the machine-readable text.

Upon identification of the first and second portions of the machine-readable text, exemplary process 9400 is complete. In certain embodiments, processor 540 may then generate an audible representation of the first portions of the machine-readable text and cause apparatus 110 to present the generated audible representation to the user, as described above in reference to steps 9312 and 9314 of FIG. 93.

Using the embodiments described above, apparatus 110 may capture image data that includes textual information, perform an OCR process to identify and retrieve machine-readable text from the textual information, and present, to a user, audible representations of portions of the machine-readable text selected in accordance with one or more contextual rules. By way of example, as illustrated in FIG. 95, a user of apparatus 110 may view a page 9500 of a printed newspaper, and apparatus 110 may capture an image that includes a portion 9502 of page 9500 corresponding to a field-of-view of sensory unit 120.

As described above, processor 540 may identify textual information within the captured image data (e.g., step 9304 of FIG. 93), may identify contextual information associated with the captured image data (e.g., step 9306 of FIG. 93), may obtain one or more contextual rules associated with the contextual information (e.g., step 9308 of FIG. 93), and further, may perform an OCR process on the textual information to identify and retrieve machine-readable text (e.g., step 9402 of FIG. 94). By way of example, processor 540 may obtain contextual information identifying a type of document associated with the captured image data (e.g., a printed newspaper article), and obtain a contextual rule indicating that processor 540 should exclude an author, the publication date, and a page number from an audible presentation of a printed newspaper article.

Figure 95:
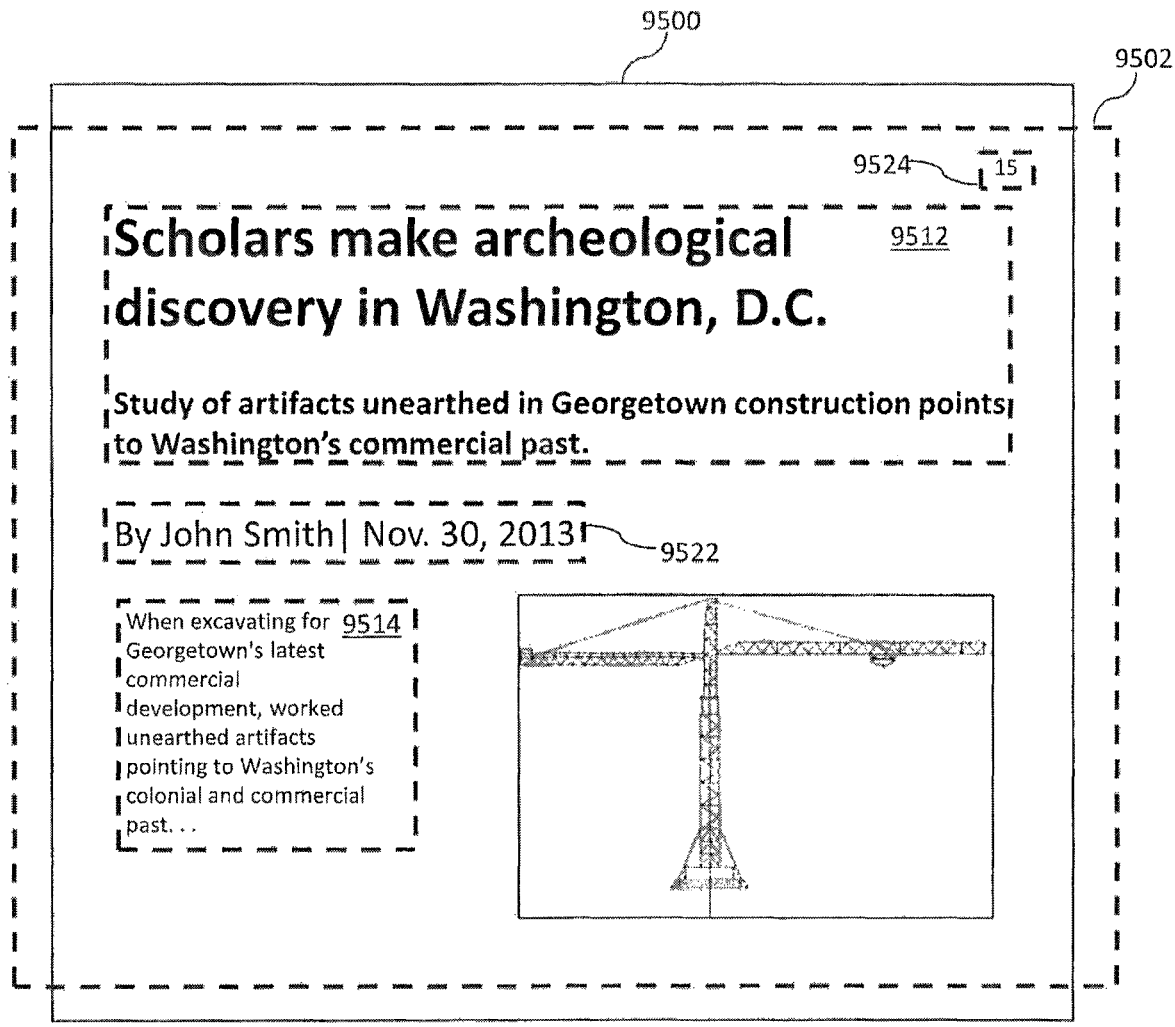

As illustrated in FIG. 95, processor 540 may apply the obtained contextual rule to the retrieved machine-readable text of the printed newspaper article to select text portion 9512 (e.g., a title of the printed newspaper article) and text portion 9514 (e.g., a body of the printed newspaper article) for inclusion within an audible representation of the printed newspaper article. Further, processor 540 may determine that text portion 9522 (e.g., an author and publication date of the printed newspaper article) and text portion 9524 (e.g., a page number of the printed newspaper article) should be excluded from the audible representation. As described above processor 540 may then generate the audible representation of text portions 9512 and 9514, and cause processor 540 to present the generated audible representation to a user through a speaker or a bone conduction headphone.

The disclosed embodiments are, however, not limited to contextual information that identifies to a type of a document associated with the captured image data. In additional embodiments, as described above, processor 540 may obtain contextual information that identifies not only the document type, but also one or more user preferences for an audible presentation of textual information disposed within the captured image data. By way of example, as illustrated in FIG. 96, a user of apparatus 110 view a printed menu 9600 provided by a restaurant, and apparatus 110 may capture an image that includes a portion 9602 of menu 9600 corresponding to a field-of-view of sensory unit 120.

As described above, processor 540 may identify textual information within the captured image data (e.g., step 9304 of FIG. 93), may identify contextual information associated with the captured image data (e.g., step 9306 of FIG. 93), may obtain one or more contextual rules associated with the contextual information (e.g., step 9308 of FIG. 93), and further, may perform an OCR process on the textual information to identify and retrieve machine-readable text (e.g., step 9402 of FIG. 94). In certain aspects, processor 540 may obtain contextual information that identifies a type of document associated with the captured image data (e.g., a menu) and one or more user preferences for an audible presentation of textual information disposed within the menu. By way of example, the user preferences within the contextual information may indicate that the user prefers an audible presentation of "vegetarian" and "vegan" items on the menu. In certain aspects, processor 540 may obtain a contextual rule indicating that processor 540 should generate audible representations of textual information corresponding to "vegan" or "vegetarian" items within menu 9600.

Figure 96:
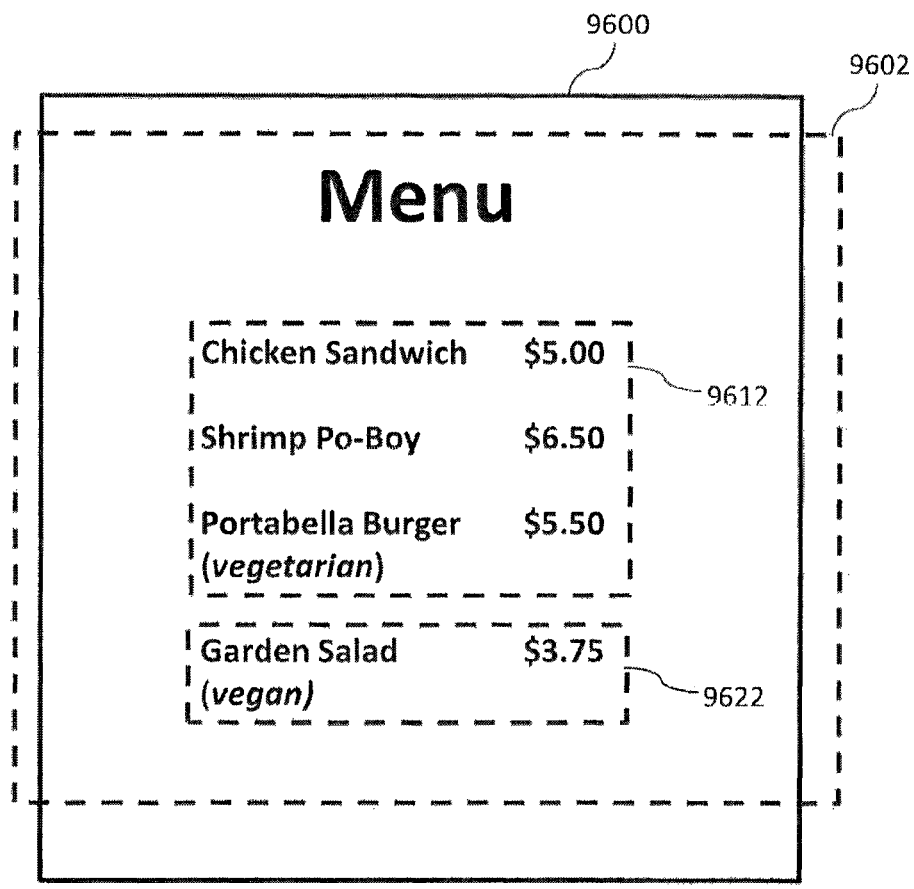

As illustrated in FIG. 96, processor 540 may apply the obtained contextual rule to the retrieved machine-readable text of menu 9600 to select text portion 9622, which corresponds to a "garden salad" identified as "vegan," for inclusion within an audible representation of menu 9600. Further, based on an application of the obtained contextual rule to the machine-readable text, processor 540 may determine that text portion 9612, which corresponds to various non-vegan and non-vegetarian menu items, should be excluded from the audible representation. As described above processor 540 may then generate the audible representation of text portion 9622, and cause processor 540 to present the generated audible representation to a user through a speaker or a bone conduction headphone.

In the embodiments described above, processor 540 may perform an OCR process that retrieves machine-readable text from textual information within captured image data, and may identify portions of the machine-readable text for audible presentation to a user based on an application of one or more contextual rules. In additional embodiments, processor 540 may leverage a logical structure of the textual information to identify portions of the textual information that should be audibly presented to the user. For example, as described below in reference to FIG. 97, the textual information within captured image data may be disposed into one or more "zones" having corresponding logical roles or purposes within a document or object associated with the captured image data. In certain aspects, processor 540 may identify portions of the textual information for audible presentation based on the application of the contextual rules to the textual information within the corresponding zones.

Figure 97:
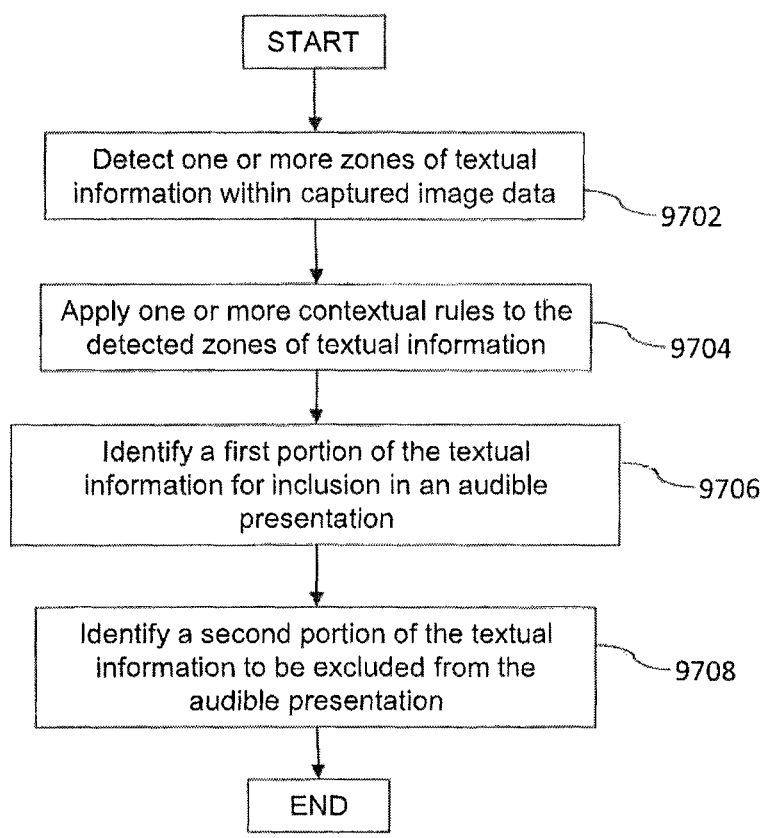

FIG. 97 is a flow diagram of an exemplary process 9700 that identifies portions of textual information for audible presentation based on a logical structure of the textual information, according to disclosed embodiments. As described above, processor 540 may leverage contextual information and corresponding contextual rules to identify a first portion of textual information suitable for inclusion within an audible representation of the textual information, and further, a second portion of the textual information to be excluded from the audible representation. In some embodiments, the first and second portions may include textual information disposed within one or more zones having corresponding logical roles or purposes within a document or object associated within the captured image data. Process 9700 provides further details on how processor 540 performs a process that detects one or more zones of textual information within captured image data, and applies one of more contextual rules to the detected zones to identified portions of textual information for audible presentation.

In step 9702, processor 540 may analyze the textual information to detect a presence of one or more zones having corresponding roles or purposes. As described above, sensory unit 120 may capture one or more images, and the captured image data may be transmitted to processing unit 140 across wired or wireless communications link 130. Processor 540 may obtain the captured image data (e.g., step 9302 of FIG. 93) and may analyze the captured image data to identify portions of the captured image data that include the textual information (e.g., step 9304 of FIG. 93). By way of example, the textual information may include, but are not limited to, paragraphs of text, blocks of text, regions that include text, logos, titles, captions, footnotes, and any additional or alternate portions of the image data that includes printed, handwritten, displayed, coded, and/or projected text.

Further, in some aspects, the logical roles or purposes that correspond to the detected zones may be defined based on an object or type of object captured within the image data. For example, the image data may capture a train schedule disposed within a field-of-view of apparatus 110, and the captured image data may include textual information disposed into discrete zones that inform a user of apparatus 110 of scheduled departures, scheduled arrivals, and messages provided to passengers by a corresponding railway carrier. Further, the textual information disposed within corresponding ones of the detected zones may include, but is not limited to, words, phrases, sentences, or other structured strings of alphanumeric characters having a logical roles or purposes consistent with the corresponding detected zone.

In step 9704, processor 540 may apply one or more contextual rules to the textual information disposed within the detected zones. In certain aspects, at least one of the contextual rules may associate contextual information with a specific portion of the textual information that will be excluded from an audible presentation of the textual information. Additionally or alternatively, at least one of the contextual rules may associate the contextual information with a specific portion of the textual information that will be included within the audible presentation. Further, in additional aspects, contextual rules consistent with the disclosed embodiments may specify an order in which processor 540 may audibly present specific portions of the textual information to the user. By way of example, the specified ordering may prioritize one or more portions of the textual information that may be of particular importance to the user, such as information relevant to the user's health, safety, and well-being (e.g., processor 540 may prioritize an audible presentation of portions of textual information relevant to an allergy of the user).

In some aspects, as described above, processor 540 may obtain the contextual information and the contextual rules from corresponding data repositories (e.g., contextual information database 9224 and contextual rules database 9226 of memory 520), and the contextual information may include any information having a direct or indirect relationship with the textual information. For example, the obtained contextual information may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

In step 9706, processor 540 may identify a first portion of the textual information that should be included within the audible representation, and in step 9708, processor 540 may identify at least one second portion of the machine readable text that will be excluded from the audible representation. In one embodiment, the identified first and second portion may include textual information disposed within one or more of the detected zones, and processor 540 may identify the first and second portions based on an application of one or more contextual rules to the textual information disposed within the detected zones. Further, in additional embodiments, processor 540 may perform an OCR process on the textual information within the detected zones to facilitate the identification of the first and second portions of the textual information.

Upon identification of the first and second portions of the machine-readable text, exemplary process 9700 is complete. In certain embodiments, processor 540 may then generate an audible representation of the first portions of the machine-readable text and cause apparatus 110 to present the generated audible representation to the user, as described above in reference to steps 9312 and 9314 of FIG. 93.

As described above in reference to FIG. 97, apparatus 110 may capture image data that includes textual information (e.g., step 9302 of FIG. 93), analyze the textual information to detect one or more zones into which the textual information is disposed (e.g., step 9702 of FIG. 97), apply one or more contextual rules to the detected zones of textual information (e.g., step 9704 of FIG. 97), and identify portions of textual information disposed within at least one of the detected zones for audible presentation to a user (e.g., steps 9706 and 9708 of FIG. 97). By way of example, as illustrated in FIG. 98, a user of apparatus 110 view a printed train schedule 9800, and apparatus 110 may capture an image that includes a portion 9802 of schedule 9800 corresponding to a field-of-view of sensory unit 120.

Figure 98:
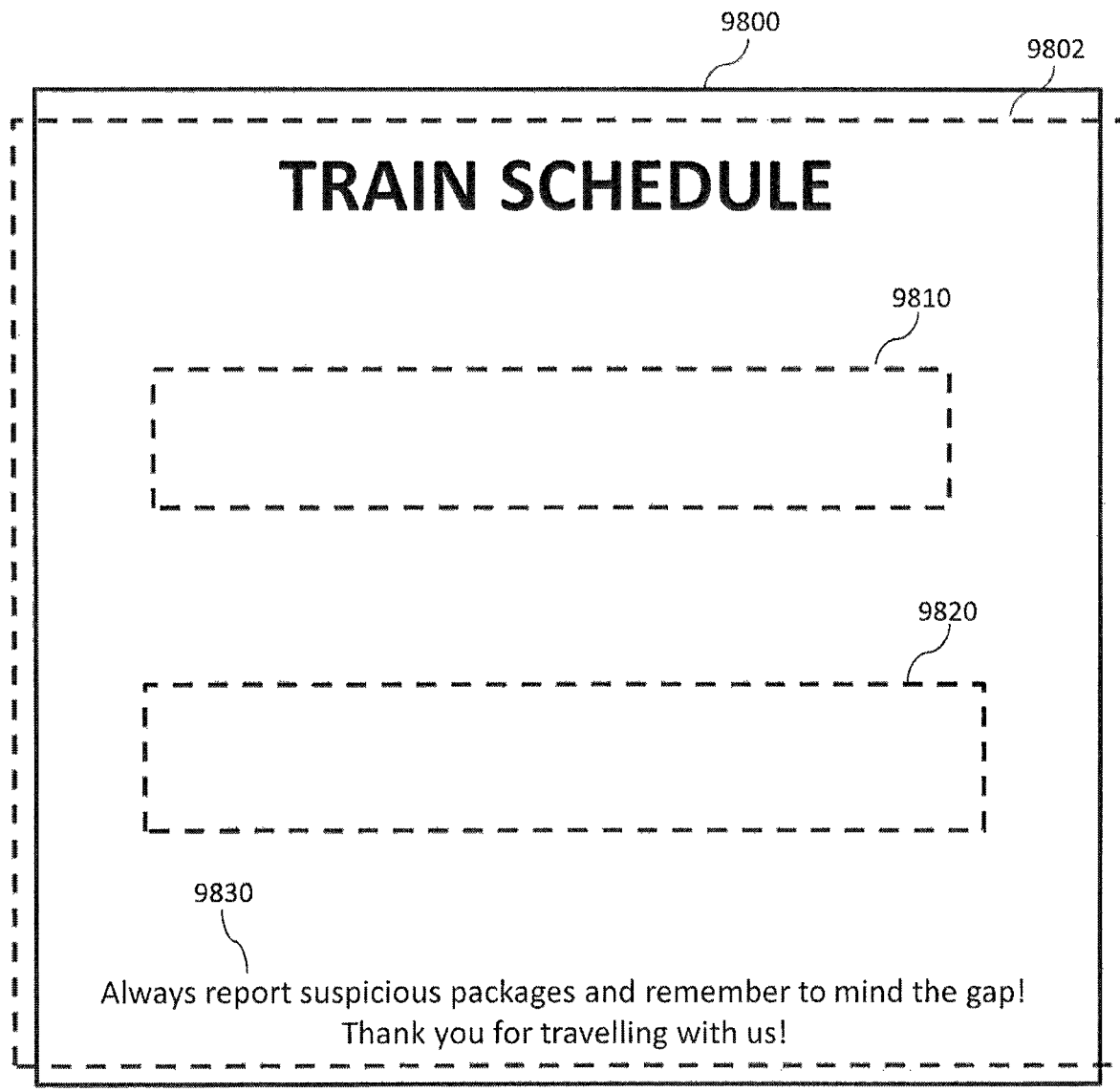

For example, in FIG. 98, processor 540 may detect within schedule 9800 a first zone 9810 that informs a user of one or more arriving trains, a second zone 9820 that informs the user of one or more departing trains, and a third zone 9830 that provides one or more general announcements to the user. In certain aspects, processor 540 obtain one or more contextual rules that explicitly exclude zones of a train schedule that inform the user of arriving trains and general announcements from a corresponding audible presentation. In such an instance, processor 540 may apply the obtained contextual rule to the detected zones of schedule 9800 to select textual information disposed within second zone 9820 (e.g., which informs the user of departing trains) for inclusion within an audible representation of schedule 9800. Further, processor 540 may determine that first and third zones 9810 and 9830 (which respectively inform the user of arriving trains and general announcements) should be excluded from the audible representation. As described above processor 540 may then generate the audible representation of the textual information within first zone 9820, and cause processor 540 to present the generated audible representation to a user through a speaker or a bone conduction headphone.

In additional embodiments, the exemplary processes of FIGS. 94 and 97 may be leveraged collectively to identify portions of textual information for audible presentation that better conform to the needs and preferences of a user of apparatus 110. In certain aspects, processor 540 may perform an OCR process on the textual information disposed within one or more of detected zones (e.g., as detected in step 9702 of FIG. 97) to generate audible representations of textual information that have specific logical roles and conform to specific user preferences.

For example, processor 540 may obtain contextual data that specifies a preference for audible presentations identifying trains that depart within a threshold time period (e.g., thirty minutes) of a time at which a user of apparatus 110 arrives at a train station. Accordingly, in such exemplary embodiments, processor 540 may obtain one or more contextual rules that explicitly exclude zones of a train schedule that inform the user of arriving trains and general announcements from a corresponding audible presentation, and further, that exclude textual information within a zone that informs the user of departing trains from the corresponding audible presentation if that textual information corresponds to a train that departs outside of the threshold time period.

Referring back to FIG. 98, and as described above, processor 540 may apply the obtained contextual rule to the detected zones of schedule 9800 to exclude first and third zones 9810 and 9830 from the audible representation. Further, for example, if the user were to arrive at the train station at 6:08 p.m., processor 540 may determine that textual information within second zone 9820 corresponding to "Train No. 2285" to "Boston, Mass.," should be excluded from the audible presentation because the departure time of "8:00 p.m." falls outside of the threshold time period of thirty minutes. Accordingly, processor 540 may generate an audible representation of a portion of textual information within second zone 9820 corresponding to "Train No. 197" departing at 6:35 p.m. for New York, N.Y., since this textual information is disposed within the specified zone and corresponds to a train departing within the pre-determined threshold time period. As described above, processor 540 may cause apparatus 110 to present the generated audible representation to a user through a speaker or a bone conduction headphone.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus for processing real time images of an environment of a user, the apparatus comprising:
 a camera including an image sensor configured to be positioned for movement with a head of the user as the head moves, and to capture real time images; and
 at least one processor device for determining contextual information based on the real time images, the processor device being configured to:
 monitor a plurality of images captured by the image sensor to determine whether relative motion occurs between a stationary object in a first portion of a scene captured in the plurality of images and other portions of the scene that appear to be moving in the plurality of images, wherein the monitoring includes determining that the user is looking at the stationary object included in the first portion of the scene;
 if the first portion of the scene moves less than at least one other portion of the scene, obtain contextual information from the first portion of the scene; and
 adjust at least one parameter associated with the camera based on at least part of the contextual information.

2. The apparatus of claim 1, wherein the contextual information is used to identify an object in the first portion of the scene.

3. The apparatus of claim 1, wherein determining the contextual information includes comparing an object in the first portion of the scene with stored image data.

4. The apparatus of claim 1, wherein the at least one parameter associated with the camera includes at least one of: a focus point, an exposure time, an aperture size, light sensitivity, an image resolution, and a frame rate.

5. The apparatus of claim 1, wherein the first portion of the scene is associated with an object in a background of the scene, and the at least one other portion of the scene is associated with an object in a foreground of the scene.

6. The apparatus of claim 1, wherein the first portion of the scene is associated with an object in a foreground and the at least one other portion of the scene is associated with an object in the background.

7. A method for processing real time images of an environment of a user, the method comprising:
- monitoring a plurality of images captured by the image sensor to determine whether relative motion occurs between a stationary object in a first portion of a scene captured in the plurality of images and other portions of the scene that appear to be moving in the plurality of images, wherein the monitoring includes determining that the a user is looking at the stationary object included in the first portion of the scene;
- if the first portion of the scene moves less than at least one other portion of the scene, obtaining contextual information from the first portion of the scene; and
- adjusting at least one parameter associated with the camera based on at least part of the contextual information.

8. The method of claim 7, wherein the contextual information is used to identify an object in the first portion of the scene.

9. The method of claim 7, the method further comprising comparing an object in the first portion of the scene with stored image data.

10. The method of claim 7, wherein the at least one parameter associated with the camera includes at least one of: a focus point, an exposure time, an aperture size, light sensitivity, an image resolution, and a frame rate.

11. The method of claim 7, wherein the first portion of the scene is associated with an object in a background of the scene, and the at least one other portion of the scene is associated with an object in a foreground of the scene.

12. The method of claim 7, wherein the first portion of the scene is associated with an object in a foreground and the at least one other portion of the scene is associated with an object in the background.

13. The method of claim 7, the method further comprising
- determining that an object appears to be stationary in the first portion of the scene across the monitored images while the other portions of the scene appear to be moving across the monitored images;
- determining, from the monitored images, based on the stationary appearance of the object in the first portion of the scene across the monitored images while the other portions of the scene appear to be moving across the monitored images, that the user is tracking the object included in the first portion of the scene,
- wherein the object appears to be stationary across the monitored images while the other portions of the scene appear to be moving across the monitored images;
- obtaining contextual information associated with the object that the user is tracking; and
- providing feedback to the user based on at least part of the contextual information.

* * * * *